(12) United States Patent
Bell et al.

(10) Patent No.: US 7,338,960 B2
(45) Date of Patent: Mar. 4, 2008

(54) PHENYLALKANOIC ACID AND PHENYLOXYALKANOIC ACID DERIVATIVES AS HPPAR ACTIVATORS

(75) Inventors: Richard Bell, Stevenage (GB); Paul John Beswick, Harlow (GB); Romain Luc Marie Gosmini, Les Ulls (FR); Richard Martin Grimes, Stevenage (GB); Christopher Charles Frederick Hamlett, Stevenage (GB); Nigel Paul King, Harlow (GB); Vipulkumar Kantibhai Patel, Stevenage (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 85 days.

(21) Appl. No.: 10/518,679

(22) PCT Filed: Jun. 18, 2003

(86) PCT No.: PCT/EP03/06415

§ 371 (c)(1),
(2), (4) Date: Aug. 16, 2005

(87) PCT Pub. No.: WO04/000315

PCT Pub. Date: Dec. 31, 2003

(65) Prior Publication Data
US 2006/0089394 A1   Apr. 27, 2006

(30) Foreign Application Priority Data
Jun. 19, 2002   (GB) ................... 0214149.7

(51) Int. Cl.
*A61K 31/435* (2006.01)
*A61K 31/12* (2006.01)
*C07C 59/00* (2006.01)
*C07D 211/70* (2006.01)

(52) U.S. Cl. ............ 514/277; 514/683; 562/465; 562/471; 546/339

(58) Field of Classification Search ........... 562/465, 562/471; 514/683, 277; 546/339
See application file for complete search history.

(56) References Cited

U.S. PATENT DOCUMENTS 4,221,919 A * 9/1980 Grimova et al. ............ 562/465
5,399,575 A * 3/1995 Friebe et al. ............... 514/340

OTHER PUBLICATIONS

Chiellini et. al., "Synthesis and Biological Activity of Novel Thyroid Hormone Analogues: 5'-Aryl Substituted GC-1 Derivatives", Bioorganic & Medicinal Chemistry 10 (2002) 333-346.*
Hcaplus 117:131082.*
Chiellini et. al., "Synthesis and Biological Activity of Novel Thyroid Hormone Analogues: 5'Aryl Substituted GC-1 Derivatives", Bioorganic & Medicinal Chemistry 10(Issue 2) (2002), pp. 333-346.*
Baker et. al., "Irreversible Enzyme Inhibitors. 195. Inhibitors of Thymidine Kinase from Walker 256 Carcinoma Dervied from Thymidine 5'-Acetate", Baker et. al., Journal of Medicinal Chemistry, 1972, vol. 15, No. 9, pp. 940-944.*
Palmer, Michael, "The Structure and Reactions of Heterocyclic Compounds", Heterocyclic Compounds, Edward Arnold Ltd. , pp. 66, 68.*

* cited by examiner

*Primary Examiner*—Janet L. Andres
*Assistant Examiner*—Binta Robinson
(74) *Attorney, Agent, or Firm*—Jennifer L. Fox

(57) ABSTRACT

A compound of formula (I) or a pharmaceutically acceptable salt, solvate, or hydrolysable ester thereof, wherein:

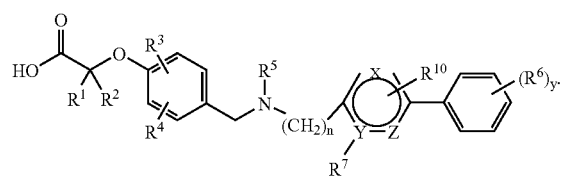

(I)

14 Claims, No Drawings

PHENYLALKANOIC ACID AND PHENYLOXYALKANOIC ACID DERIVATIVES AS HPPAR ACTIVATORS

This application is filed pursuant to 35 U.S.C. § 371 as a United States National Phase Application of International Application No. PCT/EP03/006415 filed Jun. 18, 2003, which claims priority from 0214149.7 GB filed Jun. 19, 2002.

The present invention relates to certain novel compounds. In particular, the present invention relates to compounds that activate human peroxisome proliferator activated receptors ("hPPARs"). The present invention also relates to method for preparing the compounds, their use in medicine, pharmaceutical compositions containing them and methods for the prevention or treatment of PPAR mediated diseases or conditions.

Several independent risk factors have been associated with cardiovascular disease. These include hypertension, increased fibrinogen levels, high levels of triglycerides, elevated LDL cholesterol, elevated total cholesterol, and low levels of HDL cholesterol. HMG CoA reductase inhibitors ("statins") are useful for treating conditions characterized by high LDL-c levels. It has been shown that lowering LDL-c is not sufficient for reducing the risk of cardiovascular disease in some patients, particularly those with normal LDL-c levels. This population pool is identified by the independent risk factor of low HDL-c. The increased risk of cardiovascular disease associated with low HDL-c levels has not yet been totally successfully addressed by drug therapy (Bisgaier, C. L.; Pape, M. E. Curr. Pharm. Des. 1998, 4, 53-70).

Syndrome X (including metabolic syndrome) is loosely defined as a collection of abnormalities including hyperinsulemia, obesity, elevated levels of the following: triglycerides, uric acid, fibrinogen, small dense LDL particles, and plasminogen activator inhibitor 1 (PAI-1), and decreased levels of HDL-c.

NIDDM is described as insulin resistance, which in turn causes anomalous glucose output and a decrease in glucose uptake, by skeletal muscle. These factors eventually lead to impaired glucose tolerance (IGT) and hyperinsulinemia.

Peroxisome Proliferator Activated Receptors (PPARs) are orphan receptors belonging to the steroid/retinoid receptor superfamily of ligand-activated transcription factors. See, for example Willson T. M. and Wahli, W., Curr. Opin. Chem. Biol., 1, pp 235-241 (1997) and Willson T. M. et. al., J. Med. Chem., 43, p 527-549 (2000). The binding of agonist ligands to the receptor results in changes in the expression level of mRNAs encoded by PPAR target genes.

Three mammalian Peroxisome Proliferator Activated Receptors have been isolated and termed PPAR alpha, PPAR gamma, and PPAR delta (also known as NUC1 or PPAR beta). These PPARs regulate expression of target genes by binding to DNA sequence elements, termed PPAR response elements (PPRE). To date, PPREs have been identified in the enhancers of a number of genes encoding proteins that regulate lipid metabolism suggesting that PPARs play a pivotal role in the adipogenic signalling cascade and lipid homeostasis (H. Keller and W. Wahli, Trends Endocrinol. Metab 291-296, 4 (1993)).

It has now been reported that the thiazolidinedione class of drugs are potent and selective activators of PPAR gamma and bind directly to the PPAR gamma receptor (J. M. Lehmann et. al., J. Biol. Chem. 12953-12956, 270 (1995)), providing evidence that PPAR gamma is a possible target for the therapeutic actions of the thiazolidinediones.

Activators of the nuclear receptor PPARγ, for example rosiglitazone, have been shown in the clinic to enhance insulin-action, reduce serum glucose and have small but significant effects on reducing serum triglyceride levels in patients with Type 2 diabetes. See, for example, D. E. Kelly et al., Curr. Opin. Endocrinol. Diabetes, 90-96, 5 (2), (1998); M. D. Johnson et al., Ann. Pharmacother., 337-348, 32 (3), (1997); and M. Leutenegger et al., Curr. Ther. Res., 403-416, 58 (7), (1997).

The mechanism for this triglyceride lowering effect appears to be predominantly increased clearance of very low density lipoproteins (VLDL) through induction of lipoprotein lipase (LPL) gene expression. See, for example, B. Staels et al., Arterioscler. Thromb., Vasc. Biol., 1756-1764, 17 (9), (1997).

Fibrates are a class of drugs which may lower serum triglycerides 20-50%, lower LDLc 10-15%, shift the LDL particle size from the more atherogenic small dense to normal dense LDL, and increase HDLc 10-15%. Experimental evidence indicates that the effects of fibrates on serum lipids are mediated through activation of PPARα. See, for example, B. Staels et al., Curr. Pharm. Des., 1-14, 3 (1), (1997). Activation of PPARα results in transcription of enzymes that increase fatty acid catabolism and decrease de-novo fatty acid synthesis in the liver resulting in decreased triglyceride synthesis and VLDL production/secretion. In addition, PPARα activation decreases production of apoC-III. Reduction in apoC-III, an inhibitor of LPL activity, increases clearance of VLDL. See, for example, J. Auwerx et al., Atherosclerosis, (Shannon, Irel.), S29-S37, 124 (Suppl), (1996).

Certain compounds that activate or otherwise interact with one or more of the PPARs have been implicated in the regulation of triglyceride and cholesterol levels in animal models. See, for example, U.S. Pat. No. 5,847,008 (Doebber et al.) and U.S. Pat. No. 5,859,051 (Adams et al.) and PCT publications WO 97/28149 (Leibowitz et al.), WO99/04815 (Shimokawa et al.) and WO 01/00603 (Glaxo Group Ltd.). Oliver et al, Proc Natl Acad Sci, 98, 5306-5311 (2001) reports raising of HDLc and lowering of serum triglycerides in the obese rhesus monkey following administration of a PPAR delta agonist.

Accordingly the invention provides a compound of formula 1 and pharmaceutically acceptable salts and solvates and hydrolysable esters thereof.

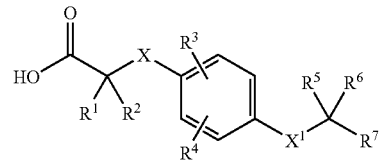

(1)

wherein:
$R^1$ and $R^2$ are independently H or $C_{1-3}$ alkyl;
X represents a O or $(CH_2)_n$ where n is 0, 1 or 2;
$R^3$ and $R^4$ independently represent H, $C_{1-3}$ alkyl, —$OCH_3$, —$CF_3$, allyl, or halogen;
$X^1$ represents O, S, $SO_2$, SO, or $CH_2$;
$R^5$ and $R^6$ independently represent hydrogen, $C_{1-6}$ alkyl (including branched alkyl and optionally substituted by one or more halogens or $C_{1-6}$alkoxy), or together with the carbon atom to which they are bonded form a 3-6 membered cycloalkyl ring;

$R^7$ represents a phenyl or a 6 membered heteroaryl group containing 1, 2 or 3 nitrogen atoms wherein the phenyl or heteroaryl group is substituted by 1, 2 or 3 moieties selected from the group consisting of halogen, $C_{1-6}$alkoxy, $C_{1-6}$alkyl, $CF_3$, hydroxy, or phenyl (which may be optionally substituted by one or more $C_{1-3}$ alkyl, —$OC_{1-3}$ alkyl, CN, acetyl, hydroxy, halogen or $CF_3$).

In another aspect, the present invention discloses a method for prevention or treatment of a disease or condition mediated by one or more human PPAR alpha, gamma or delta ("hPPARs") comprising administration of a therapeutically effective amount of a compound of this invention. hPPAR mediated diseases or conditions include dyslipidemia including associated diabetic dyslipidemia and mixed dyslipidemia, syndrome X (as defined in this application this embraces metabolic syndrome), heart failure, hypercholesterolemia, cardiovascular disease including atherosclerosis, arteriosclerosis, and hypertriglyceridemia, type II diabetes mellitus, type I diabetes, insulin resistance, hyperlipidemia, Alzheimers disease and other cognitive disorders, inflammation, epithelial hyperproliferative diseases including eczema and psoriasis and conditions associated with the lung and gut and regulation of appetite and food intake in subjects suffering from disorders such as obesity, anorexia bulimia, and anorexia nervosa. In particular, the compounds of this invention are useful in the treatment and prevention of diabetes and cardiovascular diseases and conditions including atherosclerosis, arteriosclerosis, hypertriglyceridemia, and mixed dyslipidaemia.

In another aspect, the present invention provides pharmaceutical compositions comprising a compound of the invention, preferably in association with a pharmaceutically acceptable diluent or carrier.

In another aspect, the present invention provides a compound of the invention for use in therapy, and in particular, in human medicine.

In another aspect, the present invention provides the use of a compound of the invention for the manufacture of a medicament for the treatment of a hPPAR mediated disease or condition.

As used herein, "a compound of the invention" means a compound of formula (I) or a pharmaceutically acceptable salt, or solvate, or hydrolysable ester thereof.

While hydrolyzable esters are included in the scope of this invention, the acids are preferred because the data suggests that while the esters are useful compounds, it may actually be the acids to which they hydrolyse that are the active compounds. Esters that hydrolyse readily can produce the carboxylic acid in the assay conditions or in vivo. Generally the carboxylic acid is active in both the binding and transient transfection assays, while the ester does not usually bind well but is active in the transient transfection assay presumably due to hydrolysis. Preferred hydrolysable esters are $C_{1-6}$ alkyl esters wherein the alkyl group may be straight chain or branched chain. Methyl or ethyl esters are more preferred.

Preferably $R^1$ and $R^2$ are both H or both Me. More preferably both $R^1$ and $R^2$ are H.

Preferably $R^3$ and $R^4$ are independently H or $C_{1-3}$ alkyl. More preferably, at least one of $R^3$ and $R^4$ are hydrogen and when one of $R^4$ and $R^3$ is hydrogen and the other is not, then the one that is not hydrogen is preferably ortho to the depicted moiety X. Most preferably the one that is not hydrogen is methyl.

Preferably X is O.

Preferably $X^1$ is O or S.

Preferably $R^5$ and $R^6$ are independently hydrogen or $C_{1-6}$ alkyl (optionally substituted by $C_{1-6}$ alkoxy). More preferably one of $R^5$ and $R^6$ is H. Most preferably one of $R^5$ and $R^6$ is H the other is butyl or ethyloxymethyl ($CH_3CH_2OCH_2$).

Preferably $R^7$ is phenyl or a 6 membered heterocycle selected from pyrimidine, pyridine, pyridazine, pyrazine, each of which phenyl or heterocycle is substituted by phenyl (optionally substituted by one or more $C_{1-3}$ alkyl, CN, $CF_3$, halogen). More preferably $R^7$ is a phenyl or pyridine ring which is substituted meta to the depicted moiety $X^1$ by para —$C_6H_4CF_3$, para —$C_6H_4Me$, para —$C_6H_4CN$ or para —$C_6H_4Cl$.

Preferred compounds of formula (I) include:
{[2-Methyl-4-({[4'-(trifluoromethyl)-3-biphenylyl]methyl}thio)phenyl]oxy}acetic acid
{[2-Methyl-4-({[4-methyl-4'-(trifluoromethyl)-3-biphenylyl]methyl}thio)phenyl]oxy}acetic acid
3-[2-Methyl-4-({[4'-(trifluoromethyl)-3-biphenylyl]methyl}oxy)phenyl]propanoic acid
[(2-Methyl-4-{2-[4'-(trifluoromethyl)-3-biphenylyl]ethyl}phenyl)oxy]acetic acid
({2-Methyl-4-[({6-[4-(trifluoromethyl)phenyl]-2-pyridinyl}methyl)thio]phenyl}oxy)acetic acid
{[2-Methyl-4-({1-[4'-(trifluoromethyl)-3-biphenylyl]ethyl}thio)phenyl]oxy}acetic acid
{[2-Methyl-4-({1-[4'-(trifluoromethyl)-4-biphenylyl]ethyl}thio)phenyl]oxy}acetic acid
2-Methyl-2-({2-methyl-4-[(1-{6-[4-(trifluoromethyl)phenyl]-2-pyridinyl}pentyl)oxy]phenyl}oxy)propanoic acid
{[2-Methyl-4-({1-[4'-(trifluoromethyl)-3-biphenylyl]pentyl}oxy)phenyl]oxy}acetic acid
[(4-{[1-(4'-Chloro-3-biphenylyl)pentyl]oxy}-2-methylphenyl)oxy]acetic acid
{[2-Methyl-4-({1-[4'-(trifluoromethyl)-4-biphenylyl]pentyl}oxy)phenyl]oxy}acetic acid
[(4-{[1-(4'-Chloro-4-biphenylyl)pentyl]oxy}-2-methylphenyl)oxy]acetic acid
{[2-Methyl-4-({(1R)-1-[4'-(trifluoromethyl)-4-biphenylyl]pentyl}thio)phenyl]oxy}acetic acid
{[2-Methyl-4-({(1S)-1-[4'-(trifluoromethyl)-4-biphenylyl]pentyl}thio)phenyl]oxy}acetic acid
({2-Methyl-4-[((1S)-1-{6-[4-(trifluoromethyl)phenyl]-2-pyridinyl}pentyl)oxy]phenyl}oxy)acetic acid
({2-Methyl-4-[((1R)-1-{6-[4-(trifluoromethyl)phenyl]-2-pyridinyl}pentyl)oxy]phenyl}oxy)acetic acid
({2-Methyl-4-[((1S)-1-{6-[4-(trifluoromethyl)phenyl]-2-pyridinyl}pentyl)thio]phenyl}oxy)acetic acid
({2-Methyl-4-[((1R)-1-{6-[4-(trifluoromethyl)phenyl]-2-pyridinyl}pentyl)thio]phenyl}oxy)acetic acid
({2-Methyl-4-[(1-{6-[4-(trifluoromethyl)phenyl]-2-pyridinyl}pentyl)sulfinyl]phenyl}oxy)acetic acid
({2-Methyl-4-[(1-{6-[4-(trifluoromethyl)phenyl]-2-pyridinyl}pentyl)sulfonyl]phenyl}oxy)acetic acid
{4-[(1-{6-[4-(Trifluoromethyl)phenyl]-2-pyridinyl}pentyl)oxy]phenyl}acetic acid
({2-Methyl-4-[(1-{6-[4-(trifluoromethyl)phenyl]-2-pyridinyl}butyl)oxy]phenyl}oxy)acetic acid
({4-[(1-{6-[4-(Trifluoromethyl)phenyl]-2-pyridinyl}pentyl)oxy]phenyl}oxy)acetic acid
3-{4-[(1-{6-[4-(Trifluoromethyl)phenyl]-2-pyridinyl}pentyl)oxy]phenyl}propanoic acid
{[4-({1-[6-(4-Chlorophenyl)-2-pyridinyl]pentyl}oxy)-2-methylphenyl]oxy}acetic acid
({2-Methyl-4-[(1-{6-[4-(methyloxy)phenyl]-2-pyridinyl}pentyl)oxy]phenyl}oxy)acetic acid ({4-[(1-{6-[4-(Ethyloxy)phenyl]-2-pyridinyl}pentyl)oxy]-2-methylphenyl}oxy) acetic acid
{[2-Methyl-4-({1-[6-(4-methylphenyl)-2-pyridinyl]pentyl}oxy)phenyl]oxy}acetic acid
{[4-({1-[6-(3,4-Dichlorophenyl)-2-pyridinyl]pentyl}oxy)-2-methylphenyl]oxy}acetic acid
({2-Methyl-4-[(1-{6-[3-(trifluoromethyl)phenyl]-2-pyridinyl}pentyl)oxy]phenyl}oxy)acetic acid
[(2-Methyl-4-{[1-(6-phenyl-2-pyridinyl)pentyl]oxy}phenyl)oxy]acetic acid
{[4-({1-[6-(4-Acetylphenyl)-2-pyridinyl]pentyl}oxy)-2-methylphenyl]oxy}acetic acid
{[4-({1-[6-(4-Fluorophenyl)-2-pyridinyl]pentyl}oxy)-2-methylphenyl]oxy}acetic acid
{[4-({1-[6-(4-Cyanophenyl)-2-pyridinyl]pentyl}oxy)-2-methylphenyl]oxy}acetic acid
({2-Methyl-4-[(1-{6-[4-(trifluoromethyl)phenyl]-2-pyridinyl}hexyl)oxy]phenyl}oxy)acetic acid
({2-Methyl-4-[(4-methyl-1-{6-[4-(trifluoromethyl)phenyl]-2-pyridinyl}pentyl)oxy]phenyl}oxy)acetic acid
({2-Methyl-4-[(3-methyl-1-{6-[4-(trifluoromethyl)phenyl]-2-pyridinyl}butyl)oxy]phenyl}oxy)acetic acid
[(4-{[1-(3-Biphenylyl)pentyl]oxy}-2-methylphenyl)oxy]acetic acid
{[4-({1-[4'-(Ethyloxy)-3-biphenylyl]pentyl}oxy)-2-methylphenyl]oxy}acetic acid
[(4-{[1-(4'-Cyano-3-biphenylyl)pentyl]oxy}-2-methylphenyl)oxy]acetic acid
[(2-Ethyl-4-{[1-(6-phenyl-2-pyridinyl)pentyl]oxy}phenyl)oxy]acetic acid
{[4-({1-[6-(4-Chlorophenyl)-2-pyridinyl]pentyl}oxy)-2-ethylphenyl]oxy}acetic acid
({2-Ethyl-4-[(1-{6-[4-(ethyloxy)phenyl]-2-pyridinyl}pentyl)oxy]phenyl}oxy)acetic acid
{[4-({1-[6-(4-Cyanophenyl)-2-pyridinyl]pentyl}oxy)-2-ethylphenyl]oxy}acetic acid
({2-Ethyl-4-[(1-{6-[4-(trifluoromethyl)phenyl]-2-pyridinyl}pentyl)oxy]phenyl}oxy) acetic acid
4-{4-[(1-{6-[4-(Trifluoromethyl)phenyl]-2-pyridinyl}pentyl)oxy]phenyl}butanoic acid
{[4-({(1R)-1-[6-(4-Chlorophenyl)-2-pyridinyl]pentyl}oxy)-2-methylphenyl]oxy}acetic acid
{[4-({(1R)-1-[6-(4-Cyanophenyl)-2-pyridinyl]pentyl}oxy)-2-methylphenyl]oxy}acetic acid
({2-Methyl-4-[((1R)-1-{6-[4-(methyloxy)phenyl]-2-pyridinyl}pentyl)oxy]phenyl}oxy)acetic acid
{[4-({(1R)-1-[6-(4-Acetylphenyl)-2-pyridinyl]pentyl}oxy)-2-methylphenyl]oxy}acetic acid
({4-[((1R)-1-{6-[4-Acetyl-3-(methyloxy)phenyl]-2-pyridinyl}pentyl)oxy]-2-methylphenyl}oxy)acetic acid
{[4-({(1S)-1-[6-(4-Chlorophenyl)-2-pyridinyl]pentyl}oxy)-2-methylphenyl]oxy}acetic acid
{[4-({(1S)-1-[6-(4-Cyanophenyl)-2-pyridinyl]pentyl}oxy)-2-methylphenyl]oxy}acetic acid
({2-Methyl-4-[((1S)-1-{6-[4-(methyloxy)phenyl]-2-pyridinyl}pentyl)oxy]phenyl}oxy)acetic acid
{[4-({(1S)-1-[6-(4-Acetylphenyl)-2-pyridinyl]pentyl}oxy)-2-methylphenyl]oxy}acetic acid
({4-[((1S)-1-{6-[4-Acetyl-3-(methyloxy)phenyl]-2-pyridinyl}pentyl)oxy]-2-methylphenyl}oxy)acetic acid
({2-Methyl-4-[((1R)-3-(methyloxy)-1-{6-[4-(trifluoromethyl)phenyl]-2-pyridinyl}propyl)oxy]phenyl}oxy)acetic acid
[(4-{[(1R)-1-[6-(4-Chlorophenyl)-2-pyridinyl]-3-(methyloxy)propyl]oxy}-2-methylphenyl)oxy]acetic acid
({2-Methyl-4-[((1S)-3-(methyloxy)-1-{6-[4-(trifluoromethyl)phenyl]-2-pyridinyl}propyl)oxy]phenyl}oxy)acetic acid
[(4-{[(1S)-1-[6-(4-Chlorophenyl)-2-pyridinyl]-3-(methyloxy)propyl]oxy}-2-methylphenyl)oxy]acetic acid
({4-[((1R)-2-(Ethyloxy)-1-{6-[4-(trifluoromethyl)phenyl]-2-pyridinyl}ethyl)oxy]-2-methylphenyl}oxy)acetic acid
({4-[((1R)-2-(Ethyloxy)-1-{6-[4-(methyloxy)phenyl]-2-pyridinyl}ethyl)oxy]-2-methylphenyl}oxy)acetic acid
[(4-{[(1R)-1-[6-(4-Acetylphenyl)-2-pyridinyl]-2-(ethyloxy)ethyl]oxy}-2-methylphenyl)oxy]acetic acid
[(4-{[(1R)-1-[6-(4-Cyanophenyl)-2-pyridinyl]-2-(ethyloxy)ethyl]oxy}-2-methylphenyl)oxy]acetic acid
[(4-{[(1R)-1-[6-(4-Chlorophenyl)-2-pyridinyl]-2-(ethyloxy)ethyl]oxy}-2-methylphenyl)oxy]acetic acid
({4-[((1S)-2-(Ethyloxy)-1-{6-[4-(trifluoromethyl)phenyl]-2-pyridinyl}ethyl)oxy]-2-methylphenyl}oxy)acetic acid
({4-[((1S)-2-(Ethyloxy)-1-{6-[4-(methyloxy)phenyl]-2-pyridinyl}ethyl)oxy]-2-methylphenyl}oxy)acetic acid
[(4-{[(1S)-1-[6-(4-Acetylphenyl)-2-pyridinyl]-2-(ethyloxy)ethyl]oxy}-2-methylphenyl)oxy]acetic acid
[(4-{[(1S)-1-[6-(4-Cyanophenyl)-2-pyridinyl]-2-(ethyloxy)ethyl]oxy}-2-methylphenyl)oxy]acetic acid
[(4-{([(1S)-1-[6-(4-Chlorophenyl)-2-pyridinyl]-2-(ethyloxy)ethyl]oxy}-2-methylphenyl)oxy]acetic acid
{[4-({(1R)-2-(Ethyloxy)-1-[6-(3-fluoro-4-methylphenyl)-2-pyridinyl]ethyl}oxy)-2-methylphenyl]oxy}acetic acid
{[4-({(1R)-2-(Ethyloxy)-1-[6-(4-methylphenyl)-2-pyridinyl]ethyl}oxy)-2-methylphenyl]oxy}acetic acid
({4-[((1R)-2-(Ethyloxy)-1-{6-[4-(1-methylethyl)phenyl]-2-pyridinyl}ethyl)oxy]-2-methylphenyl}oxy)acetic acid
[(4-{[(1R)-1-[6-(4-Cyano-3-fluorophenyl)-2-pyridinyl]-2-(ethyloxy)ethyl]oxy}-2-methylphenyl)oxy]acetic acid
({4-[((1R)-2-(Ethyloxy)-1-{6-[4-(ethyloxy)phenyl]-2-pyridinyl}ethyl)oxy]-2-methylphenyl}oxy)acetic acid
{[4-({(1R)-2-(Ethyloxy)-1-[6-(2-fluoro-4-methylphenyl)-2-pyridinyl]ethyl}oxy)-2-methylphenyl]oxy}acetic acid
{[4-({(1R)-2-(Ethyloxy)-1-[6-(4-fluorophenyl)-2-pyridinyl]ethyl}oxy)-2-methylphenyl]oxy}acetic acid
[(4-{[(1R)-2-(Ethyloxy)-1-(6-{4-[(1-methylethyl)oxy]phenyl}-2-pyridinyl)ethyl]oxy}-2-methylphenyl)oxy]acetic acid
[(4-{([(1R)-1-[6-(4-Chloro-3-methylphenyl)-2-pyridinyl]-2-(ethyloxy)ethyl]oxy}-2-methylphenyl)oxy]acetic acid
[(4-{[(1R)-1-[6-(3-Chloro-4-cyanophenyl)-2-pyridinyl]-2-(ethyloxy)ethyl]oxy}-2-methylphenyl)oxy]acetic acid
[(4-{[(1R)-1-[6-(4-Cyano-3-methylphenyl)-2-pyridinyl]-2-(ethyloxy)ethyl]oxy}-2-methylphenyl)oxy]acetic acid
({4-[((1R)-2-(Ethyloxy)-1-{6-[3-fluoro-4-(methyloxy)phenyl]-2-pyridinyl}ethyl)oxy]-2-methylphenyl}oxy)acetic acid
[(4-{[(1R)-1-[6-(4-Cyano-2-fluorophenyl)-2-pyridinyl]-2-(ethyloxy)ethyl]oxy}-2-methylphenyl)oxy]acetic acid
[(4-{[(1R)-1-[6-(4-Cyano-2-methylphenyl)-2-pyridinyl]-2-(ethyloxy)ethyl]oxy}-2-methylphenyl)oxy]acetic acid
{[4-({(1S)-2-(Ethyloxy)-1-[6-(3-fluoro-4-methylphenyl)-2-pyridinyl]ethyl}oxy)-2-methylphenyl]oxy}acetic acid
{[4-({(1S)-2-(Ethyloxy)-1-[6-(4-methylphenyl)-2-pyridinyl]ethyl}oxy)-2-methylphenyl]oxy}acetic acid
({4-[((1S)-2-(Ethyloxy)-1-{6-[4-(1-methylethyl)phenyl]-2-pyridinyl}ethyl)oxy]-2-methylphenyl}oxy)acetic acid
[(4-{[(1S)-1-[6-(4-Cyano-3-fluorophenyl)-2-pyridinyl]-2-(ethyloxy)ethyl]oxy}-2-methylphenyl)oxy]acetic acid
({4-[((1S)-2-(Ethyloxy)-1-{6-[4-(ethyloxy)phenyl]-2-pyridinyl}ethyl)oxy]-2-methylphenyl}oxy)acetic acid
{[4-({(1S)-2-(Ethyloxy)-1-[6-(2-fluoro-4-methylphenyl)-2-pyridinyl]ethyl}oxy)-2-methylphenyl]oxy}acetic acid {[4-({(1S)-2-(Ethyloxy)-1-[6-(4-fluorophenyl)-2-pyridinyl]ethyl}oxy)-2-methylphenyl]oxy}acetic acid

[(4-{[(1S)-2-(Ethyloxy)-1-(6-{4-[(1-methylethyl)oxy]phenyl}-2-pyridinyl)ethyl]oxy}-2-methylphenyl)oxy]acetic acid

[(4-{[(1S)-1-[6-(4-Chloro-3-methylphenyl)-2-pyridinyl]-2-(ethyloxy)ethyl]oxy}-2-methylphenyl)oxy]acetic acid

[(4-{[(1S)-1-[6-(3-Chloro-4-cyanophenyl)-2-pyridinyl]-2-(ethyloxy)ethyl]oxy}-2-methylphenyl)oxy]acetic acid

[(4-{[(1S)-1-[6-(4-Cyano-3-methylphenyl)-2-pyridinyl]-2-(ethyloxy)ethyl]oxy}-2-methylphenyl)oxy]acetic acid ({4-[((1S)-2-(Ethyloxy)-1-{6-[3-fluoro-4-(methyloxy)phenyl]-2-pyridinyl}ethyl)oxy]-2-methylphenyl}oxy)acetic acid

[(4-{[(1S)-1-[6-(4-Cyano-2-fluorophenyl)-2-pyridinyl]-2-(ethyloxy)ethyl]oxy}-2-methylphenyl)oxy]acetic acid

[(4-{[(1S)-1-{6-[4-Cyano-3-(methyloxy)phenyl]-2-pyridinyl}-2-(ethyloxy)ethyl]oxy}-2-methylphenyl)oxy]acetic acid 3-{2-Methyl-4-[((1S)-1-{6-[4-(trifluoromethyl)phenyl]-2-pyridinyl}pentyl)oxy]phenyl}propanoic acid 3-{2-Methyl-4-[((1S)-1-{6-[4-(methyloxy)phenyl]-2-pyridinyl}pentyl)oxy]phenyl}propanoic acid 3-[4-({(1S)-1-[6-(4-Acetylphenyl)-2-pyridinyl]pentyl}oxy)-2-methylphenyl]propanoic acid 3-[4-({(1S)-1-[6-(4-Cyanophenyl)-2-pyridinyl]pentyl}oxy)-2-methylphenyl]propanoic acid 3-[4-({(1S)-1-[6-(4-Chlorophenyl)-2-pyridinyl]pentyl}oxy)-2-methylphenyl]propanoic acid 3-{2-Methyl-4-[((1R)-1-{6-[4-(trifluoromethyl)phenyl]-2-pyridinyl}pentyl)oxy]phenyl}propanoic acid 3-{2-Methyl-4-[((1R)-1-{6-[4-(methyloxy)phenyl]-2-pyridinyl}pentyl)oxy]phenyl}propanoic acid 3-[4-({(1R)-1-[6-(4-Acetylphenyl)-2-pyridinyl]pentyl}oxy)-2-methylphenyl]propanoic acid 3-[4-({(1R)-1-[6-(4-Cyanophenyl)-2-pyridinyl]pentyl}oxy)-2-methylphenyl]propanoic acid 3-[4-({(1R)-1-[6-(4-Chlorophenyl)-2-pyridinyl]pentyl}oxy)-2-methylphenyl]propanoic acid 3-{3,5-Dimethyl-4-[(1-{6-[4-(trifluoromethyl)phenyl]-2-pyridinyl}pentyl)oxy]phenyl}propanoic acid 3-{3-(Methyloxy)-5-propyl-4-[(1-{6-[4-(trifluoromethyl)phenyl]-2-pyridinyl}pentyl)oxy]phenyl}propanoic acid 3-{3-Propyl-4-[(1-{6-[4-(trifluoromethyl)phenyl]-2-pyridinyl}pentyl)oxy]phenyl}propanoic acid 3-{3-(Ethyloxy)-4-[(1-{6-[4-(trifluoromethyl)phenyl]-2-pyridinyl}pentyl)oxy]phenyl}propanoic acid 3-{4-[((1R-1-{6-[4-(Trifluoromethyl)phenyl]-2-pyridinyl}pentyl)oxy]phenyl}propanoic acid 3-{3-(Methyloxy)-4-[((1R)-1-{6-[4-(trifluoromethyl)phenyl]-2-pyridinyl}pentyl)oxy]phenyl}propanoic acid {4-[((1R)-1-{6-[4-(trifluoromethyl)phenyl]-2-pyridinyl}pentyl)oxy]phenyl}acetic acid {3-Chloro-4-[((1R)-1-{6-[4-(trifluoromethyl)phenyl]-2-pyridinyl}pentyl)oxy]phenyl}acetic acid {3-(Methyloxy)-4-[((1R)-1-{6-[4-(trifluoromethyl)phenyl]-2-pyridinyl}pentyl)oxy]phenyl}acetic acid 3-{4-[((1S)-1-{6-[4-(Trifluoromethyl)phenyl]-2-pyridinyl}pentyl)oxy]phenyl}propanoic acid 3-{3-(Methyloxy)-4-[((1S)-1-{6-[4-(trifluoromethyl)phenyl]-2-pyridinyl}pentyl)oxy]phenyl}propanoic acid {4-[((1S)-1-{6-[4-(Trifluoromethyl)phenyl]-2-pyridinyl}pentyl)oxy]phenyl}acetic acid {3-Chloro-4-[((1S)-1-{6-[4-(trifluoromethyl)phenyl]-2-pyridinyl}pentyl)oxy]phenyl}acetic acid {3-(Methyloxy)-4-[((1S)-1-{6-[4-(trifluoromethyl)phenyl]-2-pyridinyl}pentyl)oxy]phenyl}acetic acid 3-{3-Fluoro-4-[((1R)-1-{6-[4-(trifluoromethyl)phenyl]-2-pyridinyl}pentyl)oxy]phenyl}propanoic acid 3-{3-Methyl-4-[((1R)-1-{6-[4-(trifluoromethyl)phenyl]-2-pyridinyl}pentyl)oxy]phenyl}propanoic acid 3-{3,5-Bis(methyloxy)-4-[((1R)-1-{6-[4-(trifluoromethyl)phenyl]-2-pyridinyl}pentyl)oxy]phenyl}propanoic acid 3-{2-(Methyloxy)-4-[((1R)-1-{6-[4-(trifluoromethyl)phenyl]-2-pyridinyl}pentyl)oxy]phenyl}propanoic acid 3-{3-Fluoro-4-[((1S)-1-{6-[4-(trifluoromethyl)phenyl]-2-pyridinyl}pentyl)oxy]phenyl}propanoic acid 3-{3-Methyl-4-[((1S)-1-{6-[4-(trifluoromethyl)phenyl]-2-pyridinyl}pentyl)oxy]phenyl}propanoic acid 3-{3,5-Bis(methyloxy)-4-[((1S)-1-{6-[4-(trifluoromethyl)phenyl]-2-pyridinyl}pentyl)oxy]phenyl}propanoic acid 3-{2-(Methyloxy)-4-[((1S)-1-{6-[4-(trifluoromethyl)phenyl]-2-pyridinyl}pentyl)oxy]phenyl}propanoic acid 3-{3-Chloro-5-(methyloxy)-4-[((1S)-1-{6-[4-(trifluoromethyl)phenyl]-2-pyridinyl}pentyl)oxy]phenyl}propanoic acid 3-{3-Chloro-4-[((1R)-1-{6-[4-(trifluoromethyl)phenyl]-2-pyridinyl}pentyl)oxy]phenyl}propanoic acid 3-{2-Chloro-4-[((1R)-1-{6-[4-(trifluoromethyl)phenyl]-2-pyridinyl}pentyl)oxy]phenyl}propanoic acid 3-{3-Chloro-4-[((1S)-1-{6-[4-(trifluoromethyl)phenyl]-2-pyridinyl}pentyl)oxy]phenyl}propanoic acid 3-{2-Chloro-4-[((1S)-1-{6-[4-(trifluoromethyl)phenyl]-2-pyridinyl}pentyl)oxy]phenyl}propanoic acid {[2-Methyl-4-({1-[2-methyl-4'-(trifluoromethyl)-3-biphenylyl]pentyl}oxy)phenyl]oxy}acetic acid

[(4-{[1-(4'-Chloro-2-methyl-3-biphenylyl)pentyl]oxy}-2-methylphenyl)oxy]acetic acid

[(4-{[1-(2,4'-Dimethyl-3-biphenylyl)pentyl]oxy}-2-methylphenyl)oxy]acetic acid

[(4-{[1-(4'-Cyano-2-methyl-3-biphenylyl)pentyl]oxy}-2-methylphenyl)oxy]acetic acid {[2-Methyl-4-({1-[2-methyl-4'-(methyloxy)-3-biphenylyl]pentyl}oxy)phenyl]oxy}acetic acid

[(4-{[1-(4'-Fluoro-2-methyl-3-biphenylyl)pentyl]oxy}-2-methylphenyl)oxy]acetic acid ({2-Methyl-4-[(2-(propyloxy)-1-{6-[4-(trifluoromethyl)phenyl]-2-pyridinyl}ethyl)oxy]phenyl}oxy)acetic acid ({4-[(2-(Ethyloxy)-1-{6-[4-(trifluoromethyl)phenyl]-2-pyridinyl}ethyl)thio]-2-methylphenyl}oxy)acetic acid While the preferred groups for each variable have generally been listed above separately for each variable, preferred compounds of this invention include those in which several or each variable in Formula (I) is selected from the preferred, more preferred, or most preferred groups for each variable. Therefore, this invention is intended to include all combinations of preferred and most preferred groups.

Those skilled in the art will recognize that stereocentres exist in compounds of formula (I). Accordingly, the present invention includes all possible stereoisomers and geometric isomers of formula (I) and includes not only racemic compounds but this invention is also intended to cover each of these isomers in their racemic, enriched, or purified forms. When a compound of formula (I) is desired as a single enantiomer, it may be obtained either by resolution of the final product or by stereospecific synthesis using an optically active catalyst or a catalytic system with optically active ligands or isomerically pure starting material or any convenient intermediate. Resolution of the final product, an intermediate or a starting material may be effected by any suitable method known in the art. See, for example, Stereochemistry of Carbon Compounds by E. L. Eliel (Mcgraw Hill, 1962) and Tables of Resolving Agents by S. H. Wilen. Additionally, in situations where tautomers of the compounds of formula (I) are possible, the present invention is intended to include all tautomeric forms of the compounds. In particular, in many of the preferred compounds of this invention the carbon atom to which $R^5$ and $R^6$ are bonded is chiral. In some of these chiral compounds the activities at the various PPAR receptors varies between the S and R isomers. Which of these isomers is preferred depends on the particular desired utility of the compound. In other words, even with the same compound, it is possible that the S isomer will be preferred for some uses, while the R isomer will be preferred for others.

The hPPAR agonists of formula (I) may be agonists of only one type ("selective agonists"), agonists for two PPAR subtypes ("dual agonists"), or agonists for all three subtypes ("pan agonists"). As used herein, by "agonist", or "activating compound", or "activator", or the like, is meant those compounds which have a pKi of at least 6.0 preferably at least 7.0 to the relevant PPAR, for example hPPARδ in the binding assay described below, and which achieve at least 50% activation of the relevant PPAR relative to the appropriate indicated positive control in the transfection assay described below at concentrations of $10^{-5}$ M or less. More preferably, the agonists of this invention achieve 50% activation of at least one human PPAR in the relevant transfection assay at concentrations of $10^{-6}$ M or less. Preferably the compounds are hPPARδ agonists. More preferably the compounds are selective hPPARδ agonists.

It will also be appreciated by those skilled in the art that the compounds of the present invention may also be utilised in the form of a pharmaceutically acceptable salt or solvate thereof. The physiologically acceptable salts of the compounds of formula (I) include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. Those skilled in the art of organic chemistry will appreciate that many organic compounds can form complexes with solvents in which they are reacted or from which they are precipitated or crystallized. These complexes are known as "solvents". For example, a complex with water is known as a "hydrate". Solvates of the compound of formula (I) are within the scope of the invention. References hereinafter to a compound according to the invention include both compounds of formula (I) and their pharmaceutically acceptable salts and solvates.

The compounds of the invention and their pharmaceutically acceptable derivatives are conveniently administered in the form of pharmaceutical compositions. Such compositions may conveniently be presented for use in conventional manner in admixture with one or more physiologically acceptable carriers or excipients.

While it is possible that compounds of the present invention may be therapeutically administered as the raw chemical, it is preferable to present the active ingredient as a pharmaceutical formulation. The carrier(s) must be "acceptable" in the sense of being compatible with the other ingredients of the formulation and not deleterious to the recipient thereof.

Accordingly, the present invention further provides for a pharmaceutical formulation comprising a compound of formula (I) or a pharmaceutically acceptable salt or solvate thereof together with one or more pharmaceutically acceptable carriers therefore and, optionally, other therapeutic and/or prophylactic ingredients.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition and disorder of the recipient. The formulations may conveniently be presented in unit dosage form and may be prepared by any of the methods well known in the art of pharmacy. All methods include the step of bringing into association the compounds ("active ingredient") with the carrier, which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a other conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The tablets may be coated according to methods well-known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g. containing conventional suppository bases such as cocoa butter or other glycerides.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

The compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

It will be appreciated by those skilled in the art that reference herein to treatment extends to prophylaxis as well as the treatment of established diseases or symptoms. Moreover, it will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02-5000 mg per day, preferably 1-1500 mg per day. The desired dose may conveniently be presented in a single dose or as divided doses administered at appropriate intervals, for example as two, three, four or more sub-doses per day. The formulations according to the invention may contain between 0.1-99% of the active ingredient, conveniently from 30-95% for tablets and capsules and 3-50% for liquid preparations.

The compound of formula (I) for use in the instant invention may be used in combination with other therapeutic agents for example, statins and/or other lipid lowering drugs for example MTP inhibitors and LDLR upregulators. The compounds of the invention may also be used in combination with antidiabetic agents, e.g. metformin, sulfonylureas and/or PPAR gamma, PPAR alpha or PPAR alpha/gamma agonists (for example thiazolidinediones such as e.g. pioglitazone and rosiglitazone). The compounds may also be used in combination with antihypertensive agents such as angiotensin antagonists e.g. telmisartan, calcium channel antagonists e.g. lacidipine and ACE inhibitors e.g. enalapril. The invention thus provides in a further aspect the use of a combination comprising a compound of formula (I) with a further therapeutic agent in the treatment of a hPPAR mediated disease.

When the compounds of formula (I) are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optimally together with a pharmaceutically acceptable carrier or excipient comprise a further aspect of the invention. The individual components of such combinations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any convenient formulation, conveniently in such a manner as are known for such compounds in the art.

When a compound of formula (I) is used in combination with a second therapeutic agent active against the same hPPAR mediated disease, the dose of each compound may differ from that when the compound is used alone. Appropriate doses will be readily appreciated by those skilled in the art.

Compounds of this invention may be conveniently prepared by a general process wherein a moiety like (A) is coupled to an alcohol (B) using the Mitsunobu protocol (O. Mitsunobu, 1981, Synthesis p1) or by alklylaton of (A) using a suitable non nucleophilic base such as $K_2CO_3$, $Cs_2CO_3$ or NaH, with an alkyl halide (C).

Compounds of this invention may be conveniently prepared by a general process wherein a moiety like (A) is coupled to an alcohol (B) using the Mitsunobu protocol (O. Mitsunobu, 1981, Synthesis p1) or by alklylaton of (A) using a suitable non nucleophilic base such as $K_2CO_3$, $Cs_2CO_3$ or NaH, with an alkyl halide (C).

Note this synthesis is preferably carried out with the acid group protected by R to give intermediate (D). Preferably R is $C_{1-6}$alkyl which can be hydrolysed to give an acid of formula (1), or if readily hydrolyzable, the resulting ester can be administered. The groups $R^1$-$R^7$ and $X^1$ of intermediate (D) can be further modified to provide further compounds of formula (1) by standard chemistry.

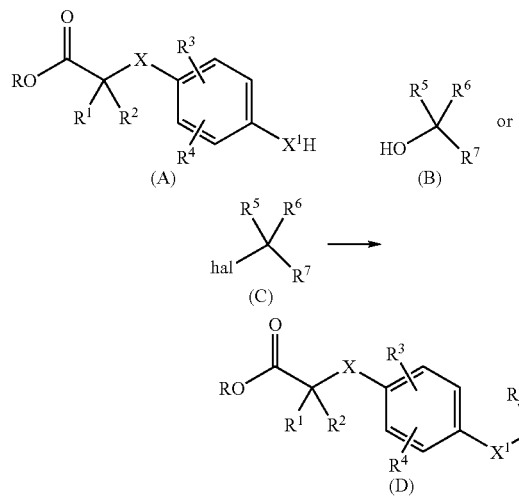

Intermediates of formulae (A), (B), (C) and (D) are commercially available or may be synthesised as outlined below. Alcohol (B) can be converted to alkyl halide (C) using standard halogenation conditions.

For example, when $X^1$ is O or S, the following synthetic schemes may be followed.

Scheme 1

Mitsunobu followed by hydrolysis

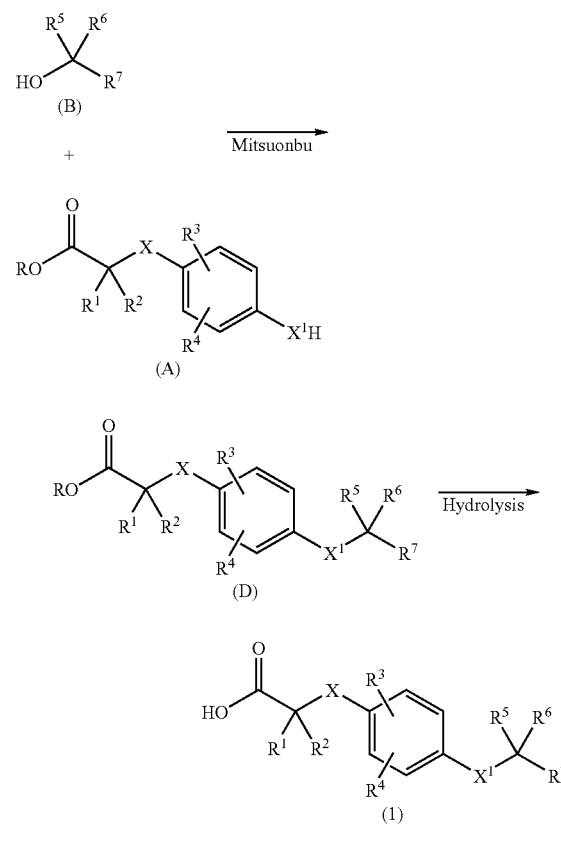

Scheme 2

Alkylation followed by hydrolysis

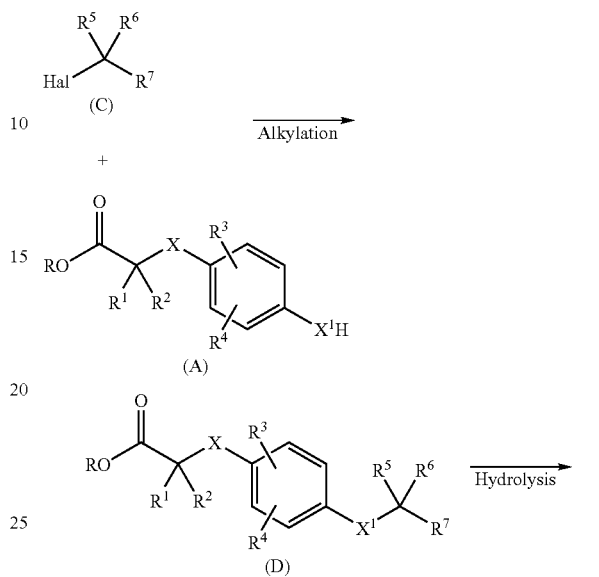

Scheme 3

Mitsunobu followed by Suzuki (to modify $R^7$) and the hydrolysis (Ar represents phenyl or a 6 membered heteroaryl group containing 1, 2 or 3 nitrogen atoms)

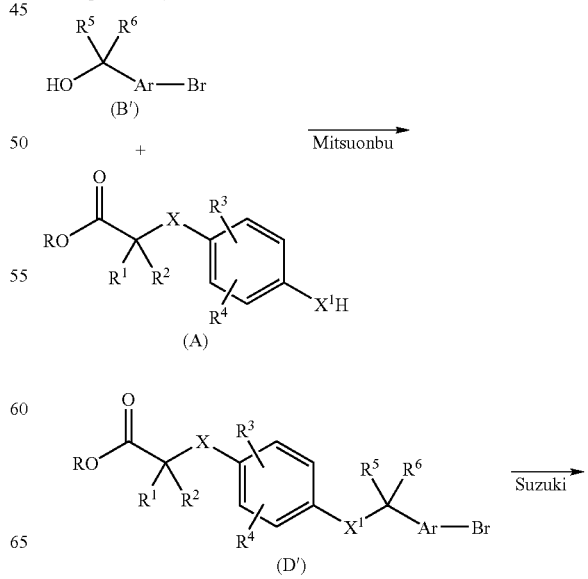

-continued

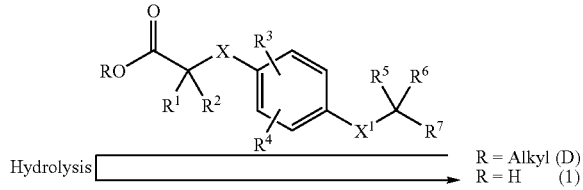

Hydrolysis → R = Alkyl (D)
R = H (1)

-continued

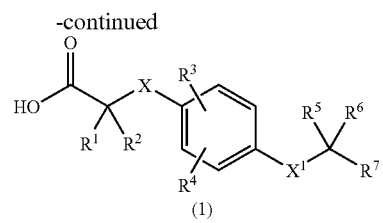

When $X^1$ represents S, the following synthetic scheme may also be followed:

Scheme 4

Mitsunobu followed by Suzuki (to modigy $R^7$) with concomitant hydrolysis

Scheme 5

Reductive alkylation followed by hydrolysis

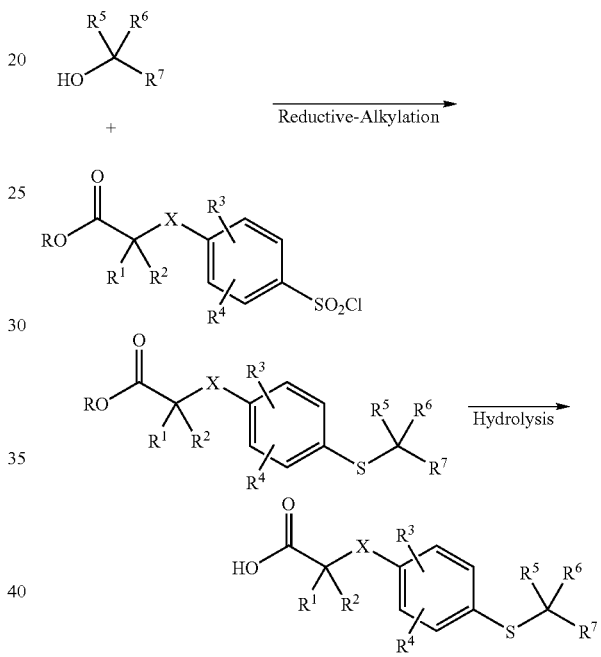

When $X^1$ is SO or $SO_2$ these are conveniently prepared by oxidation of intermediate (D) where $X^1$ is S, using standard oxidation conditions for a sulfide.

When $X^1$ represents $CH_2$ the following scheme may be followed:

Scheme 6

Wittig, Suzuki, hydrolysis, hydrogenation

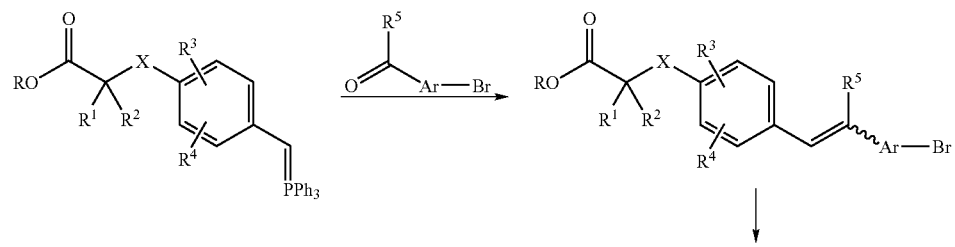

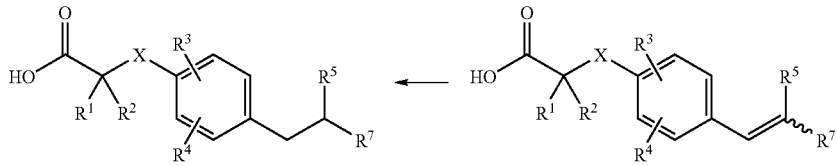

When $X^1$ is O and X represents $CH_2$ the following scheme may be followed:

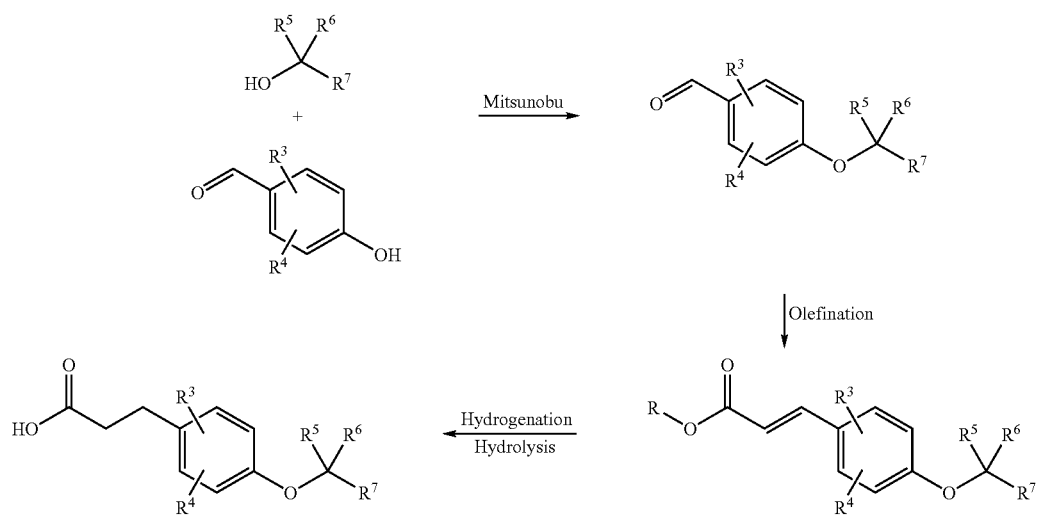

The following synthetic schemes may be followed to prepare intermediate (B) where $R^5$ is H and "ring" represents a phenyl or a 6 membered heteroaryl group containing 1, 2 or 3 nitrogen atoms:

Scheme 8

Alkylation, then Suzuki followed by reduction (or reduction followed by Suzuki) of a carboxylic acid derivative (E).

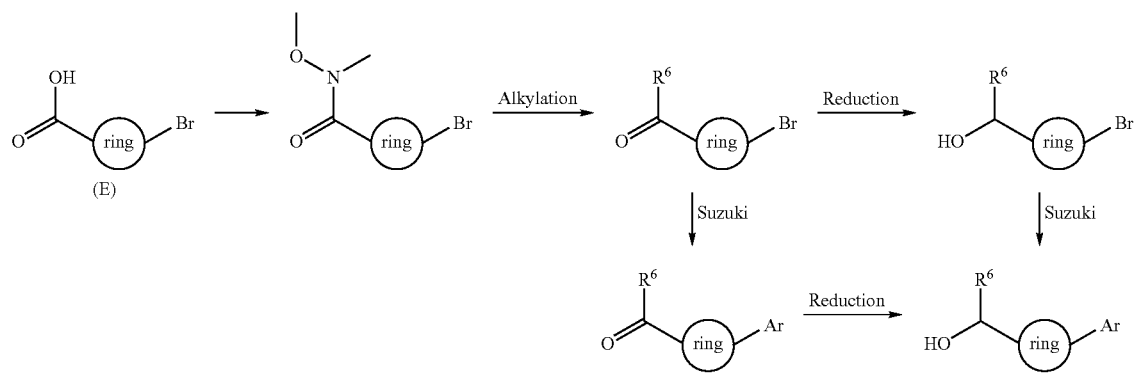

Scheme 9

Oxidation, then Suzuki followed by alkylation (or alkylation followed by Suzuki) of an alcohol derivative (F).

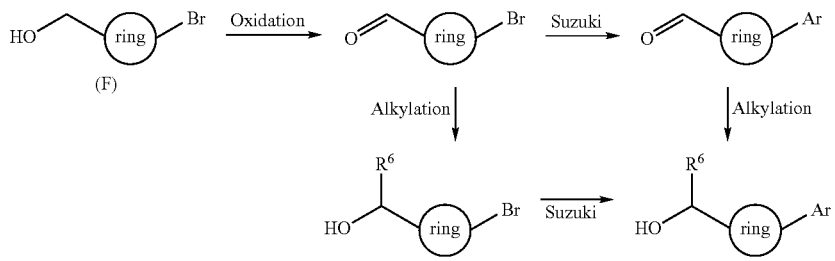

Scheme 10

Metallation, acylation, then reduction followed by Suzuki (or Suzuki followed by reduction) of a bromo derivative (G)

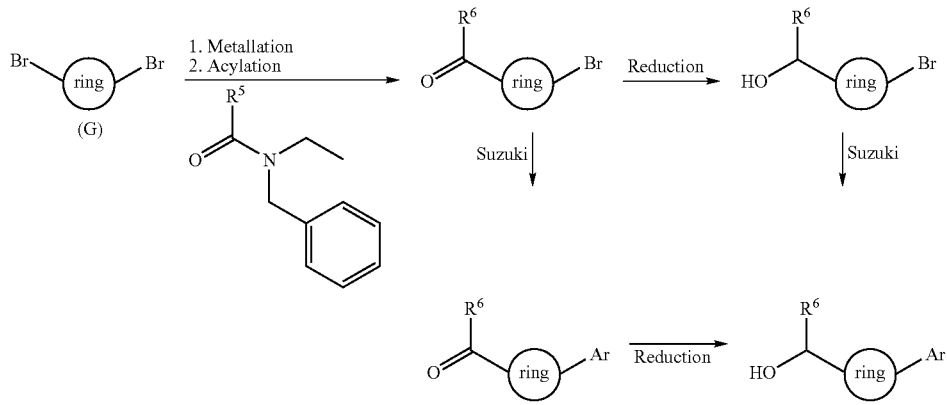

Other intermediates may be prepared as described in text below or in published literature e.g. WO 01/00603 and their synthesis will be apparent to a person skilled in the art.

The following illustrates Intermediates and Examples of Formula 1 which should not be construed as constituting a limitation thereto.

General Purification and Analytical Methods

LC/MS refers to analysis by analytical HPLC which was conducted on a Supelcosil LCABZ+PLUS column (3 μm, 3.3 cm×4.6 mm ID) eluting with 0.1% $HCO_2H$ and 0.01 M ammonium acetate in water (solvent A), and 95% acetonitrile and 0.05% $HCO_2H$ in water (solvent B), using the following elution gradient 0-0.7 minutes 0% B, 0.7-4.2 minutes 0→100% B, 4.2-5.3 minutes 100% B, 5.3-5.5 minutes 100→0% B at a flow rate of 3 ml/minute. The mass spectra (MS) were recorded on a Fisons VG Platform mass spectrometer using electrospray positive ionisation [(ES+ve to give $[M+H]^+$ and $[M+NH_4]^+$ molecular ions] or electrospray negative ionisation [(ES−ve to give $[M-H]^-$ molecular ion] modes.

$^1$H NMR spectra were recorded using a Bruker DPX 400 MHz spectrometer.

Biotage™ chromatography refers to purification carried out using equipment sold by Dyax Corporation (either the Flash 40i or Flash 150i) and cartridges pre-packed with KP-Sil™ silica.

OPTIX refers to purification using CombiFlash Optix 10 equipment provided by Isco Inc.

Mass directed auto-prep HPLC refers to the method where the material was purified by high performance liquid chromatography on a HPLCABZ+5 μm column (5 cm×10 mm i.d.) with 0.1% $HCO_2H$ in water and 95% MeCN, 5% water (0.5% $HCO_2H$) utilising the following gradient elution conditions: 0-1.0 minutes 5% B, 1.0-8.0 minutes 5→30% B, 8.0-8.9 minutes 30% B, 8.9-9.0 minutes 30→95% B, 9.0-9.9 minutes 95% B, 9.9-10 minutes 95→0% B at a flow rate of 8 ml/minute. The Gilson 202-fraction collector was triggered by a VG Platform Mass Spectrometer on detecting the mass of interest.

Hydrophobic frits refers to filtration tubes sold by Whatman.

SPE (solid phase extraction) refers to the use of cartridges sold by International Sorbent Technology Ltd.

TLC (thin layer chromatography) refers to the use of TLC plates sold by Merck coated with silica gel 60 $F_{254}$.

Abbreviations:
TLC: thin layer chromatography
DMSO-d$^6$: deuterated dimethylsulfoxide
CDCl$_3$: deuterated chloroform
MeOD-d$^4$: deuterated methanol
AcOH: acetic acid
ADDM: 1,1'-(azodicarboxylic)dimorpholide ADDP: 1,1'-(azodicarbonyl)dipiperidine
CDI: 1,1'-carbonyldiimidazole
DCM: dichloromethane
DIAD: diisopropylazodicarboxylate
4-DMAP: 4-dimethylaminopyridine
DMF: N,N-dimethylformamide
EDC: 1-(3-dimethylaminopropyl)-3-ethylcarbodiimide hydrochloride
Et$_2$O: diethyl ether
EtOAc: ethyl acetate
MeCN: acetonitrile
MeOH: methanol
nBu$_3$P: tributylphosphine
R$_t$: retention time
TBAF: tetrabutylammonium fluoride
THF: tetrahydrofuran
br: broad
s: singlet
d: doublet
dd: doublet of doublets
t: triplet
q: quartet
m: multiplet
rt: room temperature Intermediate 1

6-Bromo-N-methoxy-N-methylpyridine-2-carboxamide

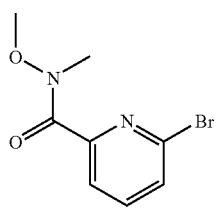

To a slurry of 6-bromopicolinic acid (5.44 g, 26.93 mmol) in DCM (100 mL) was added a solution of CDI (5.67 g, 34.97 mmol) in DCM (70 mL) drop-wise over 15 minutes under nitrogen. The solution cleared a little during the addition but remained cloudy and after 1 hour at rt the mixture was treated drop-wise over 15 minutes with N,O-dimethylhydroxylamine [solution in DCM prepared by treating N,O-dimethylhydroxylamine hydrochloride (5.35 g, 53.82 mmol) with aqueous NaOH (2M, 100 mL) and extracting with DCM (2×100 mL)]. The mixture cleared during the addition and the resulting clear pale yellow solution was left to stir under nitrogen for 20 hours. The mixture was then reduced under vacuum and the residue partitioned between EtOAc (125 mL) and saturated aqueous NaHCO$_3$ (125 mL). The layers were then separated and the organic layer washed with brine (125 mL), dried (MgSO$_4$), filtered and reduced to give the title compound as a yellow oil (5.29 g).

LC/MS: m/z 245.0 [M+H]$^+$, R$_t$ 2.27 min.

Intermediate 2

1-(6-Bromo-2-pyridinyl)-1-pentanone (Method A)

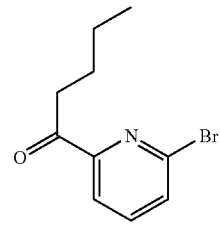

To a solution of 6-bromo-N-methoxy-N-methylpyridine-2-carboxamide (5.29 g, 21.58 mmol) in dry THF (120 mL) at −78° C. (dry ice/acetone bath) under nitrogen was added nBuMgCl (15.2 mL of a 20% wt solution in THF/toluene, 25.84 mmol) drop-wise over 15 minutes. The resulting yellow mixture was stirred at this temperature for 1 hour and was then allowed to warm to 0° C. (ice/water bath) slowly over 1.5 hours and then to rt over 18 hours. The yellow cloudy mixture was then added portion-wise to a stirred solution of aqueous HCl (2M, 200 mL) and the resulting mixture partitioned with EtOAc (200 mL) and the layers separated. The aqueous was re-extracted with EtOAc (200 mL) and the combined organic layer washed with brine (300 mL), dried (MgSO$_4$) filtered and reduced to give a yellow/orange oil. Purification by Biotage™ chromatography (silica) eluting with cyclohexane:EtOAc (gradient 20:1 to 1:2) afforded the title compound (2.51 g).

LC/MS: m/z 242.0 [M+H]$^+$, R$_t$ 3.57 min.

Intermediate 3

1-{6-[4-(Trifluoromethyl)phenyl]-2-pyridinyl}-1-pentanone

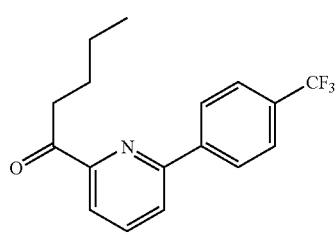

A solution of 1-(6-bromo-2-pyridinyl)-1-pentanone (2.51 g, 10.37 mmol) in DME (13 mL) was treated with 4-(trifluoromethyl)benzeneboronic acid (2.36 g, 12.43 mmol), Pd(PPh$_3$)$_4$ (1.19 g, 1.03 mmol) and then a slurry of Na$_2$CO$_3$ (3.29 g, 31.04 mmol) in water (13 mL). The resulting mixture was then heated to reflux over 30 minutes and then stirred at this temperature for 17 hours. The mixture was then allowed to cool to rt and was reduced and the residue partitioned between EtOAc (200 mL) and water (200 mL). The aqueous was re-extracted with EtOAc (100 mL) and the combined organic layer washed with saturated aqueous NaHCO$_3$ (250 mL), brine (250 mL), dried (MgSO$_4$), filtered and reduced to give a brown orange solid residue. Purification by Biotage™ chromatography (silica) eluting with cyclohexane:EtOAc (gradient 1:0 to 10:1) afforded the title compound as a white solid (3.02 g).

LC/MS: m/z 308.2 [M+H]⁺, $R_t$ 4.14 min.

Intermediate 4

1-{6-[4-(Trifluoromethyl)phenyl]-2-pyridinyl}-1-pentanol (Method A)

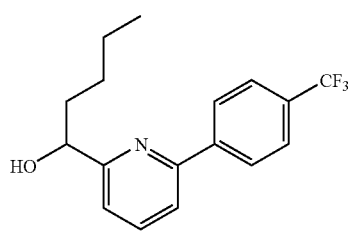

A mixture of 1-{6-[4-(trifluoromethyl)phenyl]-2-pyridinyl}-1-pentanone (2.80 g, 9.11 mmol) in THF (61 mL) at 0° C. (ice/water bath) was treated drop-wise with a mixture of sodium borohydride (689 mg, 18.21 mmol) in water (11 mL) over 5-10 minutes. The resulting mixture was stirred at this temperature for 2.5 hours and was then partitioned between EtOAc (200 mL) and water (200 mL) and the layers separated. The aqueous was re-extracted with EtOAc (200 mL) and the combined organic layer washed with brine (250 mL), dried (MgSO₄), filtered and reduced. Purification by Biotage™ chromatography (silica) eluting with cyclohexane:EtOAc (gradient 20:1 to 5:1) afforded the title compound as a colourless oil (2.81 g).

LC/MS: m/z 310.2 [M+H]⁺, $R_t$ 3.87 min.

Intermediate 5

6-[4-(Trifluoromethyl)phenyl]-2-pyridinecarbaldehyde

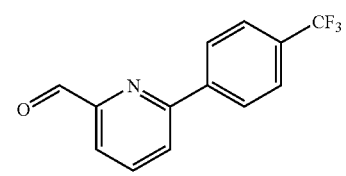

A solution of 6-bromo-2-pyridinecarboxaldehyde (512 mg, 2.75 mmol) and 4-(triflouromethyl)benzeneboronic acid (522 mg, 2.75 mmol) in DME (46 mL) was treated a slurry of Na₂CO₃ (875 mg, 8.26 mmol) in water (23 mL) followed by Pd(PPh₃)₄ (64 mg, 0.06 mmol). The resulting mixture was then heated to reflux, under nitrogen over 30 minutes and then stirred at this temperature for 17 hours. The mixture was then allowed to cool to rt, was reduced under vacuum and the residue partitioned between EtOAc (50 mL) and water (50 mL) and the layers separated. The aqueous was re-extracted with EtOAc (100 mL) and the combined organic layer washed with brine (100 mL), dried (MgSO₄), filtered and reduced to give a yellow solid residue. Purification by SPE (silica) eluting with cyclohexane:EtOAc (gradient 1:0 to 10:1) afforded the title compound as a yellow foam (565 mg).

LC/MS: m/z 251.9 [M+H]⁺, $R_t$ 3.57 min.

Intermediate 4

1-{6-[4-(Trifluoromethyl)phenyl]-2-pyridinyl}-1-pentanol (Method B)

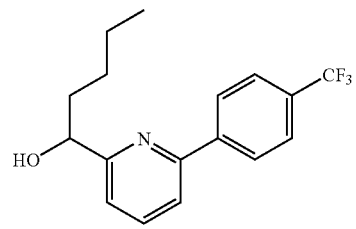

A solution of 6-[4-(trifluoromethyl)phenyl]-2-pyridinecarbaldehyde (2.50 g, 9.95 mmol) in dry THF (100 mL) was cooled to 0° C. (ice/water bath) and treated with nBuLi (6.8 mL of a 1.6M solution in hexanes, 10.88 mmol) under nitrogen drop-wise over 20 minutes. The resulting deep red coloured solution was stirred at 0° C. for 1.5 hours and then quenched by the addition of aqueous HCl (2M, 10 mL) and allowed to warm to rt over about 20 minutes. The solvents were then removed under vacuum and the residue partitioned between EtOAc (150 mL) and saturated aqueous NaHCO₃ (150 mL) and the layers separated. The aqueous was re-extracted with EtOAc (100 mL) and the combined organic layer washed with water (200 mL), brine (200 mL), dried (MgSO₄), filtered and reduced to give a pale yellow foam. Purification by Biotage™ chromatography (silica) eluting with cyclohexane:EtOAc (gradient 100:1 to 0:1) afforded the title compound as a pale yellow oil (1.99 g).

LC/MS: m/z 310.2 [M+H]⁺, $R_t$ 3.87 min.

Intermediate 6

[4'-(Trifluoromethyl)-3-biphenylyl]methanol

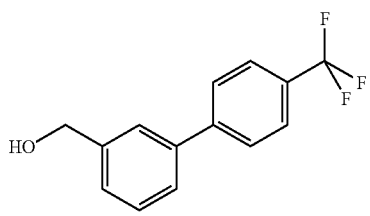

A mixture 3-bromobenzyl alcohol (500 mg, 2.70 mmol), 4-(triflouromethyl)benzeneboronic acid (1.01 g, 5.35 mmol), Pd(PPh₃)₄ (68 mg, 0.06 mmol) and Na₂CO₃ (740 mg, 7.02 mmol) in a mixture of DME (20 mL) and water (10 mL) was heated at reflux for 3 hours. The mixture was allowed to cool to rt, and then partitioned between EtOAc and water. The layers were separated and the aqueous re-extracted with EtOAc (2×) and the combined organic layer washed with water and then brine, dried (Na₂SO₄), filtered and reduced to give an oil. Purification by flash chromatography (silica) eluting with cyclohexane:EtOAc (5:2) afforded the title compound as a clear oil which crystallised on standing (654 mg).

LC/MS: $R_t$ 3.58 min, no molecular ion observed.

Intermediate 7

3-(Bromomethyl)-4'-(trifluoromethyl)biphenyl

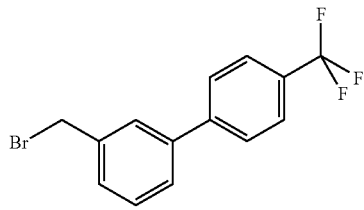

A solution of [4'-(trifluoromethyl)-3-biphenylyl]methanol (177 mg, 0.70 mmol) in dry DCM (10 mL) was cooled to 0° C. (ice/water bath) under nitrogen and treated with CBr$_4$ (256 mg, 0.77 mmol) in one portion. PPh$_3$ (202 mg, 0.77 mmol) was then added portion-wise and the resulting mixture stirred for 1 hour at this temperature and was then allowed to warm to rt. The resulting mixture was then reduced and the residue purified directly by SPE (silica, 10 g cartridge) eluting with cyclohexane:DCM afforded the title compound as a colourless oil (220 mg).

LC/MS: R$_t$ 3.94 min, no molecular ion observed.

Intermediate 8

Ethyl {[2-methyl-4-({([4'-(trifluoromethyl)-3-biphenylyl]methyl}thio)phenyl]oxy}acetate

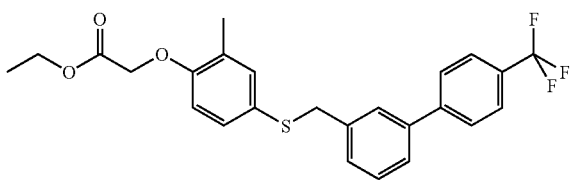

A mixture of 3-(bromomethyl)-4'-(trifluoromethyl)biphenyl (200 mg, 0.63 mmol), ethyl (4-mercapto-2-methylphenoxy)acetate (144 mg, 0.63 mmol) and polymer supported diisopropylethylamine (3 mmol/g, 423 mg, 1.27 mmol) in DCM (20 mL) was stirred at rt overnight. TLC (cyclohexane:DCM 1:1) indicated bromide still remaining so more thiol (100 mg, 0.44 mmol) was added and after 3 hours no change was observed by TLC. The mixture was then filtered, reduced and purified using SPE (silica, 10 g cartridge). The residue was dissolved in DCM (10 mL) and treated with polymer supported isocyante resin (1.43 mmol/g. 2 g, 2.46 mmol) and stirred at rt overnight. The mixture was then filtered, washing with DCM and reduced to give the title compound (209 mg).

$^1$H NMR (400 MHz; CDCl$_3$) δ: 1.29 (3H, t, J 7 Hz), 2.25 (3H, s), 4.05 (2H, s), 4.26 (2H, q, J 7 Hz), 4.60 (2H, s), 7.59 (2H, d, J 8.5 Hz), 7.68 (2H, d, J 8.5 Hz).

Intermediate 9

(5-Bromo-2-methylphenyl)methanol

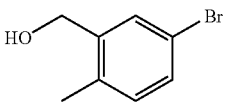

Borane (10.80 mL of a 1M solution in THF, 10.80 mmol) was added to a cooled solution of 5-bromo-2-methyl-benzoic acid (116 mg, 0.54 mmol) in THF (15 mL), under nitrogen, at 0° C. (ice water bath) and the resulting mixture allowed to warm to rt overnight. The mixture was then treated with MeOH (10 mL) followed by aqueous HCl (2M, 20 mL) and the mixture stirred for about 15 minutes, concentrated under vacuum and then partitioned with EtOAc. The organic layer was washed with aqueous HCl (2M), water and brine, dried (MgSO$_4$), filtered and reduced to give the title compound as a colourless oil (90 mg).

LC/MS: R$_t$ 3.09 min, no molecular ion observed.

Intermediate 10

Ethyl 3-[2-methyl-4-({[4'-(trifluoromethyl)-3-biphenylyl]methyl}oxy)phenyl]propanoate

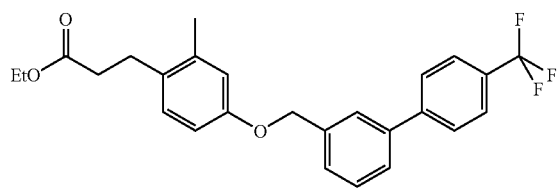

To a solution of [4'-(trifluoromethyl)-3-biphenylyl]methanol (121 mg, 0.48 mmol) in dry THF (5 mL) under nitrogen at 0° C. (ice/water bath) was added nBu$_3$P (240 µL, 0.96 mmol) followed by ethyl 3-(4-hydroxy-2-methylphenyl)propanoate (100 mg, 0.48 mmol) and then ADDM (246 mg, 0.96 mmol) portion-wise. The mixture was stirred at 0° C. for 1 hour, allowed to warm to rt over 21 hours and then partitioned between water and EtOAc, and the layers separated. The aqueous layer was then extracted with EtOAc and the combined organic extract washed with water and then brine, dried (Na$_2$SO$_4$) and the solvent removed under vacuum. Purification by flash chromatography (silica) eluting with cyclohexane:EtOAc (15:1) afforded the title compound as a clear oil (141 mg).

LC/MS: R$_t$ 4.43 min, no molecular ion observed.

Intermediate 11

Ethyl ({4-[2-(3-bromophenyl)ethenyl]-2-methylphenyl}oxy)acetate

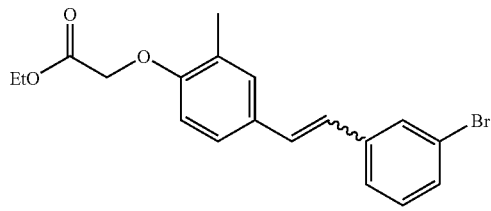

A suspension of [4-(2-ethoxy-2-oxoethoxy)-3-methylbenzyl](triphenyl)phosphonium chloride (500 mg, 0.99 mmol) in dry THF (10 mL) was cooled to 0° C. (ice/water bath) and treated with NaH (44 mg of a 60% dispersion in mineral oil, 1.10 mmol) portion-wise over 5 minutes. The resulting yellow suspension was stirred for 15 minutes and was then treated with 3-bromobenzaldehyde (184 mg, 0.99 mmol) in dry THF (5 mL). The resulting white suspension was allowed to warm to rt over 3.5 hours and was then heated at reflux for 1 hour. The reaction mixture was then allowed to cool to rt, stirred overnight and was then reduced under vacuum. The residue was then partitioned between CHCl$_3$ (20 mL) and water (20 mL) and the layers separated. The cloudy organic layer was dried through a hydrophobic frit and then concentrated to a cream coloured gum (700 mg). Purification by SPE (silica) eluting with cyclohexane:EtOAc (9:1) afforded the title compound (mixture of E:Z isomers) (258 mg).

LC/MS: R$_t$ 4.23 min and 4.31 min, no molecular ions observed.

Intermediate 12

[(2-Methyl-4-{2-[4'-(trifluoromethyl)-3-biphenylyl]ethenyl}phenyl)oxy]acetic acid

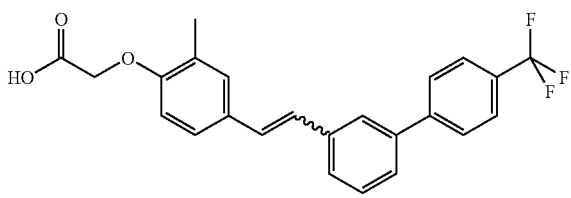

Ethyl ({4-[2-(3-bromophenyl)ethenyl]-2-methylphenyl}oxy)acetate (150 mg, 0.40 mmol), Na$_2$CO$_3$ (106 mg, 1.00 mmol), 4-(triflouromethyl)benzeneboronic acid (83.5 mg, 0.44 mmol) and Pd(PPh$_3$)$_4$ (23 mg, 0.02 mmol) was dissolved in DME and water (2:1, 6 mL) and the mixture heated at reflux for 4 hours. The mixture was allowed to cool to rt, was concentrated under reduced pressure and the residue partitioned between EtOAc (15 mL) and water (15 mL). The aqueous layer was then acidified with aqueous HCl (1N) and extracted with EtOAc and the combined organic layers dried (MgSO$_4$), filtered and reduced to give the title compound (94 mg).

LC/MS: m/z 411 [M−H]$^+$, R$_t$ 4.45 min and 4.67 min.

Intermediate 13

Ethyl ({2-methyl-4-[({6-[4-(trifluoromethyl)phenyl]-2-pyridinyl}methyl)thio]phenyl}oxy)acetate

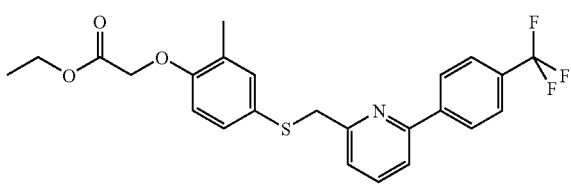

A solution of the 2-(bromomethyl)-6-[4-(trifluoromethyl)phenyl]pyridine (238 mg, 0.75 mmol), ethyl (4-mercapto-2-methylphenoxy)acetate (84 mg, 0.37 mmol) and K$_2$CO$_3$ (57 mg, 0.41 mmol) in MeCN (5 mL) was stirred at rt, under nitrogen overnight. The mixture was then partitioned between water and EtOAc and the layers separated. The organic layer was then washed with water and brine, dried (MgSO$_4$), filtered and reduced. Purification by SPE (silica, 2 g cartridge) eluting with CHCl$_3$:cyclohexane (5:1) afforded the title compound (160 mg).

LC/MS: m/z 462.3 [M+H]$^+$, R$_t$ 4.10 min.

Intermediate 14

1-[4'-(Trifluoromethyl)-3-biphenylyl]ethanone

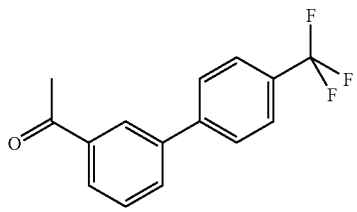

A solution of 3-bromoacetophenone (661 μL, 5.00 mmol) and 4-(triflouromethyl)benzeneboronic acid (950 mg, 5.00 mmol) in DME (50 mL) was added Na$_2$CO$_3$ (1.32 g, 12.50 mmol) and Pd(PPh$_3$)$_4$ (283 mg, 0.24 mmol) and water (25 mL). The mixture was then stirred at 100° C. for 20 hours, diluted with water and extracted with EtOAc. The organic layer was then washed with brine, dried (Na$_2$SO$_4$), filtered and reduced. Purification by flash chromatography (silica) eluting with petrol:EtOAc (gradient 19:1 to 9:1) afforded the title compound (1.01 g).

LC/MS: R$_t$ 3.62 min, no molecular ion observed.

Intermediate 15

1-[4'-(Trifluoromethyl)-3-biphenylyl]ethanol

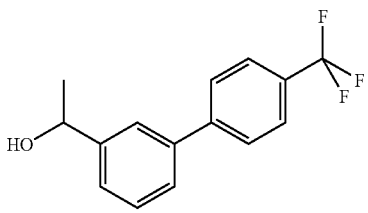

A mixture of 1-[4'-(trifluoromethyl)-3-biphenylyl]ethanone (300 mg, 1.14 mmol) in water (1 mL) and EtOH (5 mL) was treated portion-wise with sodium borohydride (57 mg, 1.50 mmol) and then stirred at rt for 1.5 hours. The reaction was then quenched by the addition of saturated aqueous NH$_4$Cl, diluted with CHCl$_3$ and the layers separated. The organic layer was then dried (Na$_2$SO$_4$), filtered and reduced to give the title compound (274 mg).

LC/MS: R$_t$ 3.50 min, no molecular ion observed.

Intermediate 16

Ethyl {[2-methyl-4-({1-[4'-(trifluoromethyl)-3-biphenylyl]ethyl}thio)phenyl]oxy}acetate

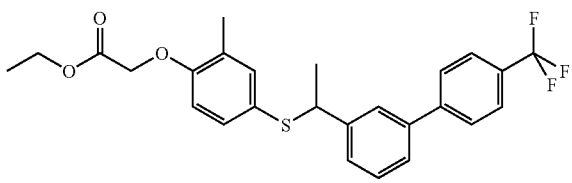

Zinc (229 mg, 3.50 mmol) was added to EtOAc (10 mL) followed by AcOH (115 µM, 2.00 mmol) and ethyl [4-(chlorosulfonyl)-2-methylphenoxy]acetate (293 mg, 1.00 mmol). After 2 hours, dichlorodimethylsilane (258 mg, 2.00 mmol) was added followed by 1-[4'-(trifluoromethyl)-3-biphenylyl]ethanol (266 mg, 1.00 mmol) and the mixture stirred for a further 1 hour and then heated at 80° C. for 5 hours. The mixture was then cooled, diluted with EtOAc and washed with saturated aqueous NaHCO₃, saturated aqueous NH₄Cl, water and brine, and then reduced. Purification by Biotage™ chromatography (silica) eluting with petrol:EtOAc (9:1) afforded the title compound as a colourless oil (238 mg).
LC/MS: m/z 492.2 [M+NH₄]⁺, $R_t$ 4.28 min.

Intermediate 17

1-[4'-(Trifluoromethyl)-4-biphenylyl]ethanone

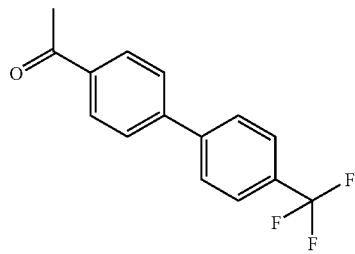

Prepared according to the procedure used for the preparation of Intermediate 14, starting from 4-bromoacetophenone (661 µL, 5.00 mmol), to give, after purification by Biotage™ chromatography (silica) eluting with petrol:EtOAc (8:1), the title compound (1.10 g).
LC/MS: $R_t$ 3.63 min, no molecular ion observed.

Intermediate 18

1-[4'-(Trifluoromethyl)-4-biphenylyl]ethanol

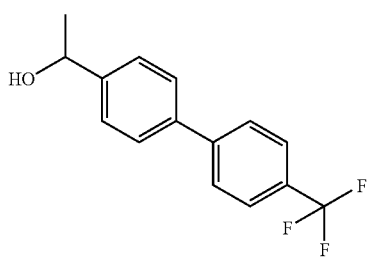

Prepared from 1-[4'-(trifluoromethyl)-4-biphenylyl]ethanone (305 mg, 1.15 mmol) according to the procedure used for the preparation of Intermediate 15 to give the title compound (324 mg).
LC/MS: $R_t$ 3.54 min, no molecular ion observed.

Intermediate 19

Ethyl {[2-methyl-4-({1-[4'-(trifluoromethyl)-4-biphenylyl]ethyl}thio)phenyl]oxy}acetate

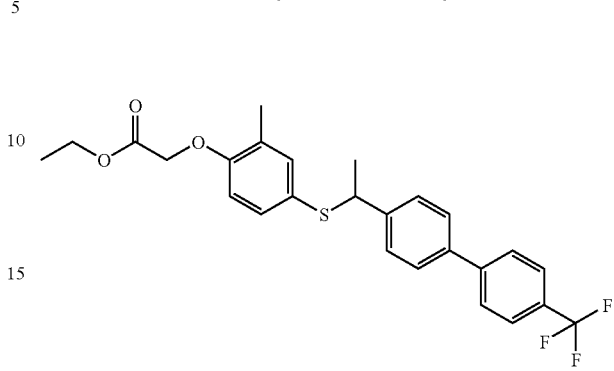

Prepared from 1-[4'-(trifluoromethyl)-4-biphenylyl]ethanol (324 mg, 1.15 mmol) according to the procedure used for the preparation of Intermediate 16, to give, after purification by Biotage™ chromatography (silica) eluting with petrol:EtOAc (8:1), the title compound as a colourless oil (333 mg).
LC/MS: m/z 492.2 [M+NH₄]⁺, $R_t$ 4.31 min.

Intermediate 20

Ethyl 2-methyl-2-({2-methyl-4-[(1-{6-[4-(trifluoromethyl)phenyl]-2-pyridinyl}pentyl)oxy]phenyl}oxy)propanoate

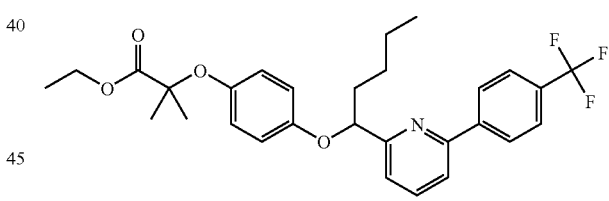

To a solution of nBu₃P (47 µL, 0.19 mmol) in dry THF (2 mL), at 0° C. (ice/water bath) under nitrogen was added DIAD (37 mL, 0.19 mmol). After stirring for 10 minutes 1-{6-[4-(trifluoromethyl)phenyl]-2-pyridinyl}-1-pentanol (50 mg, 0.16 mmol) was added, followed after another 20 minutes by ethyl 2-(4-hydroxy-2-methylphenoxy)-2-methylpropanoate (39 mg, 0.16 mmol). The mixture was then allowed to warm to rt over 16 hours and was then reduced under vacuum and the residue partitioned between EtOAc and water. The layers were separated and the organic layer washed with water (2×) then brine, dried (Na₂SO₄) and reduced to give a brown gum. Purification by Biotage™ chromatography (silica, 40 g cartridge) eluting with cyclohexane:EtOAc (19:1) afforded the title compound as a colourless gum (9 mg).
LC/MS: m/z 530.3 [M+H]⁺, $R_t$ 4.61 min.

Intermediate 21

1-(3-Bromophenyl)-1-pentanol

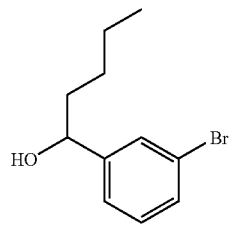

To 3-bromobenzaldehyde (5.00 g, 27.02 mmol) in dry THF (100 mL), under nitrogen at −78° C. (dry ice/acetone bath) was added nBuMgCl (16.2 mL of a 2.0M solution in THF, 0.032 mol) and the reaction stirred for 1 hour at −78° C. and then allowed to warm to rt overnight. The reaction was then quenched with water, extracted with EtOAc and the layers separated. The organic layer was washed with water then brine, dried ($Na_2SO_4$) and reduced under vacuum to give a colourless oil. Purification by Biotage™ chromatography (silica, 90 g cartridge) eluting with cyclohexane:EtOAc 9:1 afforded the title compound as a colourless oil (4.07 g).

LC/MS: $R_t$ 3.49 min, no molecular ion observed.

Intermediate 22

Ethyl [(4-{[1-(3-bromophenyl)pentyl]oxy}-2-methylphenyl)oxy]acetate

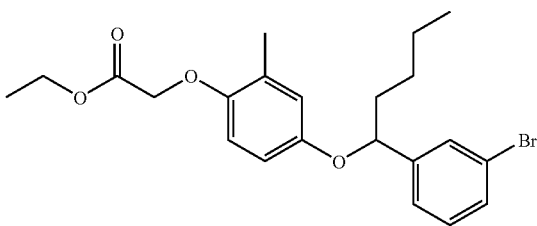

To a solution of 1-(3-bromophenyl)-1-pentanol (1.00 g, 4.11 mmol) in dry THF (40 mL) at 0° C. was added ethyl (4-hydroxy-2-methylphenoxy)acetate (865 mg, 4.11 mmol), $PPh_3$ (1.30 g, 4.94 mmol) and ADDP (1.25 g, 4.94 mmol) and the reaction stirred for 30 minutes and then allowed to warm to rt overnight. The mixture was then reduced under vacuum and the residue partitioned between EtOAc and water and the layers separated. The organic layer was washed with water (2×) then brine, dried ($Na_2SO_4$) and reduced under vacuum to give a brown oil. Purification by Biotage™ chromatography (silica, 90 g cartridge) eluting with petroleum ether 40-60° C.:EtOAc (gradient 1:0 to 9:1) afforded the title compound as colourless oil (1.15 g).

LC/MS: 454.0/455.1 $[M+NH_4]^+$, $R_t$ 4.28 min.

Intermediate 23

Ethyl {[2-methyl-4-({1-[4'-(trifluoromethyl)-3-biphenylyl]pentyl}oxy)phenyl]oxy}acetate

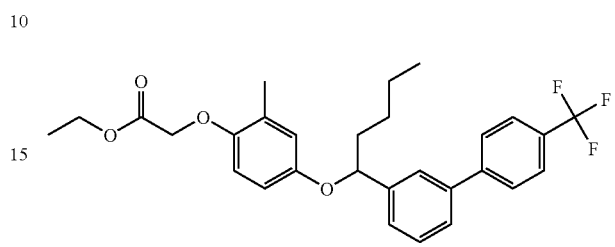

Ethyl [(4-{[1-(3-bromophenyl)pentyl]oxy}-2-methylphenyl)oxy]acetate (200 mg, 0.46 mmol) was dissolved in dry THF (3 mL), and treated with 4-(trifluoromethyl)benzeneboronic acid (104 mg, 0.55 mmol), $Pd(PPh_3)_4$ (53 mg, 0.046 mmol) and sodium carbonate (146 mg, 1.38 mmol) in water (2 mL). The mixture was then heated at 70° C. for 3 hours, cooled to rt and partitioned between EtOAc and water. The layers were separated and the organic layer washed with brine, dried ($Na_2SO_4$) and concentrated to give a brown oil. Purification by Biotage™ chromatography (silica, 40 g cartridge) eluting with petroleum ether 40-60° C.:EtOAc (19:1) afforded the title compound as a colourless gum (142 mg).

LC/MS: m/z 518.2 $[M+NH_4]^+$, $R_t$ 4.55 min.

Intermediate 24

Ethyl [(4-{[1-(4'-chloro-3-biphenylyl)pentyl]oxy}-2-methylphenyl)oxy]acetate

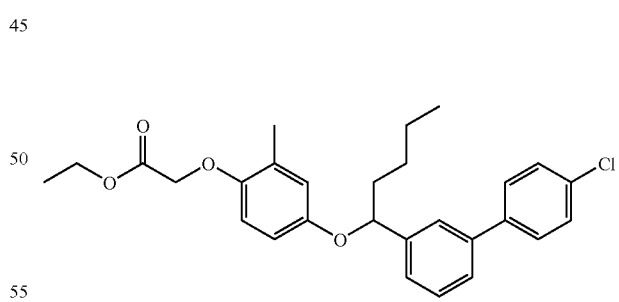

Prepared according to the procedure used for the preparation of Intermediate 23, starting from ethyl [(4-{[1-(3-bromophenyl)pentyl]oxy}-2-methylphenyl)oxy]acetate (200 mg, 0.46 mmol) and 4-chlorobenzene boronic acid (86 mg, 0.55 mmol) to give, after purification by Biotage™ chromatography (silica, 40 g cartridge) eluting with petroleum ether 40-60° C.:EtOAc (19:1), the title compound (137 mg).

LC/MS: m/z 484.2 $[M+NH_4]^+$, $R_t$ 4.55 min.

Intermediate 25

1-[4'-(Trifluoromethyl)-4-biphenylyl]-1-pentanone

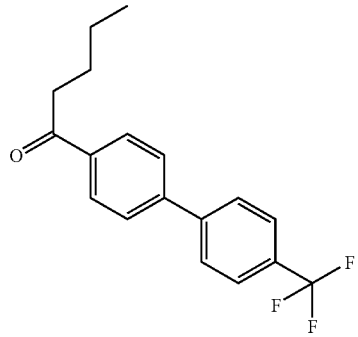

To a solution of 1-(4-methylphenyl)-1-pentanone (1.00 g, 4.15 mmol) in DME (20 mL) and water (10 mL) was added 4-(trifluoromethyl)benzeneboronic acid (870 mg, 4.57 mmol) and $Na_2CO_3$ (1.10 g, 10.38 mmol). After 10 minutes under nitrogen, $Pd(PPh_3)_4$ (480 mg, 0.42 mmol) was added portion-wise, and the mixture heated to reflux and stirred under nitrogen for 2 hours. The reaction mixture was then allowed to cool to rt and the solvents removed under vacuum. The resulting residue was partitioned between water and EtOAc, the layers separated and the aqueous re-extracted with EtOAc (3×30 mL). The combined organic extract was separated and dried ($MgSO_4$), and the solvent removed under vacuum. Purification by flash chromatography (silica), eluting with cyclohexane:EtOAc (19:1) afforded the title compound as a white solid (850 mg).

LC/MS: m/z 307.1 $[M+H]^+$, $R_t$ 4.16 min.

Intermediate 26

1-[4'-(Trifluoromethyl)-4-biphenylyl]-1-pentanol

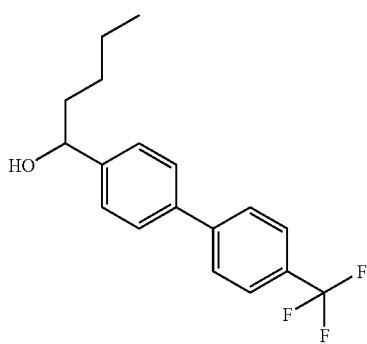

To a solution of 1-[4'-(trifluoromethyl)-4-biphenylyl]-1-pentanone (500 mg, 1.63 mmol) in THF (16 mL) and water (8 mL) under nitrogen at 0° C. (ice/water bath) was added sodium borohydride (74 mg, 1.96 mmol) portion-wise. After stirring the mixture for 1 hour at rt, the reaction was diluted with water (30 mL) and extracted into EtOAc (3×30 mL). The combined organic extract was separated, dried ($MgSO_4$) and reduced under vacuum to afford the title compound as a colourless gum (490 mg).

LC/MS: $R_t$ 3.96 min, no molecular ion observed.

Intermediate 27

Ethyl {[2-methyl-4-({1-[4'-(trifluoromethyl)-4-biphenylyl]pentyl}oxy)phenyl]oxy}acetate

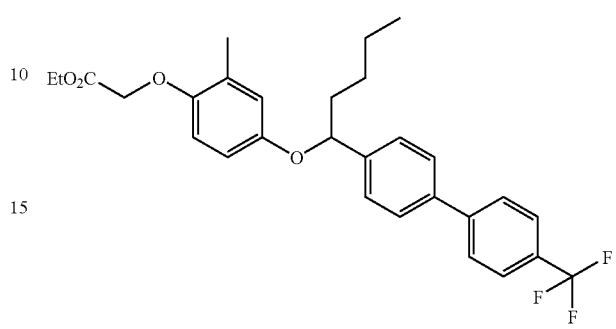

To a solution of 1-[4'-(trifluoromethyl)-4-biphenylyl]-1-pentanol (250 mg, 0.81 mmol) in dry THF (20 mL) under nitrogen at 0° C. (ice/water bath) was added $nBu_3P$ (0.41 mL, 1.64 mmol), followed by ethyl (4-hydroxy-2-methylphenoxy)acetate (170 mg, 0.81 mmol) and ADDM (420 mg, 1.64 mmol) portion-wise. After stirring the mixture for 18 hours at rt under nitrogen the solvent was removed under vacuum. The residue was partitioned between water and EtOAc and the aqueous re-extracted with EtOAc (3×30 mL). The organic combined extract was dried ($MgSO_4$) and then reduced under vacuum. Purification by flash chromatography (silica), eluting with cyclohexane:EtOAc (9:1) afforded the title compound as a colourless gum (310 mg).

LC/MS: m/z 518.2 $[M+NH_4]^+$, $R_t$ 4.55 min.

Intermediate 28

1-(4'-Chloro-4-biphenylyl)-1-pentanol

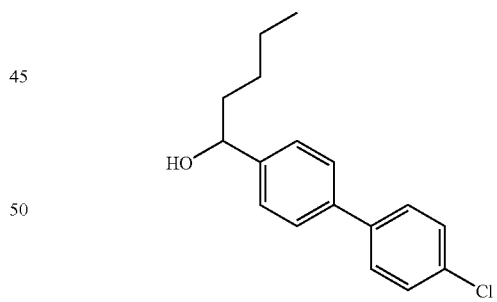

To a solution of 4'-chloro-4-biphenylcarbaldehyde (200 mg, 0.92 mmol) in anhydrous THF (10 mL) under nitrogen at −78° C. (dry ice/acetone) was added nBuMgCl (550 μL of a 2M solution in THF, 1.10 mmol). The reaction mixture was stirred at −78° C. for 1 hour and then at rt for 18 hours. The reaction was quenched by cautious addition of water (15 mL) and extracted with EtOAc (3×20 mL). The combined organic extract was then dried ($MgSO_4$) and reduced under vacuum. Purification by flash chromatography (silica), eluting with cyclohexane:EtOAc (9:1) afforded the title compound as a colourless gum (140 mg).

LC/MS: $R_t$ 3.98 min, no molecular ion observed.

Intermediate 29

Ethyl [(4-{[1-(4'-chloro-4-biphenylyl)pentyl]oxy}-2-methylphenyl)oxy]acetate

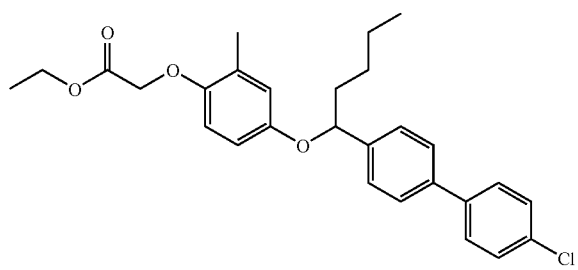

To a solution of 1-(4'-chloro-4-biphenylyl)-1-pentanol (140 mg, 0.51 mmol) in dry THF (15 mL) under nitrogen at 0° C. (ice/water bath) was added nBu$_3$P (250 μL, 1.02 mmol), followed by ethyl (4-hydroxy-2-methylphenoxy) acetate (110 mg, 0.52 mmol) and ADDP (260 mg, 1.03 mmol) portion-wise. After stirring the mixture for 18 hours at rt under nitrogen the solvent was removed under vacuum. The residue was partitioned between water and EtOAc and extracted with EtOAc (3×30 mL). The organic extract was separated and dried (MgSO$_4$) and the solvent removed under vacuum. Purification by flash chromatography (silica) eluting with cyclohexane:EtOAc (9:1) afforded the title compound as a colourless gum (150 mg).

LC/MS: m/z 484.2 [M+NH$_4$]$^+$, R$_t$ 4.51 min.

Intermediate 30

4-(1-Chloropentyl)-4'-(trifluoromethyl)biphenyl

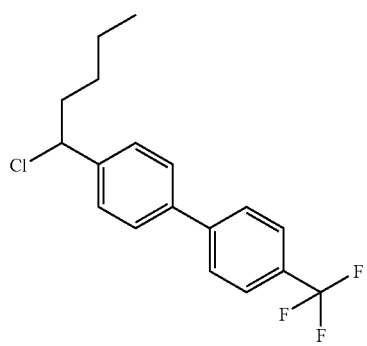

To a solution of 1-[4'-(trifluoromethyl)-4-biphenylyl]-1-pentanol (250 mg, 0.81 mmol) in dry DCM (15 mL) under nitrogen at 0° C. (ice/water bath) was added thionyl chloride (590 μL, 8.09 mmol) drop-wise. After stirring the mixture for 30 minutes at rt under nitrogen, the reaction was quenched by cautious addition of saturated aqueous NaHCO$_3$ (20 mL) and extracted with DCM (3×30 mL). The organic extract was separated, washed with brine, dried (MgSO$_4$) and the solvents removed under vacuum to afford the title compound as a yellow gum (251 mg).

LC/MS: R$_t$ 4.42 min, no molecular ion observed.

Intermediate 31 and Intermediate 32

Ethyl {[2-methyl-4-({(1R)-1-[4'-(trifluoromethyl)-4-biphenylyl]pentyl}thio)phenyl]oxy}acetate and
Ethyl {[2-methyl-4-({(1S)-1-[4'-(trifluoromethyl)-4-biphenylyl]pentyl}thio)phenyl]oxy}acetate Intermediate 31

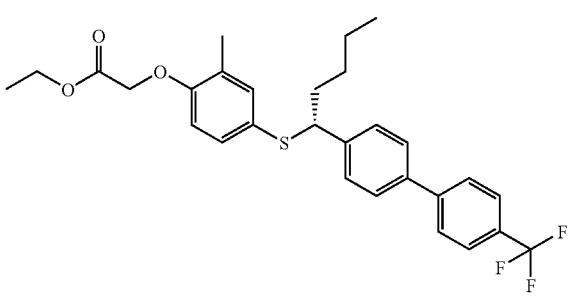

Intermediate 32

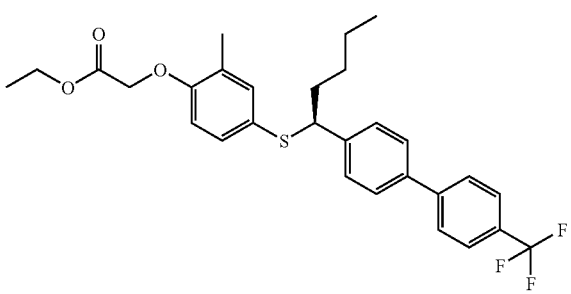

To a solution of ethyl (4-mercapto-2-methylphenoxy) acetate (170 mg, 0.75 mmol) in anhydrous MeCN (15 mL) under nitrogen was added 4-(1-chloropentyl)-4'-(trifluoromethyl)biphenyl (500 mg, 1.53 mmol) and caesium carbonate (500 mg, 1.53 mmol). After 18 hours stirring under nitrogen at room temperature, the reaction mixture was filtered and the solvent removed under vacuum. Purification by flash chromatography (silica), eluting with cyclohexane:EtOAc (9:1) afforded a colourless gum (230 mg).

LC/MS: m/z 517.1 [M+H]$^+$, R$_t$ 4.64 min.

Separation of a 20 mg sample by chiral HPLC (2×25 cm chiralpak A) eluting with 5% IPA/heptane, 15 ml/min, wavelength 215 nm afforded ethyl {[2-methyl-4-({(1R)-1-[4'-(trifluoromethyl)-4-biphenylyl]pentyl}thio)phenyl]oxy}acetate as a colourless oil (10 mg, R$_t$ 8.2 min) and ethyl {[2-methyl-4-({(1S)-1-[4'-(trifluoromethyl)-4-biphenylyl]pentyl}thio)phenyl]oxy}acetate as a colourless oil (9 mg, R$_t$ 9.8 min).

Intermediate 33 and Intermediate 34

Ethyl ({2-methyl-4-[((1S)-1-{6-[4-(trifluoromethyl) phenyl]-2-pyridinyl}pentyl)oxy]phenyl}oxy)acetate and Ethyl ({2-methyl-4-[((1R)-1-{6-[4-(trifluoromethyl)phenyl]-2-pyridinyl}pentyl)oxy]phenyl}oxy)acetate

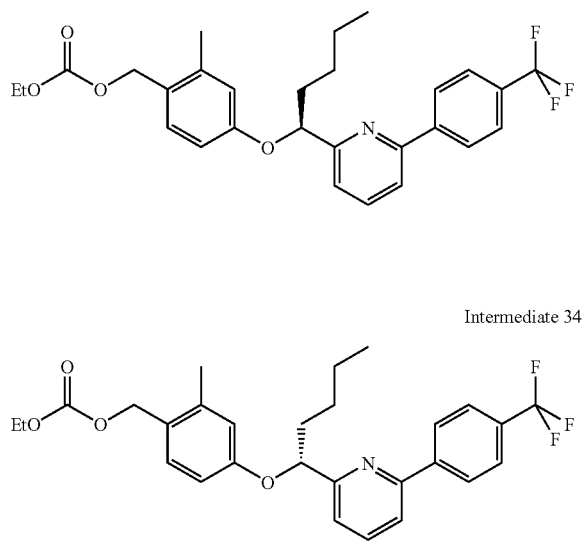

Intermediate 33

Intermediate 34

To a solution of 1-{6-[4-(trifluoromethyl)phenyl]-2-pyridinyl}-1-pentanol (711 mg, 2.30 mmol) in dry THF (46 mL) at 0° C. (ice/water bath) was added ethyl (4-hydroxy-2-methylphenoxy)acetate (483 mg, 2.30 mmol) followed one minute later by ADDM (1.18 g, 4.60 mmol) in one portion. The resulting slightly cloudy orange mixture was stirred at rt for 2-3 mins and the treated with nBu₃P (1.15 mL, 4.61 mmol) drop-wise over about 4 minutes to give a clear pale yellow solution. After 2 hours of slow warming, the solution had become slightly cloudy and was allowed to warm further to rt over 20 hours. The resulting cloudy mixture was then reduced under vacuum and the residue partitioned between EtOAc (150 mL) and water (150 mL) and the layers separated. The aqueous was re-extracted with EtOAc (150 mL) and the combined organic layers washed with brine (250 mL), dried (MgSO₄), filtered and reduced to give an oil. Purification by SPE (silica) eluting with cyclohexane:EtOAc (gradient 50:1 to 10:1) afforded a pale yellow foam (827 mg).

LC/MS: m/z 501.9 [M+H]⁺, R$_t$ 4.45 min.

Separation by chiral HPLC (2'×20 cm chiralpak) eluting with heptane:EtOH (98:2), 50 mL/min, wavelength 230 nM afforded ethyl ({2-methyl-4-[((1S)-1-{6-[4-(trifluoromethyl)phenyl]-2-pyridinyl}pentyl)oxy]phenyl}oxy)acetate (367 mg, R$_t$ 8.5 min) and ethyl ({2-methyl-4-[((1R)-1-{6-[4-(trifluoromethyl)phenyl]-2-pyridinyl}pentyl)oxy]phenyl}oxy)acetate (360 mg, R$_t$ 10.0 min).

Intermediate 35

2-(1-Chloropentyl)-6-[4-(trifluoromethyl)phenyl]pyridine

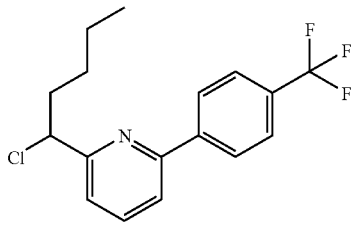

To a solution of 1-{6-[4-(trifluoromethyl)phenyl]-2-pyridinyl}-1-pentanol (1.50 g, 4.85 mmol) in dry DCM was added SOCl₂ (3.53 mL, 48.50 mmol), and the resulting solution stirred under nitrogen for 3 hours at rt. The mixture was then reduced under vacuum to afford the title compound as an oily yellow solid (1.65 g).

LC/MS: m/z 328.2 [M+H]⁺, R$_t$ 4.35 min.

Intermediate 36 and Intermediate 37

Ethyl ({2-methyl-4-[((1S)-1-{6-[4-(trifluoromethyl) phenyl]-2-pyridinyl}pentyl)thio]phenyl}oxy)acetate and Ethyl ({2-methyl-4-[((1R)-1-{6-[4-(trifluoromethyl)phenyl]-2-pyridinyl}pentyl)thio]phenyl}oxy)acetate Intermediate 36

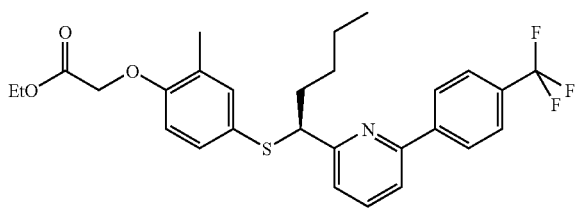

Intermediate 37

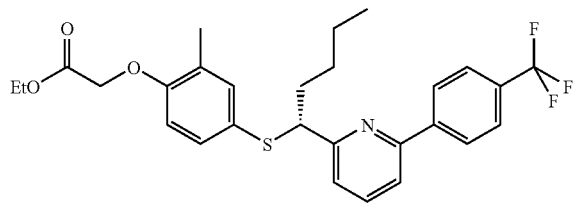

To a solution of 2-(1-chloropentyl)-6-[4-(trifluoromethyl)phenyl]pyridine (522 mg, 1.59 mmol) in dry THF (20 mL) was added caesium carbonate (621 mg, 1.91 mmol) and ethyl (4-mercapto-2-methylphenoxy)acetate (361 mg, 1.59 mmol). The resulting mixture was stirred under nitrogen for 60 hours at rt, then at 66° C. for 18 hours. The cooled reaction mixture was then diluted with water (50 mL), extracted with EtOAc (100 mL), the layers separated and the organic layer washed with brine (50 mL), dried (Na₂SO₄) and the solvents removed under vacuum. Purification by Biotage™ chromatography (silica, 40 g cartridge) eluting with cyclohexane:EtOAc (19:1) afforded a colourless oil (376 mg).

LC/MS: m/z 518.4 [M+H]⁺, R$_t$ 4.51 min.

Separation of a 100 mg sample by chiral HPLC (2 cm×25 cm chiralcel OJ) eluting with 5% EtOH/heptane, 15 ml/min, wavelength 215 nm afforded ethyl ({2-methyl-4-[((1S)-1-{6-[4-(trifluoromethyl)phenyl]-2-pyridinyl}pentyl)thio]phenyl}oxy)acetate as a colourless oil (34 mg, $R_t$ 12.4 min) and ethyl ({2-methyl-4-[((1R)-1-{6-[4-(trifluoromethyl)phenyl]-2-pyridinyl}pentyl)thio]phenyl}oxy)acetate as a colourless oil (29 mg, $R_t$ 14.7 min).

Intermediate 38

Ethyl ({2-methyl-4-[(1-{6-[4-(trifluoromethyl)phenyl]-2-pyridinyl}pentyl)sulfinyl]phenyl}oxy)acetate

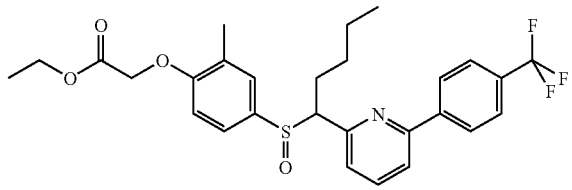

To a cooled (0° C., ice/water bath) solution of a racemic mixture of Intermediates 36 and 37 (130 mg, 0.25 mmol) in methanol (1 mL) was added Oxone (49.5% $KHSO_5$, 204 mg, 0.33 mmol) in water (1 mL). After 15 minutes the reaction was quenched with $Na_2S_2O_5$ (237 mg, 1.24 mmol) and diluted with water (10 mL). The aqueous layer was extracted with $CHCl_3$ (3×10 mL) and the combined organic layer washed with brine (10 mL), dried ($Na_2SO_4$) and concentrated under vacuum. Purification by SPE (silica, 5 g cartridge) eluting with cyclohexane:EtOAc (gradient elution 10:1 to 2:1), afforded the title compound as a mixture of isomers (60 mg).

LC/MS: m/z 534.4 [M+H]$^+$, $R_t$ 3.88 min.

Intermediate 39

Ethyl ({2-methyl-4-[(1-{6-[4-(trifluoromethyl)phenyl]-2-pyridinyl}pentyl)sulfonyl]phenyl}oxy)acetate

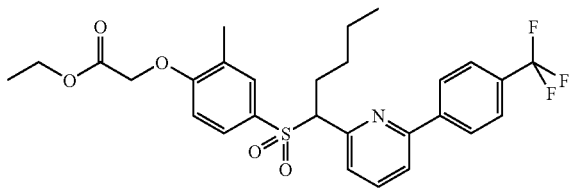

To a cooled 0° C. (ice/water bath) solution of a racemic mixture of Intermediates 36 and 37 (43 mg, 0.08 mmol) in methanol (1 mL) was added Oxone (49.5% $KHSO_5$, 153 mg, 0.25 mmol) in water (1 mL). After 4 hours 10 minutes the reaction was quenched with $Na_2S_2O_5$ (80 mg, 0.42 mmol) and diluted with water (10 mL). The aqueous layer was extracted with $CHCl_3$ (3×10 mL) and the combined organic layers washed with brine (30 mL), dried ($Na_2SO_4$) and concentrated under vacuum. Purification by SPE (silica, 5 g cartridge), eluting with cyclohexane:EtOAc (gradient 10:1 to 2:1) afforded the title compound (26 mg).

LC/MS: m/z 550.2 [M+H]$^+$, $R_t$ 4.09 min.

Intermediate 40

Methyl {4-[(1-{6-[4-(trifluoromethyl)phenyl]-2-pyridinyl}pentyl)oxy]phenyl}acetate

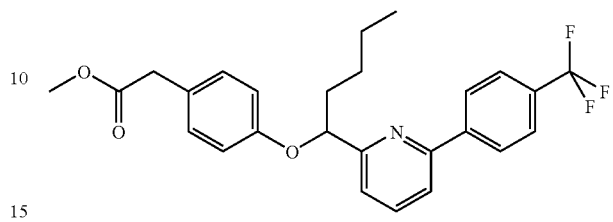

To a solution of 1-{6-[4-(trifluoromethyl)phenyl]-2-pyridinyl}-1-pentanol (349 mg, 1.13 mmol) in dry THF (22.5 mL) at 0° C. (ice/water bath) under nitrogen was added methyl-4-hydroxyphenylacetate (187 mg, 1.13 mmol) followed after 1 minute by ADDM (578 mg, 2.25 mmol) in one portion. The resulting orange cloudy mixture was stirred for 3 minutes and then treated with $nBu_3P$ (562 μL, 2.26 mmol) drop-wise over 1 minute. The resulting pale yellow/orange mixture was then allowed to warm slowly to rt over 64 hours. The cloudy mixture was then reduced under vacuum and the residue partitioned between EtOAc (50 mL) and water (50 mL) and the layers separated. The aqueous was then re-extracted with EtOAc (50 mL) and the combined organic layer washed with brine (100 mL) dried ($MgSO_4$), filtered and reduced to give an oil which was purified by SPE (silica) eluting with cyclohexane:EtOAc (gradient 100:1 to 5:1) to give the title compound (330 mg).

LC/MS: m/z 457.9 [M+H]$^+$, $R_t$ 4.32 min.

Intermediate 41

1-(6-Bromo-2-pyridinyl)-1-butanol

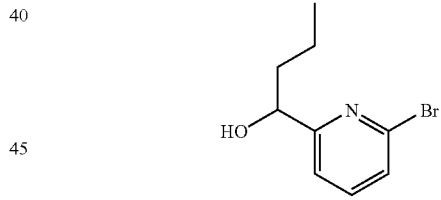

A solution of 2,6-dibromopyridine (1.00 g, 4.22 mmol) in THF (40 mL) was cooled to −78° C. (dry-ice/acetone bath) and treated with nBuLi (2.64 mL of a 1.6M solution in hexanes, 4.22 mmol) drop-wise over 10 minutes under nitrogen. After 30 minutes at this temperature the pale yellow/green solution was treated with butyraldehyde (400 μL, 4.44 mmol) drop-wise over 5 minutes and the resulting orange/red solution stirred at this temperature for 1 hour. The solution was then allowed to warm slowly to 0° C. (ice/water bath) over 20 minutes and was then quenched by the drop-wise addition of aqueous HCl (2M, 4 mL). The resulting pale yellow solution was reduced to an oil, partitioned between EtOAc (100 mL) and aqueous HCl (2M, 100 mL), and the layers separated. The aqueous was re-extracted with EtOAc (100 mL) and the combined organic layer washed with water (150 mL), brine (150 mL), dried ($MgSO_4$), filtered and reduced to an orange/yellow oil. Purification by SPE (silica) eluting with cyclohexane:EtOAc (gradient 100:1 to 2:1) afforded the title compound (626 mg).

Intermediate 42

Ethyl [(4-{[1-(6-bromo-2-pyridinyl)butyl]oxy}-2-methylphenyl)oxy]acetate

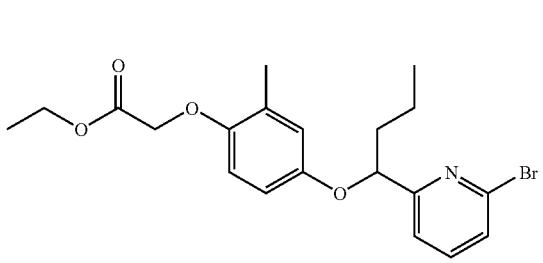

To a stirred solution of 1-(6-bromo-2-pyridinyl)-1-butanol (626 mg, 2.72 mmol) and ethyl (4-hydroxy-2-methylphenoxy)acetate (539 mg, 2.56 mmol) in dry THF (51 mL) at 0° C. (ice/water bath) under nitrogen was added ADDM (1.32 g, 5.13 mmol) followed by nBu$_3$P (1.28 mL, 4.95 mmol) drop-wise. The mixture was stirred with slow warming to rt over 18 hours and then concentrated under vacuum, diluted with EtOAc (150 mL) and washed with water (3×75 mL), dried (Na$_2$SO$_4$), filtered and reduced to give a yellow oil. Purification by SPE (silica, 20 g cartridge) eluting with cyclohexane:EtOAc (gradient 20:1 to 10:1) afforded the title compound (388 mg).

LC/MS: m/z 423.8 [M+H]$^+$, R$_t$ 3.92 min.

Intermediate 43

Ethyl ({[(1-{6-[4-(trifluoromethyl)phenyl]-2-pyridinyl}pentyl)oxy]phenyl}oxy)acetate

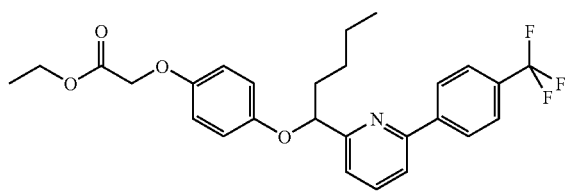

To a solution of 1-{6-[4-(trifluoromethyl)phenyl]-2-pyridinyl}-1-pentanol (99 mg, 0.32 mmol) in dry THF (6.4 mL) at 0° C. (ice/water bath) under nitrogen was added ethyl (4-hydroxyphenoxy)acetate (63 mg, 0.32 mmol) followed after 1 minute by ADDM (164 mg, 0.64 mmol) in one portion. The resulting orange slurry was stirred for 2 minutes and then treated with nBu$_3$P (159 µL, 0.64 mmol) drop-wise over 1 minute. The resulting pale yellow/orange mixture was then allowed to warm slowly to rt over 69 hours. The cloudy mixture was then reduced under vacuum and the residue purified by SPE (silica) eluting with cyclohexane:EtOAc (gradient 100:1 to 1:1) to give the title compound (42 mg).

LC/MS: m/z 487.9 [M+H]$^+$, R$_t$ 4.33 min.

Intermediate 44

Ethyl 3-{4[(1-{6-[4-(trifluoromethyl)phenyl]-2-pyridinyl}pentyl)oxy]phenyl}propanoate

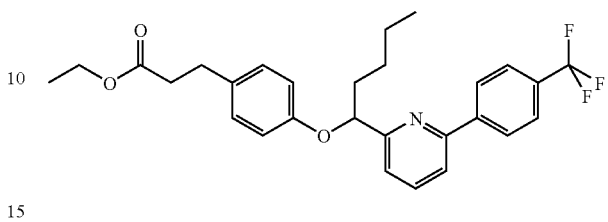

To a stirred solution of the 1-{6-[4-(trifluoromethyl)phenyl]-2-pyridinyl}-1-pentanol (50 mg, 0.16 mmol) and ethyl 3-(4-hydroxyphenyl)propanoate (31 mg, 0.16 mmol) in anhydrous THF (3.2 mL) under nitrogen at 0° C. (ice/water bath) was added ADDM (83 mg, 0.32 mmol). After a few minutes, nBu$_3$P (81 µL, 0.32 mmol) was added (drop-wise) and the solution was stirred at 0° C. warming to rt overnight. After 17.5 hours the solvent was concentrated under vacuum and the solid residue dissolved in DCM (5 mL) and washed with water (5 mL) using a hydrophobic frit. The aqueous layer was re-extracted with DCM (5 mL) and the combined organic layers concentrated under vacuum. The resulting solid residue was then purified by SPE (silica, 5 g cartridge) eluting with cyclohexane:EtOAc (gradient 100:1 to 1:1) to afford the title compound (29 mg).

LC/MS: m/z 486.1 [M+H]$^+$, R$_t$ 4.33 min.

Intermediate 45

1-(6-Bromo-2-pyridinyl)-1-pentanol

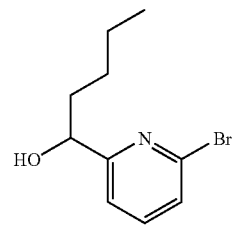

To a solution of nBuLi (26.40 mL of a 1.6M solution in hexanes, 42.24 mmol) in THF (25 mL) at −78° C. (dry-ice/acetone bath) was added a solution 2,6-dibromopyridine (10.00 g, 42.21 mmol) in THF (60 mL) drop-wise over 45 minutes under nitrogen. The resulting dark green coloured solution was stirred at −78° C. for 15 minutes and then valeraldehyde (6.70 mL, 63.01 mmol) was added drop-wise over 1 minute. The resulting dark purple coloured solution was stirred at −78° C. for 15 minutes and was then treated in one portion with a mixture of methanol (42 mL) and AcOH (2.70 mL, 47.16 mmol). The resulting pale yellow coloured solution was then allowed to warm to rt slowly over 1 hour. The mixture was then diluted with saturated aqueous NH$_4$Cl (200 mL) and the product extracted with EtOAc (2×200 mL). The combined organic layer was then washed with brine (250 mL), dried (MgSO$_4$), filtered and reduced to an orange oil (10.31 g, 100%). Purification of 7.14 g of this material by Biotage™ chromatography (silica) eluting with cyclohexane:EtOAc (gradient 100:1 to 1:1) afforded the title compound as a clear, pale yellow oil (4.48 g).

LC/MS: m/z 246.0 [M+H]$^+$, R$_t$ 3.03 min.

Intermediate 46

Ethyl [(4-{[1-(6-bromo-2-pyridinyl)pentyl]oxy}-2-methylphenyl)oxy]acetate

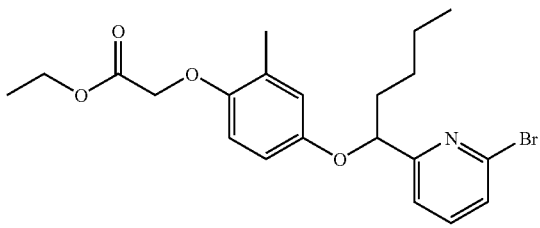

To a stirred solution of 1-(6-bromo-2-pyridinyl)-1-pentanol (2.00 g, 8.19 mmol) and ethyl (4-hydroxy-2-methylphenoxy)acetate (1.89 g, 8.99 mmol) in dry THF (160 mL) at 0° C. (ice/water bath) under nitrogen was added ADDP (4.13 g, 16.37 mmol) portion-wise over 5 min followed by nBu$_3$P (1.07 mL, 4.30 mmol) drop-wise over 1-2 min. The mixture was stirred with slow warming to rt over 21 h and then concentrated under vacuum, diluted with EtOAc (300 mL) and washed with water (200 mL). The aqueous layer was then re-extracted with EtOAc (300 mL) and the combined organic layer washed with brine (350 mL), dried (MgSO$_4$), filtered and reduced to give a orange solid residue. Purification by SPE (silica, 20 g Cartridge) eluting with cyclohexane:EtOAc (gradient 1:0 to 1:1) afforded the title compound (2.31 g).

LC/MS: m/z 438.0 [M+H]$^+$, R$_t$ 3.99 min.

Intermediate 47

1-{6-[4-(Trifluoromethyl)phenyl]-2-pyridinyl}-1-hexanol

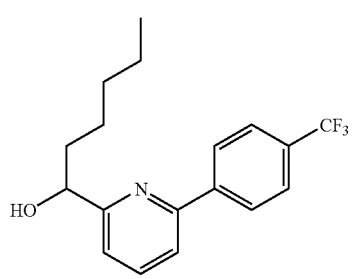

A solution of 6-[4-(trifluoromethyl)phenyl]-2-pyridinecarbaldehyde (300 mg, 1.19 mmol) in dry toluene (12 mL) under nitrogen was cooled to 0° C. (ice/water bath) and treated with n-pentylmagnesium bromide (0.66 mL of a 2M solution in Et$_2$O, 1.31 mmol) and the resulting mixture was stirred at 0° C. for 2 hours. The reaction was then quenched by the cautious addition of aqueous HCl (2M, 2 mL) and the solvent was removed under vacuum and the residue partitioned between EtOAc (2×50 mL) and aqueous HCl (2M, 50 mL). The organic solution was washed with water (60 mL) then brine (60 mL), dried (MgSO$_4$) and reduced. Purification by SPE (silica, 20 g cartridge) eluting with cyclohexane:EtOAc (gradient 99:1 to 19:1) afforded the title compound as a colourless oil (131 mg).

LC/MS: m/z 324.1[M+H]$^+$, R$_t$ 3.88 min.

Intermediate 48

Ethyl ({2-methyl-4-[(1-{6-[4-(trifluoromethyl)phenyl]-2-pyridinyl}hexyl)oxy]phenyl}oxy)acetate

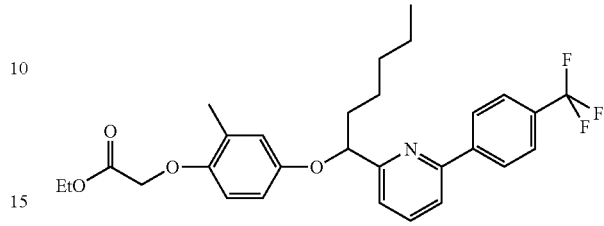

A solution of 1-{6-[4-(trifluoromethyl)phenyl]-2-pyridinyl}-1-hexanol (131 mg, 0.41 mmol) in dry THF (15 mL) under nitrogen was cooled to 0° C. and treated with ethyl (4-hydroxy-2-methylphenoxy)acetate (85 mg, 0.41 mmol), ADDM (210 mg, 0.82 mmol) and nBu$_3$P (204 µL, 0.82 mmol). The reaction mixture was then allowed to warm to rt slowly over 22 hours. The solvent was removed under vacuum and the residue partitioned between EtOAc (2×30 mL) and water (30 mL). The layers were separated and the organic layer dried (Na$_2$SO$_4$) and reduced. Purification by SPE (silica, 20 g cartridge) eluting with cyclohexane:EtOAc (49:1 to 24:1) afforded the title compound as a colourless oil (80 mg).

LC/MS: m/z 516.1 [M+H]$^+$, R$_t$ 4.37 min.

Intermediate 49

4-Methyl-1-{6-[4-(trifluoromethyl)phenyl]-2-pyridinyl}-1-pentanol

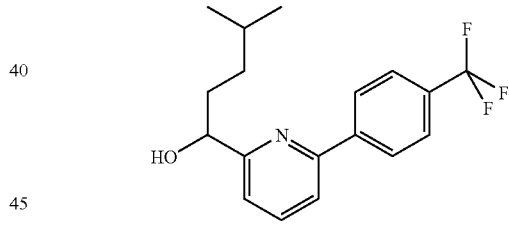

A solution of 6-[4-(trifluoromethyl)phenyl]-2-pyridinecarbaldehyde (350 mg, 1.39 mmol) in Et$_2$O (14 mL) was cooled to 0° C. To this was slowly added the freshly prepared Grignard reagent (1.26 mL, 1.53 mmol), prepared from magnesium turnings (500 mg, 0.02 mol) and 1-bromo-3-methyl butane (2.34 mL, 0.02 mol) in dry Et$_2$O (16.5 mL). The resulting mixture was stirred under nitrogen at 0° C. After 1.5 hours, more Grignard reagent (0.3 mL, 0.36 mmol) was added and the resulting mixture stirred at 0° C. for a further 1.5 hours. The reaction mixture was then quenched by cautious addition of aqueous HCl (2M, 3 mL) and the solvent removed under vacuum. The residue was partitioned between EtOAc (30 mL) and water (20 mL), the layers separated and the aqueous re-extracted with EtOAc (30 mL). The combined organic layer was washed with brine (50 mL), dried (MgSO$_4$) and reduced under vacuum. Purification by SPE (silica, 20 g cartridge), eluting with cyclohexane: EtOAc (gradient 99:1 to 1:1) followed by EtOAc then MeOH afforded the title compound as a colourless oil (179 mg).

LC/MS: m/z 324.1 [M+H]$_+$, R$_t$ 3.8 min.

Intermediate 50

Ethyl ({2-methyl-4-[(4-methyl-1-{6-[4-(trifluoromethyl)phenyl]-2-pyridinyl}pentyl)oxy]phenyl}oxy)acetate

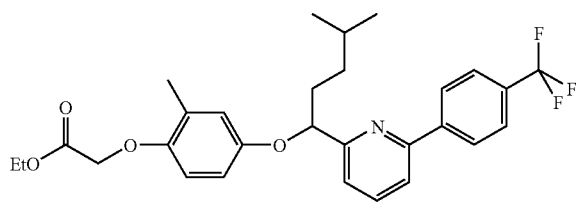

Prepared from 4-methyl-1-{6-[4-(trifluoromethyl)phenyl]-2-pyridinyl}-1-pentanol (80 mg, 0.25 mmol) according to the procedure used for the preparation of Intermediate 48 to give, after purification by SPE (silica, 10 g cartridge) eluting with cyclohexane:EtOAc (gradient 99:1 to 1:1) afforded the title compound as a colourless oil (13.2 mg).

LCMS: m/z 516.2 [M+H]$^+$, R$_t$ 4.42 min.

Intermediate 51

3-Methyl-1-{6-[4-(trifluoromethyl)phenyl]-2-pyridinyl}-1-butanol

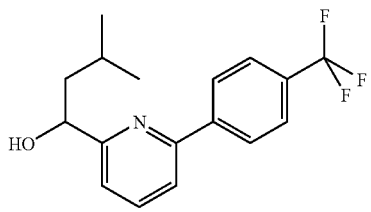

Prepared from 6-[4-(trifluoromethyl)phenyl]-2-pyridinecarbaldehyde (500 mg, 1.99 mmol) in Et$_2$O (20 mL) and isobutylmagnesium bromide (1.1 mL of a 2M solution in Et$_2$O, 2.2 mmol) according to the procedure used for the preparation of Intermediate 47 to give, after purification by SPE (silica, 10 g cartridge) eluting with cyclohexane:EtOAc (gradient 99:1 to 4:1) the title compound as a white crystalline solid (215 mg).

LC/MS: m/z 310.1 [M+H]$^+$, R$_t$ 3.74 min.

Intermediate 52

Ethyl ({2-methyl-4-[(3-methyl-1-{6-[4-(trifluoromethyl)phenyl]-2-pyridinyl}butyl)oxy]phenyl}oxy)acetate

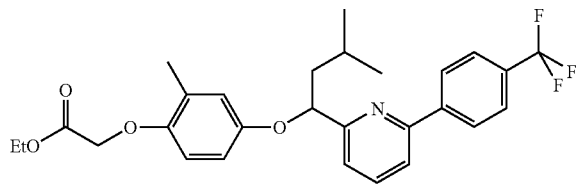

A solution of 3-methyl-1-{6-[4-(trifluoromethyl)phenyl]-2-pyridinyl}-1-butanol (180 mg, 0.58 mmol) in dry THF (12 mL) under nitrogen was treated with ethyl (4-hydroxy-2-methylphenoxy)acetate (122 mg, 0.58 mmol) and cooled to 0° C. This was treated portion-wise with ADDP (0.3 g, 1.2 mmol), then drop-wise with nBu$_3$P (0.29 mL, 1.2 mmol). The resulting pale yellow suspension allowed to warm to rt slowly over 16 hours. The solvent was removed under vacuum and the residue partitioned between EtOAc (60 mL) and water (60 mL) and the layers separated. The aqueous was re-extracted with EtOAc (60 mL) and the combined organic layer dried (Na$_2$SO$_4$) and reduced. Purification by SPE (silica, 10 g cartridge) eluting with cyclohexane:EtOAc (gradient 99:1 to 49:1) gave the title compound as a colourless oil (137 mg).

LC/MS: m/z 502.1 [M+H]$^+$, R$_t$ 4.31 min.

Intermediate 53

Ethyl [(4-{[1-(6-bromo-2-pyridinyl)pentyl]oxy}-2-ethylphenyl)oxy]acetate

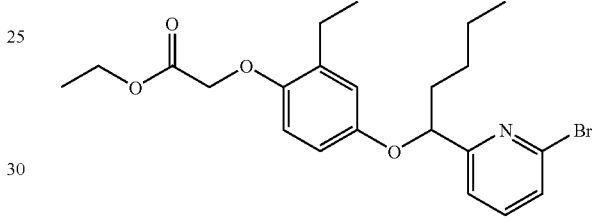

To a stirred solution of 1-(6-bromo-2-pyridinyl)-1-pentanol (250 mg, 1.02 mmol) and ethyl (4-hydroxy-2-ethylphenoxy)acetate (230 mg, 1.02 mmol) in dry THF (21 mL) at 0° C. (ice/water bath) under nitrogen was added ADDP (517 mg, 2.04 mmol) followed by nBu$_3$P (510 μL, 2.04 mmol) drop-wise. The mixture was stirred with slow warming to rt over 18 hours and then concentrated under vacuum, diluted with EtOAc (150 mL) and washed with water (3×75 mL), dried (MgSO$_4$), filtered and reduced to give an oil. Purification by SPE (silica, 10 g Cartridge) eluting with cyclohexane:EtOAc (gradient 20:1 to 5:1) afforded the title compound (307 mg).

LC/MS: m/z 452.0 [M+H]$^+$, R$_t$ 4.03 min.

Intermediate 54

2-(Trimethylsilyl)ethyl 4-(4-hydroxyphenyl)butanoate

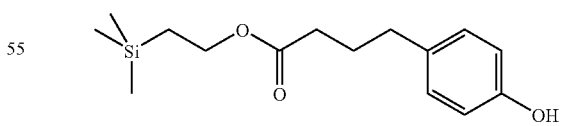

To a stirred solution of 2-(trimethylsilyl) ethanol (0.56 mL, 3.91 mmol) in THF (1 mL) at rt under nitrogen, was added 4-DMAP (113 mg, 0.92 mmol) followed by EDC (177 mg, 0.92 mmol). After about 1 minute Et$_3$N (170 μL, 1.22 mmol) was added, drop-wise followed by 4-(4-hydroxyphenyl)butanoic acid (150 mg, 0.83 mmol) in THF (4 mL) and the mixture stirred at rt for 18 hours. The mixture was then partitioned between Et$_2$O (25 mL) and aqueous HCl (2M, 30 mL) and the layers separated. The aqueous layer was re-extracted with Et₂O (20 mL) and the combined organic layer washed with brine (50 mL), dried (MgSO₄) and concentrated under vacuum to give a 'chalk-white' milky oil. Purification by SPE (silica, 5 g Cartridge) eluting with cyclohexane:EtOAc (gradient 25:1 to 1:2) afforded the title compound (55 mg).

LC/MS: m/z 298.2 [M+NH₄]⁺, R$_t$ 3.63 min.

Intermediate 55

2-(Trimethylsilyl)ethyl 4-{4-[(1-{6-[4-(trifluoromethyl)phenyl]-2-pyridinyl}pentyl)oxy]phenyl}butanoate

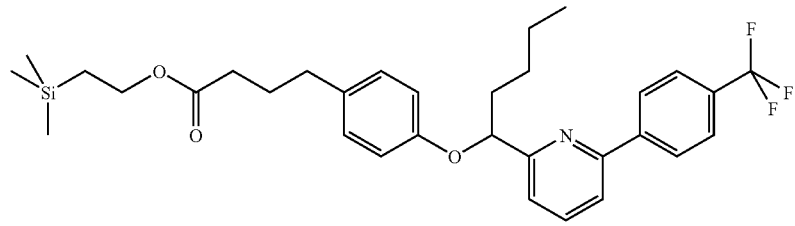

To a stirred solution of 1-{6-[4-(trifluoromethyl)phenyl]-2-pyridinyl}-1-pentanol (62 mg, 0.20 mmol) and 2-(trimethylsilyl)ethyl 4-(4-hydroxyphenyl)butanoate (55 mg, 0.20 mmol) in dry THF (4 mL) at 0° C. (ice/water bath), under nitrogen, was added ADDP (102 mg, 0.40 mmol) followed by nBu₃P (100 μL, 0.40 mmol), and the mixture stirred with slow warming to rt over 64.5 hours. The mixture was then concentrated under vacuum and the solid residue partitioned between DCM (5 mL) and water (5 mL) using a hydrophobic frit. The layers were separated and the aqueous layer re-extracted with DCM (5 mL) and the combined organic layer reduced. Purification by SPE (silica, 5 g Cartridge) eluting with cyclohexane:EtOAc (gradient 50:1 to 7.5:1) afforded the title compound (42 mg).

LC/MS: m/z 572.2 [M+H]⁺, R$_t$ 4.75 min.

Intermediate 56 and Intermediate 57

Ethyl [(4-{[(1R)-1-(6-bromo-2-pyridinyl)pentyl]oxy}-2-methylphenyl)oxy]acetate and Ethyl [(4-{[(1S)-1-(6-bromo-2-pyridinyl)pentyl]oxy}-2-methylphenyl)oxy]acetate Intermediate 56

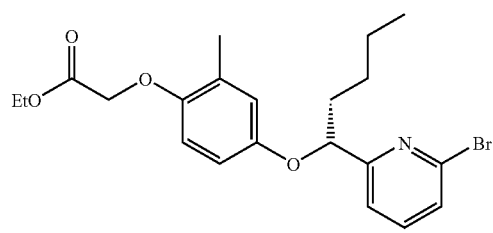

Intermediate 57

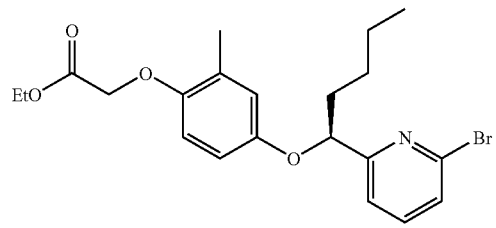

Separation of ethyl [(4-{[1-(6-bromo-2-pyridinyl)pentyl]oxy}-2-methylphenyl)oxy]acetate (Intermediate 46; 2.31 g, 5.29 mmol) by preparative chiral HPLC (1"×25 cm Chiralpak AD) eluting with 2% IPA in heptane, f=15 mL/min, afforded ethyl [(4-{[(1R)-1-(6-bromo-2-pyridinyl)pentyl]oxy}-2-methylphenyl)oxy]acetate as a pale yellow oil (962 mg), R$_t$ 10.0 min. Analytical chiral HPLC (25 cm Chiralpak AD) eluting with 10% IPA in heptane, f=1.0 mL/min, wavelength 215 nm, R$_t$ 5.3 min (96.3% ee) and ethyl [(4-{[(1S)-1-(6-bromo-2-pyridinyl)pentyl]oxy}-2-methylphenyl)oxy]acetate as a pale yellow oil (901 mg), R$_t$ 14.5 min. Analytical chiral HPLC (25 cm Chiralpak AD) eluting with 10% IPA in heptane, f=1.0 mL/min, wavelength 215 nm, R$_t$ 6.0 min (96.2% ee).

Intermediate 58

1-[2-(Methyloxy)-4-(4,4,5,5-tetramethyl-1,3,2-dioxaborolan-2-yl)phenyl]ethanone

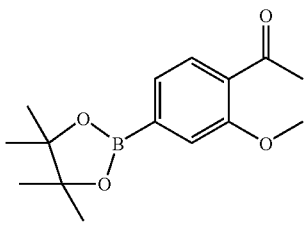

To a solution of 1-[4-bromo-2-(methyloxy)phenyl]ethanone (205 mg, 0.89 mmol), 4,4,4',4',5,5,5',5'-octamethyl-2,2'-bi-1,3,2-dioxaborolane (250 mg, 0.98 mmol), potassium acetate (263 mg, 2.68 mmol) in DMF (5.3 mL) was added PdCl₂ (dppf) (73 mg, 0.09 mmol) and the resulting mixture heated under nitrogen at 85° C., overnight. The mixture was then reduced under vacuum and the residue purified by SPE (Si) possessing a layer of celite on the top, and eluting with cyclohexane:EtOAc (gradient 50:1 to 1:2) to afford the title compound as a solid (146 mg).

LC/MS: m/z 277.1 [M+H]+, R_t 3.28 min.

Intermediate 59

N-Ethyl-3-(methyloxy)-N-(phenylmethyl)propanamide

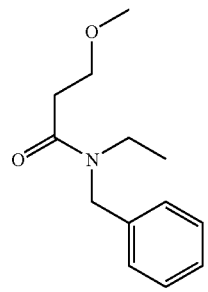

A suspension of 1,1'-carbonyldiimidazole (23.20 g, 0.14 mol) in dry DCM (240 mL) was added portion-wise over 15 min to a solution of 3-methoxypropionic acid (10.00 mL, 0.11 mol) in DCM (100 mL) under nitrogen at room temperature. The resulting solution was stirred under nitrogen for 1 h and then treated with a solution of N-ethylbenzylamine (32.70 mL, 0.22 mol) in dry DCM (140 mL) drop-wise over 50 min. The resultant pale brown solution was stirred under nitrogen at room temperature for 16 h and then reduced in vacuo. The orange residue was partitioned between EtOAc (500 mL) and saturated aqueous NaHCO3 (500 mL), the layers separated and the organic layer washed with aqueous HCl (2M, 500 mL) and brine (350 mL). Each of the aqueous washings was then re-extracted with EtOAC (250 mL) and the combined organic layer dried (MgSO4), filtered and reduced in vacuo to give a yellow oil. Purification by Biotage (silica, 5×90 g cartridges), eluting with cyclohexane:EtOAc 95:5 then 3:2 afforded the title compound as a pale yellow oil (20.39 g).

LC/MS: m/z 222.2 [M+H]+, R_t 2.54 min.

Intermediate 60

1-(6-Bromo-2-pyridinyl)-3-(methyloxy)-1-propanone

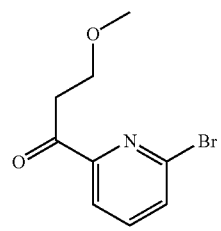

To a solution of n-Butyllithium (1.6M in hexanes, 4.06 mL, 6.50 mmol) in anhydrous THF (4.0 mL) under nitrogen at −78° C. was added a solution of 2,6-dibromopyridine (1.54 g, 6.50 mmol) in anhydrous THF (9.5 mL) drop-wise over 45 min. The resulting dark green solution was stirred at −78° C. for 15 min and then treated with N-ethyl-3-(methyloxy)-N-(phenylmethyl)propanamide (2.16 g, 9.76 mmol), washing in with anhydrous THF (3.0 mL). The resulting green solution was stirred at −78° C. for 15 min and was then treated with a solution of AcOH (0.40 mL) in MeOH (6.60 mL) to give a pale brown solution. This mixture was removed from the cooling bath and allowed to warm to room temperature, then stirred for 2 h. The mixture was then treated with saturated aqueous. NH4Cl (40 mL) and the products extracted with EtOAc (2×50 mL). The combined organic layer was then washed with brine (60 mL), dried (MgSO4) and the reduced in vacuo to give an orange oil. Purification by Biotage (silica, 90 g cartridge) eluting with cyclohexane:EtOAc (10:1) afforded the title compound as a white solid (547 mg).

LC/MS: m/z 244.1/246.1 [M+H]+, R_t 2.65 min.

Intermediate 61

1-(6-Bromo-2-pyridinyl)-3-(methyloxy)-1-propanol

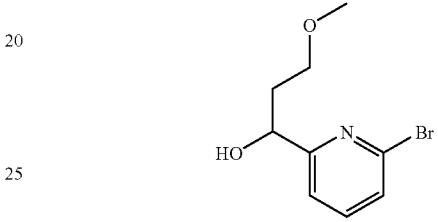

To a solution of 1-(6-bromo-2-pyridinyl)-3-(methyloxy)-1-propanone (547 mg, 2.24 mmol) in anhydrous MeOH (15 mL) under nitrogen at 0° C. was treated portion-wise with sodium borohydride (127 mg, 3.36 mmol) over 10 min. The resulting solution was stirred under nitrogen and gradually allowed to warm to room temperature over 2 h. The reaction mixture was then diluted with aqueous HCl (0.5M, 20 mL) and the resulting mixture extracted with EtOAc (2×50 mL). The combined organic layer was dried (MgSO4) and reduced under vacuum to afford the title compound as an off-white gum (551 mg).

LC/MS: m/z 246.0/248.0 [M+H]+, R_t 2.22 min.

Intermediate 62

Ethyl [(4-{[1-(6-bromo-2-pyridinyl)-3-(methyloxy)propyl]oxy}-2-methylphenyl)oxy]acetate

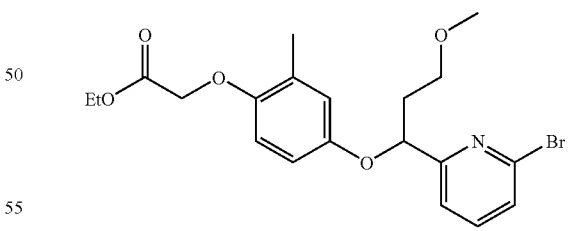

A solution of diisopropylazodicarboxylate (1.44 mL, 7.31 mmol) in dry THF (50 mL) was added drop-wise, under nitrogen, over 1.5 h (using a syringe pump) to a solution ethyl (4-hydroxy-2-methylphenoxy)acetate (1.10 g, 5.21 mmol), 1-(6-bromo-2-pyridinyl)-3-(methyloxy)-1-propanol (1.29 g, 5.24 mmol) and triphenylphosphine (1.92 g, 7.32 mmol) in dry THF (50 mL) at 0° C. The resulting mixture was stirred under nitrogen and gradually allowed to warm to room temperature over 19 h. The solvent was then removed in vacuo and the residue purified by Biotage (silica, 90 g cartridge), eluting with cyclohexane:EtOAc 85:15 to afford the title compound as a pale yellow oil (1.32 g).

LC/MS: m/z 438.1/440.1 [M+H]$^+$, R$_t$ 3.47 min.

Intermediate 63 and Intermediate 64

Ethyl [(4-{[(1R)-1-(6-bromo-2-pyridinyl)-3-(methyloxy)propyl]oxy}-2-methylphenyl)oxy]acetate and Ethyl [(4-{[(1S)-1-(6-bromo-2-pyridinyl)-3-(methyloxy)propyl]oxy}-2-methylphenyl)oxy]acetate Intermediate 63

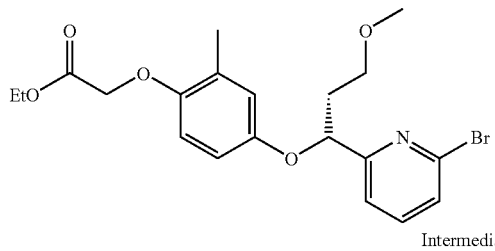

Intermediate 64

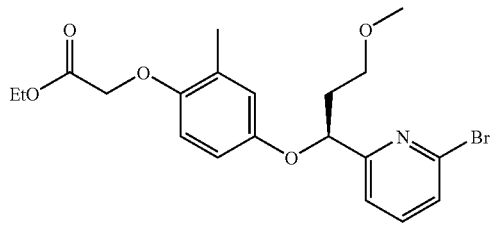

Separation of ethyl [(4-{[1-(6-bromo-2-pyridinyl)-3-(methyloxy)propyl]oxy}-2-methylphenyl)oxy]acetate (1.32 g, 3.01 mmol) by preparative chiral HPLC (2"×20 cm Chiralpak AD) eluting with 5% EtOH in heptane, f=40 mL/min, afforded ethyl [(4-{[(1R)-1-(6-bromo-2-pyridinyl)-3-(methyloxy)propyl]oxy}-2-methylphenyl)oxy]acetate as a colourless oil (556 mg), R$_t$ 10.0 min. Analytical chiral HPLC (25 cm Chiralpak AD) eluting with 5% EtOH in heptane, f=1.0 mL/min, wavelength 215 nm, R$_t$ 9.9 min (98.2% ee) and ethyl [(4-{[(1S)-1-(6-bromo-2-pyridinyl)-3-(methyloxy)propyl]oxy}-2-methylphenyl)oxy]acetate as a colourless oil (566 mg), R$_t$ 12.5 min. Analytical chiral HPLC (25 cm Chiralpak AD) eluting with 5% EtOH in heptane, f=1.0 mL/min, wavelength 215 nm, R$_t$ 11.7 min (94.9% ee).

Intermediate 65

N-Ethyl-2-(ethyloxy)-N-(phenylmethyl)acetamide

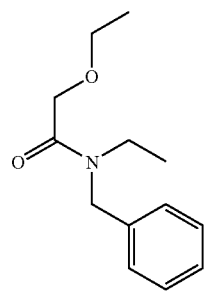

A suspension of 1,1'-carbonyldiimidazole (4.68 g, 28.86 mmol) in dry DCM (15 mL) was added portion-wise over 15 min to a solution of ethoxyacetic acid (2.09 mL, 22.12 mmol) in DCM (30 mL) under nitrogen at room temperature. The resulting solution was stirred under nitrogen for 1 h and then treated with a solution of N-ethylbenzylamine (6.60 mL, 44.37 mol) in dry dichloromethane (30 mL) drop-wise over 15 min. The resultant solution was stirred under nitrogen at room temperature for 18 h and then partitioned with aqueous HCl (2M, 2×75 mL) and the combined organic layer dried (MgSO$_4$), filtered and reduced in vacuo to give an oil. Purification by SPE (silica, 2×50 g cartridges), eluting with cyclohexane:EtOAc gradient 15:1 to 1:1 afforded the title compound as a pale yellow oil (4.36 g).

LC/MS: m/z 222.2 [M+H]$^+$, R$_t$ 2.59 min.

Intermediate 66

1-(6-Bromo-2-pyridinyl)-2-(ethyloxy)ethanol

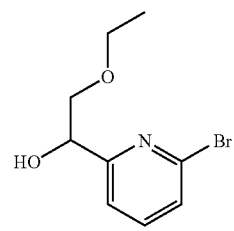

To a solution of n-butyllithium (1.6M in hexanes, 4.19 mL, 6.70 mmol) in anhydrous THF (4.0 mL) under nitrogen at −78° C. was added a solution of 2,6-dibromopyridine (1.59 g, 6.71 mmol) in anhydrous THF (9.5 mL) drop-wise over 1 h. The resulting dark green solution was stirred at −78° C. for 15 min and then treated with N-ethyl-2-(ethyloxy)-N-(phenylmethyl)acetamide (1.93 g, 8.70 mmol), washing in with anhydrous THF (1.0 mL). The resulting green solution was stirred at −78° C. for 15 min and was then treated with a solution of AcOH (0.42 mL) in MeOH (7.00 mL) to give a orange solution which was then treated with NaBH$_4$ (0.38 g, 10.04 mmol). This mixture was removed from the cooling bath and allowed to warm to room temperature over 2 h. The mixture was then treated with saturated aqueous. NH$_4$Cl (50 mL) and the products extracted with EtOAc (2×50 mL). The combined organic layer was then washed with brine (100 mL), dried (MgSO$_4$) and the reduced in vacuo to give a yellow oil. Purification by SPE (silica, 20 g cartridge) eluting with cyclohexane:EtOAc (gradient 50:1 to 1:1) afforded the title compound as a white solid (612 mg).

LC/MS: m/z 246.0/248.0 [M+H]$^+$, R$_t$ 2.30 min.

Intermediate 67

Ethyl [(4-{[1-(6-bromo-2-pyridinyl)-2-(ethyloxy)ethyl]oxy}-2-methylphenyl)oxy]acetate

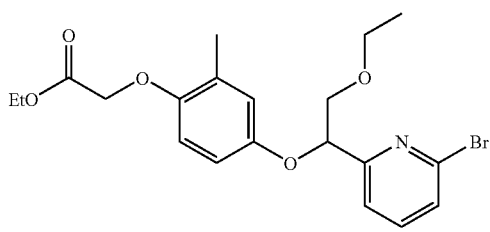

A solution of diisopropylazodicarboxylate (0.96 mL, 4.89 mmol) in dry THF (35 mL) was added drop-wise, under nitrogen, over 2 h (using a syringe pump) to a solution of ethyl (4-hydroxy-2-methylphenoxy)acetate (735 mg, 3.50 mmol), 1-(6-bromo-2-pyridinyl)-2-(ethyloxy)ethanol (860 mg, 3.49 mmol) and triphenylphosphine (1.28 g, 4.88 mmol) in dry THF (35 mL) at 0° C. The resulting mixture was stirred under nitrogen and gradually allowed to warm to room temperature over 21 h. The solvent was then removed in vacuo and the residue purified by SPE (silica, 2×50 g cartridge), eluting with cyclohexane:EtOAc (gradient 20:1 to 1:1) to afford the title compound as an oil (966 mg).
LC/MS: m/z 438.1/440.0 [M+H]$^+$, R$_t$ 3.67 min.

Intermediate 68 and Intermediate 69

Ethyl [(4{[(1R)-1-(6-bromo-2-pyridinyl)-2-(ethyloxy)ethyl]oxy}-2-methylphenyl)oxy]acetate and
Ethyl [(4-{[(1S)-1-(6-bromo-2-pyridinyl)-2-(ethyloxy)ethyl]oxy}-2-methylphenyl)oxy]acetate Intermediate 68

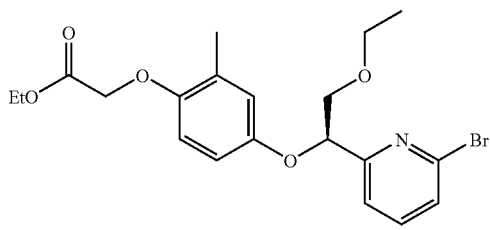

Intermediate 69

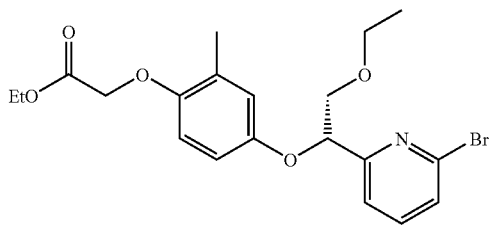

Separation of ethyl [(4-{[1-(6-bromo-2-pyridinyl)-2-(ethyloxy)ethyl]oxy}-2-methylphenyl)oxy]acetate (966 mg, 2.20 mmol) by preparative chiral HPLC (2"×20 cm Chiralcel OD) eluting with 5% IPA in heptane, f=50 mL/min, afforded ethyl [(4-{[[(1R)-1-(6-bromo-2-pyridinyl)-2-(ethyloxy)ethyl]oxy}-2-methylphenyl)oxy]acetate as a colourless oil (284 mg), R$_t$ 14.0 min. Analytical chiral HPLC (25 cm Chiralcel ODH) eluting with 5% IPA in heptane, f=1.0 mL/min, wavelength 215 nm, R$_t$ 12.1 min (94.7% ee) and ethyl [(4-{[(1S)-1-(6-bromo-2-pyridinyl)-2-(ethyloxy)ethyl]oxy}-2-methylphenyl)oxy]acetate as a colourless oil (273 mg), R$_t$ 16.0 min. Analytical chiral HPLC (25 cm Chiralcel ODH) eluting with 5% EtOH in heptane, f=1.0 mL/min, wavelength 215 nm, R$_t$ 14.0 min (99.3% ee).

Intermediate 2

1-(6-Bromo-2-pyridinyl)-1-pentanone (Method B)

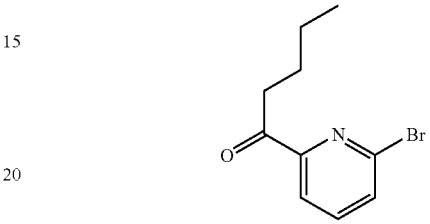

To a stirring solution of 1-(6-bromo-2-pyridinyl)-1-pentanol (1.01 g, 4.15 mmol) in chloroform (27 mL) was added manganese oxide (14.24 g, 0.16 mol) portion-wise over 4 h. The mixture was then left to stir for an additional 3.5 h and was then filtered through celite placed directly on the top of a SPE (silica, 20 g cartridge) eluting with chloroform. The filtrate was reduce under vacuum and then purified further by SPE (silica, 20 g cartridge) eluting with cyclohexane:EtOAc (gradient 100:1 to 5:1) afforded the title compound as an oil (625 mg).
LC/MS: m/z 242.1/244.1 [M+H]$^+$, R$_t$ 3.50 min.

Intermediate 70

(1R)-1-(6-Bromo-2-pyridinyl)-1-pentanol

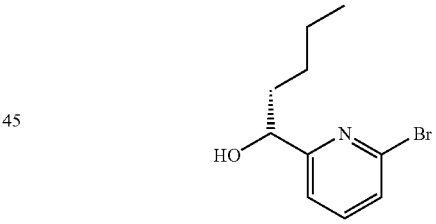

To a stirring solution of (S)-(−)-α,α-diphenyl-2-pyrrolidinemethanol (α,α-diphenyl-L-prolinol) (840 mg, 3.32 mmol) in THF (3 mL) was added drop-wise trimethylborate (0.45 mL, 3.97 mmol) at ambient temperature under nitrogen. After stirring for 1 h at this temperature, borane dimethylsulfide (2M in THF, 2.5 mL, 5.00 mmol) drop-wise over 3-4 minutes. After the effervescence had stopped, 1-(6-bromo-2-pyridinyl)-1-pentanone (797 mg, 3.29 mmol) in THF (3.6 mL) was added over 1 h using a syringe pump. The mixture was stirred for an additional 5 minutes and the reaction was then quenched with aqueous HCl (2N, 5 mL) and the reaction mixture stirred overnight at ambient temperature. The mixture was then reduced under vacuum and the residue partitioned between EtOAc (30 mL) and water (30 mL) and the layers separated. The aqueous was then re-extracted with EtOAc (30 mL) and the combined organic layer washed with brine (50 mL) and then reduced under vacuum to give an oil. Purification by SPE (silica, 20 g cartridge) eluting with cyclohexane:EtOAc (gradient 100:1 to 3:1) afforded the title compound as an oil (712 mg).

LC/MS: m/z 244.1/246.1 [M+H]$^+$, R$_t$ 3.01 min.

Analytical chiral HPLC (25 cm Chiralpak AD) eluting with 2% EtOH in heptane, f=1.0 mL/min, wavelength 215 nm, R$_t$ 11.7 min (97% ee).

Intermediate 71

(1S)-1-(6-Bromo-2-pyridinyl)-1-pentanol

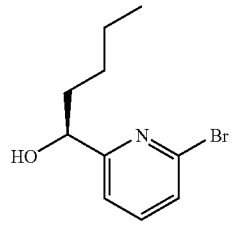

To a gently shaking solution of 1-(6-bromo-2-pyridinyl)-1-pentanol (1.00 g, 4.10 mmol) in dry cyclohexane (100 mL) was added Lipase PS-C "Amano" (*Pseudomonas cepacia*) (9.97 g) followed by vinyl acetate (1.5 mL, 16.27 mmol). Shaking was continued for 7.5 h with continual monitoring by chiral HPLC. The mixture was then filtered and the filtrate reduced under vacuum to give an oil which was purified by SPE (silica, 20 g cartridge) eluting with cyclohexane:EtOAc (gradient 50:1 to 2:1) to afford (1R)-1-(6-bromo-2-pyridinyl)pentyl acetate as an oil (737 mg, 63%). LC/MS: m/z 286.1/288.1 [M+H]$^+$, R$_t$ 3.38 min. Analytical chiral HPLC (25 cm Chiralpak AD) eluting with 2% EtOH in heptane, f=1.0 mL/min, wavelength 215 nm, (S-) R$_t$ 5.1 min and (R-) R$_t$ 5.4 min (43% ee) and the title compound as an oil (349 mg).

LC/MS: m/z 244.1/246.1 [M+H]$^+$, R$_t$ 3.01 min.

Analytical chiral HPLC (25 cm Chiralpak AD) eluting with 2% EtOH in heptane, f=1.0 mL/min, wavelength 215 nm, R$_t$ 12.7 min (95% ee).

Intermediate 72

Ethyl (2E)-3-{2-methyl-4-[(phenylmethyl)oxy]phenyl}-2-propenoate

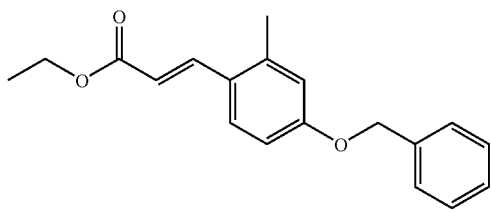

To a stirred solution of triethyl phosphonoacetate (1.40 mL, 7.06 mmol) in THF (40 mL) was added portion-wise NaH (60% dispersion in mineral oil, 399 mg, 9.98 mmol) over 2-3 mins. After effervescence had ceased, 2-methyl-4-benzyloxybenzaldehyde (1.50 g, 6.62 mmol) was added, washing in with THF (4 mL), and the resulting mixture heated to reflux. After 4 h at this temperature, the mixture was allowed to cool slowly to ambient temperature over night. Saturated aqueous NH$_4$Cl (45 mL) was then added carefully and the organic solvent removed under vacuum. The resulting aqueous mixture was then extracted with DCM (2×40 mL) and the combined organic layer washed with brine (60 mL) and then concentrated under vacuum to give a cream coloured solid. Purification by SPE (silica, 50 g cartridge) eluting with cyclohexane:EtOAc (gradient 20:1 to 0:1) then EtOAc:MeOH (gradient 95:5 to 90:10) afforded the title compound as an oil (1.22 g).

LC/MS: m/z 297.2 [M+H]$^+$, R$_t$ 3.80 min.

Intermediate 73

Ethyl 3-(4-hydroxy-2-methylphenyl)propanoate

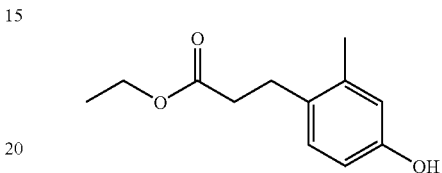

To a flask containing 10% Pd/C catalyst under nitrogen was added ethyl (2E)-3-{2-methyl-4-[(phenylmethyl)oxy]phenyl}-2-propenoate (1.22 g, 4.12 mmol) in EtOH (15 mL) washing in with more EtOH (2×4 mL). The reaction vessel was placed under an atmosphere of hydrogen and stirred rapidly at ambient temperature for 19 h. The mixture was then filtered through a pad of celite washing with EtOH and the filtrate reduced under vacuum. The residue was the purified by SPE (silica, 20 g cartridge) eluting with cyclohexane:EtOAc (gradient 10:1 to 2:1) to afford the title compound (548 mg).

LC/MS: m/z 436.2 [M+H]$^+$, R$_t$ 4.07 min.

Intermediate 74

Ethyl 3-(4-{[(1S)-1-(6-bromo-2-pyridinyl)pentyl]oxy}-2-methylphenyl)propanoate

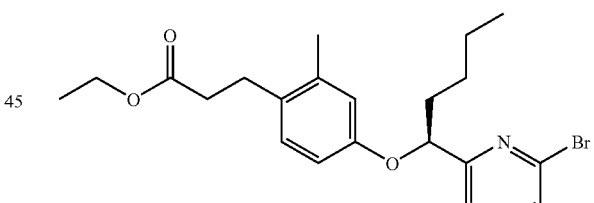

To a stirring solution of (1R)-1-(6-bromo-2-pyridinyl)-1-pentanol (261 mg, 1.07 mmol) and ethyl 3-(4-hydroxy-2-methylphenyl)propanoate (329 mg, 1.58 mmol) in THF (13 mL) at 0° C. under nitrogen was added ADDP (531 mg, 2.10 mmol) followed by tri-N-butylphosphine (0.525 mL, 2.10 mmol) drop-wise. The resulting mixture was then stirred with slow warming to ambient temperature over 15 h. The reaction mixture was then concentrated under vaccum and the solid residue purified directly by SPE (silica, 10 g cartridge) with a pad of celite on the top, eluting with cyclohexane:EtOAc (gradient 100:1 to 20:1) to afford the title compound (350 mg).

LC/MS: m/z 434.1/436.1 [M+H]$^+$, R$_t$ 4.07 min.

Analytical chiral HPLC (25 cm Chiralcel OD-H) eluting with 2% IPA in heptane, f=1.0 mL/min, wavelength 215 nm, R$_t$ 5.7 min (96% ee).

Intermediate 75

Ethyl 3-(4-{[(1R)-1-(6-bromo-2-pyridinyl)pentyl]oxy}-2-methylphenyl)propanoate

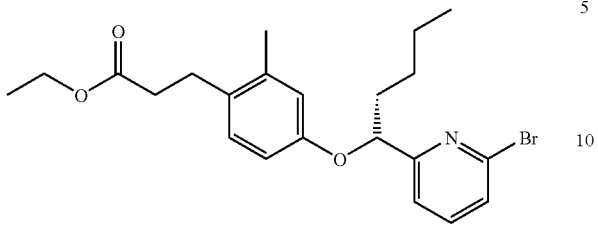

Prepared according to the procedure described for Intermediate 74, except starting from (1S)-1-(6-bromo-2-pyridinyl)-1-pentanol (237 mg, 0.97 mmol) to give the title compound as an oil (237 mg).
LC/MS: m/z 434.1/436.1 [M+H]$^+$, R$_t$ 4.07 min.
Analytical chiral HPLC (25 cm Chiralcel OD-H) eluting with 2% IPA in heptane, f=1.0 mL/min, wavelength 215 nm, R$_t$ 6.7 min (96% ee).

Intermediate 76

3-Fluoro-4-[(phenylmethyl)oxy]benzaldehyde

To a stirring solution of 3-fluoro-4-hydroxybenzaldehyde (508 mg, 3.63 mmol) and CsCO$_3$ (1.25 g, 3.84 mmol) in dry MeCN (5.6 mL) under nitrogen at ambient temperature was added benzyl chloride (0.45 mL, 3.91 mmol) and the mixture heated at 40° C. for 27 h. The mixture was then allowed to cool to rt, was quenched by the addition of aqueous NaOH (2N, 30 mL) and the product extracted with EtOAc (2×50 mL). The combined organic layer was then washed with brine (80 mL) and reduced under vacuum. The residue was then purified by SPE (silica, 10 g cartridge) eluting with cyclohexane:EtOAc (gradient 50:1 to 0:1) to afford the title compound as a colourless solid (623 mg).
LC/MS: m/z 231.1 [M+H]$^+$, R$_t$ 3.26 min.

Intermediate 77

Ethyl (2E)-3-{3-fluoro-4-[(phenylmethyl)oxy]phenyl}-2-propenoate

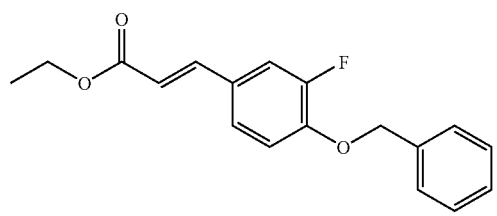

Prepared according to the procedure used to prepare Intermediate 72 starting from 3-fluoro-4-[(phenylmethyl)oxy]benzaldehyde (620 mg, 2.69 mmol) except using 1.5 eq of triethyl phosphonoacetate and heating for 18 h. The product was isolated and purified as described for Intermediate 72, but contained some of the aldehyde starting material. Therefore, this crude material was re-subjected to the reaction conditions described above and was isolated and purified to give the title compound (605 mg).
LC/MS: m/z 301.2 [M+H]$^+$, R$_t$ 3.66 min.

Intermediate 78

Ethyl 3-(3-fluoro-4-hydroxyphenyl)propanoate

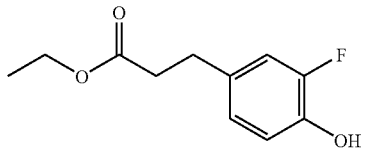

A mixture of ethyl (2E)-3-{3-fluoro-4-[(phenylmethyl)oxy]phenyl}-2-propenoate (205 mg, 0.68 mmol) and 10% Pd/C catalyst (40 mg) in EtOH (4 mL) was stirred under an atmosphere of hydrogen at ambient temperature for 16.5 h. The mixture was then filtered through celite placed directly on the top of a SPE (silica, 5 g cartridge) eluting with EtOH. The filtrate was reduced under vacuum and the residue purified further by SPE (silica, 5 g cartridge) eluting with cyclohexane:EtOAc (gradient 25:1 to 3:1) to afford the title compound (140 mg).
LC/MS: m/z 213.1 [M+H]$^+$, R$_t$ 2.80 min.

Intermediate 79

Ethyl (2E)-3-{3-methyl-4-[(phenylmethyl)oxy]phenyl}-2-propenoate

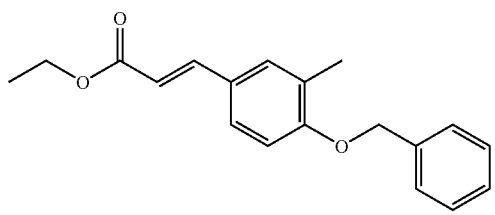

Prepared according to the procedure used to prepare Intermediate 77 starting from 3-methyl-4-[(phenylmethyl)oxy]benzaldehyde (1.00 g, 4.44 mmol) except that the reaction was re-subjected to the reaction conditions twice before final purification. The title compound was isolated as a cream coloured solid (1.10 g).
LC/MS: m/z 297.2 [M+H]$^+$, R$_t$ 3.86 min.

Intermediate 80

Ethyl 3-(4-hydroxy-3-methylphenyl)propanoate

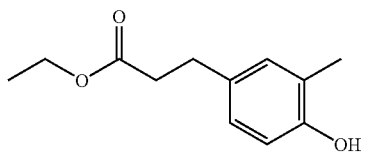

Prepared according to the procedure used to prepare Intermediate 78 starting from ethyl (2E)-3-{3-methyl-4-[(phenylmethyl)oxy]phenyl}-2-propenoate (202 mg, 0.68 mmol) to give the title compound (136 mg).

LC/MS: m/z 209.1 [M+H]$^+$, R$_t$ 2.91 min.

Intermediate 81

Ethyl (2E)-3-[4-hydroxy-3,5-bis(methyloxy)phenyl]-2-propenoate

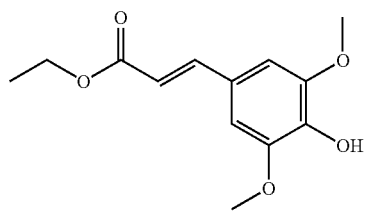

To a stirred solution of triethyl phosphonoacetate (0.60 mL, 3.02 mmol) in THF (5 mL) was added portion-wise NaH (60% dispersion in mineral oil, 360 mg, 9.00 mmol) over 2-3 mins. After effervescence had ceased, 4-hydroxy-3,5-dimethoxybenzaldehyde (547 mg, 3.00 mmol) was added portion-wise, washing in with THF (3 mL). More THF (2×2 mL) was added to the thick slurry and the resulting mixture was then heated to reflux for 21 hours. The mixture was then allowed to cool slowly to ambient temperature and the reaction quenched by the careful addition of saturated aqueous NH$_4$Cl (20 mL). The organic solvent was then removed under vacuum and the resulting aqueous mixture was then extracted with DCM (10 mL, 5 mL and then 2 mL) using hydrophobic frits. The filtrate was then treated with Polymer Supported-TsNHNH2 resin (loading 3.22 mmol/g, 1.62 g, 5.23 mmol (3 eq wrt unreacted aldehyde)) and the mixture stirred for 16 hours to remove any unreacted aldehyde. The resin was then removed by filtration washing with DCM (5 mL, 10 mL and then 5 mL) and the filtrate reduced under vacuum to give the title compound (221 mg).

LC/MS: m/z 253.2 [M+H]$^+$, R$_t$ 2.76 min.

Intermediate 82

Ethyl (2E)-3-(4-hydroxy-3,5-dimethylphenyl)-2-propenoate

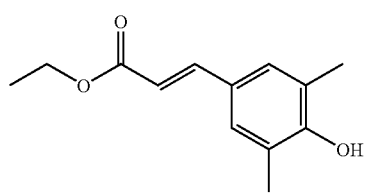

Prepared according to the procedure Intermediate 81 starting 3,5-dimethyl-4-hydroxybenzaldehyde (450 mg, 3.00 mmol) to give the title compound (347 mg).

LC/MS: m/z 221.2 [M+H]$^+$, R$_t$ 3.22 min.

Intermediate 83

Ethyl (2E)-3-[4-hydroxy-3-(methyloxy)-5-(2-propen-1-yl)phenyl]-2-propenoate

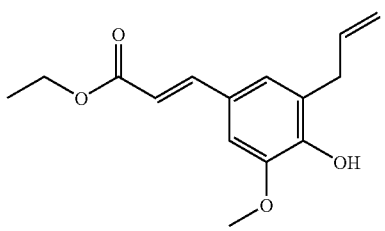

Prepared according to the procedure Intermediate 81 starting from 4-hydroxy-3-(methyloxy)-5-(2-propen-1-yl)benzaldehyde (577 mg, 3.00 mmol) to give the title compound (436 mg, 55%).

LC/MS: m/z 263.2 [M+H]$^+$, R$_t$ 3.31 min.

Intermediate 84

Ethyl (2E)-3-[4-hydroxy-3-(2-propen-1-yl)phenyl]-2-propenoate

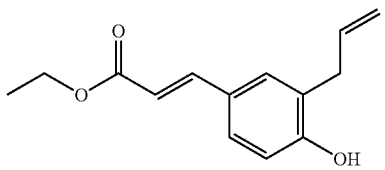

Prepared according to the procedure Intermediate 81 starting from 4-hydroxy-3-(2-propen-1-yl)benzaldehyde (324 mg, 2.00 mmol) to give the title compound (159 mg).

LC/MS: m/z 233.2 [M+H]$^+$, R$_t$ 3.33 min.

Intermediate 85

Ethyl (2E)-3-[3-(ethyloxy)-4-hydroxyphenyl]-2-propenoate

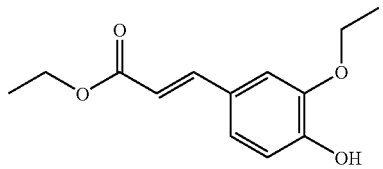

Prepared according to the procedure for Intermediate 81 starting from 3-ethoxy-4-hydroxybenzaldehyde (500 mg, 3.00 mmol) to give the title compound (557 mg).

LC/MS: m/z 237.2 [M+H]$^+$, R$_t$ 3.03 min.

Intermediate 86

Ethyl 3-[4-hydroxy-3,5-bis(methyloxy)phenyl]propanoate

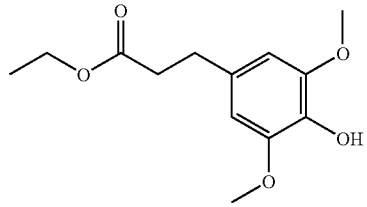

Prepared according to the procedure used to prepare Intermediate 78 starting from ethyl (2E)-3-{3-methyl-4-[(phenylmethyl)oxy]phenyl}-2-propenoate (130 mg, 0.52 mmol) to give the title compound (80 mg).

LC/MS: m/z 255.1 [M+H]$^+$, R$_t$ 2.58 min.

Intermediate 87

(2E)-3-[4-Hydroxy-2-(methyloxy)phenyl]-2-propenoic acid

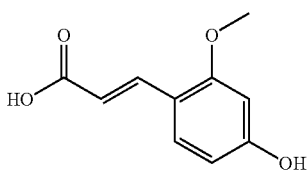

To a stirring solution of 4-hydroxy-2-methoxybenzaldehyde (1.02 g, 6.70 mmol) and malonic acid (728 mg, 7.00 mmol) in pyridine (9.2 mL) at ambient temperature under nitrogen was added piperidine (0.20 mL, 2.02 mmol) dropwise. The mixture was then heated to 80° C. over 20 mins and then stirred at this temperature for 2 h. The reaction was then quenched with water (50 mL), acidified to pH 1 with concentrated HCl and then partitioned with EtOAc (50 mL) and the layers separated. The aqueous layer was re-extracted with EtOAc (50 mL) and the combined organic layer washed with brine (80 mL) and then concentrated under vacuum to give a bright yellow solid. Purification by SPE (silica, 20 g cartridge) eluting with cyclohexane:EtOAc (gradient 25:1 to 0:1) afforded the title compound (674 mg).

LC/MS: m/z 195.1 [M+H]$^+$, R$_t$ 2.48 min.

Intermediate 88

3-[4-Hydroxy-2-(methyloxy)phenyl]propanoic acid

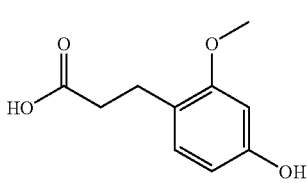

Prepared according to the procedure used to prepare Intermediate 78 starting from (2E)-3-[4-hydroxy-2-(methyloxy)phenyl]-2-propenoic acid (335 mg, 1.73 mmol) to give the title compound (225 mg).

LC/MS: m/z 197.2 [M+H]$^+$, R$_t$ 2.25 min.

Intermediate 89

Ethyl 3-[4-hydroxy-2-(methyloxy)phenyl]propanoate

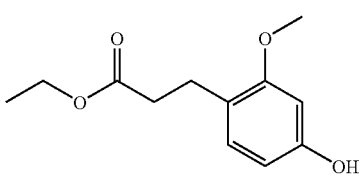

To a stirring solution of 3-[4-hydroxy-2-(methyloxy)phenyl]propanoic acid (229 mg, 1.17 mmol) in EtOH (14 mL) was added concentrated H$_2$SO$_4$ (0.031 mL, 0.58 mmol) and the reaction heated at reflux under nitrogen for 1 h. The mixture was then cooled to ambient temperature poured into ice (ca. 30 mL) and saturated aqueous Na$_2$CO$_3$ (60 mL) added. The mixture was then extracted with EtOAc (2×50 mL) and the combined organic layer washed with brine (70 mL) and concentrated under vacuum. The residue was then purified by SPE (silica, 5 g cartridge) eluting with cyclohexane:EtOAc (gradient 10:1 to 2:1) to afford the title compound (217 mg).

LC/MS: m/z 225.2 [M+H]$^+$, R$_t$ 2.83 min.

Intermediate 90

Ethyl (2E)-3-{3,5-dimethyl-4-[(1-{6-[4-(trifluoromethyl)phenyl]-2-pyridinyl}pentyl)oxy]phenyl}-2-propenoate

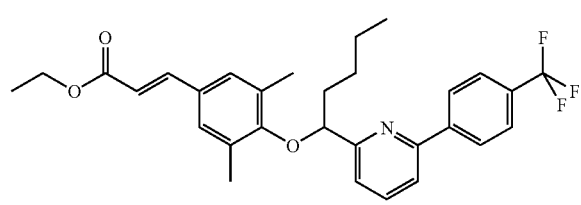

A stirred solution of 1-{6-[4-(trifluoromethyl)phenyl]-2-pyridinyl}-1-pentanol (62 mg, 0.20 mmol) and ethyl (2E)-3-(4-hydroxy-3,5-dimethylphenyl)-2-propenoate (79 mg, 0.36 mmol) in THF (4 mL) at 0° C. under nitrogen was added ADDP (101 mg, 0.40 mmol) followed by tri-N-butylphosphine (0.100 mL, 0.40 mmol). The resulting mixture was then allowed to warm slowly to ambient temperature overnight. After 66 h the solvent was removed under vacuum (Genevac) and the resulting solid partitioned between DCM (5 mL) and water (5 mL), the layers separated and the aqueous re-extracted with DCM (5 mL). The combined organic layer was then reduced under vacuum and purified by SPE (silica, 10 g cartridge) eluting with cyclohexane:EtOAc (gradient 20:1 to 1:1) to give the title compound (35 mg).

LC/MS: m/z 512.2 [M+H]$^+$, R$_t$ 4.53 min.

Intermediate 91

Ethyl (2E)-3-{3-(methyloxy)-5-(2-propen-1-yl)-4-[(1-{6-[4-(trifluoromethyl)phenyl]-2-pyridinyl}pentyl)oxy]phenyl}-2-propenoate

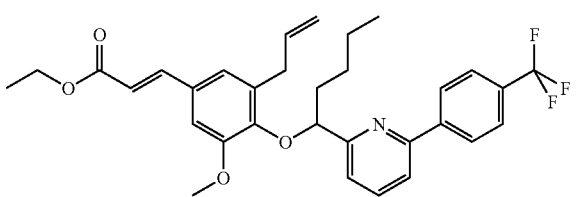

Prepared according to the procedure used to prepare Intermediate 90 starting from ethyl (2E)-3-[4-hydroxy-3-(methyloxy)-5-(2-propen-1-yl)phenyl]-2-propenoate (94 mg, 0.36 mmol) to give the title compound (102 mg).

LC/MS: m/z 554.2 [M+H]$^+$, R$_t$ 4.51 min.

Intermediate 92

Ethyl (2E)-3-{3-(2-propen-1-yl)-4-[(1-{6-[4-(trifluoromethyl)phenyl]-2-pyridinyl}pentyl)oxy]phenyl}-2-propenoate

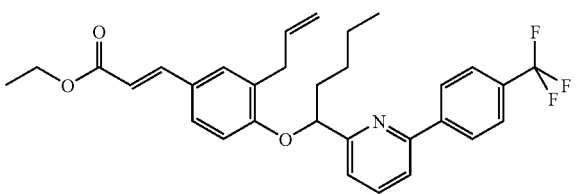

Prepared according to the procedure used to prepare Intermediate 90 starting from ethyl (2E)-3-[4-hydroxy-3-(2-propen-1-yl)phenyl]-2-propenoate (116 mg, 0.50 mmol) to give the title compound (103 mg).

LC/MS: m/z 524.2 [M+H]$^+$, R$_t$ 4.60 min.

Intermediate 93

Ethyl (2E)-3-{3-(ethyloxy)-4-[(1-{6-[4-(trifluoromethyl)phenyl]-2-pyridinyl}pentyl)oxy]phenyl}-2-propenoate

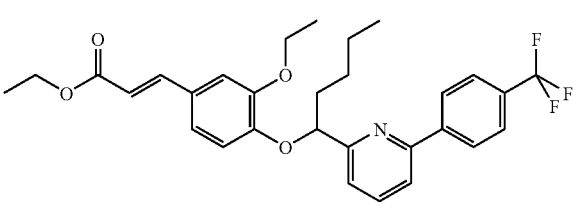

Prepared according to the procedure used to prepare Intermediate 90 starting from ethyl (2E)-3-[3-(ethyloxy)-4-hydroxyphenyl]-2-propenoate (557 mg, 2.36 mmol) to give the title compound (479 mg).

LC/MS: m/z 528.2 [M+H]$^+$, R$_t$ 4.41 min.

Intermediate 94

(2E)-3-{3,5-Dimethyl-4-[(1-{6-[4-(trifluoromethyl)phenyl]-2-pyridinyl}pentyl)oxy]phenyl}-2-propenoic acid

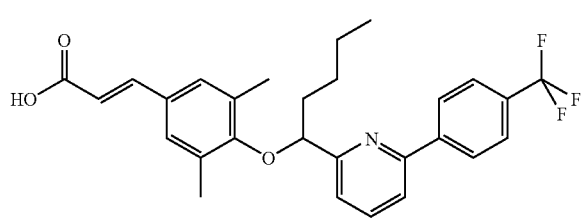

To a stirring solution of ethyl (2E)-3-{3,5-dimethyl-4-[(1-{6-[4-(trifluoromethyl)phenyl]-2-pyridinyl}pentyl)oxy]phenyl}-2-propenoate (35 mg, 0.07 mmol) in THF (5 mL) and MeOH (5 mL) at ambient temperature was added NaOH (2N, 5 mL) and the mixture stirred for 2 h and then left to stand overnight. HCl (2N, 5 mL) was then added and the mixture reduced under vacuum. The residue was then purified by SPE (silica, 5 g cartridge) with a pad of celite on the top, eluting with cyclohexane:EtOAc (gradient 3:1 to 0:1) the EtOAc:MeOH (gradient 95:5 to 0:1) to give the title compound (28 mg).

LC/MS: m/z 484.2 [M+H]$^+$, R$_t$ 4.40 min.

Intermediate 95

(2E)-3-{3-(Methyloxy)-5-(2-propen-1-yl)-4-[(1-{6-[4-(trifluoromethyl)phenyl]-2-pyridinyl}pentyl)oxy]phenyl}-2-propenoic acid

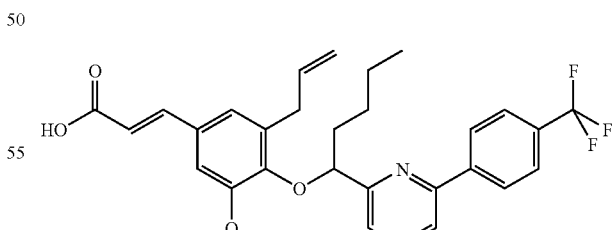

Prepared according to the procedure used to prepare Intermediate 94 starting from ethyl (2E)-3-{3-(methyloxy)-5-(2-propen-1-yl)-4-[(1-{6-[4-(trifluoromethyl)phenyl]-2-pyridinyl}pentyl)oxy]phenyl}-2-propenoate (102 mg, 0.18 mmol) to give the title compound (82 mg).

LC/MS: m/z 526.2 [M+H]$^+$, R$_t$ 4.30 min.

Intermediate 96

(2E)-3-{3-(2-Propen-1-yl)-4-[(1-{6-[4-(trifluoromethyl)phenyl]-2-pyridinyl}pentyl)oxy]phenyl}-2-propenoic acid

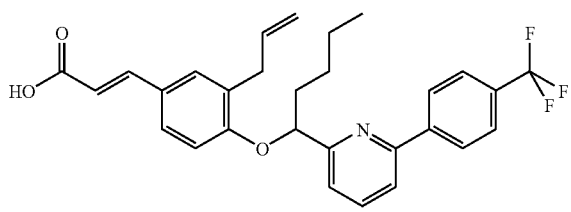

Prepared according to the procedure used to prepare Intermediate 94 starting from ethyl (2E)-3-{3-(2-propen-1-yl)-4-[(1-{6-[4-(trifluoromethyl)phenyl]-2-pyridinyl}pentyl)oxy]phenyl}-2-propenoate (103 mg, 1.97 mmol) to give the title compound (39 mg).

LC/MS: m/z 496.2 [M+H]$^+$, R$_t$ 4.45 min.

Intermediate 97

(2E)-3-{3-(Ethyloxy)-4-[(1-{6-[4-(trifluoromethyl)phenyl]-2-pyridinyl}pentyl)oxy]phenyl}-2-propenoic acid

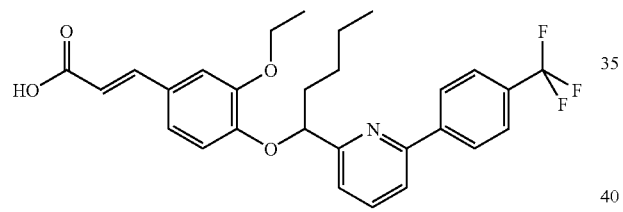

Prepared according to the procedure used to prepare Intermediate 94 starting from ethyl (2E)-3-{3-(ethyloxy)-4-[(1-{6-[4-(trifluoromethyl)phenyl]-2-pyridinyl}pentyl)oxy]phenyl}-2-propenoate (479 mg, 0.91 mmol) to give the title compound (407 mg).

LC/MS: m/z 500.2 [M+H]$^+$, R$_t$ 4.21 min.

Intermediate 98 and Intermediate 99

(1S)-1-{6-[4-(Trifluoromethyl)phenyl]-2-pyridinyl}-1-pentanol and (1R)-1-{6-[4-(Trifluoromethyl)phenyl]-2-pyridinyl}-1-pentanol Intermediate 98

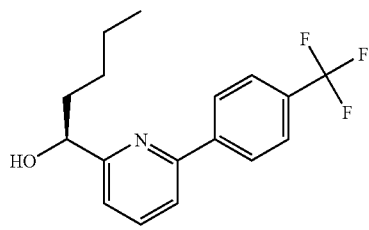

Intermediate 99

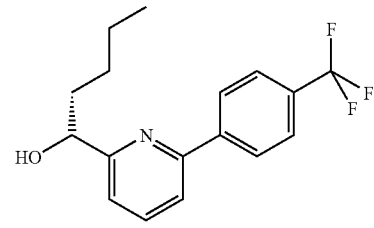

Separation of 1-{6-[4-(trifluoromethyl)phenyl]-2-pyridinyl}-1-pentanol (2.50 g, 8.08 mmol) by preparative chiral HPLC (2"×20 cm Chiralpak AD) eluting with 5% IPA in heptane, f=60 mL/min, afforded (1S)-1-{6-[4-(trifluoromethyl)phenyl]-2-pyridinyl}-1-pentanol as a pale yellow oil (1.03 g), R$_t$ 15.5 min. Analytical chiral HPLC (25 cm Chiralpak AD) eluting with 10% EtOH in heptane, f=1.0 mL/min, wavelength 215 nm, R$_t$ 8.7 min (95.2% ee) and (1R)-1-{6-[4-(trifluoromethyl)phenyl]-2-pyridinyl}-1-pentanol as a pale yellow oil (0.94 g), R$_t$ 23 min. Analytical chiral HPLC (25 cm Chiralpak AD) eluting with 10% EtOH in heptane, f=1.0 mL/min, wavelength 215 nm, R$_t$ 7.7 min (97.1% ee).

Intermediate 100

3-Chloro-5-(methyloxy)-4-[(phenylmethyl)oxy]benzaldehyde

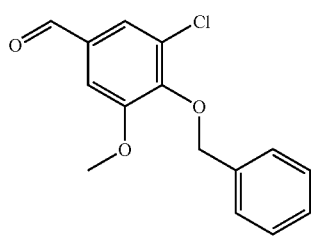

To a stirring solution of 3-chloro-4-hydroxy-5-methoxybenzaldehyde (599 mg, 3.21 mmol) in DMF (5 mL) under nitrogen was added Cs$_2$CO$_3$ (1.10 g, 3.38 mmol) followed by benzyl chloride (0.40 mL, 3.48 mmol) and the mixture heated at reflux for 1 h. After allowing the mixture to cool to ambient temperature the reaction was quenched by the addition of aqueous NaOH (2N, 30 mL) and the mixture concentrated under vacuum. The residue was then partitioned between NaOH (2N, 30 mL) and EtOAc (50 mL) and the layers separated. The aqueous layer was then re-extracted with EtOAc (50 mL), the layers separated and the combined organic layer washed with brine and then concentrated under vacuum. Purification by SPE (silica, 20 g cartridge) eluting with cyclohexane:EtOAc (gradient 50:1 to 10:1) afforded the title compound (632 mg).

LC/MS: m/z 277.1 [M+H]$^+$, R$_t$ 3.47 min.

Intermediate 101

Ethyl (2E)-3-{3-chloro-5-(methyloxy)-4-[(phenylmethyl)oxy]phenyl}-2-propenoate

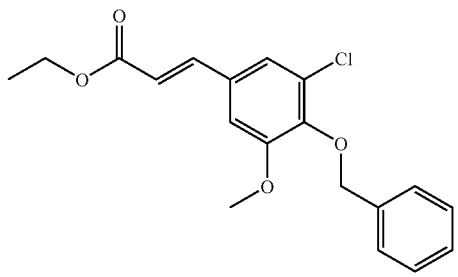

To a stirring solution of triethylphosphonoacetate (530 µL, 2.67 mmol) in dry THF (12 mL) at ambient temperature under nitrogen was added NaH (60% dispersion in mineral oil, 107 mg, 2.68 mmol). After stirring for an additional few minutes 3-chloro-5-(methyloxy)-4-[(phenylmethyl)oxy]benzaldehyde (495 mg, 1.79 mmol) was added in THF (10 mL) and the resulting mixture heated at 80° C. for 21 h. The mixture was then allowed to cool to ambient temperature and the reaction then quenched with saturated aqueous NH$_4$Cl (12 mL) and the product extracted with EtOAc (2×30 mL) and the combined organic layer washed with brine (50 mL) and then reduced under vacuum. Purification by SPE (silica, 10 g cartridge) eluting with cyclohexane:EtOAc (gradient 50:1 to 5:1) afforded a mixture of product and starting material (515 mg). This mixture was then subjected to the conditions described above to push the reaction further and was then worked-up as described. Purification by SPE (silica, 10 g cartridge) eluting with cyclohexane:EtOAc (gradient 50:1 to 1:1) afforded the title compound (535 mg).

LC/MS: m/z 364.2 [M+NH$_4$]$^+$, R$_t$ 3.84 min.

Intermediate 102

Ethyl 3-[3-chloro-4-hydroxy-5-(methyloxy)phenyl]propanoate

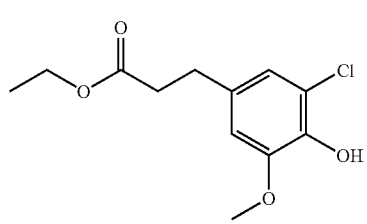

To a stirring solution of ethyl (2E)-3-{3-chloro-5-(methyloxy)-4-[(phenylmethyl)oxy]phenyl}-2-propenoate (441 mg, 1.27 mmol) in EtOAc (9 mL) under nitrogen at ambient temperature was added PtO$_2$ (20 wt %, 88 mg) and the mixture stirred under an atmosphere of hydrogen for 18 h.

The resulting mixture was then purified by SPE (silica, 5 g cartridge) with a pad of celite on the top, eluting with EtOAc. The filtrate was then reduced and purified further by SPE (silica, 10 g cartridge) eluting with cyclohexane:EtOAc (gradient 20:1 to 3:1) to give the title compound (287 mg).

LC/MS: m/z 276.1 [M+NH$_4$]$^+$, R$_t$ 2.97 min.

Intermediate 103

Ethyl 3-{3-chloro-5-(methyloxy)-4-[((1S)-1-{6-[4-(trifluoromethyl)phenyl]-2-pyridinyl}pentyl)oxy]phenyl}propanoate

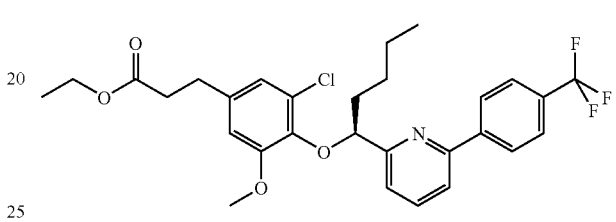

To a stirring solution of (1R)-1-{6-[4-(trifluoromethyl)phenyl]-2-pyridinyl}-1-pentanol (66 mg, 0.21 mmol) and ethyl 3-[3-chloro-4-hydroxy-5-(methyloxy)phenyl]propanoate (78 mg, 0.30 mmol) in THF (4 mL) at 0° C. under nitrogen was added ADDP (100 mg, 0.40 mmol) followed by nBu$_3$P (0.10 mL, 0.40 mmol). The resulting mixture was then stirred at 0° C. with slow warming to ambient temperature over 19 h and then reduced under vacuum (Genevac). The residue was then purified by SPE (silica, 10 g cartridge) with a pad of celite on the top, eluting with cyclohexane:EtOAc (gradient 100:1 to 3:1) to afford the title compound (118 mg).

LC/MS: m/z 550.1 [M+H]$^+$, R$_t$ 4.41 min.

Intermediate 104

2-Chloro-4-[((1R)-1-{[4-(trifluoromethyl)phenyl]-2-pyridinyl}pentyl)oxy]benzaldehyde

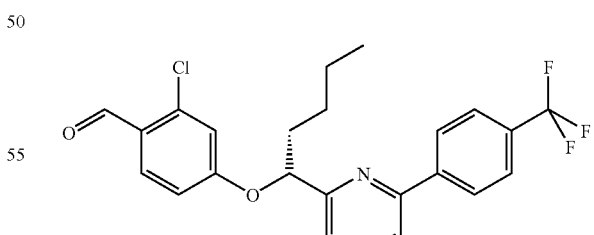

Prepared according to the procedure used to prepare Intermediate 103 starting from (1S)-1-{6-[4-(trifluoromethyl)phenyl]-2-pyridinyl}-1-pentanol (208 mg, 0.67 mmol) and 2-chloro-4-hydroxybenzaldehyde (140, 0.89 mmol) to afford the title compound (103 mg).

LC/MS: m/z 448.0 [M+H]$^+$, R$_t$ 4.38 min.

Intermediate 105

3-Chloro-4-[((1R)-1-{6-[4-(trifluoromethyl)phenyl]-2-pyridinyl}pentyl)oxy]benzaldehyde

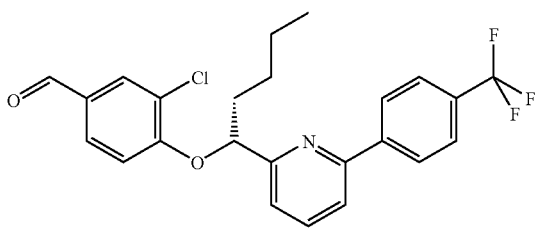

Prepared according to the procedure used to prepare Intermediate 103 starting from (1S)-1-{6-[4-(trifluoromethyl)phenyl]-2-pyridinyl}-1-pentanol (196 mg, 0.63 mmol) and 3-chloro-4-hydroxybenzaldehyde (141, 0.90 mmol) to afford the title compound (55 mg).

LC/MS: m/z 448.0 [M+H]$^+$, R$_t$ 4.33 min.

Intermediate 106

2-Chloro-4-[((1S)-1-{6-[4-(trifluoromethyl)phenyl]-2-pyridinyl}pentyl)oxy]benzaldehyde

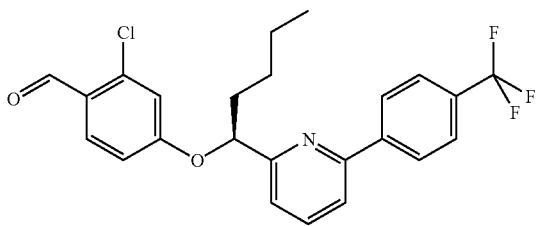

Prepared according to the procedure used to prepare Intermediate 103 starting from (1R)-1-{6-[4-(trifluoromethyl)phenyl]-2-pyridinyl}-1-pentanol (202 mg, 0.65 mmol) and 2-chloro-4-hydroxybenzaldehyde (140, 0.89 mmol) to afford the title compound (102 mg).

LC/MS: m/z 448.0 [M+H]$^+$, R$_t$ 4.40 min.

Intermediate 107

3-Chloro-4-[((1S)-1-{6-[4-(trifluoromethyl)phenyl]-2-pyridinyl}pentyl)oxy]benzaldehyde

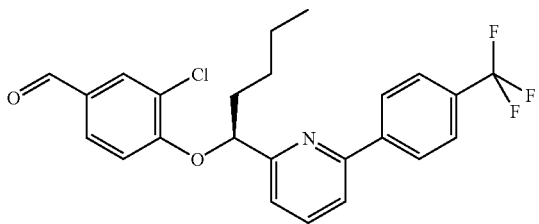

Prepared according to the procedure used to prepare Intermediate 103 from (1R)-1-{6-[4-(trifluoromethyl)phenyl]-2-pyridinyl}-1-pentanol (208 mg, 0.67 mmol) and 3-chloro-4-hydroxybenzaldehyde (141, 0.90 mmol) to afford the title compound (59 mg).

LC/MS: m/z 448.1 [M+H]$^+$, R$_t$ 4.33 min.

Intermediate 108

Ethyl (2E)-3-{2-chloro-4-[((1R)-1-{6-[4-(trifluoromethyl)phenyl]-2-pyridinyl}pentyl)oxy]phenyl}-2-propenoate

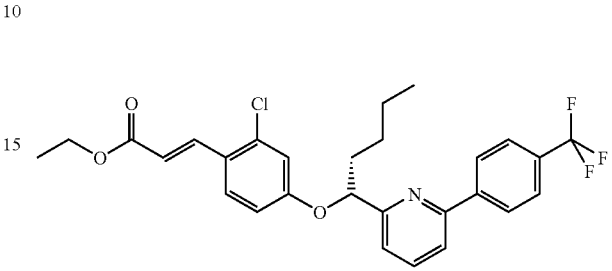

To a stirring solution of triethylphosphonoacetate (64 μL, 0.32 mmol) in dry THF (0.20 mL) at ambient temperature under nitrogen was added NaH (60% dispersion in mineral oil, 13 mg, 0.33 mmol). After stirring for an additional few minutes 2-chloro-4-[((1R)-1-{6-[4-(trifluoromethyl)phenyl]-2-pyridinyl}pentyl)oxy]benzaldehyde (103 mg, 0.23 mmol) was added in THF (0.8 mL) and the resulting mixture heated at 80° C. for 17 h. The mixture was then allowed to cool to ambient temperature and the reaction then quenched with saturated aqueous NH$_4$Cl (3 mL) and the product extracted with EtOAc (2×20 mL) and the combined organic layer washed with brine (50 mL) and then reduced under vacuum. The crude reaction mixture was then subjected to the conditions described above to push the reaction further and was then worked-up as described. Purification by SPE (silica, 5 g cartridge) eluting with cyclohexane:EtOAc (gradient 50:1 to 15:1) afforded the title compound (103 mg).

LC/MS: m/z 518.1 [M+H]$^+$, R$_t$ 4.58 min.

Intermediate 109

Ethyl (2E)-3-{3-chloro-4-[((1R)-1-{6-[4-(trifluoromethyl)phenyl]-2-pyridinyl}pentyl)oxy]phenyl}-2-propenoate

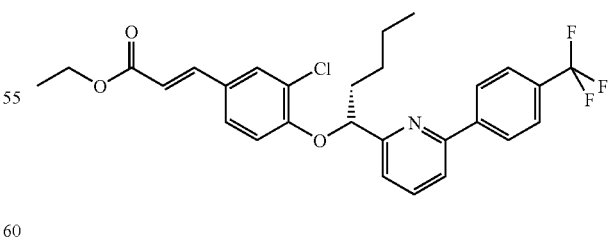

Prepared according to the procedure used to prepare Intermediate 108 starting from 3-chloro-4-[((1R)-1-{6-[4-(trifluoromethyl)phenyl]-2-pyridinyl}pentyl)oxy]benzaldehyde (55 mg, 0.12 mmol) to afford the title compound (54 mg).

LC/MS: m/z 518.2 [M+H]$^+$, R$_t$ 4.54 min.

Intermediate 110

Ethyl (2E)-3-{2-chloro-4[((1S)-1-{6-[4-(trifluoromethyl)phenyl]-2-pyridinyl}pentyl)oxy]phenyl}-2-propenoate

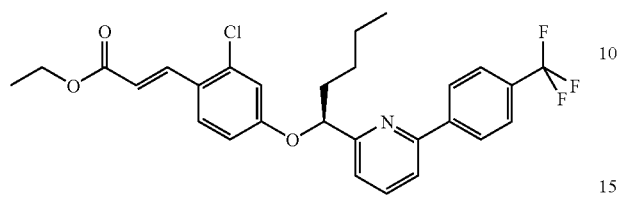

Prepared according to the procedure used to prepare Intermediate 108 starting from 2-chloro-4-[((1S)-1-{6-[4-(trifluoromethyl)phenyl]-2-pyridinyl}pentyl)oxy]benzaldehyde (102 mg, 0.23 mmol) to afford the title compound (111 mg).

LC/MS: m/z 518.1 [M+H]$^+$, R$_t$ 4.58 min.

Intermediate 111

Ethyl (2E)-3-{3-chloro-4-[((1S)-1-{6-[4-(trifluoromethyl)phenyl]-2-pyridinyl}pentyl)oxy]phenyl}-2-propenoate

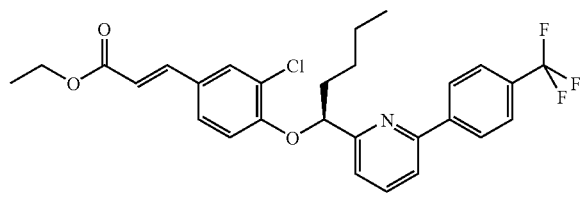

Prepared according to the procedure used to prepare Intermediate 108 starting from 3-chloro-4-[((1S)-1-{6-[4-(trifluoromethyl)phenyl]-2-pyridinyl}pentyl)oxy]benzaldehyde (58 mg, 0.13 mmol) to afford the title compound (41 mg).

LC/MS: m/z 518.1 [M+H]$^+$, R$_t$ 4.53 min.

Intermediate 112

3-Bromo-N,2-dimethyl-N-(methyloxy)benzamide

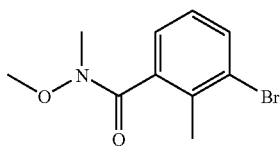

To a solution of 3-bromo-2-methyl benzoic acid (430 mg, 2.00 mmol) in anhydrous DCM, under nitrogen at ambient temperature was added N,O-dimethylhydroxylamine hydrochloride (215 mg, 2.20 mmol), pyridine (0.18 mL, 2.23 mmol) and CBr$_4$ (662 mg, 2.00 mmol). Triphenyl phosphine (576 mg, 2.20 mmol) was added portion-wise over 10 min and the resulting mixture stirred at ambient temperature for 2.5 h. The reaction mixture then reduced under vacuum and purified by SPE (silica, 10 g cartridge) eluting with cyclohexane:EtOAc (gradient 99:1 to 4:1) to afford the title compound as a colourless oil (310 mg).

LC/MS: m/z 258.0/260.0 [M+H]$^+$, R$_t$ 2.73 min.

Intermediate 113

1-(3-Bromo-2-methylphenyl)-1-pentanone

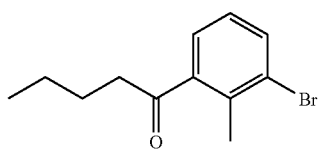

To a solution of 3-bromo-N,2-dimethyl-N-(methyloxy)benzamide (2.55 g, 9.88 mmol) in anhydrous THF (28 mL) under nitrogen at −78° C. was added a butylmagnesium chloride (20% wt in THF/toluene, 6.94 mL, 11.90 mmol) drop-wise over 15 min. The resulting solution was stirred at −78° C. for 1 h, was allowed to warm to 0° C. and then stirred with slow warming to ambient temperature over 20 h. The reaction was then quenched with water (50 mL) and extracted with EtOAc (2×60 mL). Some saturated aqueous NH$_4$Cl was added to disperse the emulsion formed. The resulting organic layer was then washed with brine (100 mL), dried (Na$_2$SO$_4$), filtered and reduced under vacuum. Purification by SPE (silica, 50 g cartridge), eluting with cyclohexane:EtOAc (gradient 49:1 to 9:1) afforded the title compound as a colourless oil (706 mg).

LC/MS: m/z 272.1/274.0 [M+NH$_4$]$^+$, R$_t$ 3.71 min.

Intermediate 114

1-(3-Bromo-2-methylphenyl)-1-pentanol

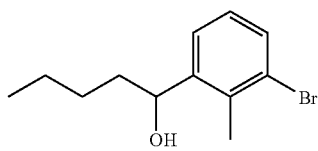

To a solution of 1-(3-bromo-2-methylphenyl)-1-pentanone (706 mg, 2.77 mmol) in anhydrous THF (12 mL) under nitrogen at 0° C. was added sodium borohydride (209 mg, 5.53 mmol) in water (8 mL) and the resulting mixture stirred at 0° C. for 2 h. Additional sodium borohydride (105 mg, 2.77 mmol) was then added, along with more THF (40 mL), and the resulting mixture stirred at 0° C. for an additional 30 min. The reaction mixture was then partitioned between EtOAc (50 mL) and water (50 mL), the layers separated, and the aqueous re-extracted with EtOAc (50 mL). The combined organic solution was then dried (Na$_2$SO$_4$) filtered, and reduced under vacuum. Purification by SPE (silica, 20 g cartridge), eluted with cyclohexane:EtOAc (gradient 99:1 to 19:1) afforded the title compound as a colourless oil (495 mg).

LC/MS: m/z 274.1/276.1 [M+NH$_4$]$^+$, R$_t$ 3.55 min.

Intermediate 115

Ethyl [(4-{[1-(3-bromo-2-methylphenyl)pentyl]oxy}-2-methylphenyl)oxy]acetate

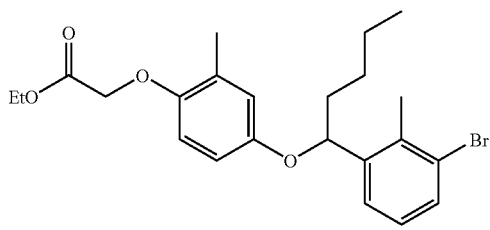

To a solution of 1-(3-bromo-2-methylphenyl)-1-pentanol (495 mg, 1.92 mmol) in anhydrous THF (40 mL) under nitrogen at 0° C. was added portion-wise ethyl (4-hydroxy-2-methylphenoxy)acetate (405 mg, 1.93 mmol), followed by slow addition (over 25 min) of ADDP (971 mg, 3.85 mmol) and drop-wise addition of tributylphosphine (0.96 mL, 3.85 mmol). The resulting mixture was then stirred for 16 h with gradual warming to ambient temperature. The solvent was then removed under vacuum and the residue partitioned between EtOAc (100 mL) and water (150 mL), the layers separated, and the aqueous re-extracted with EtOAc (100 mL). The combined organic layer was then dried ($Na_2SO_4$), filtered and reduced under vacuum and the resulting residue purified by SPE (silica, 50 g cartridge), eluting with cyclohexane:EtOAc (gradient 99:1 to 4:1) to afford the title compound as a colourless oil (495 mg).

LC/MS: m/z 466.0/468.1 $[M+NH_4]^+$, $R_t$ 4.25 min.

Intermediate 116

1-(6-Bromo-2-pyridinyl)-2-{[(1,1-dimethylethyl)(dimethyl)silyl]oxy}ethanol

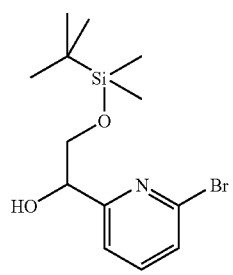

A solution of nBuLi (7.90 mL of a 1.6M solution in hexanes, 12.64 mmol) in THF (7.6 mL) was cooled to −78° C. (dry-ice/acetone bath) under nitrogen and then treated with a solution of 2,6-dibromopyridine (3.00 g, 12.66 mmol) in THF (17.8 mL) drop-wise over 30 min. The resulting green solution was stirred at −78° C. for 20 min and then treated with {[(1,1-dimethylethyl)(dimethyl)silyl]oxy}acetaldehyde (3.00 mL, 15.75 mmol) over 1 min to give a deep purple/brown coloured solution which was stirred at this temperature for 15 min. The reaction was then quenched by the addition of a mixture of MeOH (12.5 mL) and AcOH (0.8 mL, 13.90 mmol) in one portion and the resulting clear, pale yellow solution allowed to warm slowly to ambient temperature over 1.25 h. The mixture was then partitioned between EtOAc (100 mL) and saturated aqueous $NH_4Cl$ (100 mL), and the layers separated. The aqueous was re-extracted with EtOAc (100 mL) and the combined organic layer washed with brine (200 mL), dried ($MgSO_4$), filtered and reduced to give the title compound as a clear, pale yellow oil which was used directly without further purification (4.61 g).

LC/MS: m/z 332.0/334.0 $[M+H]^+$, $R_t$ 3.64 min.

Intermediate 117

Ethyl ({4-[(1-(6-bromo-2-pyridinyl)-2-{[(1,1-dimethylethyl)(dimethyl)silyl]oxy}ethyl)oxy]-2-methylphenyl}oxy)acetate

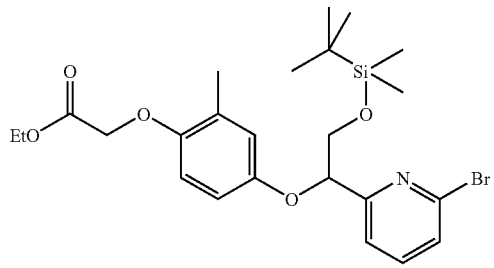

To a solution of $Ph_3P$ (1.10 g, 4.19 mmol) in dry THF (30 mL), was treated with ethyl [(4-hydroxy-2-methylphenyl)oxy]acetate (696 mg, 3.31 mmol) and 1-(6-bromo-2-pyridinyl)-2-{[(1,1-dimethylethyl)(dimethyl)silyl]oxy}ethanol (1.00 g, 3.01 mmol) and the resulting solution cooled to 0° C. (ice/water bath) under nitrogen. DIAD (0.829 ml, 4.21 mmol) in THF (30 ml) was then added drop-wise over 2 h using a syringe pump. The resulting mixture was then allowed to warm to ambient temperature over 22.5 h and was then reduced under vacuum to give an orange oily residue. Purification by SPE (silica, 10 g cartridge) eluting with cyclohexane:EtOAc (gradient, 1:1 to 0:1) afforded the title compound (429 mg).

LC/MS: m/z 524.1/526.1 $[M+H]^+$, $R_t$ 4.37 min.

Intermediate 118

Ethyl ({4-[(2-{[(1,1-dimethylethyl)(dimethyl)silyl]oxy}-1-{6-[4-(trifluoromethyl)phenyl]-2-pyridinyl}ethyl)oxy]-2-methylphenyl}oxy)acetate

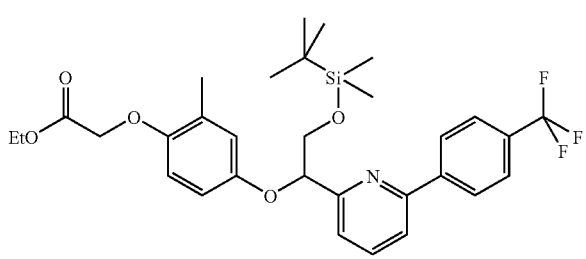

To a stirred solution of ethyl ({4-[(1-(6-bromo-2-pyridinyl)-2-{[(1,1-dimethylethyl)(dimethyl)silyl]oxy}ethyl)oxy]-2-methylphenyl}oxy)acetate (273 mg, 0.52 mmol) in DME (2.3 mL) was added 4-(trifluoromethyl)benzeneboronic (129 mg, 0.68 mmol), Pd(PPh₃)₄ (60 mg, 0.052 mmol) and Na₂CO₃ (165 mg, 1.56 mmol) and water (1.13 mL) was heated at 45° C. for 21 hours and then allowed to cool to ambient temperature. The resulting mixture was then reduced under vacuum, partitioned between water (90 mL) and EtOAc (100 mL), and the layers separated. The organic layer was re-extracted with EtOAc (100 mL) and the combined organic layer washed with brine (100 mL), dried (MgSO₄) filtered and reduced under vacuum. The residue was then purified by SPE (silica, 10 g cartridge) eluting with cyclohexane:EtOAc (gradient, 30:1 to 3:1) to give the title compound (208 mg).

LC/MS: m/z 590.6 [M+H]⁺, R$_t$ 4.59 min.

Intermediate 119

Ethyl ({4-[(2-hydroxy-1-{6-[4-(trifluoromethyl) phenyl]-2-pyridinyl}ethyl)oxy]-2-methylphenyl}oxy)acetate

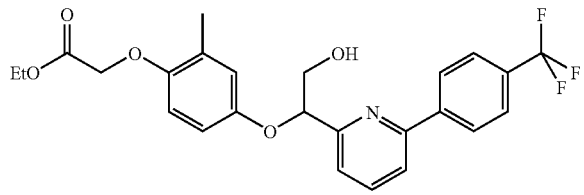

To a stirred solution of ethyl ({4-[(2-{[(1,1-dimethylethyl)(dimethyl)silyl]oxy}-1-{6-[4-(trifluoromethyl)phenyl]-2-pyridinyl}ethyl)oxy]-2-methylphenyl}oxy)acetate (208 mg, 0.352 mmol) in THF (3.5 mL) was added TBAF (1M in THF, 0.458 mL) dropwise over 1 min. The resulting solution was then stirred at ambient temperature for 18 h. The mixture was then reduced under vacuum and the residue purified by SPE (silica, 10 g cartridge) eluting with cyclohexane:EtOAc (gradient 15:1 to 2:1) to afford the title compound (89 mg).

LC/MS: m/z 476.1 [M+H]⁺, R$_t$ 3.78 min.

Intermediate 120

Ethyl [(4-{[1-(6-bromo-2-pyridinyl)-2-(ethyloxy) ethyl]thio}-2-methylphenyl)oxy]acetate

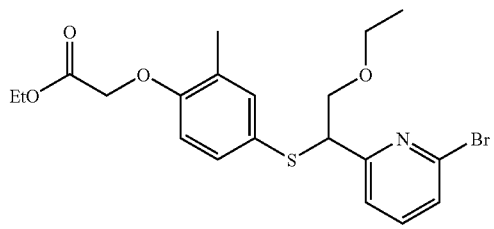

A solution of (ethyl [(4-mercapto-2-methylphenyl)oxy] acetate) (386 mg, 1.71 mmol), 1-(6-bromo-2-pyridinyl)-2-(ethyloxy)ethanol (352 mg, 1.43 mmol) and PPh₃ (450 mg, 1.72 mmol) in DCM (17 mL) at 0° C. under nitrogen was stirred for 10 mins and then treated drop-wise with DIAD (0.34 mL, 1.73 mmol). The resulting mixture was then stirred, with slow warming to ambient temperature over 18 h. The mixture was then reduced under vacuum and the resulting yellow oil purified by SPE (silica, 20 g cartridge), eluting with cyclohexane:EtOAc (gradient 15:1 to 5:1). Further purification using the OPTIX-SPE (C18 cartridge, 50 g) eluting with 60-80% MeCN (+0.05% HCOOH) in H₂O (+0.01% HCOOH) over 56 mins afforded the title compound as an oil (232 mg).

LC/MS: m/z 454.1/456.1 [M+H]⁺, R$_t$ 3.64 min.

Intermediate 121

Ethyl ({4-[(2-(ethyloxy)-1-{6-[4-(trifluoromethyl) phenyl]-2-pyridinyl}ethyl)thio]-2-methylphenyl}oxy)acetate

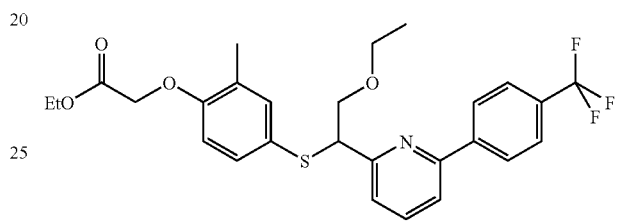

To a mixture of palladium (II) acetate (6 mg, 0.027 mmol), 1,3-bis(2,4,6-trimethylphenyl)imidazoliumchloride (9 mg, 0.026 mmol) and Cs₂CO₃ (266 mg, 0.816 mmol) in 1,4-dioxane (1 mL) was added ethyl [(4-{[1-(6-bromo-2-pyridinyl)-2-(ethyloxy)ethyl]thio}-2-methylphenyl)oxy]acetate (125 mg, 0.275 mmol) in 1,4-dioxane (1.75 mL) and the resulting mixture stirred under nitrogen at ambient temperature for 10 min. 2-[4-(Trifluoromethyl)phenyl]-1,3,2-dioxaborolane (69 mg, 0.300 mmol) was then added and the resulting mixture heated to 85° C. and kept at this temperature for 16 h. The reaction mixture was then reduced and the residue partitioned between EtOAc (15 mL) and saturated aqueous NH₄Cl (15 mL) and the layers separated. The aqueous layer was then re-extracted with EtOAc (15 mL) and the combined organic layers washed with brine (50 mL) dried (MgSO₄) and filtered. The mixture was then reduced under vacuum and the resulting residue purified by SPE (silica, 10 g cartridge), eluting with cyclohexane:EtOAc (gradient 50:1 to 3:1). Further purification by mass directed autoprep HPLC afforded the title compound as an oil (35 mg).

LC/MS: m/z 520.2 [M+H]⁺, R$_t$ 4.04 min.

Separation of racemic material (35 mg, 0.067 mmol) by preparative chiral HPLC (1″×25 cm Chiralcel OJ) eluting with 30% EtOH in heptane, f=15 mL/min, afforded Enantiomer 1 as an oil (12 mg), R$_t$ 9.0 min, analytical chiral HPLC (25 cm Chiralcel OJ) eluting with 30% IPA in heptane, f=1.0 mL/min, wavelength 215 nm, R$_t$ 8.4 min (>99.9% ee) and Enantiomer 2 as an oil (13.7 mg) R$_t$ 14.4 min, analytical chiral HPLC (25 cm Chiralcel OJ) eluting with 30% IPA in heptane, f=1.0 mL/min, wavelength 215 nm, R$_t$ 15.5 min (99.7% ee).

Intermediate 122 and Intermediate 123

(1R)-1-(6-Bromo-2-pyridinyl)-2-(ethyloxy)ethanol and (1S)-1-(6-Bromo-2-pyridinyl)-2-(ethyloxy)ethanol

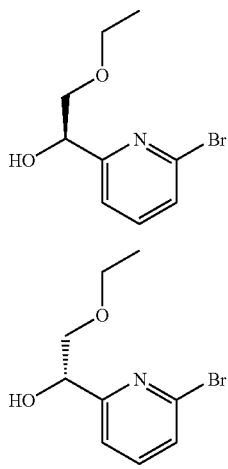

Intermediate 122

Intermediate 123

Separation of 1-(6-bromo-2-pyridinyl)-2-(ethyloxy)ethanol (100 g) by preparative chiral HPLC (2"×20 cm Chiralcel OD) eluting with 2% EtOH in heptane, f=60 mL/min, afforded (1R)-1-(6-bromo-2-pyridinyl)-2-(ethyloxy)ethanol as a white solid (45.9 g), $R_t$ 11.5 min. Analytical chiral HPLC (25 cm Chiralcel OD-H) eluting with 5% EtOH in heptane, f=1.0 mL/min, wavelength 215 nm, $R_t$ 6.8 min (>99% ee) and (1S)-1-(6-bromo-2-pyridinyl)-2-(ethyloxy)ethanol as a white solid (46.8 g), $R_t$ 14.5 min. Analytical chiral HPLC (25 cm Chiralcel OD-H) eluting with 5% EtOH in heptane, f=1.0 mL/min, wavelength 215 nm, $R_t$ 8.3 min (96% ee).

Intermediate 124

4-{6-[(1R)-2-(Ethyloxy)-1-hydroxyethyl]-2-pyridinyl}benzonitrile

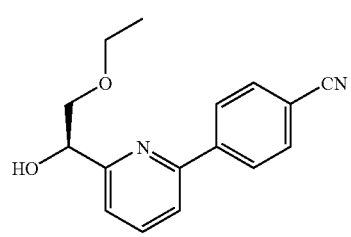

Pd(PPh$_3$)$_4$ (187 mg, 0.162 mmol) and Na$_2$CO$_3$ (1.29 g, 12.2 mmol) was treated with DME (20 mL) and stirred under nitrogen for 2 min. Water (10 mL), (1R)-1-(6-bromo-2-pyridinyl)-2-(ethyloxy)ethanol (1.0 g, 4.1 mmol) and (4-cyanophenyl)boronic acid (656 mg, 4.47 mmol) were added and the stirred reaction mixture heated at 80° C. for 17 h. The mixture was then allowed to cool to ambient temperature and the residue partitioned between saturated NH$_4$Cl (100 mL) and EtOAc (100 mL). The aqueous phase was extracted with EtOAc (2×100 mL) and the combined organic extracts washed with brine (100 mL), dried (Na$_2$SO$_4$) and evaporated to give a yellow oil (1.43 g). Purification by Biotage™ chromatography (silica, 40 g cartridge) eluting with cyclohexane:EtOAc (4:1) afforded the title compound as a pale yellow oil (945 mg).

LC/MS: m/z 269.2 [M+H]$^+$, $R_t$ 2.83 min.

Intermediate 125

Ethyl [(4-{[(1S)-1-[6-(4-cyanophenyl)-2-pyridinyl]-2-(ethyloxy)ethyl]oxy}-2-methylphenyl)oxy]acetate

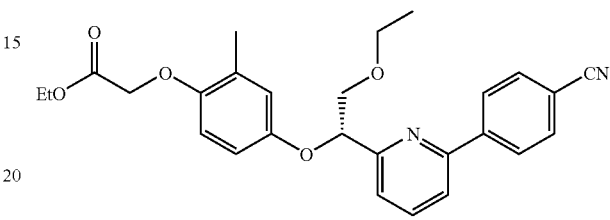

A stirred mixture of ethyl [(4-hydroxy-2-methylphenyl)oxy]acetate (664 mg, 3.16 mmol), 4-{6-[(1R)-2-(ethyloxy)-1-hydroxyethyl]-2-pyridinyl}benzonitrile (719 mg, 2.68 mmol) and triphenylphosphine (857 mg, 3.27 mmol) in dry DCM (35 mL) was cooled to 0° C. under nitrogen. DIAD (633 μL, 3.21 mmol) was added dropwise over 10 min, and the reaction mixture stirred at 0° C. for a further 2 h. DCM (120 mL) was added to the reaction mixture, washed with aq 1M NaOH (50 mL) and water (100 mL), dried (Na$_2$SO$_4$) and evaporated to give a yellow oil. Purification by Biotage™ chromatography (silica, 90 g cartridge) eluting with cyclohexane:EtOAc (8:1) afforded the title compound as a colourless oil (765 mg).

LC/MS: m/z 461.2 [M+H]$^+$, $R_t$ 3.67 min.

EXAMPLE 1

{[2-Methyl-4-({[4'-(trifluoromethyl)-3-biphenylyl]methyl}thio)phenyl]oxy}acetic acid

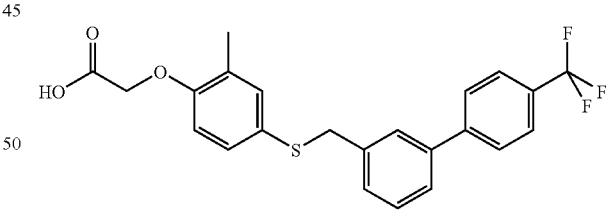

A solution of ethyl {[2-methyl-4-({[4'-(trifluoromethyl)-3-biphenylyl]methyl}thio)phenyl]oxy}acetate (209 mg) in THF (20 mL) and aqueous NaOH (2M, 20 mL) was stirred at rt overnight and then heated to 60° C. for 2 hours. The mixture was then allowed to cool to rt and the THF removed under vacuum. The resulting aqueous mixture was then acidified and extracted with EtOAc (3×) and the organic layer washed with brine dried (MgSO$_4$), filtered and reduced. Purification by mass directed auto-prep HPLC afforded the title compound as a white solid (24 mg).

LC/MS: m/z 431.0 [M−H]$^+$, $R_t$ 4.80 min.

$^1$H NMR (400 MHz; CDCl$_3$) δ: 2.22 (3H, s), 4.06 (2H, s), 4.66 (2H, s), 6.63 (1H, d, J 8.5 Hz), 7.14 (1H, dd, J 8.5, 2.5

Hz), 7.16, (1H, m), 7.24-7.28 (1H, m), 7.34-7.41 (2H, m), 7.46 (1H, m), 7.60 (2H, d, J 8.0 Hz), 7.67 (2H, d, J 8.0 Hz).

EXAMPLE 2

{[2-Methyl-4-({[4-methyl-4'-(trifluoromethyl)-3-biphenylyl]methyl}thio)phenyl]oxy}acetic acid

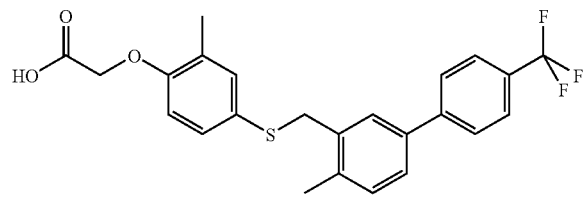

A mixture of (5-bromo-2-methylphenyl)methanol (90 mg, 0.45 mmol), 4-(triflouromethyl)benzeneboronic (94 mg, 0.49 mmol), Pd(PPh$_3$)$_4$ (5 mg, 0.004 mmol) and Na$_2$CO$_3$ (123 mg, 1.16 mmol) in a mixture of DME (20 mL) and water (10 mL) was heated at reflux for 7 hours and then allowed to cool to rt. The resulting mixture was then reduced under vacuum, partitioned between water and EtOAc and the layers separated. The organic layer was then washed with brine, reduced under vacuum and then purified by SPE (silica, 10 g cartridge) eluting with cyclohexane:CHCl$_3$ then cyclohexane:EtOAc to give a crude product containing a mixture of (5-bromo-2-methylphenyl)methanol and product. The mixture was then dissolved in DCM (10 mL) and then treated with thionyl chloride (200 μL, 2.74 mmol) and the mixture stirred for 5 hours. Additional thionyl chloride (200 μL, 2.74 mmol) was then added and after a further 2 hours, the reaction was quenched by the careful addition of aqueous K$_2$CO$_3$ (1N) and the resulting layers separated using a hydrophobic frit. The organic layer was reduced and the resulting crude mixture (98 mg) dissolved in MeCN (20 mL) was and treated ethyl (4-mercapto-2-methylphenoxy)acetate (92 mg, 0.41 mmol) and K$_2$CO$_3$ (55 mg, 0.40 mmol). The resulting mixture was then stirred under nitrogen over the 72 hours and the resulting mixture partitioned between water and EtOAc and the layers separated. The aqueous was re-extracted with EtOAc and the combined organic layers washed with brine, dried (MgSO$_4$), filtered and reduced. Purification by SPE (silica) eluting with cyclohexane:CHCl$_3$ (1:1) afforded the crude ester as a clear oil (125 mg). A solution of the ester in THF (10 mL) and aqueous NaOH (2M, 10 mL) was heated at 60° C. for 1 hour and was then allowed to cool to rt overnight. The THF was then removed under vacuum and the resulting aqueous mixture was then acidified and extracted with EtOAc (2×). The organic layer was then washed with brine, dried (MgSO$_4$), filtered and reduced. Purification by mass directed auto-prep HPLC afforded the title compound as a white solid (41 mg).

LC/MS: m/z 445.0 [M−H]$^+$, R$_t$ 4.32 min.

$^1$H NMR (400 MHz; DMSO-d$^6$) δ: 2.07 (3H, s), 2.35 (3H, s), 4.10 (2H, s), 4.64 (2H, s), 6.74 (1H, d, J 8.5 Hz), 7.09 (1H, m), 7.14 (1H, dd, J 8.0, 2.5 Hz), 7.24-7.30 (2H, m), 7.46 (1H, dd, J 8.0, 2.0 Hz), 7.64 (2H, d, J 8.5 Hz), 7.67 (2H, d, J 8.5 Hz).

EXAMPLE 3

3-[2-Methyl-4-({[4'-trifluoromethyl)-3-biphenylyl]methyl}oxy)phenyl]propanoic acid

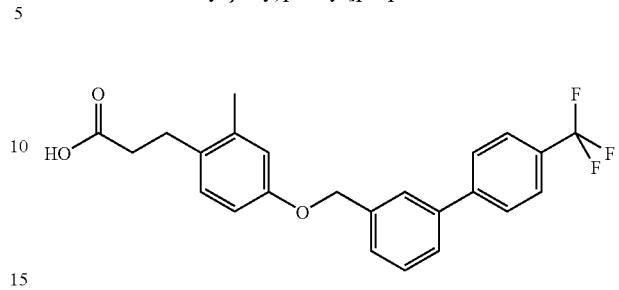

A solution of ethyl 3-[2-methyl-4-({[4'-(trifluoromethyl)-3-biphenylyl]methyl}oxy)phenyl]propanoate (135 mg, 0.31 mmol) in THF (4 mL) at rt was treated with aqueous NaOH (2M, 4 mL) and the resulting solution heated to 75° C. for 7 hours and then allowed to cool to rt over 21 hours. The mixture was then reduced and the residue partitioned between CHCl$_3$ and water and the aqueous phase separated and acidified to pH2 with aqueous HCl (2 N). The mixture was then extracted with CHCO$_3$ (3×) and the combined organic layer washed with brine, dried (Na$_2$SO$_4$), filtered and reduced to give the title compound as a white crystalline solid (123 mg).

LC/MS: m/z 413.1 [M−H]$^+$, R$_t$ 4.21 min.

$^1$H NMR (400 MHz; CDCl$_3$) δ: 2.31 (3H, s), 2.62 (2H, m), 2.91 (2H, m), 5.10 (2H, s), 6.79 (1H, dd, J 8.5, 3.0 Hz), 6.83 (1H, d, 3.0 Hz), 7.08 (1H, d, J 8.5 Hz), 7.44-7.53 (2H, m), 7.56 (1H, m), 7.66 (1H, m), 7.70 (4H, s).

EXAMPLE 4

[(2-Methyl-4-{2-[4'-(trifluoromethyl)-3-biphenylyl]ethyl}phenyl)oxy]acetic acid

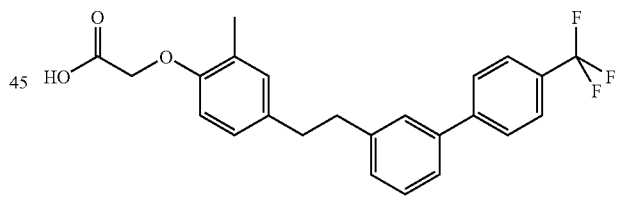

A suspension of [(2-methyl-4-{2-[4'-(trifluoromethyl)-3-biphenylyl]ethenyl}phenyl)oxy]acetic acid (90 mg, 0.22 mmol) in EtOH (10 mL) was added to Pd/C (Degussa type E101 NE/N) (10 mg, 11 wt %) and the resulting mixture stirred under an atmosphere of hydrogen for 6 hours. The mixture was then filtered through celite J2 washing with copious amounts of EtOH and the filtrate reduced under vacuum to give a sticky solid (100 mg) which was purified by mass directed auto-prep HPLC to give the title compound as a fluffy white solid (25 mg).

LC/MS: m/z 413.1 [M−H]$^+$, R$_t$ 4.48 min.

$^1$H NMR (400 MHz; MeOD-d$^4$) δ: 2.21 (3H, s), 2.85 (2H, m), 2.95 (2H, m), 4.62 (2H, s), 6.70 (1H, d, J 8.0 Hz), 6.91-6.95 (2H, m), 7.22 (1H, dt, J 7.5, 1.0 Hz), 7.35 (1H, m), 7.37 (1H, t, J 7.5 Hz), 7.46 (1H, ddd, J 7.5, 2.0, 1.0 Hz), 7.72 (4H, s).

EXAMPLE 5

({2-Methyl-4[({6-[4-(trifluoromethyl)phenyl]-2-pyridinyl}methyl)thio]phenyl}oxy)acetic acid

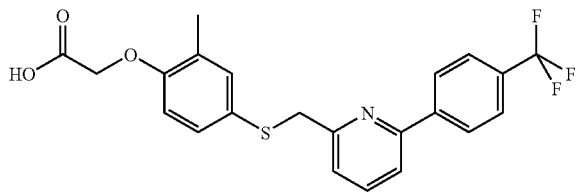

A solution of ethyl ({2-methyl-4-[({6-[4-(trifluoromethyl)phenyl]-2-pyridinyl}methyl)thio]phenyl}oxy)acetate (367 mg, 0.80 mmol) in THF (5 mL) was treated with aqueous NaOH (2M, 5 mL) and the resulting solution stirred at rt for 4 hours. The mixture was poured into a mixture of aqueous HCl (2M) and EtOAc and the layers separated. The organic layer was then washed with water and brine, dried MgSO$_4$, filtered and then reduced under vacuum. Purification by mass-directed auto-prep HPLC afforded the title compound as an oil.

LC/MS: m/z 434.2 [M+H]$^+$, R$_t$ 3.97 min.

$^1$H NMR (400 MHz; CDCl$_3$) δ: 2.22 (3H, s), 4.24 (2H, s), 4.63 (2H, s), 6.61 (1H, d, J 8.5 Hz), 7.16 (1H, dd, J 8.5, 2.0 Hz), 7.22-7.28 (2H, m), 7.60 (1H, d, J 8.5 Hz), 7.68-7.74 (3H, m), 8.02 (2H, d, J 8.0 Hz).

EXAMPLE 6

{[2-Methyl-4-({1-[4'-(trifluoromethyl)-3-biphenylyl]ethyl}thio)phenyl]oxy}acetic acid

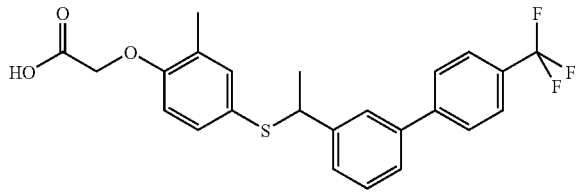

A mixture of ethyl {[2-methyl-4-({1-[4'-(trifluoromethyl)-3-biphenylyl]ethyl}thio)phenyl]oxy}acetate (235 mg, 0.50 mmol) in dioxane (6 mL) was treated with aqueous NaOH (0.5N, 2.0 mL, 1.00 mmol) and the mixture heated at reflux for 1 hour. The resulting mixture was then cooled and treated with Dowex 50WX2 (pre-washed with dioxan), filtered and washed with more dioxan and reduced to give the title compound as a colourless gum (220 mg).

LC/MS: m/z 445.2 [M−H]$^+$, R$_t$ 4.20 min.

$^1$H NMR (400 MHz; CDCl$_3$) δ: 1.65 (3H, d, J 7.0 Hz), 2.18 (3H, s), 4.25 (1H, q, J 7.0 Hz), 4.64 (2H, s), 6.57 (1H, d, J 9.0 Hz), 7.08-7.13 (2H, m), 7.29 (1H, m), 7.33-7.41 (2H, m), 7.43 (1H, m), 7.59 (2H, d, J 8.5 Hz), 7.67 (2H, m, J 8.5 Hz).

EXAMPLE 7

{[2-Methyl-4-({1-[4'-(trifluoromethyl)-4-biphenylyl]ethyl}thio)phenyl]oxy}acetic acid

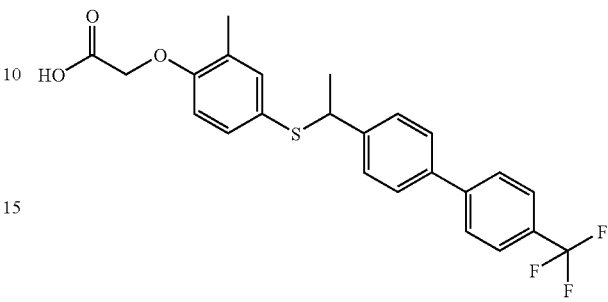

Prepared from ethyl {[2-methyl-4-({1-[4'-(trifluoromethyl)-4-biphenylyl]ethyl}thio)phenyl]oxy}acetate (333 mg, 0.70 mmol) according to the procedure used for the preparation of Example 6 to give the title compound as a white solid (283 mg).

LC/MS: m/z 445.2 [M−H]$^+$, R$_t$ 4.28 min.

$^1$H NMR (400 MHz; CDCl$_3$) δ: 1.63 (3H, d, J 7.0 Hz), 2.19 (3H, s), 4.24 (1H, q, J 7.0 Hz), 4.65 (2H, s), 6.58 (1H, d, J 8.5 Hz), 7.08-7.14 (2H, m), 7.33 (2H, d, J 8.5 Hz), 7.50 (2H, d, J 8.5 Hz), 7.67 (4H, m).

EXAMPLE 8

2-Methyl-2-({2-methyl-4-[(1-{6-[4-(trifluoromethyl)phenyl]-2-pyridinyl}pentyl)oxy]phenyl}oxy)propanoic acid

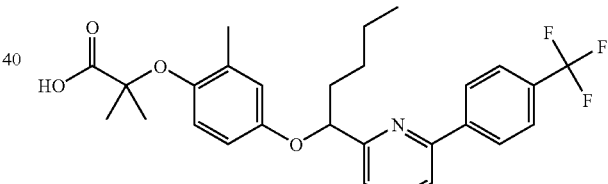

Ethyl 2-methyl-2-({2-methyl-4-[(1-{6-[4-(trifluoromethyl)phenyl]-2-pyridinyl}pentyl)oxy]phenyl}oxy)propanoate (9 mg, 0.02 mmol) was dissolved in THF (0.75 mL), water (0.25 mL) and aqueous NaOH (2M, 35 μl, 0.07 mmol) and the mixture heated at 80° C. for 16 hours. More aqueous NaOH (2M, 420 μl, 0.84 mmol) was then added and heating continued for an additional 24 hours. The mixture was then cooled, neutralised with aqueous HCl (2M), partitioned between EtOAc and water and the layers separated. The organic layer was then washed with brine, dried (Na$_2$SO$_4$) and reduced to give a pale yellow oil. Purification by SPE (aminopropyl, 1 g cartridge) loading in CHCl$_3$ and eluting with dioxane and then 10% aqueous ammonia in dioxane afforded the title compound as a colourless gum (4.5 mg).

LC/MS: m/z 502.3 [M+H]$^+$, R$_t$ 4.49.

$^1$H NMR (400 MHz; CDCl$_3$) δ: 0.91 (3H, t, J 7.0 Hz), 1.50 (6H, s), 1.32-1.61 (4H, m), 2.00 (2H, m), 2.15 (3H, s), 5.23 (1H, t, J 6.0 Hz), 6.57 (1H, dd, J 8.5, 3.0 Hz), 6.69 (1H, d, J 8.5 Hz), 6.76 (1H, d, J 3.0 Hz), 7.37 (1H, dd, J 8.0, 1.0 Hz), 7.62 (1H, dd, J 8.0, 1.0 Hz), 7.73 (1H, t, J 8.0 Hz), 7.74 (2H, d, J 8.0 Hz), 8.12 (2H, d, J 8.0 Hz).

EXAMPLE 9

{[2-Methyl-4-({1-[4'-(trifluoromethyl)-3-biphenylyl]pentyl}oxy)phenyl]oxy}acetic acid

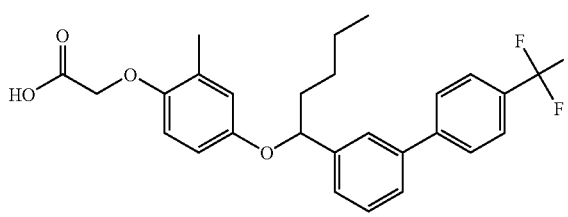

Ethyl {[2-methyl-4-({1-[4'-(trifluoromethyl)-3-biphenylyl]pentyl}oxy)phenyl]oxy}acetate (138 mg, 0.28 mmol) was dissolved in THF (1.5 mL), water (0.5 mL) and aqueous NaOH (2M, 0.52 mL, 1.04 mmol) and the mixture stirred at 70° C. for 2 hours, cooled to rt and acidified to pH4 with aqueous hydrochloric acid (2M). The mixture was then partitioned between EtOAc and water, the layers separated and the organic layer washed with brine, dried ($Na_2SO_4$) and concentrated to give the title compound as a colourless gum (130 mg).

LC/MS: m/z 471.2 [M−H]$^+$, $R_t$ 4.57 min.

$^1$H NMR (400 MHz; $CDCl_3$) δ: 0.90 (3H, t, J 7.0 Hz), 1.31-1.45 (3H, m), 1.45-1.60 (1H, m), 1.76-1.90 (1H, m), 1.93-2.07 (1H, m), 2.20 (3H, s), 4.55 (2H, s), 5.03 (2H, dd, J 8.0, 5.0 Hz), 6.55 (1H, d, J 9.0 Hz), 6.58 (1H, dd, J 9.0, 2.5 Hz), 6.75 (1H, 2.5 Hz), 7.36 (1H, m), 7.42 (1H, t, J 7.5 Hz), 7.48 (1H, dt, J 7.5, 1.5 Hz), 7.5 (1H, m), 7.67 (4H, m).

EXAMPLE 10

[(4-{[1-(4'-Chloro-3-biphenylyl)pentyl]oxy}-2-methylphenyl)oxy]acetic acid

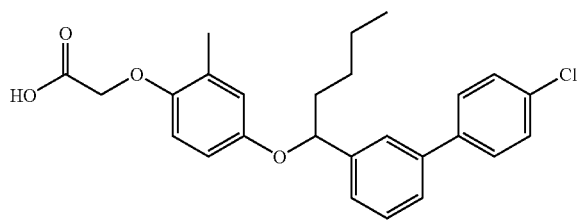

Prepared according to the procedure used for the preparation of Example 9 starting from ethyl [(4-{[1-(4'-chloro-3-biphenylyl)pentyl]oxy}-2-methylphenyl)oxy]acetate (137 mg, 0.29 mmol) to give the title compound (130 mg).

LC/MS m/z 456.1 [M+$NH_4$]$^+$, $R_t$ 4.55 min.

$^1$H NMR (400 MHz; $CDCl_3$) δ: 0.90 (3H, t, J 7.0 Hz), 1.30-1.44 (3H, m), 1.44-1.59 (1H, m), 1.76-1.88 (1H, m), 1.94-2.06 (1H, m), 2.21 (3H, s), 4.51 (2H, s), 5.02 (2H, dd, J 8.0, 5.0 Hz), 6.53 (1H, d, J 9.0 Hz), 6.56 (1H, dd, J 9.0, 2.5 Hz), 6.74 (1H, 2.5 Hz), 7.32 (1H, dt, J 7.5, 1.5 Hz), 7.36-7.41 (3H, m), 7.43 (1H, dt, J 7.5, 1.5 Hz), 7.47-7.53 (4H, m).

EXAMPLE 11

{[2-Methyl-4-({1-[4'-(trifluoromethyl)-4-biphenylyl]pentyl}oxy)phenyl]oxy}acetic acid

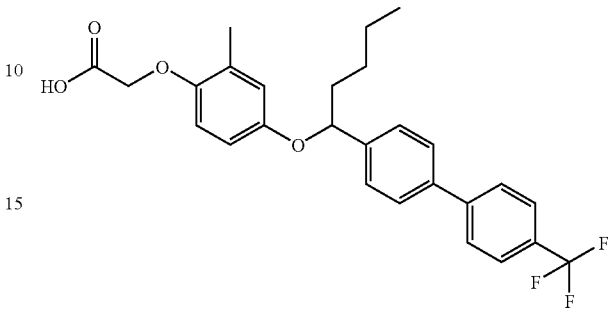

To a solution of ethyl {[2-methyl-4-({1-[4'-(trifluoromethyl)-4-biphenylyl]pentyl}oxy)phenyl]oxy}acetate (310 mg, 0.62 mmol) in dioxan (6 mL) and water (3 mL), was added aqueous NaOH (2M, 2.43 mL, 1.22 mmol), and the mixture stirred at rt for 1 hour. The dioxan was removed under vacuum and brine (5 mL) added to the residue. The precipitate was collected by filtration and dried under vacuum to give the title compound as a white solid (250 mg).

LC/MS: m/z 471.3 [M−H]$^+$, $R_t$ 4.57 min.

$^1$H NMR (400 MHz; MeOD-d$^4$) δ: 0.91 (3H, t, J 7.0 Hz), 1.37 (2H, m), 1.39 (1H, m), 1.49 (1H, m), 1.80 (1H, m), 1.95 (1H, m), 2.17 (3H, s), 4.26 (2H, s), 5.11 (1H, dd, J 5.5, 5.5 Hz), 6.55 (1H, dd, J 8.5, 2.0 Hz), 6.58 (1H, d, J 8.5 Hz), 6.68 (1H, d, J 2.0 Hz), 7.44 (2H, d, J 8.0 Hz), 7.61 (2H, d, J 8.0 Hz), 7.70 (2H, d, J 8.0 Hz), 7.77 (2H, d, J 8.0 Hz).

EXAMPLE 12

[(4-{[1-(4'-Chloro-4-biphenylyl)pentyl]oxy}-2-methylphenyl)oxy]acetic acid

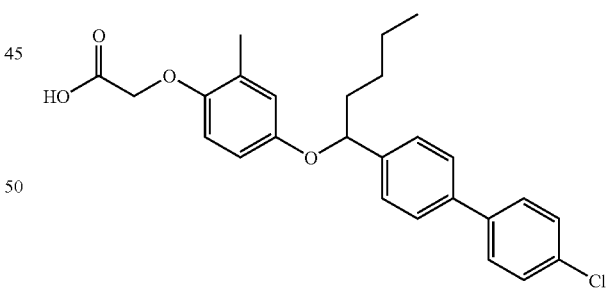

Prepared from ethyl [(4-{[1-(4'-chloro-4-biphenylyl)pentyl]oxy}-2-methylphenyl)oxy]acetate (150 mg, 0.32 mmol) according to the procedure used for the preparation of Example 11, to give the title compound as a white solid (140 mg).

LC/MS: m/z 437.2 [M−H]$^+$, $R_t$ 4.83 min.

$^1$H NMR (400 MHz; MeOD-d$^4$) δ: 0.90 (3H, t, J 7.0 Hz), 1.36 (2H, m), 1.39 (1H, m), 1.49 (1H, m), 1.80 (1H, m), 1.95 (1H, m), 2.16 (3H, s), 4.26 (2H, s), 5.11 (1H, dd, J 7.5, 5.5 Hz), 6.54 (1H, dd, J 9.0, 2.5 Hz), 6.58 (1H, d, J 9.0 Hz), 6.68 (1H, d, J 2.5 Hz), 7.39 (4H, d, J 8.5 Hz), 7.53 (2H, d, J 8.5 Hz), 7.57 (2H, d, J 8.5 Hz).

EXAMPLE 13

{[2-Methyl-4-({(1R)-1-[4'-(trifluoromethyl)-4-biphenylyl]pentyl}thio)phenyl]oxy}acetic acid

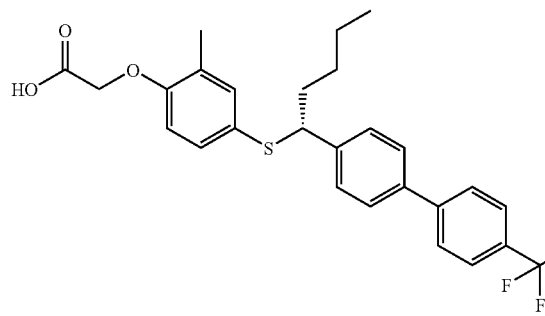

To a solution of ethyl {[2-methyl-4-({(1R)-1-[4'-(trifluoromethyl)-4-biphenylyl]pentyl}thio)phenyl]oxy}acetate (10 mg, 0.02 mmol) in THF (1 mL) and MeOH (1 mL) was added aqueous NaOH (2M, 1 mL) and the resulting mixture agitated for 1.5 hours at rt. The mixture was then reduced under vacuum, acidified with aqueous HCl (2M), extracted with DCM (2 mL) and reduced to afford the title compound as colourless oil (9 mg).

LC/MS: m/z 487.3 [M−H]+ $R_t$ 4.84 min.

$^1$H NMR (400 MHz; MeOD-d$^4$) δ: 0.85 (3H, t, J 7.0 Hz), 1.21-1.44 (4H, m), 1.84-2.02 (2H, m), 2.12 (3H, s), 4.06 (1H, dd, J 8.5, 6.5 Hz), 4.62 (2H, s), 6.64 (1H, d, J 8.5 Hz), 7.01 (1H, d, J 2.0 Hz), 7.04 (1H, dd, J 8.5, 2.0 Hz), 7.26 (2H, d, J 8.0 Hz), 7.55 (2H, d, J 8.0 Hz), 7.70 (2H, d, J 8.0 Hz), 7.77 (2H, d, J 8.0 Hz).

EXAMPLE 14

{[2-Methyl-4-({(1S)-1-[4'-(trifluoromethyl)-4-biphenylyl]pentyl}thio)phenyl]oxy}acetic acid

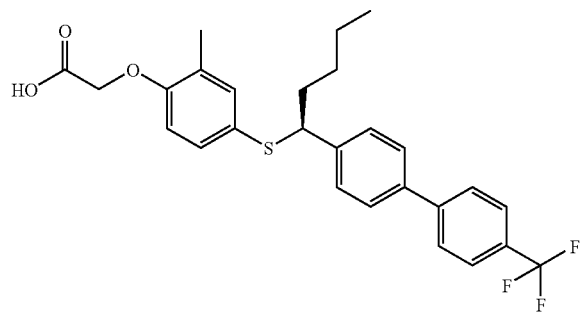

Prepared from ethyl {[2-methyl-4-({(1S)-1-[4'-(trifluoromethyl)-4-biphenylyl]pentyl}thio)phenyl]oxy}acetate (9 mg, 0.02 mmol) according to the procedure used for the preparation of Example 13 to give the title compound (8 mg).

LC/MS: m/z 487.3 [M−H]+ $R_t$ 4.84 min.

$^1$H NMR (400 MHz; MeOD-d$^4$) δ: 0.85 (3H, t, J 7.0 Hz), 1.21-1.44 (4H, m), 1.84-2.02 (2H, m), 2.12 (3H, s), 4.06 (1H, dd, J 8.5, 6.5 Hz), 4.62 (2H, s), 6.64 (1H, d, J 8.5 Hz), 7.01 (1H, d, J 2.0 Hz), 7.04 (1H, dd, J 8.5, 2.0 Hz), 7.26 (2H, d, J 8.0 Hz), 7.55 (2H, d, J 8.0 Hz), 7.70 (2H, d, J 8.0 Hz), 7.77 (2H, d, J 8.0 Hz).

EXAMPLE 15

({2-Methyl-4-[((1S)-1-{6-[4-(trifluoromethyl)phenyl]-2-pyridinyl}pentyl)oxy]phenyl}oxy)acetic acid

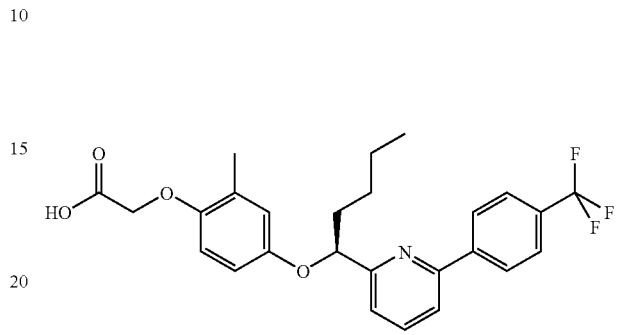

A solution of ethyl ({2-methyl-4-[((1S)-1-{6-[4-(trifluoromethyl)phenyl]-2-pyridinyl}pentyl)oxy]phenyl}oxy)acetate (367 mg, 0.73 mmol) in THF (9 mL) and methanol (9 mL) was treated with aqueous NaOH (2M, 9 mL) drop-wise and the resulting solution stirred at rt for 3 h. The volatile solvents were then removed under vacuum and the resulting aqueous residue diluted with water (100 mL) and then acidified with aqueous HCl (2M, 11 mL). The product was extracted with DCM (2×50 mL). The combined organic layers were then washed with brine (150 mL), dried (MgSO$_4$), filtered and then reduced under vacuum to give a pale yellow foam (341 mg). Purification by SPE (silica) eluting with heptane:EtOAc (gradient 10:1 to 0:1) afforded the title compound as a pale yellow foam (256 mg).

LC/MS: m/z 473.9 [M+H]+, $R_t$ 4.38 min.

$^1$H NMR (400 MHz; CDCl$_3$) δ: 0.91 (3H, t, J 7.0 Hz), 1.32-1.63 (4H, m), 2.00 (2H, m), 4.55 (2H, s), 5.22 (1H, m), 6.53-6.63 (2H, m), 6.79 (1H, d, J 2.0 Hz), 7.37 (1H, d, J 8.0 Hz), 7.62 (1H, d, J 8.0 Hz), 7.73 (3H, m), 8.13 (2H, d, J 8.0 Hz).

Analytical chiral HPLC, 25 cm chiralpak AD, 5% EtOH/heptane [0.1% TFA], 1.0 mL/min, wavelength 215 nm, $R_t$ 9.53 min.

EXAMPLE 16

({2-Methyl-4-[((1R)-1-{6-[4-(trifluoromethyl)phenyl]-2-pyridinyl}pentyl)oxy]phenyl}oxy)acetic acid

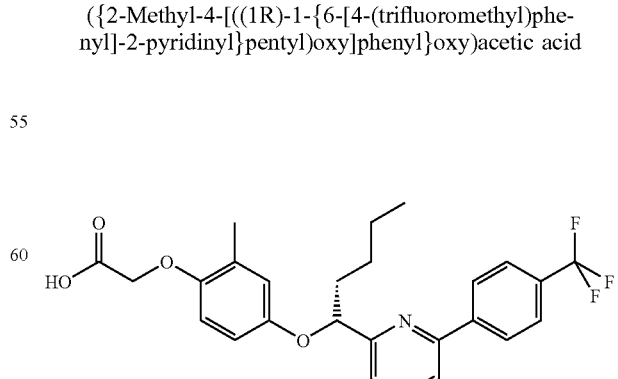

Prepared from ethyl ({2-methyl-4-[((1R)-1-{6-[4-(trifluoromethyl)phenyl]-2-pyridinyl}pentyl)oxy]phenyl}oxy)acetate (360 mg, 0.72 mmol) according to the procedure used for the preparation of Example 15 to give the title compound as a pale yellow foam (269 mg).

LC/MS: m/z 473.9 [M+H]⁺, R$_t$ 4.38 min.

¹H NMR (400 MHz; CDCl₃) δ: 0.91 (3H, t, J 7.0 Hz), 1.32-1.63 (4H, m), 2.00 (2H, m), 4.55 (2H, s), 5.22 (1H, m), 6.53-6.63 (2H, m), 6.79 (1H, d, J 2.0 Hz), 7.37 (1H, d, J 8.0 Hz), 7.62 (1H, d, J 8.0 Hz), 7.73 (3H, m), 8.13 (2H, d, J 8.0 Hz).

Analytical chiral HPLC 25 cm chiralpak AD 5% EtOH/heptane [0.1% TFA], 1.0 mL/min, wavelength 215 nm, R$_t$ 10.87 min

EXAMPLE 17

({2-Methyl-4-[((1S)-1-{6-[4-(trifluoromethyl)phenyl]-2-pyridinyl}pentyl)thio]phenyl}oxy)acetic acid

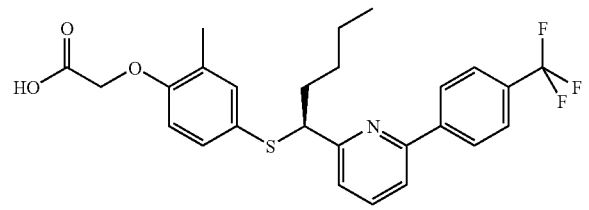

To a solution of ethyl ({2-methyl-4-[((1S)-1-{6-[4-(trifluoromethyl)phenyl]-2-pyridinyl}pentyl)thio]phenyl}oxy)acetate (34 mg, 0.07 mmol) in THF (1 mL) and MeOH (1 mL) was added aqueous NaOH (2M, 1 mL) and the resulting mixture agitated for 1.5 hours at rt. The mixture was then reduced under vacuum, acidified with aqueous HCl (2M) and extracted with DCM (2 mL) and reduced to afford the title compound as a colourless oil (31 mg).

LC/MS: m/z 490.0 [M+H]⁺ R$_t$ 4.60 min.

¹H NMR (400 MHz; MeOD-d⁴) δ: 0.86 (3H, t, 7.0 Hz), 1.23-1.48 (4H, m), 1.95-2.18 (2H, m), 2.08 (3H, s) 4.23 (1H, dd, J 8.5, 6.5 Hz), 4.54 (2H, s), 6.62 (1H, d, J 8.5 Hz), 6.97 (1H, d, J 1.5 Hz), 7.04 (1H, dd, J 8.5 Hz, 1.5 Hz), 7.26 (1H, d, J 8.0 Hz), 7.70 (1H, d, J 8.0 Hz), 7.73 (2H, d, J 8.0 Hz), 7.77 (1H, t, J 8.0 Hz), 8.04 (2H, d, J 8.0 Hz).

Analytical chiral HPLC; 25 cm chiralcel OJ-R, flow 0.5 ml/min, wavelength 215 nm, 50% acetonitrile/H₃PO₄—KH₂PO₄ [0.2M] pH2, R$_t$ 27.25 min.

EXAMPLE 18

({(2-Methyl-4-[((1R)-1-{6-[4-(trifluoromethyl)phenyl]-2-pyridinyl}pentyl)thio]phenyl}oxy)acetic acid

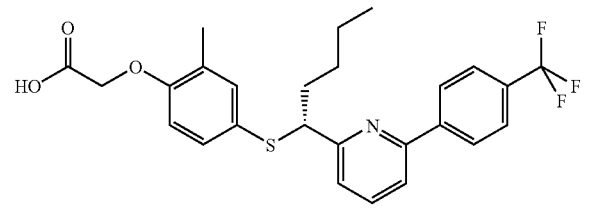

Prepared from ethyl ({2-methyl-4-[((1R)-1-{6-[4-(trifluoromethyl)phenyl]-2-pyridinyl}pentyl)thio]phenyl}oxy)acetate (29 mg, 0.06 mmol) according to the procedure used for the preparation of Example 17 to give the title compound (28 mg).

LC/MS: m/z 490.0 [M+H]⁺ R$_t$ 4.60 min.

¹H NMR (400 MHz; MeOD-d⁴) δ: 0.86 (3H, t, 7.0 Hz), 1.23-1.48 (4H, m), 1.95-2.18 (2H, m), 2.08 (3H, s) 4.23 (1H, dd, J 8.5, 6.5 Hz), 4.54 (2H, s), 6.62 (1H, d, J 8.5 Hz), 6.97 (1H, d, J 1.5 Hz), 7.04 (1H, dd, J 8.5 Hz, 1.5 Hz), 7.26 (1H, d, J 8.0 Hz), 7.70 (1H, d, J 8.0 Hz), 7.73 (2H, d, J 8.0 Hz), 7.77 (1H, t, J 8.0 Hz), 8.04 (2H, d, J 8.0 Hz).

Analytical chiral HPLC; 25 cm chiralcel OJ-R, flow 0.5 ml/min, wavelength 215 nm, 50% acetonitrile/H₃PO₄—KH₂PO₄ [0.2M] pH2, R$_t$ 30.34 min.

EXAMPLE 19

({2-Methyl-4-[(1-{6-[4-(trifluoromethyl)phenyl]-2-pyridinyl}pentyl)sulfinyl]phenyl}oxy)acetic acid

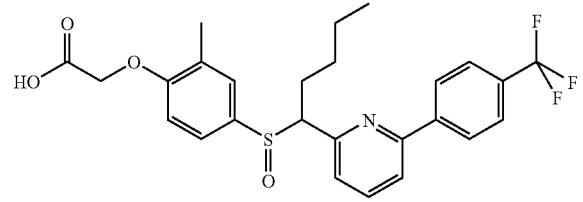

A stirred solution of ethyl ({2-methyl-4-[(1-{6-[4-(trifluoromethyl)phenyl]-2-pyridinyl}pentyl)sulfinyl]phenyl}oxy)acetate (27 mg, 0.05 mmol) in THF (1 mL) and methanol (1 mL) was added, drop-wise, aqueous NaOH (2M, 1 mL). After 2 hours 50 minutes the mixture was concentrated producing a 'chalk-white' solid which was diluted with water (2 mL) and acidified with aqueous HCl (2M, 2 mL). The aqueous layer was extracted with DCM (2×2 mL then 1 mL) using a hydrophobic frit and the combined organic layer concentrated under vacuum yielding the title compound as a mixture of two diastereoisomers (24 mg).

LC/MS: m/z 506.2 [M+H]⁺, R$_t$ 4.24 min.

¹H NMR (400 MHz; CDCl₃) δ: isomer 1 (70%) 0.83 (3H, t, J 7.0 Hz), 1.17-1.41 (4H, m), 2.06 (3H, s), 1.97-2.42 (2H, m), 4.07 (1H, dd, J 11.0, 4.0 Hz), 4.48 (1H, d, J 17.0 Hz), 4.53 (1H, d, J 17.0 Hz), 6.49 (1H, d, J 8.5 Hz), 6.86 (1H, d, J 2.0 Hz), 6.90 (1H, m), 7.11 (1H, dd, J 8.5, 2.0 Hz), 7.59-7.80 (4H, m), 7.94 (2H, d, 8.0 Hz); isomer 2 (30%) 0.83 (3H, t, J 7.0 Hz), 1.17-1.41 (4H, m), 2.16 (3H, s), 1.97-2.42 (2H, m), 4.14 (1H, m), 4.44 (1H, d, J 17.0 Hz), 4.53 (1H, d, J 17.0 Hz), 6.51 (1H, d, J 8.5 Hz), 7.03 (1H, d, J 2.0 Hz), 7.13 (1H, dd, J 8.5, 2.0 Hz), 7.32 (1H, d, J 8.0 Hz), 7.59-7.80 (6H, m).

EXAMPLE 20

(\{2-Methyl-4-[(1-\{6-[4-(trifluoromethyl)phenyl]-2-pyridinyl\}pentyl)sulfonyl]phenyl\}oxy)acetic acid

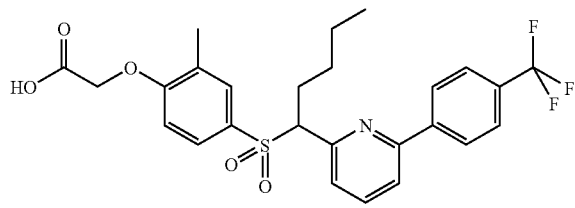

Prepared from ethyl (\{2-methyl-4-[(1-\{6-[4-(trifluoromethyl)phenyl]-2-pyridinyl\}pentyl)sulfonyl]phenyl\}oxy)acetate (26 mg, 0.05 mmol) according to the procedure used for the preparation of Example 19 to give the title compound as a clear oil (22 mg).

LC/MS: m/z 522.2 [M+H]$^+$, R$_t$ 4.23 min.

$^1$H NMR (400 MHz; CDCl$_3$) δ: 0.82 (3H, t, 7.0 Hz), 1.12-1.44 (4H, m), 2.11 (3H, s), 2.26-2.47 (2H, m), 4.40 (1H, dd, 11.5, 4.0 Hz), 4.57 (2H, s), 6.56 (1H, d, 8.5 Hz), 7.27 (1H, m), 7.34 (1H, dd, J 8.5 Hz, 2.0 Hz), 7.47 (1H, d, 7.0 Hz), 7.62 (2H, d, J 8.0 Hz), 7.67 (1H, d, 7.0 Hz), 7.73 (2H, d, J 8.0 Hz), 7.81 (1H, dd, J 7.0, 7.0 Hz).

EXAMPLE 21

\{4-[(1 \{6-[4-(Trifluoromethyl)phenyl]-2-pyridinyl\}pentyl)oxy]phenyl\}acetic acid

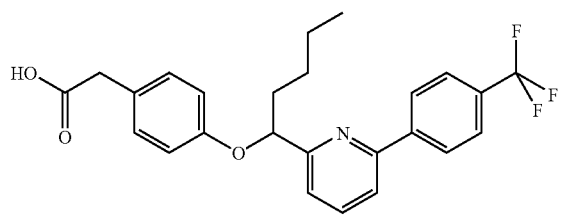

A solution of methyl \{4-[(1-\{6-[4-(trifluoromethyl)phenyl]-2-pyridinyl\}pentyl)oxy]phenyl\}acetate (329 mg, 0.72 mmol) in THF (9.5 mL) and methanol (9.5 mL) was treated with aqueous NaOH (2M, 9.5 mL) drop-wise and the resulting solution stirred at rt for 17 hours. The volatile solvents were then removed under vacuum and the resulting aqueous mixture acidified with aqueous HCl (2M, 15 mL), diluted with water (100 mL) and the product extracted with DCM (2×100 mL). The combined organic layers were then washed with brine (100 mL), dried (MgSO$_4$), filtered and then reduced under vacuum to give the title compound as a pale yellow foam (314 mg).

LC/MS: m/z 443.9 [M+H]$^+$, R$_t$ 4.15 min.

$^1$H NMR (400 MHz; CDCl$_3$) δ: 0.91 (3H, t, J 7.0 Hz), 1.32-1.63 (4H, m), 2.01 (2H, m), 3.52 (2H, s), 5.28 (1H, t, J 6.5 Hz), 6.84 (2H, d, J 9.0 Hz), 7.09 (2H, d, J 9.0 Hz), 7.36 (1H, d, J 7.5 Hz), 7.62 (1H, d, J 8.0 Hz), 7.72 (1H, dd, J 8.0, 7.5 Hz), 7.74 (2H, d, J 8.0 Hz), 8.14 (2H, d, J 8.0 Hz).

EXAMPLE 22

(\{2-Methyl-4-[(1-\{6-[4-(trifluoromethyl)phenyl]-2-pyridinyl\}butyl)oxy]phenyl\}oxy)acetic acid

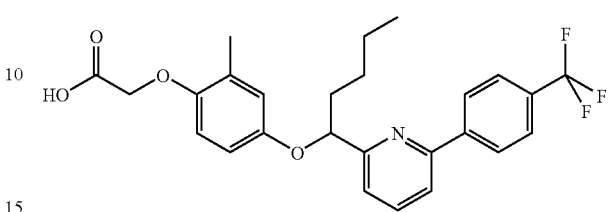

A stirred solution of ethyl [(4-\{[1-(6-bromo-2-pyridinyl)butyl]oxy\}-2-methylphenyl)oxy]acetate (50 mg, 0.12 mmol) in DME (0.5 mL) was treated with phenyl 4-(trifluoromethyl)benzeneboronic acid (23 mg, 0.12 mmol) followed by Pd(PPh$_3$)$_4$ (14 mg, 0.01 mmol) and a solution of Na$_2$CO$_3$ (38 mg, 0.36 mmol) in water (0.5 mL), and the resulting mixture was heated at 70° C. for 18 hours under nitrogen. The solvent was then removed under vacuum and the resulting mixture acidified with aqueous HCl (2M) and then partitioned between water and EtOAc, the layers separated and the organic layer reduced to an oil. Purification by mass directed auto-prep HPLC afforded the title compound (12 mg).

LC/MS: m/z 459.9 [M+H]$^+$, R$_t$ 4.30 min.

$^1$H NMR (400 MHz; CDCl$_3$) δ: 0.97 (3H, t, J 7.5 Hz), 1.56 (2H, m), 1.97 (2H, m), 2.19 (3H, s), 4.53 (2H, s), 5.23 (1H, dd, J 6.5, 6.5 Hz), 6.55 (1H, d, J 9.0 Hz), 6.59 (1H, dd, J 9.0, 3.0 Hz), 6.78 (1H, d, 3.0 Hz), 7.37 (1H, d, 7.5 Hz), 7.61 (1H, d, 7.5 Hz), 7.72 (3H, m), 8.13 (2H, d, 8.5 Hz).

EXAMPLE 23

(\{4-[(1-\{6-[4-(Trifluoromethyl)phenyl]-2-pyridinyl\}pentyl)oxy]phenyl\}oxy)acetic acid

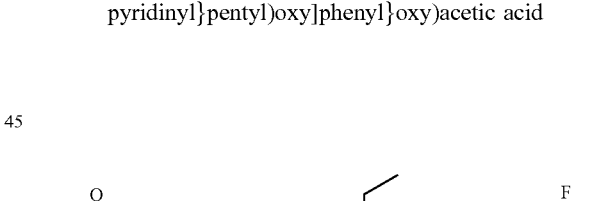

Prepared from ethyl (\{4-[(1-\{6-[4-(trifluoromethyl)phenyl]-2-pyridinyl\}pentyl)oxy]phenyl\}oxy)acetate (42 mg, 0.09 mmol) according to the procedure used for the preparation of Example 21 to give the title compound as a gum (40 mg).

LC/MS: m/z 459.9 [M+H]$^+$, R$_t$ 4.31 min.

$^1$H NMR (400 MHz; MeOD-d$^4$) δ: 0.92 (3H, t, J 7.5 Hz), 1.34-1.60 (4H, m), 2.00 (2H, m), 4.51 (2H, s), 5.25 (1H, dd, J 7.5, 5.5 Hz), 6.77 (2H, m), 6.82 (2H, m), 7.41 (1H, dd, J 7.5, 1.5 Hz), 7.78 (2H, d, J 8.0 Hz), 7.78-7.86 (2H, m), 8.13 (2H, d, J 8.0 Hz).

EXAMPLE 24

3-({4-[(1-{6-[4-(Trifluoromethyl)phenyl]-2-pyridinyl}pentyl)oxy]phenyl}propanoic acid

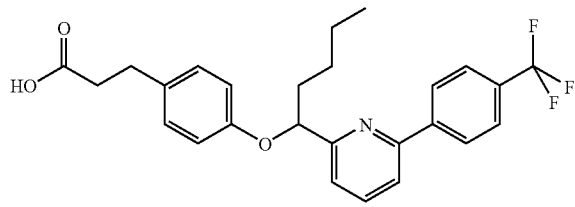

To a stirred solution of ethyl 3-{4-[(1-{6-[4-(trifluoromethyl)phenyl]-2-pyridinyl}pentyl)oxy]phenyl}propanoate (92 mg, 0.19 mmol) in THF (3 mL) and methanol (3 mL) was added, drop-wise, aqueous NaOH (2M, 3 mL). After 17 hours the mixture was concentrated under vacuum and the solid residue acidified with aqueous HCl (2M, 3.5 mL), diluted with water (10 mL) and extracted with DCM (2×10 mL). The combined organic layer was washed with brine (20 mL), dried (MgSO$_4$) and concentrated under vacuum. The acid was loaded onto a PE-AX isolute SPE cartridge (pre-conditioned with 1 column volume of methanol) in 9 mL of methanol and a few drops of Et$_3$N. The cartridge was washed with 3 column volumes of methanol followed by 10% aqueous HCl (2M) in methanol (2×5 mL) and 20% aqueous HCl (2M) in methanol (2×5 mL), yielding the title compound (38 mg).

LC/MS: m/z 458.0 [M+H]$^+$, R$_t$ 4.11 min.

$^1$H NMR (400 MHz; MeOD-d$^4$) δ: 0.90 (3H, t, J 7.0 Hz), 1.32-1.59 (4H, m), 1.94-2.05 (2H, m), 2.47 (2H, t, J 7.5 Hz), 2.76 (2H, t, J 7.5 Hz), 5.29 (1H, dd, 6.5, 5.5 Hz), 6.78 (2H, d, 8.5 Hz), 7.01 (2H, d, 8.5 Hz), 7.39 (1H, d, J 7.5 Hz), 7.78 (4H, m), 8.21 (2H, d, J 8.0 Hz).

General Procedure for the Preparation of Examples 25-34

A stirred solution of ethyl [(4-{[1-(6-bromo-2-pyridinyl)pentyl]oxy}-2-methylphenyl)oxy]acetate (50 mg, 0.12 mmol) in DME (0.5 mL) was treated with the appropriate aryl boronic acid (0.12 mmol) followed by Pd(PPh$_3$)$_4$ (13 mg, 0.01 mmol) and a solution of Na$_2$CO$_3$ (37 mg, 0.34 mmol) in water (0.25 mL). The reaction mixture was heated at 70° C. for 18 hours under nitrogen, allowed to cool to rt and then reduced under vacuum (Genevac). The residue was loaded in the minimum volume of methanol onto a SPE (C18 cartridge) (pre-conditioned with 1 column volume of methanol and then 1 column volume of 5% MeCN in water) eluting with 5% MeCN in water, then MeCN followed by methanol to give the crude product. Further purification by mass directed auto-prep HPLC afforded the title compounds.

EXAMPLE 25

{[4-({1-[6-(4-Chlorophenyl)-2-pyridinyl]pentyl}oxy)-2-methylphenyl]oxy}acetic acid

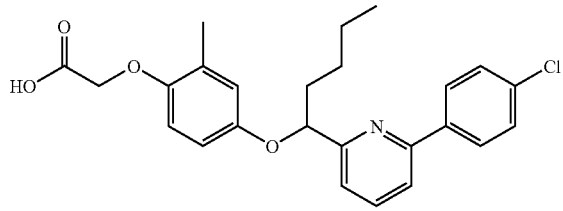

LC/MS: m/z 437.9 [M−H]$^+$, R$_t$ 4.45 min.

$^1$H NMR (400 MHz; CDCl$_3$) δ: 0.91 (3H, t, J 7.5 Hz), 1.32-1.61 (4H, m), 1.90-2.05 (2H, m), 2.19 (3H, s), 4.53 (2H, s), 5.21 (1H, dd, J 7.5, 5.5 Hz), 6.54 (1H, d, J 9.0 Hz), 6.58 (1H, dd, J 9.0, 3.0 Hz), 6.77 (1H, d, J 3.0 Hz), 7.32 (1H, d, J 8.0 Hz), 7.44 (2H, d, J 8.5 Hz), 7.54 (1H, d, J 8.0 Hz), 7.68 (1H, t, J 8.0 Hz), 7.95 (2H, d, J 8.5 Hz).

EXAMPLE 26

({2-Methyl-4-[(1-{6-[4-(methyloxy)phenyl]-2-pyridinyl}pentyl)oxy]phenyl}oxy)acetic acid

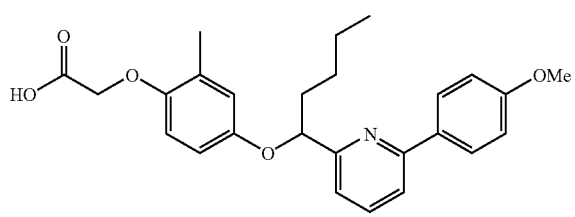

LC/MS: m/z 436.0 [M+H]$^+$, R$_t$ 4.18 min.

$^1$H NMR (400 MHz; CDCl$_3$) δ: 0.90 (3H, t, J 7.5 Hz), 1.31-1.62 (4H, m), 1.90-2.06 (2H, m), 2.19 (3H, s), 3.87 (3H, s), 4.53 (2H, s), 5.21 (1H, dd, J 8.0, 5.0 Hz), 6.55 (1H, d, J 9.0 Hz), 6.60 (1H, dd, J 9.0, 3.0 Hz), 6.78 (1H, d, J 3.0 Hz), 7.01 (2H, d, J 9.0 Hz), 7.26 (1H, d, J 7.5 Hz), 7.51 (1H, d, J 7.5 Hz), 7.66 (1H, t, J 7.5 Hz), 7.95 (2H, d, J 9.0 Hz).

EXAMPLE 27

({4-[(1-{6-[4-(Ethyloxy)phenyl]-2-pyridinyl}pentyl)oxy]-2-methylphenyl}oxy)acetic acid

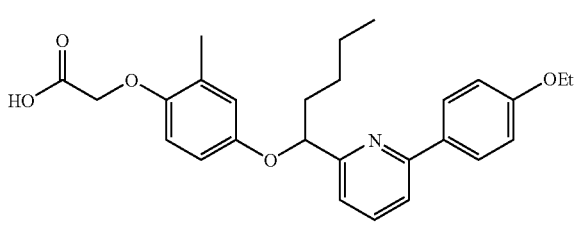

LC/MS: m/z 449.9 [M+H]$^+$, R$_t$ 4.32 min.

$^1$H NMR (400 MHz; CDCl$_3$) δ: 0.90 (3H, t, J 7.5 Hz) 1.32-1.62 (4H, m), 1.45 (3H, t, J 7.0 Hz), 1.90-2.05 (2H, m), 2.17 (3H, s), 4.10 (2H, q, J 7.0 Hz), 4.50 (2H, s), 5.19 (1H, dd, J 8.0, 5.0 Hz), 6.54 (1H, d, J 9.0 Hz), 6.58 (1H, dd J 9.0, 3.0), 6.77 (1H, d, J 3.0), 6.99 (2H, d, J 9.0 Hz), 7.23 (1H, d, J 7.5 Hz), 7.49 (1H, d, J 7.5 Hz), 7.63 (1H, t, J 7.5 Hz), 7.94 (2H, d, J 9.0 Hz).

EXAMPLE 28

{[2-Methyl-4-({1-[6-(4-methylphenyl)-2-pyridinyl]pentyl}oxy)phenyl]oxy}acetic acid

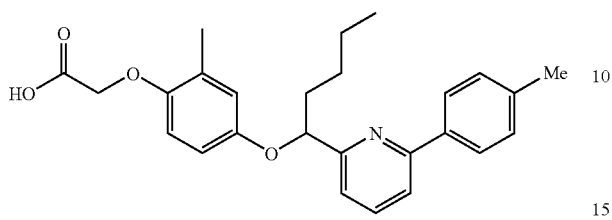

LC/MS: m/z 419.9 [M+H]⁺, R_t 4.34 min.

$^1$H NMR (400 MHz; CDCl$_3$) δ: 0.90 (3H, t, 7.0 Hz), 1.32-1.61 (4H, m), 1.90-2.06 (2H, m), 2.19 (3H, s), 2.41 (3H, s), 4.52 (2H, s), 5.21 (1H, dd, J 8.0, 5.0 Hz), 6.54 (1H, d, J 9.0 Hz), 6.59 (1H, dd, J 9.0, 3.0 Hz), 6.78 (1H, d, J 3.0 Hz), 7.27 (1H, dd, J 8.0, 1.0 Hz), 7.28 (2H, d, J 8.0 Hz), 7.53 (1H, dd, J 8.0, 1.0 Hz), 7.65 (1H, t, J 8.0 Hz), 7.89 (2H, d, J 8.0 Hz).

EXAMPLE 29

{[4-({1-[6-(3,4-Dichlorophenyl)-2-pyridinyl]pentyl}oxy)-2-methylphenyl]oxy}acetic acid

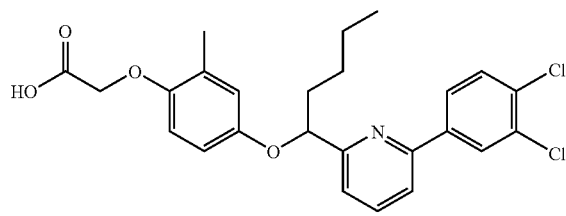

LC/MS: m/z 473.8 [M+H]⁺, R_t 4.82 min.

$^1$H NMR (400 MHz; CDCl$_3$) δ: 0.91 (3H, t, J 7.0 Hz), 1.33-1.61 (4H, m), 1.98 (2H, m), 2.20 (3H, s), 4.54 (2H, s), 5.20 (1H, dd, J 6.5, 6.5 Hz), 6.55 (1H, d, J 9.0 Hz), 6.58 (1H, d, J 9.0, 2.5 Hz), 6.77 (1H, d, J 2.5 Hz), 7.34 (1H, d, J 8.0 Hz), 7.54 (2H, d, J 8.5 Hz), 7.69 (1H, t, J 8.0 Hz), 7.83 (1H, dd, J 8.5, 2.0 Hz), 8.14 (1H, d, J 2.0 Hz).

EXAMPLE 30

({2-Methyl-4-[(1-{6-[3-(trifluoromethyl)phenyl]-2-pyridinyl}pentyl)oxy]phenyl}oxy)acetic acid

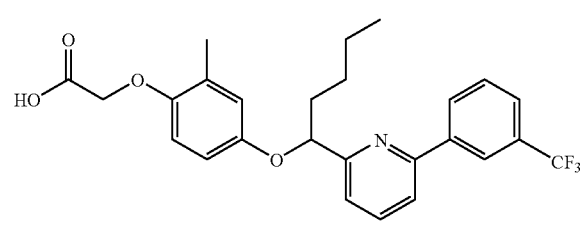

LC/MS: m/z 473.9 [M+H]⁺, R_t 4.50 min.

$^1$H NMR (400 MHz; CDCl$_3$) δ: 0.91 (3H, t, J 7.0 Hz), 1.34-1.62 (4H, m), 1.96-2.04 (2H, m), 2.19 (3H, s), 4.54 (2H, s), 5.22 (1H, m), 6.55 (1H, d, J 9.0 Hz), 6.60 (1H, dd, J 9.0, 3.0 Hz), 6.78 (1H, d, J 3.0 Hz), 7.36 (1H, d, J 7.5 Hz), 7.60 (1H, m), 7.61 (1H, d, J 8.0 Hz), 7.67 (1H, d, 8.0 Hz) 7.72 (1H, t, J 8.0 Hz), 8.20 (1H, d, J 8.0 Hz), 8.28 (1H, s).

EXAMPLE 31

[(2-Methyl-4-{[1-(6-phenyl-2-pyridinyl)pentyl]oxy}phenyl)oxy]acetic acid

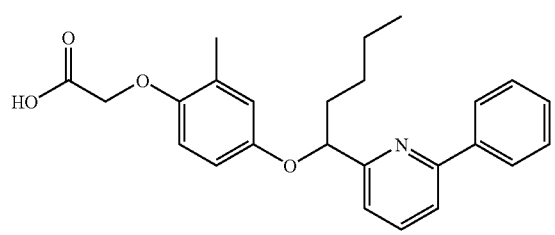

LC/MS: m/z 406.0 [M+H]⁺, R_t 4.20 min.

$^1$H NMR (400 MHz; CDCl$_3$) δ: 0.91 (3H, t, J 7.0 Hz), 1.32-1.62 (4H, m), 1.92-2.06 (2H, m), 2.18 (3H, s), 4.49 (2H, s), 5.21 (1H, dd, J 7.5, 5.0 Hz), 6.53 (1H, d, J 9.0 Hz), 6.59 (1H, dd, J 9.0, 3.0 Hz), 6.77 (1H, d, J 3.0 Hz), 7.30 (1H, d, 8.0 Hz), 7.41 (1H, m), 7.48 (2H, m), 7.56 (1H, dd, J 8.0, 1.0 Hz), 7.67 (1H, t, J 8.0 Hz), 8.00 (2H, m).

EXAMPLE 32

{[4-({1-[6-(4-Acetylphenyl)-2-pyridinyl]pentyl}oxy)-2-methylphenyl]oxy}acetic acid

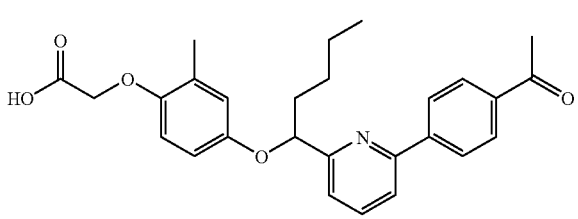

LC/MS: m/z 448.1 [M+H]⁺, R_t 3.93 min.

$^1$H NMR (400 MHz; CDCl$_3$) δ: 0.91 (3H, t, J 7.0 Hz), 1.32-1.63 (4H, m), 2.00 (2H, m), 2.19 (3H, s), 2.66 (3H, s), 4.53 (2H, s), 5.22 (1H, m), 6.55 (1H, d, J 9.0 Hz), 6.60 (1H, dd, J 9.0, 3.0 Hz), 6.78 (1H, d, J 3.0 Hz), 7.36 (1H, dd, J 7.5, 1.0 Hz), 7.63 (1H, dd, J 7.5, 1.0 Hz), 7.72 (1H, t, J 7.5 Hz), 8.07 (2H, d, J 8.5 Hz), 8.12 (2H, d, J 8.5 Hz).

EXAMPLE 33

{[4-({1-[6-(4-Fluorophenyl)-2-pyridinyl]pentyl}oxy)-2-methylphenyl]oxy}acetic acid

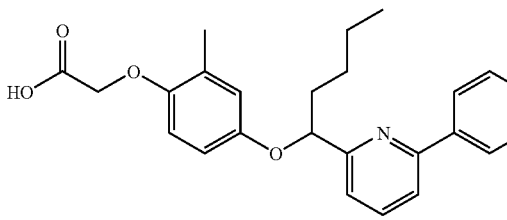

LC/MS: m/z 424.1 [M+H]$^+$, R$_t$ 4.16 min.

$^1$H NMR (400 MHz; CDCl$_3$) δ: 0.91 (3H, t, J 7.0 Hz), 1.32-1.61 (4H, m), 1.99 (2H, m), 2.18 (3H, s), 4.51 (2H, s), 5.19 (1H, dd, J 7.5, 5.5 Hz), 6.53 (1H, d, J 9.0 Hz), 6.58 (1H, dd, J 9.0, 3.0 Hz), 6.77 (1H, d, J 3.0 Hz), 7.16 (2H, m), 7.30 (1H, d, J 7.5 Hz), 7.52 (1H, d, J 7.5 Hz), 7.67 (1H, t, J 7.5 Hz), 7.98 (2H, m).

EXAMPLE 34

{[4-({1-[6-(4-Cyanophenyl)-2-pyridinyl]pentyl}oxy)-2-methylphenyl]oxy}acetic acid

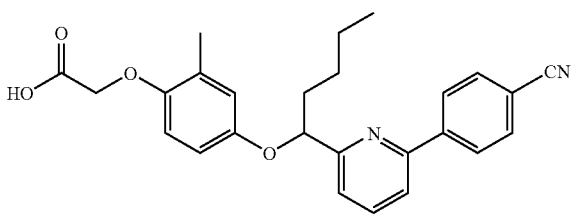

LC/MS: m/z 431.1 [M+H]$^+$, R$_t$ 4.02 min.

$^1$H NMR (400 MHz; CDCl$_3$) δ: 0.91 (3H, t, 7.0 Hz), 1.32-1.61 (4H, m), 1.99 (2H, m), 2.19 (3H, s), 4.53 (2H, s), 5.21 (1H, dd, J 6.5, 6.5 Hz), 6.54 (1H, d, J 9.0 Hz), 6.58 (1H, dd, J 9.0, 2.5 Hz), 6.77 (1H, d, J 2.5 Hz), 7.39 (1H, d, J 7.0 Hz), 7.62 (1H, d, J 8.0 Hz), 7.74 (1H, m), 7.77 (2H, d, J 8.5 Hz), 8.14 (2H, dd, J 8.5 Hz).

EXAMPLE 35

({2-Methyl-4-[(1-{6-[4-(trifluoromethyl)phenyl]-2-pyridinyl}hexyl)oxy]phenyl}oxy)acetic acid

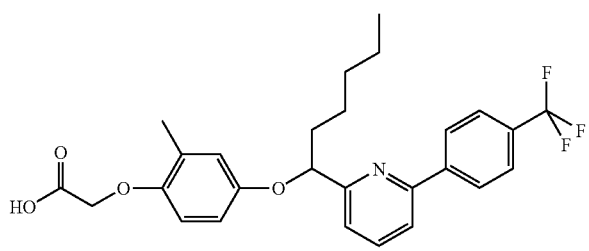

To a solution of ethyl ({2-methyl-4-[(1-{6-[4-(trifluoromethyl)phenyl]-2-pyridinyl}hexyl)oxy]phenyl}oxy)acetate (80 mg, 0.16 mmol) in MeOH (2 mL) and THF (2 mL) at rt was added aqueous NaOH (2M, 1 mL, 2.0 mmol) and the resulting mixture stirred for 2.5 hours. The solvents were then removed under vacuum and the residue partitioned between DCM (20 mL) and aqueous HCl (2M, 20 mL), the layers separated and the aqueous re-extracted with DCM (20 mL). The combined organic solution was passed through a hydrophobic frit and then reduced affording the title compound as colourless oil (57 mg).

LC/MS: m/z 488.3 [M+H]$^+$, R$_t$ 4.54 min.

$^1$H NMR (400 MHz; CDCl$_3$) δ: 0.88 (3H, t, J 7.0 Hz), 1.27-1.40 (4H, m), 1.41-1.64 (2H, m), 1.99 (2H, m), 2.20 (3H, s), 4.55 (2H, s), 5.25 (1H, dd, J 6.5, 6.5 Hz), 6.56 (1H, d, J 9.0 Hz), 6.60 (1H, dd, J 9.0 Hz, 3.0 Hz), 6.78 (1H, d, J 3 Hz), 7.38 (1H, d, J 7.5 Hz), 7.62 (1H, d, J 7.5 Hz), 7.74 (1H, t, J 7.5 Hz), 7.74 (2H, d, J 8.0 Hz), 8.13 (2H, d, J 8.0 Hz).

EXAMPLE 36

({2-Methyl-4-[(4-methyl-1-{6-[4-(trifluoromethyl)phenyl]-2-pyridinyl}pentyl)oxy]phenyl}oxy)acetic acid

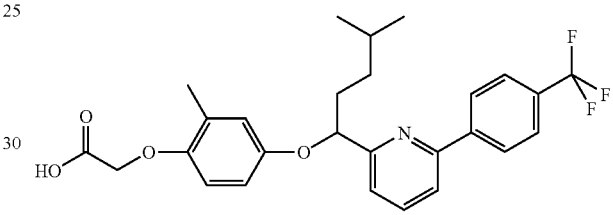

Prepared from ethyl ({2-methyl-4-[(4-methyl-1-{6-[4-(trifluoromethyl)phenyl]-2-pyridinyl}pentyl)oxy]phenyl}oxy)acetate (15 mg, 0.03 mmol) according to the procedure used for the preparation of Example 35 to give the title compound as a colourless oil (10 mg).

LC/MS: m/z 488.1 [M+H]$^+$, R$_t$ 4.49 min.

$^1$H NMR (400 MHz; CDCl$_3$) δ: 0.89 (3H, d, J 6.5 Hz), 0.90 (3H, d, J 6.5 Hz), 1.31-1.42 (1H, m), 1.43-1.54 (1H, m), 1.55-1.56 (1H, m), 2.00 (2H, m), 2.20 (3H, s), 4.55 (2H, s), 5.26 (1H, m), 6.56 (1H, d, J 9.0 Hz), 6.61 (1H, dd, J 9.0, 3.0 Hz), 6.79 (1H, d, J 3.0 Hz), 7.40 (1H, d, J 7.5 Hz), 7.63 (1H, d, J 7.5 Hz), 7.75 (2H, d, J 8.5 Hz), 7.76 (1H, m), 8.13 (2H, d, J 8.5 Hz).

EXAMPLE 37

({2-Methyl-4-[(3-methyl-1-{6-[4-(trifluoromethyl)phenyl]-2-pyridinyl}butyl)oxy]phenyl}oxy)acetic acid

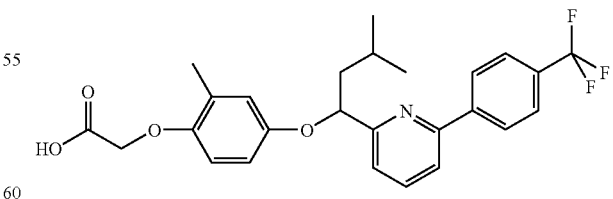

Prepared from ethyl ({2-methyl-4-[(3-methyl-1-{6-[4-(trifluoromethyl)phenyl]-2-pyridinyl}butyl)oxy]phenyl}oxy)acetate (132 mg, 0.26 mmol) according to the procedure used for the preparation of Example 35 to give the title compound as a pale orange solid (124 mg).

LC/MS: m/z 474.1 [M+H]$^+$, R$_t$ 4.25 min.

¹H NMR (400 MHz; CDCl₃) δ: 1.03 (6H, m), 1.71-2.05 (3H, m), 2.20 (3H, s), 4.55 (2H, s), 5.57 (1H, m), 6.57 (1H, d, J 9.0 Hz), 6.66 (1H, dd, J 8.5 Hz, 3.0 Hz), 6.81 (1H, d, J 3.0 Hz), 7.47 (1H, d, J 8.0 Hz), 7.66 (1H, d, J 8.0 Hz), 7.77 (2H, d, J 8.0 Hz), 7.83 (1H, t, J 8.0 Hz), 8.16 (2H, d, J 8.0 Hz).

General Procedure for Examples 38-40

A stirred solution of ethyl [(4-{[1-(3-bromophenyl)pentyl]oxy}-2-methylphenyl)oxy]acetate (50 mg, 0.11 mmol) in DME (0.5 mL) was treated with the appropriate aryl boronic acid (0.11 mmol) followed by Pd(PPh₃)₄ (13 mg, 0.01 mmol) and a solution of Na₂CO₃ (37 mg, 0.33 mmol) in water (0.25 mL). The reaction mixture was heated at 70° C. for 18 hours under nitrogen, allowed to cool to rt and then reduced under vacuum (Genevac). The residue was loaded in the minimum volume of methanol onto a SPE (C18 cartridges) (pre-conditioned with 1 column volume of methanol and then 1 column volume of 5% MeCN in water) eluting with 5% MeCN in water, then MeCN followed by methanol to give the crude product. Further purification by mass directed auto-prep HPLC afforded the title compounds.

EXAMPLE 38

[(4-{[1-(3-Biphenylyl)pentyl]oxy}-2-methylphenyl) oxy]acetic acid

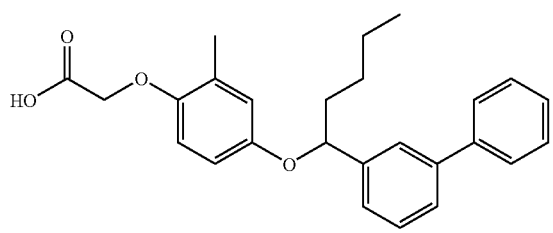

LC/MS: m/z 422.1 [M+H]⁺, R$_t$ 4.24 min.
¹H NMR (400 MHz; CDCl₃) δ: 0.89 (3H, t, J 7.0 Hz), 1.29-1.42 (3H, m), 1.44-1.57 (1H, m), 1.75-1.87 (1H, m), 1.93-2.05 (1H, m), 2.09 (3H, s), 4.35 (2H, s), 4.99 (1H, dd, J 8.0, 5.0 Hz), 6.46 (1H, d, J 9.0 Hz), 6.53 (1H, d, 9.0, 3.0 Hz), 6.69 (1H, d, 3.0 Hz), 7.24-7.46 (6H, m), 7.51-7.58 (3H, m).

EXAMPLE 39

{[4-({1-[4'-(Ethyloxy)-3-biphenylyl]pentyl}oxy)-2-methylphenyl]oxy}acetic acid

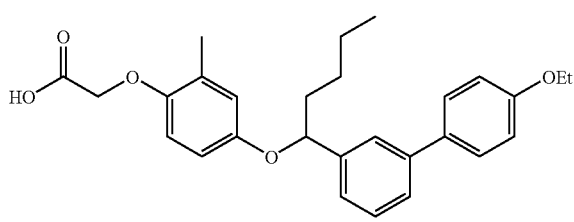

LC/MS: m/z 466.1 [M+NH₄]⁺, R$_t$ 4.29 min.
¹H NMR (400 MHz; CDCl₃) δ: 0.89 (3H, t, J 7.0 Hz), 1.35 (3H, m), 1.42 (3H, t, J 7.0 Hz), 1.46-1.58 (1H, m), 1.75-1.86 (1H, m), 1.92-2.03 (1H, m), 2.10 (3H, s), 4.05 (2H, q, J 7.0 Hz), 4.38 (2H, s), 4.98 (1H, dd, J 8.0, 5.5 Hz), 6.47 (1H, d, J 9.0 Hz), 6.54 (1H, dd, J 9.0, 2.5 Hz), 6.70 (1H, d, J 2.5 Hz), 6.93 (2H, d, J 9.0 Hz), 7.23 (1H, d, J 7.5 Hz), 7.32 (1H, t, J 7.5 Hz), 7.40 (1H, d, J 7.5 Hz), 7.47 (2H, d, J 9.0 Hz), 7.49 (1H, m).

EXAMPLE 40

[(4-{[1-(4'-Cyano-3-biphenylyl)pentyl]oxy}-2-methylphenyl)oxy]acetic acid

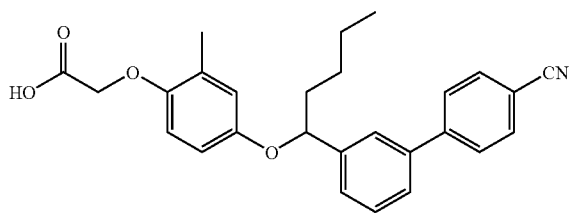

LC/MS: m/z 447.3 [M+NH₄]⁺, R$_t$ 4.20 min.
¹H NMR (400 MHz; CDCl₃) δ: 0.90 (3H, t, 7.0 Hz), 1.36 (3H, m), 1.45-1.57 (1H, m), 1.81 (1H, m), 1.98 (1H, m), 2.11 (3H, s), 4.39 (2H, s), 5.02 (1H, dd, J 8.0, 5.0 Hz), 6.48 (1H, d, J 9.0 Hz), 6.52 (1H, dd, J 9.0, 2.5 Hz), 6.70 (1H, d, J 2.5 Hz), 7.34-7.47 (3H, m), 7.53 (1H, s), 7.62 (2H, d, J 8.0 Hz), 7.68 (2H, d, J 8.0 Hz).

General Procedure for Examples 41-45

A stirred solution of ethyl [(4-{[1-(6-bromo-2-pyridinyl)pentyl]oxy}-2-ethylphenyl)oxy]acetate (50 mg, 0.11 mmol) in DME (0.5 mL) was treated with the appropriate aryl boronic acid (0.11 mmol) followed by Pd(PPh₃)₄ (13 mg, 0.01 mmol) and a solution of Na₂CO₃ (37 mg, 0.33 mmol) in water (0.25 mL). The reaction mixture was heated at 70° C. for 18 hours under nitrogen, allowed to cool to rt and then reduced under vacuum (Genevac). The residue was loaded in the minimum volume of methanol onto a SPE (C18 cartridges) (pre-conditioned with 1 column volume of methanol and then 1 column volume of 5% MeCN in water) eluting with 5% MeCN in water, then MeCN followed by methanol to give the crude product. Further purification by mass directed auto-prep HPLC afforded the title compounds.

EXAMPLE 41

[(2-Ethyl-4-{[1-(6-phenyl-2-pyridinyl)pentyl] oxy}phenyl)oxy]acetic acid

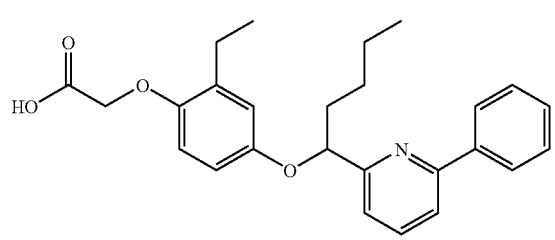

LC/MS: m/z 420.2 [M+H]⁺, R$_t$ 4.33 min.
¹H NMR (400 MHz; CDCl₃) δ: 0.90 (3H, t, J 7.5 Hz), 1.07 (3H, t, J 7.5 Hz), 1.32-1.62 (4H, m), 1.99 (2H, m), 2.51 (2H, q, J 7.5 Hz), 4.37 (2H, s), 5.21 (1H, m), 6.48 (1H, d, J 9.0 Hz), 6.55 (1H, d, J 9.0 Hz), 6.76 (1H, dd, J 9.0, 3.0 Hz), 7.28 (1H, d, J 7.5 Hz), 7.40 (1H, m), 7.46 (2H, m), 7.53 (1H, d, J 7.5 Hz), 7.62 (1H, t, J 7.5 Hz), 7.99 (2H, m).

EXAMPLE 42

{[4-({1-[6-(4-Chlorophenyl)-2-pyridinyl]pentyl}oxy)-2-ethylphenyl]oxy}acetic acid

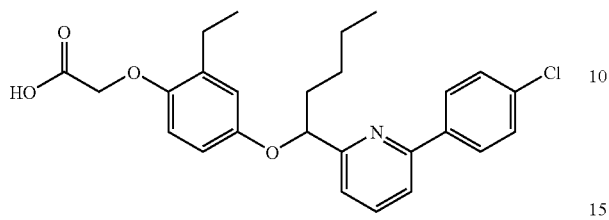

LC/MS: m/z 454.1 [M+H]$^+$, R$_t$ 4.55 min.
$^1$H NMR (400 MHz; CDCl$_3$) δ: 0.90 (3H, t, J 7.5 Hz), 1.10 (3H, t, J 7.5 Hz), 1.32-1.61 (4H, m), 1.99 (2H, m), 2.55 (2H, q, J 7.5 Hz), 4.45 (2H, s), 5.20 (1H, dd, J 6.5, 6.5 Hz), 6.51 (1H, d, J 9.0 Hz), 6.56 (1H, dd, J 9.0, 3.0 Hz), 6.78 (1H, d, J 3.0 Hz), 7.30 (1H, d, J 7.5 Hz), 7.44 (2H, d, J 8.5 Hz), 7.52 (1H, d, J 7.5 Hz), 7.65 (1H, t, J 7.5 Hz), 7.95 (2H, d, J 8.5 Hz).

EXAMPLE 43

({2-Ethyl-4-[(1-{6-[4-(ethyloxy)phenyl]-2-pyridinyl}pentyl)oxy]phenyl}oxy)acetic acid

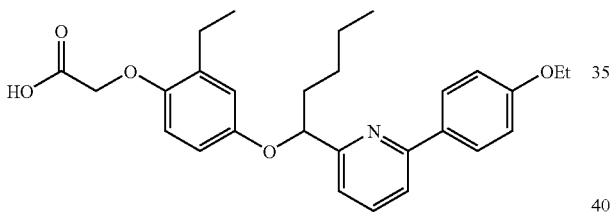

LC/MS: m/z 464.2 [M+H]$^+$, R$_t$ 4.39 min.
$^1$H NMR (400 MHz; CDCl$_3$) δ: 0.90 (3H, t, J 7.0 Hz), 1.08 (3H, t, J 7.5 Hz), 1.44 (3H, t, J 7.0 Hz), 1.32-1.61 (4H, m), 1.98 (2H, m), 2.53 (2H, q, J 7.5 Hz), 4.09 (2H, q, J 7.0 Hz), 4.41 (2H, s), 5.19 (1H, dd, J 7.5, 5.0 Hz), 6.49 (1H, d, J 9.0 Hz), 6.56 (1H, dd, J 9.0, 3.0 Hz), 6.77 (1H, d, J 3.0 Hz), 6.98 (2H, d, J 9.0 Hz), 7.22 (1H, d J 7.5 Hz), 7.47 (1H, d, J 7.5 Hz), 7.59 (1H, t, J 7.5 Hz), 7.94 (2H, d, J 9.0 Hz).

EXAMPLE 44

{[4-({1-[6-(4-Cyanophenyl)-2-pyridinyl]pentyl}oxy)-2-ethylphenyl]oxy}acetic acid

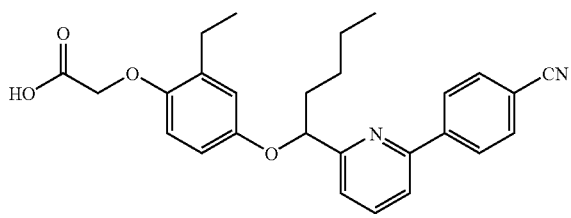

LC/MS: m/z 445.0 [M+H]$^+$, R$_t$ 4.09 min.
$^1$H NMR (400 MHz; CDCl$_3$) δ: 0.90 (3H, t, J 7.0 Hz), 1.09 (3H, t, J 7.5 Hz), 1.32-1.62 (4H, m), 1.99 (2H, m), 2.54 (2H, q, J 7.5 Hz), 4.43 (2H, s), 5.21 (1H, dd, J 6.0 Hz), 6.50 (1H, d, J 9.0 Hz), 6.54 (1H, dd, J 9.0, 2.5 Hz), 6.77 (1H, d, J 2.5 Hz), 7.38 (1H, d, J 8.0 Hz), 7.60 (1H, d, J 8.0 Hz), 7.71 (1H, t, J 8.0 Hz), 7.70 (2H, d, J 8.5 Hz), 8.13 (2H, d, J 8.5 Hz).

EXAMPLE 45

({2-Ethyl-4-[(1-{6-[4-(trifluoromethyl)phenyl]-2-pyridinyl}pentyl)oxy]phenyl}oxy)acetic acid

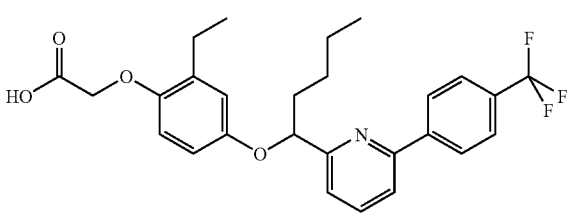

LC/MS: m/z 488.1 [M+H]$^+$, R$_t$ 4.51 min.
$^1$H NMR (400 MHz; CDCl$_3$) δ: 0.91 (3H, t, J 7.0 Hz), 1.13 (3H, t, J 7.5 Hz), 1.32-1.63 (4H, m), 2.00 (2H, m), 2.59 (2H, q, J 7.5 Hz), 4.52 (2H, s), 5.23 (1H, dd, J 6.5, 6.5 Hz), 6.54 (1H, d, J 9.0 Hz), 6.58 (1H, dd, J 9.0, 3.0 Hz), 6.80 (1H, d, J 3.0 Hz), 7.37 (1H, d, J 8.0 Hz), 7.61 (1H, d, J 8.0 Hz), 7.72 (1H, t, J 8.0 Hz), 7.73 (2H, d, J 8.0 Hz), 8.13 (2H, d, J 8.0 Hz).

EXAMPLE 46

4-{4-[(1-{6-[4-(Trifluoromethyl)phenyl]-2-pyridinyl}pentyl)oxy]phenyl}butanoic acid

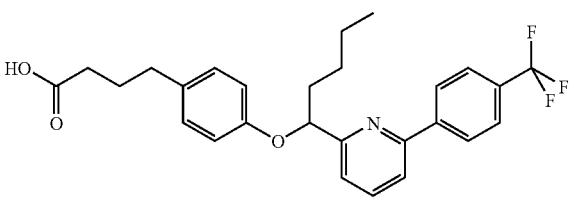

To a stirred solution of 2-(trimethylsilyl)ethyl 4-{4-[(1-{6-[4-(trifluoromethyl)phenyl]-2-pyridinyl}pentyl)oxy]phenyl}butanoate (42 mg, 0.07 mmol) in THF at rt was added, drop-wise, TBAF (70 μL of a 1.0M solution in THF, 0.07 mmol) and the mixture stirred at rt for 1.5 hours. Additional TBAF (35 μL of a 1.0M solution in THF, 0.04 mmol) was then added and the mixture left to stir at rt for 17.5 hours. The mixture was then concentrated under vacuum and the residue purified by SPE (silica, 1 g Cartridge) eluting with cyclohexane:EtOAc (gradient 25:1 to 0:1), then EtOAc:MeOH (gradient 10:1 to 0:1) to give a crude product which was purified further by mass directed auto-prep HPLC to give the title compound (6.4 mg).
LC/MS: m/z 472.15 [M+H]$^+$, R$_t$ 4.21 min.
$^1$H NMR (400 MHz; MeOD-d$^4$) δ: 0.92 (3H, t, 7.0 Hz), 1.34-1.61 (4H, m), 1.80 (2H, m), 2.00 (2H, m), 2.22 (2H, t, 7.5 Hz), 2.51 (2H, t, 7.5 Hz), 5.29 (1H, dd, 7.0, 6.0 Hz), 6.79

(2H, d, 9.0 Hz), 7.00 (2H, d, 9.0 Hz), 7.40 (1H, dd, J 7.0, 1.5 Hz), 7.75-7.85 (4H, m), 8.23 (2H, d, J 8.5 Hz).

General Procedures for Examples 47-50

Ethyl [(4-{[(1R)-1-(6-bromo-2-pyridinyl)pentyl]oxy}-2-methylphenyl)oxy]acetate (50 mg, 0.11 mmol) was dissolved in DME (0.50 mL) and then treated with the appropriate boronic acid (0.15 mmol) followed by Pd(PPh$_3$)$_4$ (13 mg, 0.01 mmol) and then a solution of Na$_2$CO$_3$ (36.5 mg, 0.34 mmol) in water (0.25 mL). The resulting mixture was then placed under nitrogen and heated at 70° C. for 18 h. The solvents were the removed under vacuum (Genevac) and the residue purified using the OPTIX-SPE (C18 cartridge, 5 g) eluting with 10-95% MeCN (+0.05% HCOOH) in H$_2$O (+0.01% HCOOH) over 15 mins to afford the desired product which, if appropriate, were further purified by mass directed autoprep HPLC.

EXAMPLE 47

{([4-({(1R)-1-[6-(4-Chlorophenyl)-2-pyridinyl]pentyl}oxy)-2-methylphenyl]oxy}acetic acid

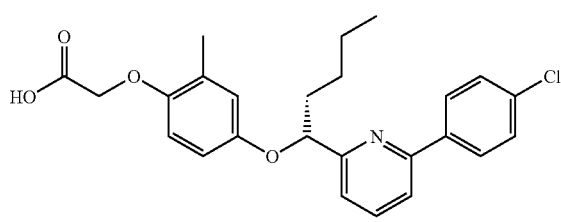

LC/MS and $^1$H NMR as described for Example 25.

Analytical chiral HPLC (25 cm Chiralpak AD) eluting with 15% IPA in heptane with 0.1% TFA, f=1.0 mL/min, wavelength 215 nm, R$_t$ 6.6 min (>99% ee).

EXAMPLE 48

{4-({(1R)-1-[6-(4-Cyanophenyl)-2-pyridinyl]pentyl}oxy)-2-methylphenyl]oxy}acetic acid

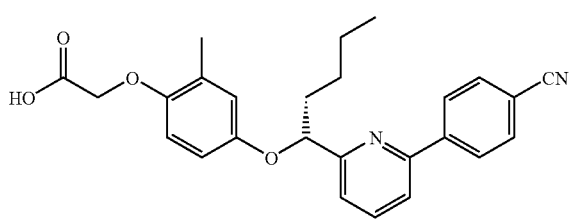

LC/MS and $^1$H NMR as described for Example 34.

Analytical chiral HPLC (25 cm Chiralpak AD) eluting with 15% IPA in heptane with 0.1% TFA, f=1.0 mL/min, wavelength 215 nm, R$_t$ 9.8 min (98.9% ee).

EXAMPLE 49

({2-Methyl-4-[((1R)-1-{6-[4-(methyloxy)phenyl]-2-pyridinyl}pentyl)oxy]phenyl}oxy)acetic acid

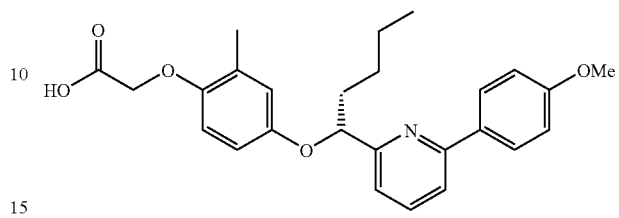

LC/MS and $^1$H NMR as described for Example 26.

Analytical chiral HPLC (25 cm Chiralpak AD) eluting with 15% IPA in heptane with 0.1% TFA, f=1.0 mL/min, wavelength 215 nm, R$_t$ 7.5 min (98.5% ee).

EXAMPLE 50

{[4-({(1R)-1-[6-(4-Acetylphenyl)-2-pyridinyl]pentyl}oxy)-2-methylphenyl]oxy}acetic acid

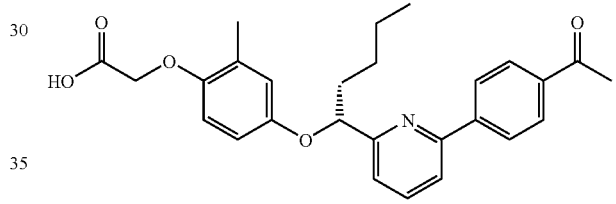

LC/MS and $^1$H NMR as described for Example 32.

Analytical chiral HPLC (25 cm Chiralpak AD) eluting with 15% IPA in heptane with 0.1% TFA, f=1.0 mL/min, wavelength 215 nm, R$_t$ 9.5 min (99.3% ee).

EXAMPLES 51

({4-[((1R)-1-{6-[4-Acetyl-3-(methyloxy)phenyl]-2-pyridinyl}pentyl)oxy]-2-methylphenyl}oxy)acetic acid

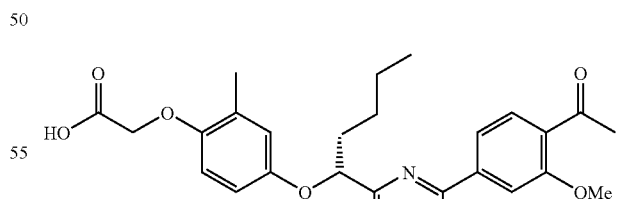

Ethyl [(4-{[(1R)-1-(6-bromo-2-pyridinyl)pentyl]oxy}-2-methylphenyl)oxy]acetate (50 mg, 0.11 mmol) was dissolved in DME (0.76 mL) and then treated with 1-[2-(methyloxy)-4-(4,4,5,5-tetramethyl-1,3,2-dioxaborolan-2-yl)phenyl]ethanone (41 mg, 0.15 mmol) followed by Pd(PPh$_3$)$_4$ (13 mg, 0.01 mmol) and then a solution of Na$_2$CO$_3$ (49 mg, 0.46 mmol) in water (0.42 mL). The resulting mixture was then placed under nitrogen and heated at 80° C. for 18 h. The solvents were the removed under vacuum (Genevac) and the residue purified by mass directed autoprep HPLC) to give the title compound as an oil (39 mg).

LC/MS: m/z 478.1 [M+H]$^+$, R$_t$ 4.04 min.

$^1$H NMR (400 MHz; CDCl$_3$) δ: 0.91 (3H, t, J 7.5 Hz), 1.33-1.44 (2H, m), 1.44-1.61 (2H, m), 1.95-2.05 (2H, m), 2.19 (3H, s), 2.66 (3H, s), 4.03 (3H, s), 4.53 (2H, s), 5.22 (1H, dd, J 6.5, 6.5 Hz), 6.55 (1H, d, J 9.0 Hz), 6.58 (1H, dd, J 9.0, 2.5 Hz), 6.78 (1H, d, J 2.5 Hz), 7.36 (1H, d, J 7.5 Hz), 7.55 (1H, dd J 8.0, 1.5 Hz), 7.61 (1H, d, J 7.5 Hz), 7.71 (1H, t, J 7.5 Hz), 7.71 (1H, d, J 1.5 Hz), 7.85 (1H, d, J 8.0 Hz).

General Procedures for Examples 52-55

The following compounds were prepared as described for Examples 47-50 except starting from ethyl [(4-{[(1S)-1-(6-bromo-2-pyridinyl)pentyl]oxy}-2-methylphenyl)oxy]acetate.

EXAMPLE 52

{[4-({(1S)-1-[6-(4-Chlorophenyl)-2-pyridinyl]pentyl}oxy)-2-methylphenyl]oxy}acetic acid

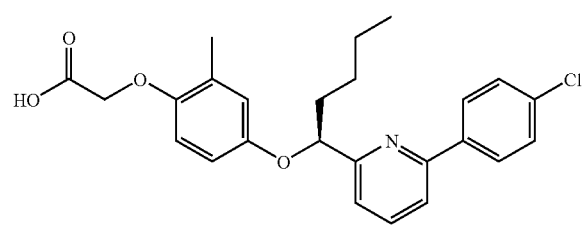

LC/MS and $^1$H NMR as described for Example 25.

Analytical chiral HPLC (25 cm Chiralpak AD) eluting with 15% IPA in heptane with 0.1% TFA, f=1.0 mL/min, wavelength 215 nm, R$_t$ 8.0 min (92.9% ee).

EXAMPLE 53

{[4-({(1S)-1-[6-(4-Cyanophenyl)-2-pyridinyl]pentyl}oxy)-2-methylphenyl]oxy}acetic acid

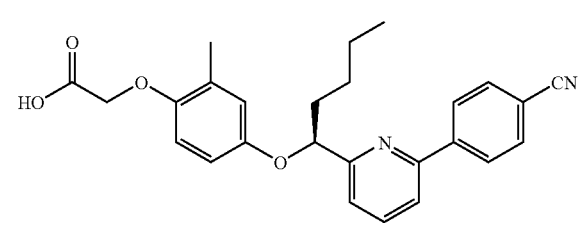

LC/MS and $^1$H NMR as described for Example 34.

Analytical chiral HPLC (25 cm Chiralpak AD) eluting with 15% IPA in heptane with 0.1% TFA, f=1.0 mL/min, wavelength 215 nm, R$_t$ 12.4 min (95.9% ee).

EXAMPLE 54

({2-Methyl-4-[((1S)-1-{6-[4-(methyloxy)phenyl]-2-pyridinyl}pentyl)oxy]phenyl}oxy)acetic acid

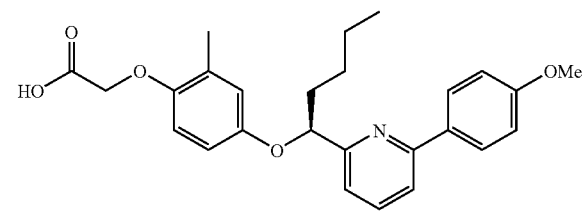

LC/MS and $^1$H NMR as described for Example 26.

Analytical chiral HPLC (25 cm Chiralpak AD) eluting with 15% IPA in heptane with 0.1% TFA, f=1.0 mL/min, wavelength 215 nm, R$_t$ 8.6 min (95.1% ee).

EXAMPLE 55

{[4-({(1S)-1-[6-(4-Acetylphenyl)-2-pyridinyl]pentyl}oxy)-2-methylphenyl]oxy}acetic acid

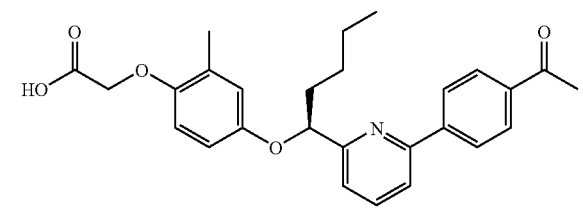

LC/MS and $^1$H NMR as described for Example 32.

Analytical chiral HPLC (25 cm Chiralpak AD) eluting with 15% IPA in heptane with 0.1% TFA, f=1.0 mL/min, wavelength 215 nm, R$_t$ 11.9 min (96.6% ee).

EXAMPLE 56

({4-[((1S)-1-{6-[4-Acetyl-3-(methyloxy)phenyl]-2-pyridinyl}pentyl)oxy]-2-methylphenyl}oxy)acetic acid

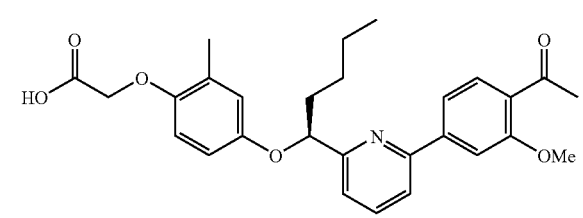

Prepared according to the procedure used to prepare Example 51 starting from ethyl [(4-{[(1S)-1-(6-bromo-2-pyridinyl)pentyl]oxy}-2-methylphenyl)oxy]acetate (50 mg, 0.11 mmol) to give the title compound (27 mg).

LC/MS and $^1$H NMR as described for Example 51.

General Procedure for Examples 57-58

A stirred solution of bromide ethyl [(4-{[(1R)-1-(6-bromo-2-pyridinyl)-3-(methyloxy)propyl]oxy}-2-methylphenyl)oxy]acetate (50 mg, 0.11 mmol) in DME (0.75 mL) was treated with the appropriate aryl boronic acid (0.15 mmol) followed by Pd(PPh$_3$)$_4$ (13 mg, 0.01 mmol) and a solution of Na$_2$CO$_3$ (48 mg, 0.46 mmol) in water (0.42 mL). The reaction mixture was heated at 80° C. for 17 h under nitrogen, allowed to cool to rt and then reduced under vacuum (Genevac). The residue was then purified using the OPTIX-SPE (C18 cartridge, 5 g) eluting with 20-75% (or 20-60%) MeCN (+0.05% HCOOH) in H$_2$O (+0.01% HCOOH) over 20 mins afforded the desired target molecules which, if appropriate, were purified further by mass directed autoprep HPLC.

EXAMPLE 57

({2-Methyl-4-[((1R)-3-(methyloxy)-1-{6-[4-(trifluoromethyl)phenyl]-2-pyridinyl}propyl)oxy]phenyl}oxy)acetic acid

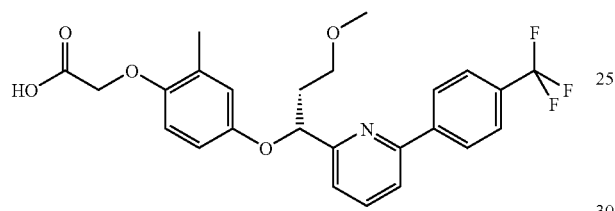

LC/MS: m/z 476.2 [M+H]$^+$, R$_t$ 3.83 min.

$^1$H NMR (400 MHz; CDCl$_3$) δ: 2.19 (3H, s), 2.17-2.28 (1H, m), 2.28-2.40 (1H, m), 3.35 (3H, s), 3.58 (1H, m), 3.68 (1H, m), 4.51 (2H, br.s), 5.39 (1H, dd, J 9.0, 4.0 Hz), 6.54 (1H, d, J 9.0 Hz), 6.60 (1H, dd, J 9.0, 3.0 Hz), 6.78 (1H, d, J 3.0 Hz), 7.37 (1H, d, J 7.5 Hz), 7.62 (1H, d, J 7.5 Hz), 7.72 (2H, d, J 8.0 Hz), 7.72 (1H, t, J 7.5 Hz), 8.14 (2H, d, J 8.0 Hz).

EXAMPLE 58

[(4-{[(1R)-1-[6-(4-Chlorophenyl)-2-pyridinyl]-3-(methyloxy)propyl]oxy}-2-methylphenyl)oxy]acetic acid

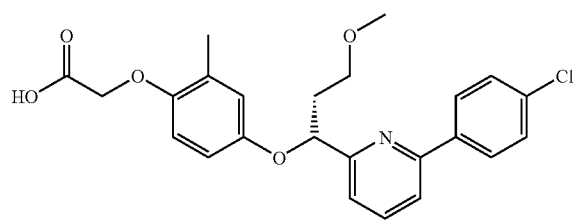

LC/MS: m/z 442.2 [M+H]$^+$, R$_t$ 3.84 min.

$^1$H NMR (400 MHz; CDCl$_3$) δ: 2.18 (3H, s), 2.14-2.26 (1H, m), 2.27-2.39 (1H, m), 3.35 (3H, s), 3.57 (1H, m), 3.67 (1H, m), 4.51 (2H, br.s), 5.36 (1H, dd, J 9.0, 4.0 Hz), 6.53 (1H, d, J 9.0 Hz), 6.59 (1H, dd, J 9.0, 2.5 Hz), 6.78 (1H, d, J 2.5 Hz), 7.32 (1H, d, J 8.0 Hz), 7.43 (2H, d, J 8.5 Hz), 7.55 (1H, d, J 8.0 Hz), 7.68 (1H, t, J 8.0 Hz), 7.96 (2H, d, J 8.5 Hz).

General Procedure for Examples 59-60

The following compounds were prepared as described for Examples 57-58 except starting from ethyl [(4-{[(1S)-1-(6-bromo-2-pyridinyl)-3-(methyloxy)propyl]oxy}-2-methylphenyl)oxy]acetate.

EXAMPLE 59

({2-Methyl-4-[((1S)-3-(methyloxy)-1-{6-[4-(trifluoromethyl)phenyl]-2-pyridinyl}propyl)oxy]phenyl}oxy)acetic acid

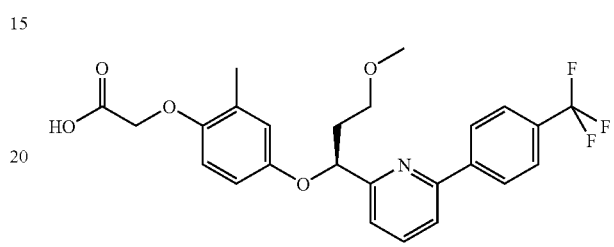

LC/MS and $^1$H NMR as described for Example 57.

EXAMPLE 60

[(4-{[(1S)-1-[6-(4-Chlorophenyl)-2-pyridinyl]-3-(methyloxy)propyl]oxy}-2-methylphenyl)oxy]acetic acid

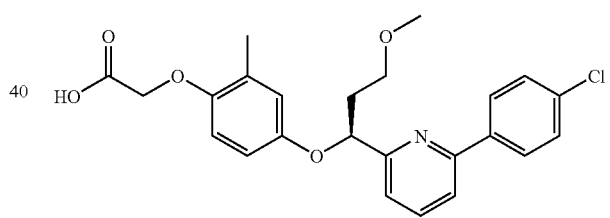

LC/MS and $^1$H NMR as described for Example 58.

General Procedure for Examples 61-65

A stirred solution of ethyl [(4-{[(1R)-1-(6-bromo-2-pyridinyl)-3-(methyloxy)propyl]oxy}-2-methylphenyl)oxy]acetate (50 mg, 0.11 mmol) in DME (0.50 mL) was treated with the appropriate aryl boronic acid (0.15 mmol) followed by Pd(PPh$_3$)$_4$ (13 mg, 0.01 mmol) and a solution of Na$_2$CO$_3$ (37 mg, 0.35 mmol) in water (0.25 mL). The reaction mixture was heated at 70° C. for 16 h under nitrogen and then allowed to cool to rt and stirred at rt for 7 h. LC/MS analysis indicated a mixture of the desired acid and the ethyl ester, so MeOH (1 mL), THF (1 mL) and aqueous sodium hydroxide (2M, 1 mL) were added and the mixture stirred at rt for 18 h. The reaction was then quenched by the addition of aqueous HCl (2N, 2 mL) and the solvents then removed under vacuum (Genevac). The residue was then dissolved in MeCN:H$_2$O (1:2, 1.8 mL) and loaded onto an SPE (C18 cartridge, 5 g) which had been pre-conditioned with 2 column volumes of MeOH and then equilibrated with 20% MeCN (+0.05% HCOOH) in H₂O (+0.01% HCOOH). Elution with 20-75% (or 20-60%) MeCN (+0.05% HCOOH) in H₂O (+0.01% HCOOH) over 20 mins afforded the desired target molecules which, if appropriate, were purified further by mass directed autoprep HPLC.

EXAMPLE 61

({4[((1R)-2-(Ethyloxy)-1-{6-[4-(trifluoromethyl)phenyl]-2-pyridinyl}ethyl)oxy]-2-methylphenyl}oxy)acetic acid

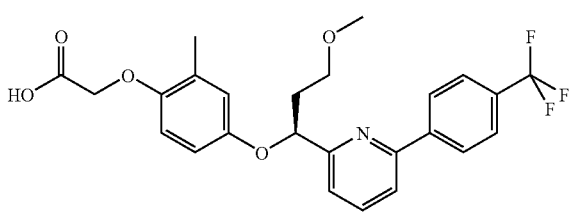

LC/MS: m/z 476.1 [M+H]$^+$, R$_t$ 4.01 min.

$^1$H NMR (400 MHz; CDCl$_3$) δ: 1.20 (3H, t, J 7.0 Hz), 2.20 (3H, s), 3.62 (2H, m), 3.91 (1H, dd, J 11.0, 7.0 Hz), 3.98 (1H, dd, J 11.0, 3.0 Hz), 4.53 (2H, s), 5.45 (1H, dd, J 7.0, 3.0 Hz), 6.55 (1H, d, J 9.0 Hz), 6.64 (1H, dd, J 9.0, 3.0 Hz), 6.83 (1H, d, J 3.0 Hz), 7.42 (1H, d, J 8.0 Hz), 7.65 (1H, d, J 8.0 Hz), 7.73 (2H, d, J 8.0 Hz), 7.74 (1H, t, J 8.0 Hz), 8.14 (2H, d, J 8.0 Hz).

Analytical chiral HPLC (25 cm Chiralcel OJ) eluting with 20% EtOH in heptane with 0.1% TFA, f=1.0 mL/min, wavelength 215 nm, R$_t$ 9.5 min (>99.9% ee).

EXAMPLE 62

({4-[((1R)-2-(Ethyloxy)-1-{6-[4-(methyloxy)phenyl]-2-pyridinyl}ethyl)oxy]-2-methylphenyl}oxy)acetic acid

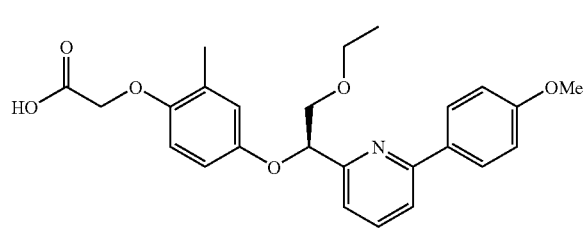

LC/MS: m/z 438.2 [M+H]$^+$, R$_t$ 3.70 min.

$^1$H NMR (400 MHz; CDCl$_3$) δ: 1.19 (3H, t, J 7.0 Hz), 2.19 (3H, s), 3.62 (2H, m), 3.89 (1H, dd, J 11.0, 7.5 Hz), 3.97 (1H, dd, J 11.0, 3.0 Hz), 4.51 (2H, s), 5.43 (1H, dd, J 7.5, 3.0 Hz), 6.54 (1H, d, J 9.0 Hz), 6.63 (1H, dd, J 9.0, 3.0 Hz), 6.82 (1H, d, J 3.0 Hz), 7.00 (2H, d, J 9.0 Hz), 7.29 (1H, d, J 8.0 Hz), 7.54 (1H, d, J 8.0 Hz), 7.65 (1H, t, J 8.0 Hz), 7.97 (2H, d, J 9.0 Hz).

Analytical chiral HPLC (25 cm Chiralpak AD) eluting with 10% EtOH in heptane with 0.1% TFA, f=1.0 mL/min, wavelength 215 nm, R$_t$ 13.9 min (>99.9% ee).

EXAMPLE 63

[(4-{[(1R)-1-[6-(4-Acetylphenyl)-2-pyridinyl]-2-(ethyloxy)ethyl]oxy}-2-methylphenyl)oxy]acetic acid

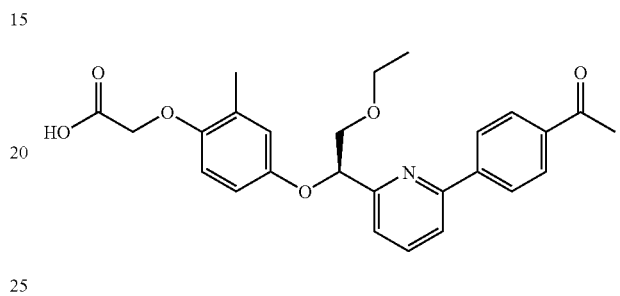

LC/MS: m/z 450.1 [M+H]$^+$, R$_t$ 3.45 min.

$^1$H NMR (400 MHz; CDCl$_3$) δ: 1.19 (3H, t, J 7.0 Hz), 2.19 (3H, s), 2.66 (3H, s), 3.62 (2H, m), 3.91 (1H, dd, J 11.0, 7.0 Hz), 3.99 (1H, dd, J 11.0, 3.0 Hz), 4.52 (2H, s), 5.45 (1H, dd, J 7.0, 3.0 Hz), 6.55 (1H, d, J 9.0 Hz), 6.64 (1H, dd, J 9.0, 3.0 Hz), 6.83 (1H, d, J 3.0 Hz), 7.41 (1H, d, J 7.5 Hz), 7.67 (1H, dd, J 7.5, 1.0 Hz), 7.73 (1H, t, J 7.5 Hz), 8.07 (2H, d, J 8.5 Hz), 8.13 (2H, d, J 8.5 Hz).

EXAMPLE 64

[(4-{[(1R)-1-[6-(4-Cyanophenyl)-2-pyridinyl]-2-(ethyloxy)ethyl]oxy}-2-methylphenyl)oxy]acetic acid

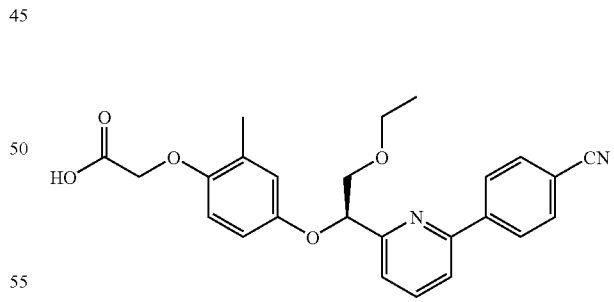

LC/MS: m/z 433.2 [M+H]$^+$, R$_t$ 3.64 min.

$^1$H NMR (400 MHz; CDCl$_3$) δ: 1.19 (3H, t, J 7.0 Hz), 2.19 (3H, s), 3.62 (2H, m), 3.90 (1H, dd, J 11.0, 7.0 Hz), 3.97 (1H, dd, J 11.0, 3.0 Hz), 4.51 (2H, s), 5.43 (1H, dd, J 7.0, 3.0 Hz), 6.55 (1H, d, J 9.0 Hz), 6.63 (1H, dd, J 9.0, 3.0 Hz), 6.82 (1H, d, J 3.0 Hz), 7.44 (1H, d, J 7.5 Hz), 7.65 (1H, d, J 7.5 Hz), 7.75 (1H, t, J 7.5 Hz), 7.77 (2H, d, J 8.5 Hz), 8.15 (2H, d, J 8.5 Hz).

EXAMPLE 65

[(4-{[(1R)-1-[6-(4-Chlorophenyl)-2-pyridinyl]-2-(ethyloxy)ethyl]oxy}-2-methylphenyl)oxy]acetic acid

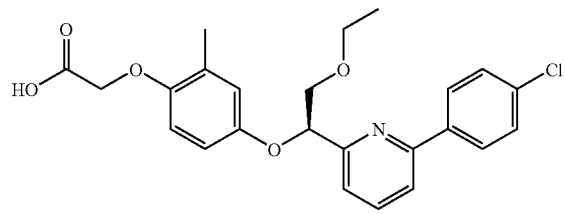

LC/MS: m/z 442.1 [M+H]$^+$, R$_t$ 3.95 min.

$^1$H NMR (400 MHz; CDCl$_3$) δ: 1.19 (3H, t, J 7.0 Hz), 2.19 (3H, s), 3.62 (2H, m), 3.90 (1H, dd, J 11.0, 7.0 Hz), 3.97 (1H, dd, J 11.0, 3.0 Hz), 4.52 (2H, s), 5.43 (1H, dd, J 7.0, 3.0 Hz), 6.54 (1H, d, J 9.0 Hz), 6.63 (1H, dd, J 9.0, 3.0 Hz), 6.82 (1H, d, J 3.0 Hz), 7.37 (1H, d, J 7.5 Hz), 7.44 (2H, d, J 8.5 Hz), 7.57 (1H, d, J 7.5 Hz), 7.69 (1H, t, J 7.5 Hz), 7.96 (2H, d, J 8.5 Hz).

General Procedure for Examples 66-70

The following compounds were prepared as described for Examples 61-65 except starting from ethyl [(4-{[(1S)-1-(6-bromo-2-pyridinyl)-3-(methyloxy)propyl]oxy}-2-methylphenyl)oxy]acetate.

EXAMPLE 66

({4[((1S)-2-(Ethyloxy)-1-{6-[4-(trifluoromethyl)phenyl]-2-pyridinyl}ethyl)oxy]-2-methylphenyl}oxy)acetic acid

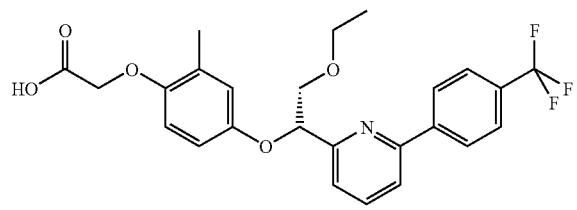

LC/MS and $^1$H NMR as described for Example 61.

Analytical chiral HPLC (25 cm Chiralcel OJ) eluting with 20% EtOH in heptane with 0.1% TFA, f=1.0 mL/min, wavelength 215 nm, R$_t$ 13.5 min (>99.9% ee).

EXAMPLE 67

({4-[((1S)-2-(Ethyloxy)-1-{6-[4-(methyloxy)phenyl]-2-pyridinyl}ethyl)oxy]-2-methylphenyl}oxy)acetic acid

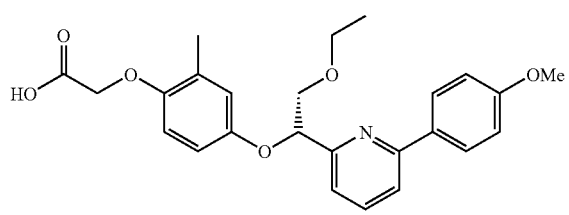

LC/MS and $^1$H NMR as described for Example 62.

Analytical chiral HPLC (25 cm Chiralpak AD) eluting with 10% EtOH in heptane with 0.1% TFA, f=1.0 mL/min, wavelength 215 nm, R$_t$ 16.2 min (>99.9% ee).

EXAMPLE 68

[(4-{[(1S)-1-[6-(4-Acetylphenyl)-2-pyridinyl]-2-(ethyloxy)ethyl]oxy}-2-methylphenyl)oxy]acetic acid

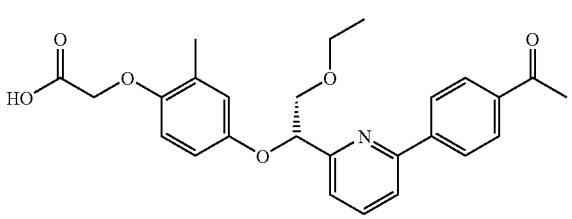

LC/MS and $^1$H NMR as described for Example 63.

EXAMPLE 69

Method A

[(4-{[(1S)-1-[6-(4-Cyanophenyl)-2-pyridinyl]-2-(ethyloxy)ethyl]oxy}-2-methylphenyl)oxy]acetic acid

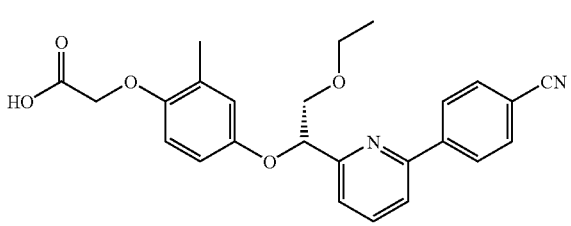

LC/MS and $^1$H NMR as described for Example 64.

EXAMPLE 70

[(4-{[(1S)-1-[6-(4-Chlorophenyl)-2-pyridinyl]-2-(ethyloxy)ethyl]oxy}-2-methylphenyl)oxy]acetic acid

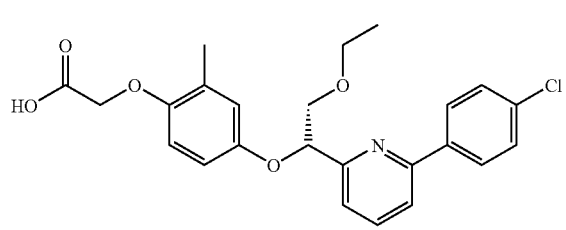

LC/MS and $^1$H NMR as described for Example 65.

EXAMPLE 69

Method B

[(4-{[(1S)-1-[6-(4-cyanophenyl)-2-pyridinyl]-2-(ethyloxy)ethyl]oxy}-2-methylphenyl)oxy]acetic acid

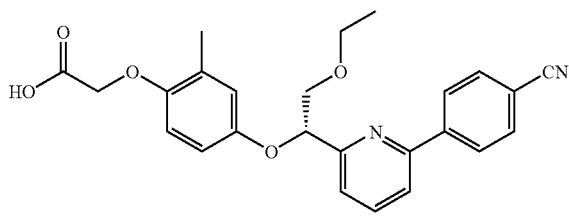

Ethyl [(4-{[(1S)-1-[6-(4-cyanophenyl)-2-pyridinyl]-2-(ethyloxy)ethyl]oxy}-2-methylphenyl)oxy]acetate (0.886 g) was dissolved in THF (8.8 mL). Water (8.8 mL) and aq 2M NaOH (1.8 mL) were added and the mixture stirred at ambient temperature for 30 mins. The reaction mixture was acidified to pH 1 by the addition of aq 2M HCl and extracted with EtOAc (2×10 mL). The organic extracts were washed with brine (20 mL), dried ($Na_2SO_4$) and evaporated to give the title compound as a white foam (729 mg).

LC/MS: m/z 433.2 [M+H]$^+$, $R_t$ 3.57 min.

$^1$H NMR (400 MHz; CDCl$_3$) δ: 1.20 (3H, t, J 7.0 Hz), 2.21 (3H, s), 3.63 (2H, m), 3.92 (1H, dd, J 11.0, 7.0 Hz), 3.99 (1H, dd, J 11.0, 3.0 Hz), 4.56 (2H, s), 5.45 (1H, dd, J 7.0, 3.0 Hz), 6.57 (1H, d, J 9.0 Hz), 6.65 (1H, dd, J 9.0, 3.0 Hz), 6.84 (1H, d, J 3.0 Hz), 7.45 (1H, d, J 7.5 Hz), 7.67 (1H, d, J 7.5 Hz), 7.77 (1H, t, J 7.5 Hz), 7.78 (2H, d, J 8.5 Hz), 8.17 (2H, d, J 8.5 Hz).

General Procedure for Examples 71-84

A mixture of the boronic acid (or ester) (0.09 mmol) and Pd(PPh$_3$)$_4$ (7.5 mg, 0.006 mmol) in an 8 ml test tube within a greenhouse was purged with nitrogen and then treated with a solution of ethyl [(4-{[(1R)-1-(6-bromo-2-pyridinyl)-2-(ethyloxy)ethyl]oxy}-2-methylphenyl)oxy]acetate (30 mg, 0.068 mmol) in DME (1.5 mL) and then with aqueous Na$_2$CO$_3$ (1M, 1.0 mL). The resulting mixture was heated to 60° C. with vigorous stirring for 2 h then at 80° C. for a further 3 h. The mixture was then allowed to cool to ambient temperature then the solvent evaporated in a Genevac. The residue was treated cautiously with aqueous HCl (2M, 1.5 mL) and then the product extracted into DCM (2×3 mL). The combined organic solution was evaporated and the product purified either by mass directed autoprep HPLC or using the Optix (C18 SPE).

EXAMPLE 71

{[4-({(1R)-2-(Ethyloxy)-1-[6-(3-fluoro-4-methylphenyl)-2-pyridinyl]ethyl}oxy)-2-methylphenyl]oxy}acetic acid

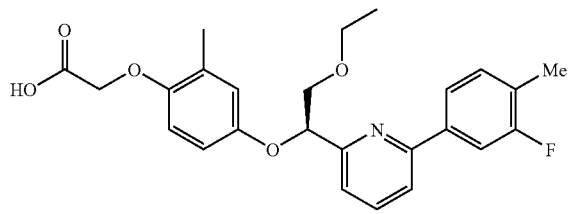

LC/MS: m/z 440.3 [M+H]$^+$, $R_t$ 3.86 min.

$^1$H NMR (400 MHz; CDCl$_3$) δ: 1.19 (3H, t, J 7.0 Hz), 2.19 (3H, s), 2.33 (3H, s), 3.62 (2H, m), 3.90 (1H, dd, J 11.0, 7.5 Hz), 3.98 (1H, dd, J 11.0, 3.0 Hz), 4.52 (2H, s), 5.43 (1H, dd, J 7.0, 3.0 Hz), 6.54 (1H, d, J 9.0 Hz), 6.63 (1H, dd, J 9.0, 3.0 Hz), 6.82 (1H, d, J 3.0 Hz), 7.27 (1H, dd, J 8.0, 8.0 Hz), 7.35 (1H, d, J 7.5 Hz), 7.56 (1H, d, J 7.5 Hz), 7.68 (1H, t, J 7.5 Hz), 7.67 (1H, dd, J 8.0, 1.5 Hz), 7.71 (1H, dd, J 11.0, 1.5 Hz).

EXAMPLE 72

{[4-({(1R)-2-(Ethyloxy)-1-[6-(4-methylphenyl)-2-pyridinyl]ethyl}oxy)-2-methylphenyl]oxy}acetic acid

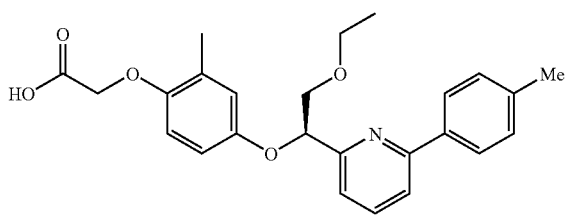

LC/MS: m/z 422.4 [M+H]$^+$, $R_t$ 3.75 min.

$^1$H NMR (400 MHz; CDCl$_3$) δ: 1.19 (3H, t, J 7.0 Hz), 2.17 (3H, s), 2.41 (3H, s), 3.61 (2H, m), 3.90 (1H, dd, J 11.0, 7.5 Hz), 3.97 (1H, dd, J 11.0, 3.0 Hz), 4.47 (2H, s), 5.44 (1H, dd, J 7.0, 3.0 Hz), 6.52 (1H, d, J 9.0 Hz), 6.62 (1H, dd, J 9.0, 3.0 Hz), 6.81 (1H, d, J 3.0 Hz), 7.28 (2H, d, J 8.0 Hz), 7.32 (1H, d, J 7.5 Hz), 7.56 (1H, d, J 7.5 Hz), 7.65 (1H, t, J 7.5 Hz), 7.90 (2H, d, J 8.0 Hz).

EXAMPLE 73

({4-[((1R)-2-(Ethyloxy)-1-{6-[4-(1-methylethyl)phenyl]-2-pyridinyl}ethyl)oxy]-2-methylphenyl}oxy)acetic acid

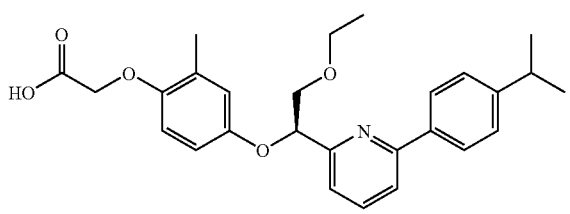

LC/MS: m/z 450.4 [M+H]$^+$, $R_t$ 4.04 min.

$^1$H NMR (400 MHz; CDCl$_3$) δ: 1.19 (3H, t, J 7.0 Hz), 1.29 (6H, d, J 7.0 Hz), 2.18 (3H, s), 2.97 (1H, sept, J 7.0 Hz), 3.62 (2H, m), 3.90 (1H, dd, J 11.0, 7.5 Hz), 3.98 (1H, dd, J 11.0, 3.0 Hz), 4.50 (2H, s), 5.45 (1H, dd, J 7.5, 3.0 Hz), 6.53 (1H, d, J 9.0 Hz), 6.63 (1H, dd, J 9.0, 3.0 Hz), 6.81 (1H, d, J 3.0 Hz), 7.33 (3H, m), 7.57 (1H, d, J 7.5 Hz), 7.66 (1H, t, J 7.5 Hz), 7.93 (2H, d, J 8.5 Hz).

EXAMPLE 74

[(4-{[(1R)-1-[6-(4-Cyano-3-fluorophenyl)-2-pyridinyl]-2-(ethyloxy)ethyl]oxy}-2-methylphenyl)oxy]acetic acid

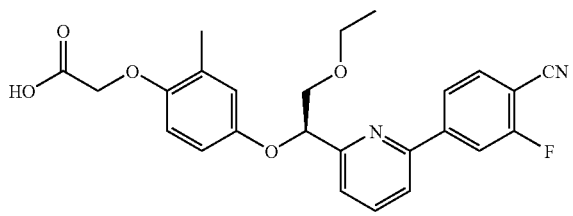

LC/MS: m/z 451.3 [M+H]$^+$, R$_t$ 3.63 min.
$^1$H NMR (400 MHz; CDCl$_3$) δ: 1.19 (3H, t, J 7.0 Hz), 2.18 (3H, s), 3.62 (2H, m), 3.91 (1H, dd, J 11.0, 7.0 Hz), 3.97 (1H, dd, J 11.0, 3.5 Hz), 4.50 (2H, s), 5.43 (1H, dd, J 7.0, 3.5 Hz), 6.53 (1H, d, J 9.0 Hz), 6.61 (1H, dd, J 9.0, 3.0 Hz), 6.80 (1H, d, J 3.0 Hz), 7.47 (1H, d, J 7.5 Hz), 7.65 (1H, d, J 7.5 Hz), 7.71 (1H, dd, J 8.0, 7.0 Hz), 7.76 (1H, t, J 7.5 Hz), 7.91 (1H, dd, J 8.0, 1.5 Hz), 7.96 (1H, dd, J 10.5, 1.5 Hz).

EXAMPLE 75

({4-[((1R)-2-(Ethyloxy)-1-{6-[4-(ethyloxy)phenyl]-2-pyridinyl}ethyl)oxy]-2-methylphenyl}oxy)acetic acid

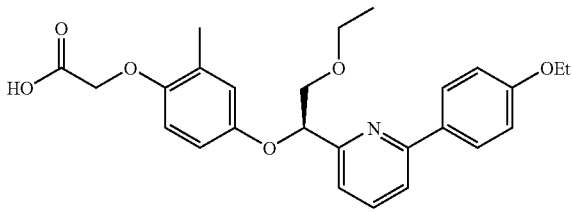

LC/MS: m/z 452.4 [M+H]$^+$, R$_t$ 3.71 min.
$^1$H NMR (400 MHz; CDCl$_3$) δ: 1.19 (3H, t, J 7.0 Hz), 1.45 (3H, t, J 7.0 Hz), 2.18 (3H, s), 3.62 (2H, m), 3.89 (1H, dd, J 11.0, 7.5 Hz), 3.97 (1H, dd, J 11.0, 3.0 Hz), 4.09 (2H, q, J 7.0 Hz), 4.49 (2H, s), 5.43 (1H, dd, J 7.0, 3.0 Hz), 6.53 (1H, d, J 9.0 Hz), 6.62 (1H, dd, J 9.0, 3.0 Hz), 6.81 (1H, d, J 3.0 Hz), 6.99 (2H, d, J 9.0 Hz), 7.29 (1H, d, J 7.5 Hz), 7.52 (1H, d, J 7.5 Hz), 7.64 (1H, t, J 7.5 Hz), 7.94 (2H, d, J 9.0 Hz).

EXAMPLE 76

{[4-({(1R)-2-(Ethyloxy)-1-[6-(2-fluoro-4-methylphenyl)-2-pyridinyl]ethyl}oxy)-2-methylphenyl]oxy}acetic acid

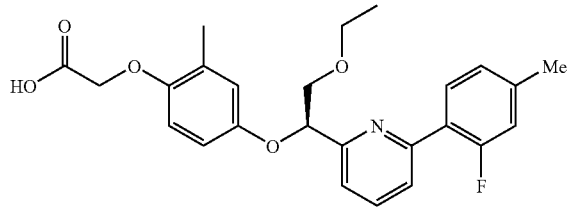

LC/MS: m/z 440.3 [M+H]$^+$, R$_t$ 3.80 min.
$^1$H NMR (400 MHz; CDCl$_3$) δ: 1.19 (3H, t, J 7.0 Hz), 2.20 (3H, s), 2.40 (3H, s), 3.61 (2H, m), 3.89 (1H, dd, J 11.0, 7.0 Hz), 3.96 (1H, dd, J 11.0, 3.5 Hz), 4.53 (2H, s), 5.44 (1H, dd, J 7.0, 3.0 Hz), 6.56 (1H, d, J 9.0 Hz), 6.64 (1H, dd, J 9.0, 3.0 Hz), 6.83 (1H, d, J 3.0 Hz), 6.98 (1H, d, J 13.0 Hz), 7.08 (1H, d, J 8.0 Hz), 7.35 (1H, dd, J 7.0, 1.5 Hz), 7.62-7.71 (2H, m), 7.90 (1H, t, J 8.0 Hz).

EXAMPLE 77

{[4-({(1R)-2-(Ethyloxy)-1-[6-(4-fluorophenyl)-2-pyridinyl]ethyl}oxy)-2-methylphenyl]oxy}acetic acid

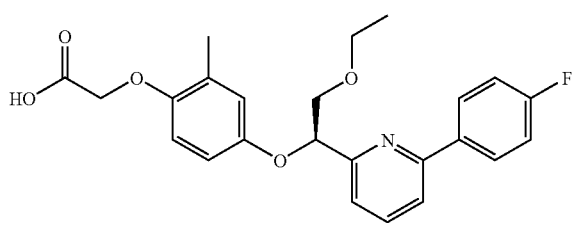

LC/MS: m/z 426.3 [M+H]$^+$, R$_t$ 3.67 min.
$^1$H NMR (400 MHz; CDCl$_3$) δ: 1.19 (3H, t, J 7.0 Hz), 2.18 (3H, s), 3.62 (2H, m), 3.90 (1H, dd, J 11.0, 7.0 Hz), 3.97 (1H, dd, J 11.0, 3.0 Hz), 4.49 (2H, s), 5.43 (1H, dd, J 7.0, 3.0 Hz), 6.52 (1H, d, J 9.0 Hz), 6.62 (1H, dd, J 9.0, 3.0 Hz), 6.81 (1H, d, J 3.0 Hz), 7.16 (2H, dd, J 8.5, 8.5 Hz), 7.35 (1H, d, J 8.0 Hz), 7.55 (1H, d, J 8.0 Hz), 7.68 (1H, t, J 8.0 Hz) 7.99 (2H, dd, J 8.5, 6.0 Hz).

EXAMPLE 78

[(4-{[(1R)-2-(Ethyloxy)-1-(6-{4-[(1-methylethyl)oxy]phenyl}-2-pyridinyl)ethyl]oxy}-2-methylphenyl)oxy]acetic acid

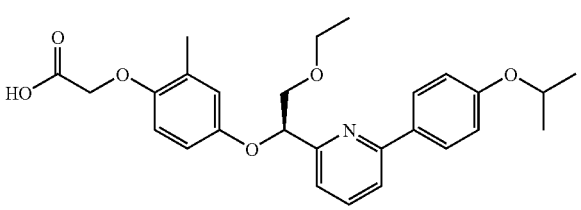

LC/MS: m/z 466.4 [M+H]$^+$, R$_t$ 3.86 min.
$^1$H NMR (400 MHz; CDCl$_3$) δ: 1.19 (3H, t, J 7.0 Hz), 1.37 (6H, d, J 6.0 Hz), 2.18 (3H, s), 3.61 (2H, m), 3.89 (1H, dd, J 11.0, 7.5 Hz), 3.97 (1H, dd, J 11.0, 3.0 Hz), 4.49 (2H, s), 4.63 (1H, sept, J 6.0 Hz), 5.43 (1H, dd, J 7.0, 3.0 Hz), 6.53 (1H, d, J 9.0 Hz), 6.62 (1H, dd, J 9.0, 3.0 Hz), 6.81 (1H, d, J 3.0 Hz), 6.98 (2H, d, J 9.0 Hz), 7.28 (1H, d, J 8.0 Hz), 7.52 (1H, d, J 8.0 Hz), 7.64 (1H, t, J 8.0 Hz), 7.94 (2H, d, J 9.0 Hz).

EXAMPLE 79

[(4-{[(1R)-1-[6-(4-Chloro-3-methylphenyl)-2-pyridinyl]-2-(ethyloxy)ethyl]oxy}-2-methylphenyl)oxy]acetic acid

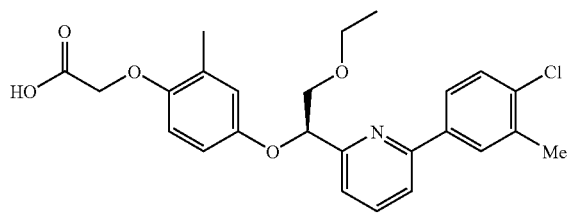

LC/MS: m/z 456.3 [M+H]$^+$, R$_t$ 4.06 min.
$^1$H NMR (400 MHz; CDCl$_3$) δ: 1.19 (3H, t, J 7.0 Hz), 2.19 (3H, s), 2.46 (3H, s), 3.62 (2H, m), 3.89 (1H, dd, J 11.0, 7.5 Hz), 3.97 (1H, dd, J 11.0, 3.5 Hz), 4.51 (2H, s), 5.43 (1H, dd, J 7.5, 3.0 Hz), 6.54 (1H, d, J 9.0 Hz), 6.62 (1H, dd, J 9.0, 3.0 Hz), 6.82 (1H, d, J 3.0 Hz), 7.35 (1H, d, J 7.5 Hz), 7.43 (1H, d, J 8.5 Hz), 7.56 (1H, d, J 7.5 Hz), 7.68 (1H, t, J 7.5 Hz), 7.75 (1H, dd, J 8.5, 2.0 Hz), 7.89 (1H, d, J 2.0 Hz).

EXAMPLE 80

[(4-{[(1R)-1-[6-(3-Chloro-4-cyanophenyl)-2-pyridinyl]-2-(ethyloxy)ethyl]oxy}-2-methylphenyl)oxy]acetic acid

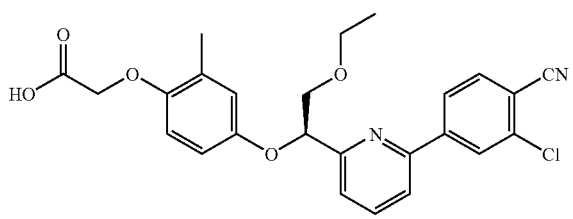

LC/MS: m/z 467.2 [M+H]$^+$, R$_t$ 3.76 min.
$^1$H NMR (400 MHz; CDCl$_3$) δ: 1.19 (3H, t, J 7.0 Hz), 2.18 (3H, s), 3.62 (2H, m), 3.90 (1H, dd, J 11.0, 7.0 Hz), 3.97 (1H, dd, J 11.0, 3.5 Hz), 4.51 (2H, s), 5.43 (1H, dd, J 7.0, 3.5 Hz), 6.53 (1H, d, J 9.0 Hz), 6.61 (1H, dd, J 9.0, 3.0 Hz), 6.81 (1H, d, J 3.0 Hz), 7.47 (1H, d, J 7.5 Hz), 7.65 (1H, d, J 7.5 Hz), 7.76 (1H, t, J 7.5 Hz), 7.76 (1H, d, J 8.0 Hz), 8.01 (1H, dd, J 8.0, 1.5 Hz), 8.23 (1H, d, J 1.5 Hz).

EXAMPLE 81

[(4{[(1R)-1-[6-(4-Cyano-3-methylphenyl)-2-pyridinyl]-2-(ethyloxy)ethyl]oxy}-2-methylphenyl)oxy]acetic acid

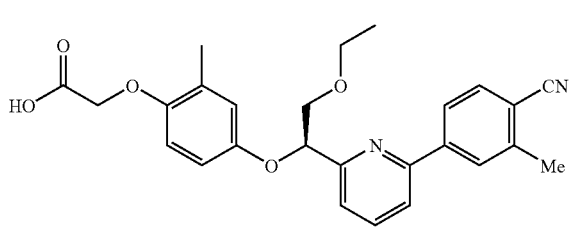

LC/MS: m/z 447.3 [M+H]$^+$, R$_t$ 3.65 min.
$^1$H NMR (400 MHz; CDCl$_3$) δ: 1.19 (3H, t, J 7.0 Hz), 2.18 (3H, s), 2.64 (3H, s), 3.62 (2H, m), 3.90 (1H, dd, J 11.0, 7.0 Hz), 3.97 (1H, dd, J 11.0, 3.5 Hz), 4.50 (2H, s), 5.44 (1H, dd, J 7.0, 3.5 Hz), 6.54 (1H, d, J 9.0 Hz), 6.62 (1H, dd, J 9.0, 3.0 Hz), 6.81 (1H, d, J 3.0 Hz), 7.43 (1H, d, J 7.5 Hz), 7.63 (1H, d, J 7.5 Hz), 7.70 (1H, d, J 8.0 Hz), 7.73 (1H, t, J 7.5 Hz), 7.89 (1H, dd, J 8.0, 1.0 Hz), 7.99 (1H, d, J 1.0 Hz).

EXAMPLE 82

({4-[((1R)-2-(Ethyloxy)-1-{6-[3-fluoro-4-(methyloxy)phenyl]-2-pyridinyl}ethyl)oxy]-2-methylphenyl}oxy)acetic acid

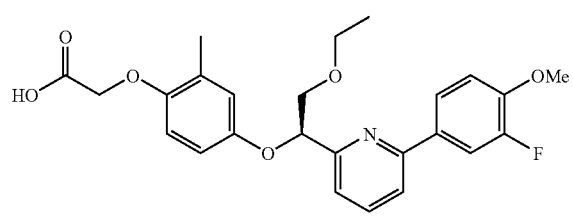

LC/MS: m/z 456.3 [M+H]$^+$, R$_t$ 3.63 min.
$^1$H NMR (400 MHz; CDCl$_3$) δ: 1.20 (3H, t, J 7.0 Hz), 2.19 (3H, s), 3.62 (2H, m), 3.90 (1H, dd, J 11.0, 7.0 Hz), 3.95 (3H, s), 3.94-3.99 (1H, m), 4.52 (2H, s), 5.42 (1H, dd, J 7.5, 3.0 Hz), 6.54 (1H, d, J 9.0 Hz), 6.63 (1H, dd, J 9.0, 3.0 Hz), 6.82 (1H, d, J 3.0 Hz), 7.04 (1H, dd, J 8.5, 8.5 Hz), 7.32 (1H, d, J 7.5 Hz), 7.53 (1H, d, J 7.5 Hz), 7.66 (1H, t, J 7.5 Hz), 7.74 (1H, bd, J 8.5 Hz) 7.82 (1H, dd, J 13.0, 2.0 Hz).

EXAMPLE 83

[(4-{[(1R)-1-[6-(4-Cyano-2-fluorophenyl)-2-pyridinyl]-2-(ethyloxy)ethyl]oxy}-2-methylphenyl)oxy]acetic acid

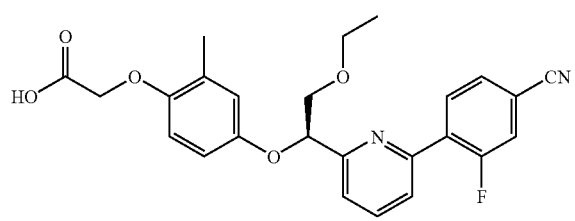

LC/MS: m/z 451.3 [M+H]$^+$, R$_t$ 3.56 min.
$^1$H NMR (400 MHz; CDCl$_3$) δ: 1.19 (3H, t, J 7.0 Hz), 2.19 (3H, s), 3.61 (2H, m), 3.90 (1H, dd, J 11.0, 7.0 Hz), 3.96 (1H, dd, J 11.0, 3.5 Hz), 4.52 (2H, s), 5.43 (1H, dd, J 7.0, 3.5 Hz), 6.55 (1H, d, J 9.0 Hz), 6.62 (1H, dd, J 9.0, 3.0 Hz), 6.81 (1H, d, J 3.0 Hz), 7.44-7.51 (2H, m), 7.58 (1H, dd, J 8.0, 1.5 Hz), 7.71-7.79 (2H, m), 8.21 (1H, t, J 8.0 Hz).

EXAMPLE 84

[(4-{[(1R)-1-[6-(4-Cyano-2-methylphenyl)-2-pyridinyl]-2-(ethyloxy)ethyl]oxy}-2-methylphenyl)oxy] acetic acid

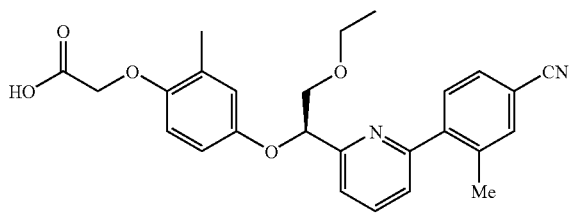

LC/MS: m/z 447.3 [M+H]+, R$_t$ 3.49 min.
$^1$H NMR (400 MHz; CDCl$_3$) δ: 1.17 (3H, t, J 7.0 Hz), 2.18 (3H, s), 2.38 (3H, s), 3.59 (2H, m), 3.90 (2H, m), 4.52 (2H, s), 5.44 (1H, dd, J 5.0, 5.0 Hz), 6.55 (1H, d, J 9.0 Hz), 6.62 (1H, dd, J 9.0, 3.0 Hz), 6.79 (1H, d, J 3.0 Hz), 7.29 (1H, d, J 7.5 Hz), 7.47 (1H, d, J 7.5 Hz), 7.48 (1H, d, J 8.5 Hz), 7.54-7.62 (2H, m), 7.76 (1H, t, J 7.5 Hz).

General Procedure for Examples 85-98

The following compounds were prepared as described for Examples 71-84 except starting from ethyl [(4-{[(1S)-1-(6-bromo-2-pyridinyl)-2-(ethyloxy)ethyl]oxy}-2-methylphenyl)oxy]acetate bromide.

EXAMPLE 85

{[4-({(1S)-2-(Ethyloxy)-1-[6-(3-fluoro-4-methylphenyl)-2-pyridinyl]ethyl}oxy)-2-methylphenyl]oxy}acetic acid

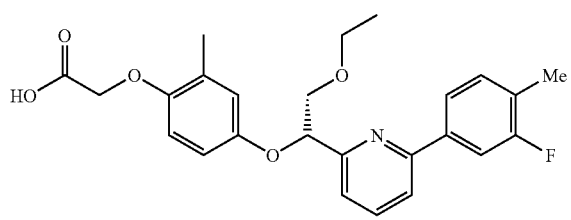

LC/MS and $^1$H NMR as described for Example 71.

EXAMPLE 86

{[4-({(1S)-2-(Ethyloxy)-1-[6-(4-methylphenyl)-2-pyridinyl]ethyl}oxy)-2-methylphenyl]oxy}acetic acid

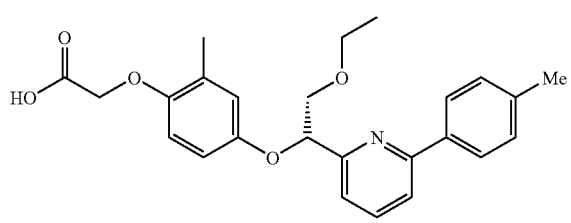

LC/MS and $^1$H NMR as described for Example 72.

EXAMPLE 87

({4[((1S)-2-(Ethyloxy)-1-{6-[4-(1-methylethyl)phenyl]-2-pyridinyl}ethyl)oxy]-2-methylphenyl}oxy) acetic acid

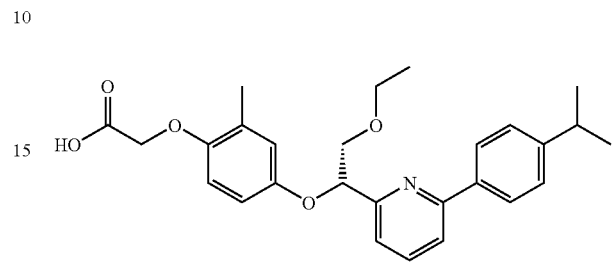

LC/MS and $^1$H NMR as described for Example 73.

EXAMPLE 88

[(4-{[(1S)-1-[6-(4-Cyano-3-fluorophenyl)-2-pyridinyl]-2-(ethyloxy)ethyl]oxy}-2-methylphenyl)oxy] acetic acid

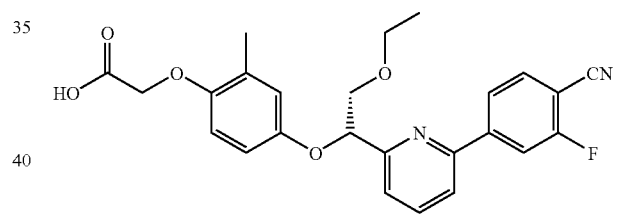

LC/MS and $^1$H NMR as described for Example 74.

EXAMPLE 89

({4-[((1S)-2-(Ethyloxy)-1-{6-[4-(ethyloxy)phenyl]-2-pyridinyl}ethyl)oxy]-2-methylphenyl}oxy)acetic acid

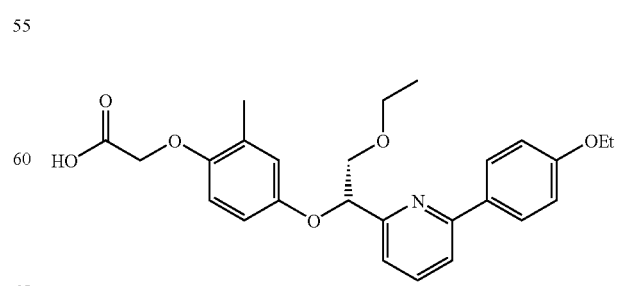

LC/MS and $^1$H NMR as described for Example 75.

EXAMPLE 90

{[4-({(1S)-2-(Ethyloxy)-1-[6-(2-fluoro-4-methylphenyl)-2-pyridinyl]ethyl}oxy)-2-methylphenyl]oxy}acetic acid

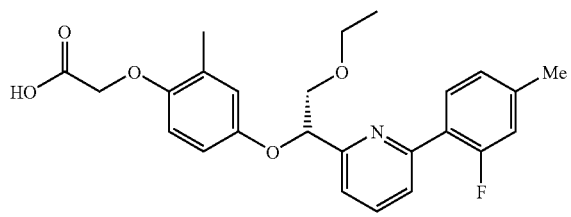

LC/MS and ¹H NMR as described for Example 76.

EXAMPLE 91

{[4-({(1S)-2-(Ethyloxy)-1-[6-(4-fluorophenyl)-2-pyridinyl]ethyl}oxy)-2-methylphenyl]oxy}acetic acid

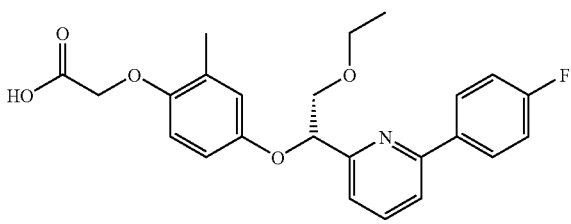

LC/MS and ¹H NMR as described for Example 77.

EXAMPLE 92

[(4-{[(1S)-2-(Ethyloxy)-1-(6-{4-[(1-methylethyl)oxy]phenyl}-2-pyridinyl)ethyl]oxy}-2-methylphenyl)oxy]acetic acid

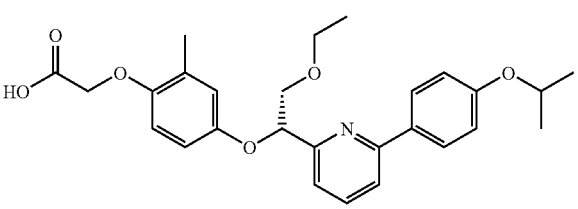

LC/MS and ¹H NMR as described for Example 78.

EXAMPLE 93

[(4-{[(1S)-1-[6-(4-Chloro-3-methylphenyl)-2-pyridinyl]-2-(ethyloxy)ethyl]oxy}-2-methylphenyl)oxy]acetic acid

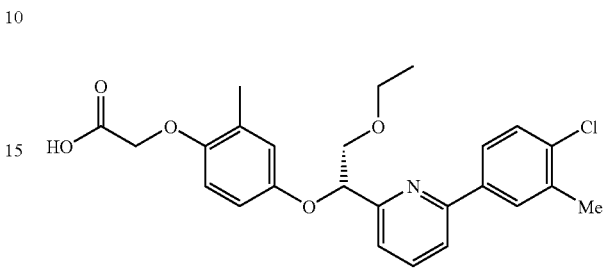

LC/MS and ¹H NMR as described for Example 79.

EXAMPLE 94

[(4-{[(1S)-1-[6-(3-Chloro-4-cyanophenyl)-2-pyridinyl]-2-(ethyloxy)ethyl]oxy}-2-methylphenyl)oxy]acetic acid

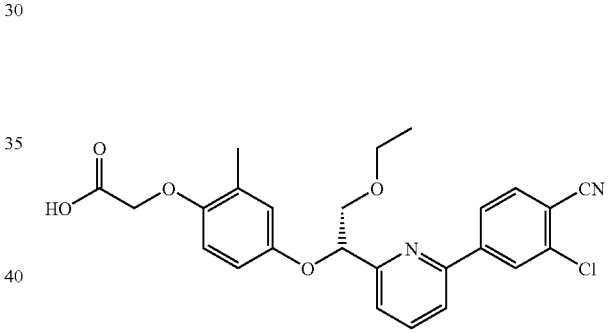

LC/MS and ¹H NMR as described for Example 80.

EXAMPLE 95

[(4-{[(1S)-1-[6-(4-Cyano-3-methylphenyl)-2-pyridinyl]-2-(ethyloxy)ethyl]oxy}-2-methylphenyl)oxy]acetic acid

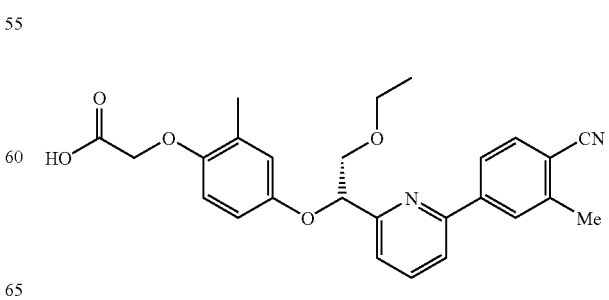

LC/MS and ¹H NMR as described for Example 81.

EXAMPLE 96

({4-[((1S)-2-(Ethyloxy)-1-{6-[3-fluoro-4-(methyloxy)phenyl]-2-pyridinyl}ethyl)oxy]-2-methylphenyl}oxy)acetic acid

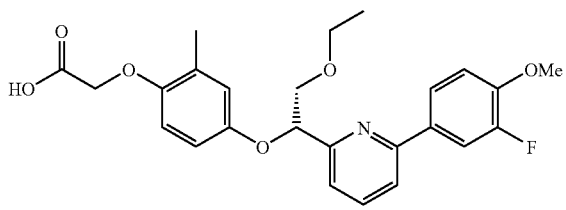

LC/MS and ¹H NMR as described for Example 82.

EXAMPLE 97

[(4-{[(1S)-1-[6-(4-Cyano-2-fluorophenyl)-2-pyridinyl]-2-(ethyloxy)ethyl]oxy}-2-methylphenyl)oxy]acetic acid

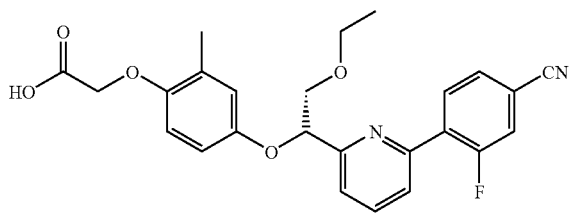

LC/MS and ¹H NMR as described for Example 83.

EXAMPLE 98

[(4-{[(1S)-1-{6-[4-Cyano-3-(methyloxy)phenyl]-2-pyridinyl}-2-(ethyloxy)ethyl]oxy}-2-methylphenyl)oxy]acetic acid

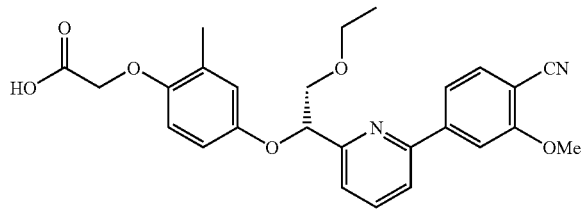

LC/MS and ¹H NMR as described for Example 84.

General Procedure for Examples 99-103

A stirred solution of ethyl 3-(4-{[(1S)-1-(6-bromo-2-pyridinyl)pentyl]oxy}-2-methylphenyl)propanoate (76 mg, 0.17 mmol) in DME (1.2 mL) was treated with the appropriate aryl boronic acid (0.23 mmol) followed by and a solution of $Na_2CO_3$ (74 mg, 0.70 mmol) in water (0.7 mL). The reaction mixture was heated at 73° C. for 21 h under nitrogen, allowed to cool to rt and then reduced under vacuum (Genevac). The residue was then treated with THF (2 mL), MeOH (2 mL) followed by aqueous NaOH (2N, 2 mL) and the resulting mixture stirred at ambient temperature for 4 h. The solvents were then removed under vacuum and the residue purified using the OPTIX-SPE (C18 cartridge, 5 g) eluting with 25-100% MeCN (+0.05% HCOOH) in $H_2O$ (+0.01% HCOOH) over 18 mins to afford the desired product which, if appropriate, were further purified by mass directed autoprep HPLC.

EXAMPLE 99

3-{2-Methyl-4-[((1S)-1-{6-[4-(trifluoromethyl)phenyl]-2-pyridinyl}pentyl)oxy]phenyl}propanoic acid

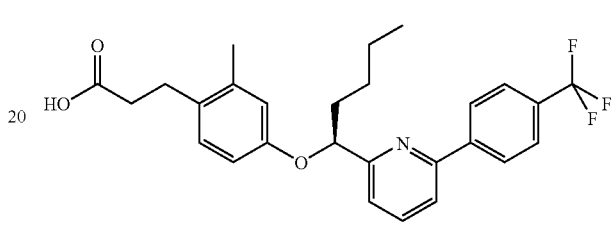

LC/MS: m/z 472.2 [M+H]⁺, $R_t$ 4.26 min.

¹H NMR (400 MHz; CDCl₃) δ: 0.92 (3H, t, J 7.5 Hz), 1.34-1.45 (2H, m), 1.45-1.64 (2H, m), 1.96-2.08 (2H, m), 2.23 (3H, s), 2.55 (2H, m), 2.83 (2H, m), 5.28 (1H, dd, J 7.5, 5.5 Hz), 6.64 (1H, dd, J 8.5, 2.5 Hz), 6.77 (1H, d, J 2.5 Hz), 6.95 (1H, d, J 8.5 Hz), 7.38 (1H, d, J 7.5 Hz), 7.62 (1H, d, J 7.5 Hz), 7.72 (1H, t, J 7.5 Hz), 7.75 (2H, d, J 8.5 Hz), 8.14 (2H, d, J 8.5 Hz).

Analytical chiral HPLC (25 cm Chiralpak AD) eluting with 20% IPA in heptane with 0.1°/TFA, f=1.0 mL/min, wavelength 215 nm, $R_t$ 7.5 min (94% ee).

EXAMPLE 100

3-{2-Methyl-4-[((1S)-1-{6-[4-(methyloxy)phenyl]-2-pyridinyl}pentyl)oxy]phenyl}propanoic acid

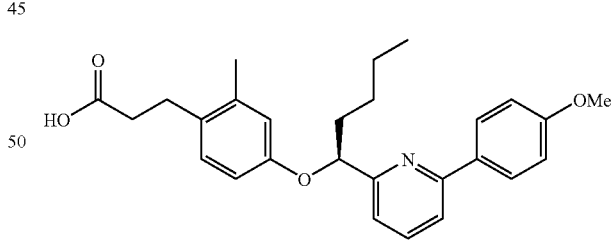

LC/MS: m/z 434.3 [M+H]⁺, $R_t$ 4.05 min.

¹H NMR (400 MHz; CDCl₃) δ: 0.92 (3H, t, J 7.5 Hz), 1.33-1.44 (2H, m), 1.44-1.64 (2H, m), 1.94-2.09 (2H, m), 2.22 (3H, s), 2.54 (2H, m), 2.82 (2H, m), 3.88 (3H, s), 5.25 (1H, dd, J 8.0, 4.5 Hz), 6.65 (1H, dd, J 8.5, 2.5 Hz), 6.77 (1H, d, J 2.5 Hz), 6.94 (1H, d, J 8.5 Hz), 7.02 (2H, d, J 9.0 Hz), 7.25 (1H, d, J 8.0 Hz), 7.51 (1H, d, J 8.0 Hz), 7.63 (1H, t, J 8.0 Hz), 7.98 (2H, d, J 0.0 Hz).

Analytical chiral HPLC (25 cm Chiralcel OD) eluting with 2% EtOH in heptane with 0.1% TFA, f=1.0 mL/min, wavelength 254 nm, $R_t$ 22.2 min (97% ee).

EXAMPLE 101

3-[4-({(1S)-1-[6-(4-Acetylphenyl)-2-pyridinyl]pentyl}oxy)-2-methylphenyl]propanoic acid

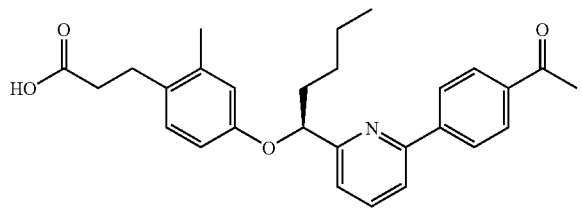

LC/MS: m/z 446.3 [M+H]$^+$, R$_t$ 3.93 min.
$^1$H NMR (400 MHz; CDCl$_3$) δ: 0.92 (3H, t, J 7.5 Hz), 1.33-1.45 (2H, m), 1.45-1.65 (2H, m), 1.94-2.09 (2H, m), 2.23 (3H, s), 2.55 (2H, m), 2.66 (3H, s), 2.82 (2H, m), 5.29 (1H, dd, J 7.5, 5.5 Hz), 6.64 (1H, dd, J 8.5, 2.5 Hz), 6.77 (1H, d, J 2.5 Hz), 6.95 (1H, d, J 8.5 Hz), 7.37 (1H, d, J 7.5 Hz), 7.64 (1H, d, J 7.5 Hz), 7.71 (1H, t, J 7.5 Hz), 8.08 (2H, d, J 8.5 Hz), 8.14 (2H, d, J 8.5 Hz).

EXAMPLE 102

3-[4-({(1S)-1-[6-(4-Cyanophenyl)-2-pyridinyl]pentyl}oxy)-2-methylphenyl]propanoic acid

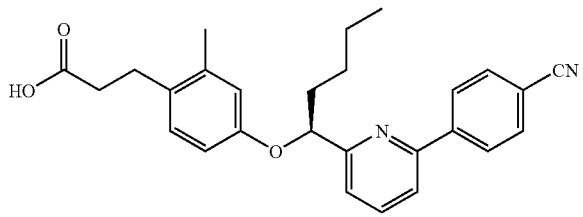

LC/MS: m/z 429.3 [M+H]$^+$, R$_t$ 3.97 min.
$^1$H NMR (400 MHz; CDCl$_3$) δ: 0.91 (3H, t, J 7.5 Hz), 1.33-1.43 (2H, m), 1.43-1.63 (2H, m), 1.94-2.07 (2H, m), 2.54 (2H, m), 2.82 (2H, m), 5.27 (1H, m), 6.62 (1H, d, J 8.5, 2.5 Hz), 6.75 (1H, d, J 2.5 Hz), 7.94 (1H, d, J 8.5 Hz), 7.40 (1H, d, J 7.5 Hz), 7.62 (1H, d, J 7.5 Hz), 7.74 (1H, t, J 7.5 Hz), 7.78 (2H, d, J 8.5 Hz), 8.16 (2H, d, J 8.5 Hz).

EXAMPLE 103

3-[4-({(1S)-1-[6-(4-Chlorophenyl)-2-pyridinyl]pentyl}oxy)-2-methylphenyl]propanoic acid

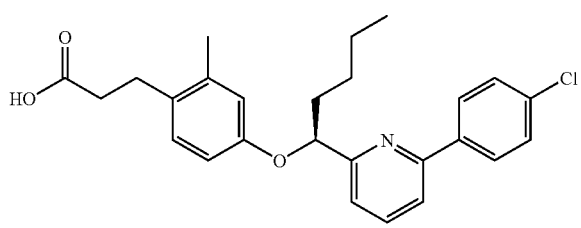

LC/MS: m/z 438.2 [M+H]$^+$, R$_t$ 4.28 min.
$^1$H NMR (400 MHz; CDCl$_3$) δ: 0.91 (3H, t, J 7.5 Hz), 1.32-1.44 (2H, m), 1.44-1.63 (2H, m), 1.92-2.07 (2H, m), 2.22 (3H, s), 2.54 (2H, m), 2.82 (2H, m), 5.25 (1H, dd, J 8.0, 5.0 Hz), 6.63 (1H, dd, J 8.5, 2.5 Hz), 6.75 (1H, d, J 2.5 Hz), 6.94 (1H, d, J 8.5 Hz), 7.32 (1H, d, J 7.5 Hz), 7.45 (2H, d, J 8.5 Hz), 7.54 (1H, d, J 7.5 Hz), 7.67 (1H, t, J 7.5 Hz), 7.97 (2H, d, J 8.5 Hz).

General Procedure for Examples 104-108

The following compounds were prepared as described for Examples 99-103, except starting from ethyl 3-(4-{[(1R)-1-(6-bromo-2-pyridinyl)pentyl]oxy}-2-methylphenyl)propanoate.

EXAMPLE 104

3-{2-Methyl-4-[((1R)-1-{6-[4-(trifluoromethyl)phenyl]-2-pyridinyl}pentyl)oxy]phenyl}propanoic acid

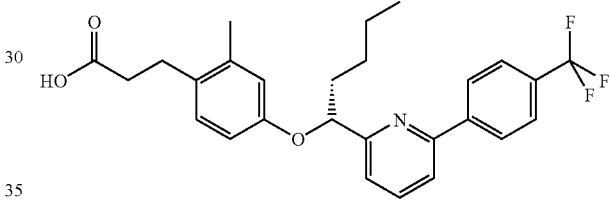

LC/MS and $^1$H NMR as described for Example 99.
Analytical chiral HPLC (25 cm Chiralpak AD) eluting with 20% IPA in heptane with 0.1% TFA, f=1.0 mL/min, wavelength 215 nm, R$_t$ 4.2 min (99% ee).

EXAMPLE 105

3-{2-Methyl-4-[((1R)-1-{6-[4-(methyloxy)phenyl]-2-pyridinyl}pentyl)oxy]phenyl}propanoic acid

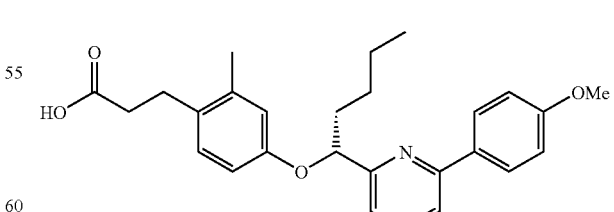

LC/MS and $^1$H NMR as described for Example 100.
Analytical chiral HPLC (25 cm Chiralcel OD) eluting with 2% EtOH in heptane with 0.1% TFA, f=1.0 mL/min, wavelength 254 nm, R$_t$ 17.2 min (>99% ee).

EXAMPLE 106

3-[4-({(1R)-1-[6-(4-Acetylphenyl)-2-pyridinyl]pentyl}oxy)-2-methylphenyl]propanoic acid

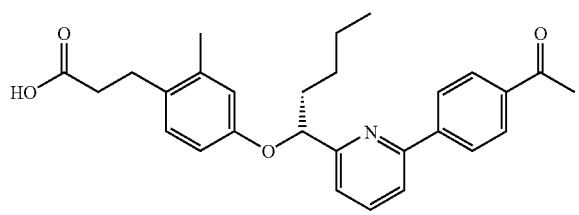

LC/MS and ¹H NMR as described for Example 101.

EXAMPLE 107

3-[4-({(1R)-1-[6-(4-Cyanophenyl)-2-pyridinyl]pentyl}oxy)-2-methylphenyl]propanoic acid

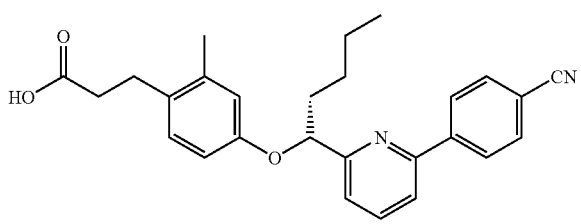

LC/MS and ¹H NMR as described for Example 102.

EXAMPLE 108

3-[4-({(1R)-1-[6-(4-Chlorophenyl)-2-pyridinyl]pentyl}oxy)-2-methylphenyl]propanoic acid

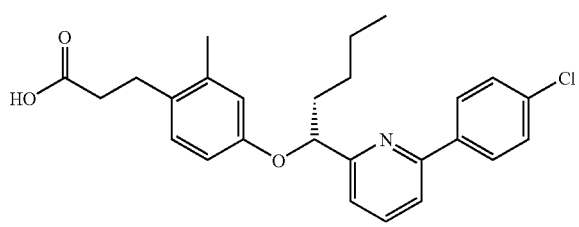

LC/MS and ¹H NMR as described for Example 103

EXAMPLE 109

3-{3,5-Dimethyl-4-[(1-{6-[4-(trifluoromethyl)phenyl]-2-pyridinyl}pentyl)oxy]phenyl}propanoic acid

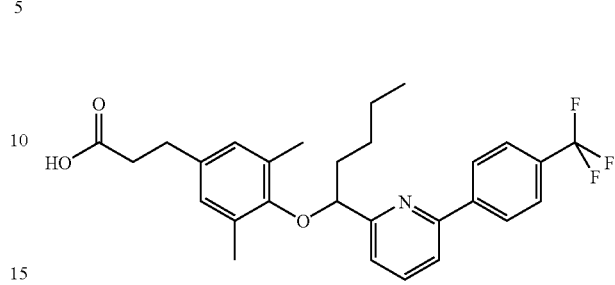

Prepared according to the procedure used to prepare Intermediate 73 starting from (2E)-3-{3,5-dimethyl-4-[(1-{6-[4-(trifluoromethyl)phenyl]-2-pyridinyl}pentyl)oxy]phenyl}-2-propenoic acid (28 mg, 0.06 mmol) to give, after further purification by mass directed autoprep HPLC, the title compound (15 mg).

LC/MS: m/z 486.3 [M+H]⁺, $R_t$ 4.20 min.

¹H NMR (400 MHz; CDCl₃) δ: 0.85 (3H, t, J 7.0 Hz), 1.18-1.39 (4H, m), 2.11 (6H, s), 2.14-2.28 (2H, m), 2.62 (2H, m), 2.83 (2H, m), 4.96 (1H, dd, J 7.5, 6.0 Hz), 6.79 (2H, s), 7.40 (1H, d, J 7.5 Hz), 7.68 (1H, d, J 7.5 Hz), 7.71 (2H, d, J 8.5 Hz), 7.77 (1H, t, J 7.5 Hz), 8.10 (2H, d, J 8.5 Hz).

EXAMPLE 110

3-{3-(Methyloxy)-5-propyl-4-[(1-{6-[4-(trifluoromethyl)phenyl]-2-pyridinyl}pentyl)oxy]phenyl}propanoic acid

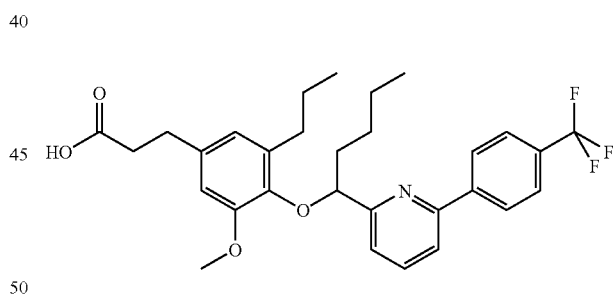

Prepared according to the procedure used to prepare Intermediate 73 starting from (2E)-3-{3-(methyloxy)-5-(2-propen-1-yl)-4-[(1-{6-[4-(trifluoromethyl)phenyl]-2-pyridinyl}pentyl)oxy]phenyl}-2-propenoic acid (68 mg, 0.13 mmol) to give, after further purification by mass directed autoprep HPLC, the title compound (36 mg).

LC/MS: m/z 430.2 [M+H]⁺, $R_t$ 4.24 min.

¹H NMR (400 MHz; CDCl₃) δ: 0.83 (3H, t, J 7.5 Hz), 0.87 (3H, m), 1.26-1.38 (4H, m), 1.38-1.59 (2H, m), 2.03-2.14 (1H, m), 2.16-2.28 (1H, m), 2.43 (2H, t, J 8.0 Hz), 2.63 (2H, m), 2.85 (2H, m), 3.69 (3H, s), 4.96 (1H, dd, J 7.0, 5.5 Hz), 6.55 (2H, s), 7.46 (1H, d, J 7.5 Hz), 7.64 (1H, d, J 7.5 Hz), 7.70 (2H, d, J 8.0 Hz), 7.75 (1H, t, J 7.5 Hz), 8.10 (2H, d, J 8.0) Hz).

EXAMPLE 111

3-{3-Propyl-4-[(1-{6-[4-(trifluoromethyl)phenyl]-2-pyridinyl}pentyl)oxy]phenyl}propanoic acid

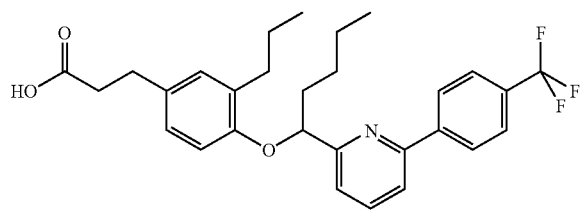

Prepared according to the procedure used to prepare Intermediate 73 starting from (2E)-3-{3-(2-propen-1-yl)-4-[(1-{6-[4-(trifluoromethyl)phenyl]-2-pyridinyl}pentyl)oxy]phenyl}-2-propenoic acid (39 mg, 0.08 mmol) to give, after further purification by mass directed autoprep HPLC, the title compound (25 mg).

LC/MS: m/z 500.2 [M+H]$^+$, R$_t$ 4.37 min.

$^1$H NMR (400 MHz; CDCl$_3$) δ: 0.92 (3H, t, J 7.5 Hz), 1.02 (3H, t, J 7.5 Hz), 1.34-1.45 (2H, m), 1.46-1.59 (2H, m), 1.71 (2H, m), 2.04 (2H, m), 2.59 (2H, m), 2.71 (2H, t, J 8.0 Hz), 2.81 (2H, m), 5.30 (1H, dd, J 6.5, 6.5 Hz), 6.54 (1H, d, J 8.5 Hz), 6.78 (1H, dd, J 8.5, 2.5 Hz), 6.97 (1H, d, J 2.5 Hz), 7.31 (1H, d, J 7.5 Hz), 7.62 (1H, d, J 7.5 Hz), 7.71 (1H, t, J 7.5 Hz), 7.75 (2H, d, J 8.0 Hz), 8.15 (2H, d, J 8.0 Hz).

EXAMPLE 112

3-{3-(Ethyloxy)-4-[(1-{6-[4-(trifluoromethyl)phenyl]-2-pyridinyl}pentyl)oxy]phenyl}propanoic acid

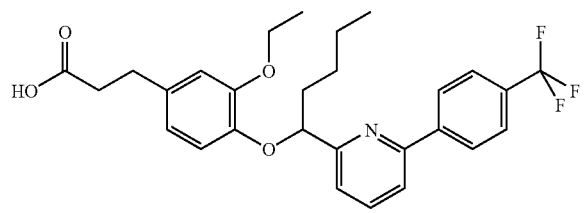

Prepared according to the procedure used to prepare Intermediate 73 starting from (2E)-3-{3-(ethyloxy)-4-[(1-{6-[4-(trifluoromethyl)phenyl]-2-pyridinyl}pentyl)oxy]phenyl}-2-propenoic acid (305 mg, 0.61 mmol) to give, after further purification by mass directed autoprep HPLC, the title compound (26 mg).

LC/MS: m/z 502.2 [M+H]$^+$, R$_t$ 4.10 min.

$^1$H NMR (400 MHz; MeOD-d$^4$) δ: 0.87 (3H, t, J 7.5 Hz), 1.30-1.58 (4H, m), 1.36 (3H, t, J 7.0 Hz), 1.90-2.09 (2H, m), 2.46 (2H, t, J 7.5 Hz), 2.72 (2H, t, J 7.5 Hz), 4.03 (2H, d, J 7.0 Hz), 5.23 (1H, dd, J 7.5, 5.0 Hz), 6.52 (1H, dd, J 8.5, 2.0 Hz), 6.64 (1H, d, J 8.5 Hz), 6.78 (1H, d, J 2.0 Hz), 7.46 (1H, dd, J 7.5, 1.0 Hz), 7.72 (2H, d, J 8.5 Hz), 7.73 (1H, dd, J 7.5, 1.0 Hz), 7.78 (1H, t, J 7.5 Hz), 8.16 (2H, d, J 8.5 Hz).

General Procedure for Examples 113-117

A stirred solution of alcohol (1S)-1-{6-[4-(trifluoromethyl)phenyl]-2-pyridinyl}-1-pentanol (65 mg, 0.21 mmol) and the appropriate phenol (0.33 mmol) in THF (4 mL) at 0° C. under nitrogen was added ADDP (106 mg, 0.42 mmol) followed by tri-N-butylphosphine (0.105 mL, 0.42 mmol). The resulting mixture was then allowed to warm slowly to ambient temperature overnight. After 21 h the solvent was removed under vacuum (Genevac) and the solid residue dissolved in THF (2 mL), MeOH (2 mL) and treated with aqueous NaOH (2N, 2 mL). The resulting mixture was then stirred at rt for 2-3 h and then treated with aqueous HCl (2N, 2 mL) and the solvents removed under vacuum (Genevac). The residue was then purified using the OPTIX-SPE (018 cartridge, 5 g) eluting with 50-100% MeCN (+0.05% HCOOH) in H$_2$O (+0.01% HCOOH) over 15 mins to afford the crude product OPTIX. The sulting crude product containing un-reacted alcohol was further purified using an SPE (silica, 2 or 5 g cartridge) eluting with cyclohexane:EtOAc (gradient 50:1 or 20:1 to 0:1) to give the desired product.

EXAMPLE 113

3-{4-[((1R)-1-{6-[4-(Trifluoromethyl)phenyl]-2-pyridinyl}pentyl)oxy]phenyl}propanoic acid

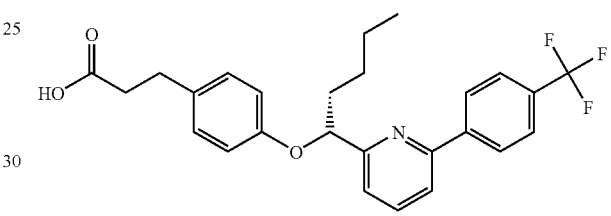

LC/MS: m/z 458.2 [M+H]$^+$, R$_t$ 4.17 min.

$^1$H NMR (400 MHz; CDCl$_3$) δ: 0.93 (3H, t, J 7.5 Hz), 1.36-1.46 (2H, m), 1.46-1.64 (2H, m), 2.03 (2H, m), 2.60 (2H, t, J 7.5 Hz), 2.84 (2H, t, J 7.5 Hz), 5.30 (1H, dd, J 6.5, 6.5 Hz), 6.83 (2H, d, J 8.5 Hz), 7.04 (2H, d, J 8.5 Hz), 7.38 (1H, d, J 8.0 Hz), 7.62 (1H, d, J 8.0 Hz), 7.72 (1H, t, J 8.0 Hz), 7.75 (2H, d, J 8.0 Hz), 8.15 (2H, d, J 8.0 Hz),

EXAMPLE 114

3-{3-Methyloxy)-4-[((1R)-1-{6-[4-(trifluoromethyl)phenyl]-2-pyridinyl}pentyl)oxy]phenyl}propanoic acid

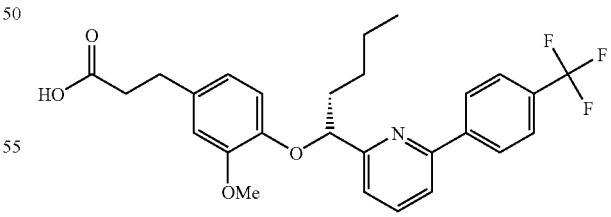

LC/MS: m/z 488.2 [M+H]$^+$, R$_t$ 4.02 min.

$^1$H NMR (400 MHz; CDCl$_3$) δ: 0.92 (3H, t, J 7.5 Hz), 1.34-1.46 (2H, m), 1.45-1.55 (1H, m), 1.55-1.68 (1H, m), 2.01-2.20 (2H, m), 2.61 (2H, t, J 7.5 Hz), 2.84 (2H, t, J 7.5 Hz), 3.89 (3H, s), 5.29 (1H, dd, J 7.0, 6.0 Hz), 6.56 (1H, dd, J 8.0, 1.5 Hz), 6.68 (1H, dd, J 8.0 Hz), 6.74 (1H, d, J 1.5 Hz), 7.48 (1H, d, J 7.5 Hz), 7.61 (1H, d, J 7.5 Hz), 7.70-7.77 (3H, m), 8.14 (2H, d, J 8.0 Hz).

EXAMPLE 115

{4-[((1R)-1-{6-[4-(Trifluoromethyl)phenyl]-2-pyridinyl}pentyl)oxy]phenyl}acetic acid

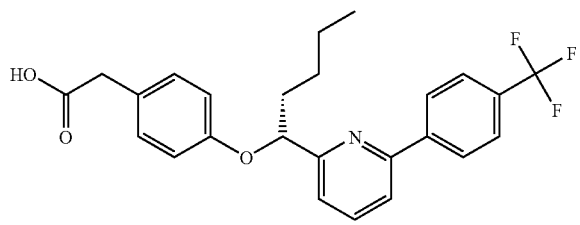

LC/MS: m/z 444.2 [M+H]$^+$, R$_t$ 4.09 min.

$^1$H NMR (400 MHz; CDCl$_3$) δ: 0.92 (3H, t, J 7.5 Hz), 1.34-1.45 (2H, m), 1.45-1.65 (2H, m), 2.03 (2H, m), 3.51 (2H, s), 5.30 (1H, dd, J 6.5, 6.5 Hz), 6.86 (2H, d, J 8.5 Hz), 7.10 (2H, d, J 8.5 Hz), 7.37 (1H, d, J 7.5 Hz), 7.62 (1H, d, J 7.5 Hz), 7.72 (1H, t, J 7.5 Hz), 7.75 (2H, d, J 8.0 Hz), 8.14 (2H, d, J 8.0 Hz),

EXAMPLE 116

{3-Chloro-4-[((1R)-1-{6-[4-(trifluoromethyl)phenyl]-2-pyridinyl}pentyl)oxy]phenyl}acetic acid

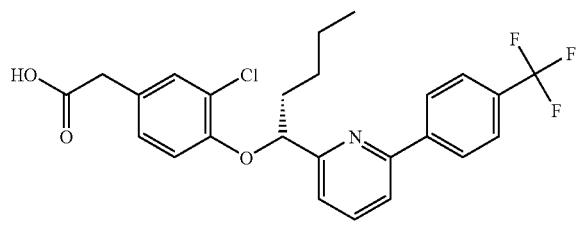

LC/MS: m/z 478.1 [M+H]$^+$, R$_t$ 4.23 min.

$^1$H NMR (400 MHz; CDCl$_3$) δ: 0.92 (3H, t, J 7.5 Hz), 1.34-1.46 (2H, m), 1.46-1.68 (2H, m), 2.01-2.16 (2H, m), 3.49 (2H, s), 5.36 (1H, dd, J 7.5, 5.0 Hz), 6.74 (1H, d, J 8.5 Hz), 6.92 (1H, dd, J 8.5, 2.0 Hz), 7.30 (1H, d, J 2.0 Hz), 7.42 (1H, d, J 7.5 Hz), 7.64 (1H, d, J 7.5 Hz), 7.75 (1H, t, J 7.5 Hz), 7.75 (2H, d, J 8.0 Hz), 8.14 (2H, d, J 8.0 Hz).

EXAMPLE 117

{3-(Methyloxy)-4-[((1R)-1-{6-[4-(trifluoromethyl)phenyl]-2-pyridinyl}pentyl)oxy]phenyl}acetic acid

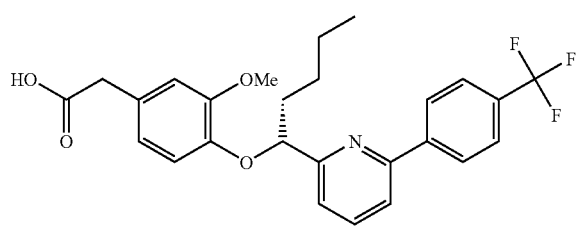

LC/MS: m/z 474.2 [M+H]$^+$, R$_t$ 3.96 min.

$^1$H NMR (400 MHz; CDCl$_3$) δ: 0.91 (3H, t, J 7.5 Hz), 1.34-1.44 (2H, m), 1.44-1.54 (1H, m), 1.54-1.67 (1H, m), 2.00-2.18 (2H, m), 3.51 (2H, s), 3.90 (3H, s), 5.29 (1H, dd, J 8.0, 5.0 Hz), 6.62 (1H, dd, J 8.0, 1.5 Hz), 6.70 (1H, d, J 8.0 Hz), 6.81 (1H, d, J 1.5 Hz), 7.46 (1H, d, J 7.5 Hz), 7.61 (1H, d, J 7.5 Hz), 7.69-7.77 (3H, m), 8.13 (2H, d, J 8.0 Hz).

General Procedure for Examples 118-121

The following compounds were prepared in a similar way to that described for Examples 113-117 except starting from alcohol (1R)-1-{6-[4-(trifluoromethyl)phenyl]-2-pyridinyl}-1-pentanol.

EXAMPLE 118

3-{4[((1S)-1-{6-[4-(Trifluoromethyl)phenyl]-2-pyridinyl}pentyl)oxy]phenyl}propanoic acid

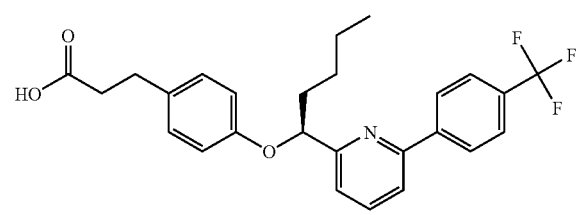

LC/MS and $^1$H NMR as described for Example 113.

EXAMPLE 119

3-{3-(Methyloxy)-4-[((1S)-1-{6-[4-(trifluoromethyl)phenyl]-2-pyridinyl}pentyl)oxy]phenyl}propanoic acid

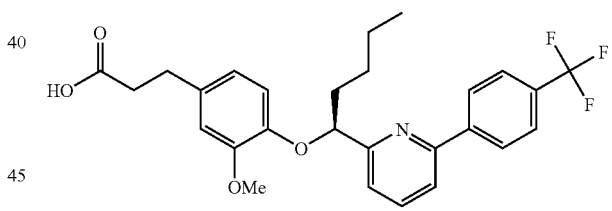

LC/MS and $^1$H NMR as described for Example 114.

EXAMPLE 120

{4-[((1S)-1-{6-[4-(Trifluoromethyl)phenyl]-2-pyridinyl}pentyl)oxy]phenyl}acetic acid

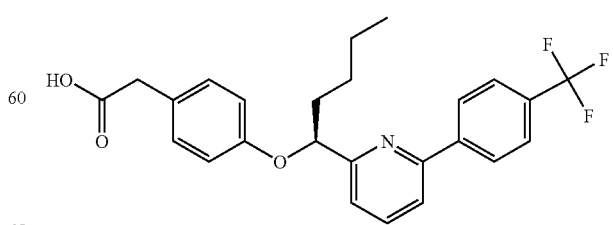

LC/MS and $^1$H NMR as described for Example 115.

EXAMPLE 121

{3-Chloro-4-[((1S)-1-{6-[4-(trifluoromethyl)phenyl]-2-pyridinyl}pentyl)oxy]phenyl}acetic acid

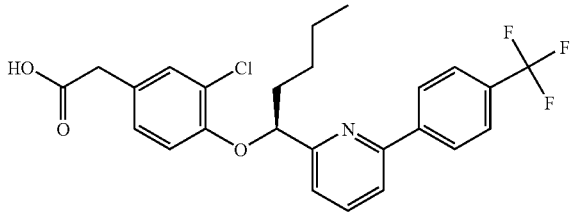

LC/MS and ¹H NMR as described for Example 116.

EXAMPLE 122

{3-(Methyloxy)-4-[((1S)-1-{6-[4-(trifluoromethyl)phenyl]-2-pyridinyl}pentyl)oxy]phenyl}acetic acid

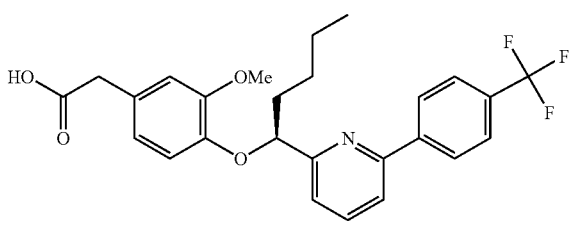

LC/MS and ¹H NMR as described for Example 117.

General Procedure for Examples 123-126

The following compounds were prepared using a similar procedure to Examples 113-117 except the mixtures were not reduced after the Mitsunobu reaction but were treated directly with MeOH (2 mL) and aqueous NaOH (2 mL), stirred for 3 h and then quenched with aqueous HCl (2N, 2 mL) and reduced. The residue was then suspended in a DCM (ca. 1 mL) and filtered through a bond elut cartridge directly onto a SPE (silica, 5 g cartridge) washing with a more DCM (2×0.5 mL). The cartridge was left to dry and the compound purified using the OPTIX-SPE (Si cartridge, 5 g) eluting with cyclohexane:EtOAc (gradient 85:15 to 0:1) over 15 mins to afford the desired products which were purified further by repeated SPE or mass directed autoprep HPLC as appropriate.

EXAMPLE 123

3-{3-Fluoro-4-[((1R)-1-{6-[4-(trifluoromethyl)phenyl]-2-pyridinyl}pentyl)oxy]phenyl}propanoic acid

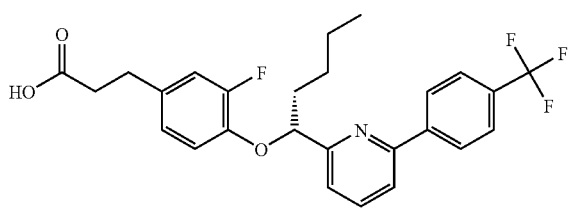

LC/MS: m/z 476.1 [M+H]⁺, $R_t$ 4.14 min.

¹H NMR (400 MHz; CDCl₃) δ: 0.92 (3H, t, J 7.5 Hz), 1.33-1.45 (2H, m), 1.45-1.54 (1H, m), 1.54-1.66 (1H, m), 1.99-2.16 (2H, m), 2.58 (2H, t, J 7.5 Hz), 2.82 (2H, t, J 7.5 Hz), 5.31 (1H, dd, J 8.0, 5.0 Hz), 6.72 (1H, dd, J 8.5, 2.0 Hz), 6.75 (1H, dd, J 16.0, 8.5 Hz), 6.93 (1H, dd, J 12.0, 2.0 Hz), 7.45 (1H, d, J 8.0 Hz), 7.64 (1H, d, J 8.0 Hz), 7.74 (2H, d, J 8.5 Hz), 7.76 (1H, t, J 8.5 Hz), 8.13 (2H, d, J 8.5 Hz).

EXAMPLE 124

3-{3-Methyl-4-[((1R)-1-{6-[4-(trifluoromethyl)phenyl]-2-pyridinyl}pentyl)oxy]phenyl}propanoic acid

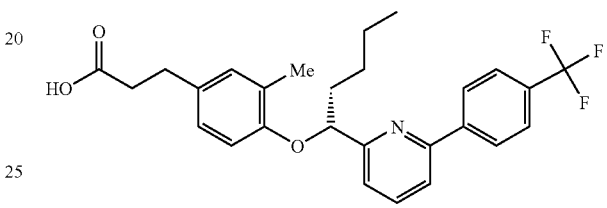

LC/MS: m/z 472.2 [M+H]⁺, $R_t$ 4.30 min.

¹H NMR (400 MHz; CDCl₃) δ: 0.92 (3H, t, J 7.5 Hz), 1.35-1.46 (2H, m), 1.46-1.65 (2H, m), 2.01-2.10 (2H, m), 2.35 (3H, s), 2.59 (2H, t, J 7.5 Hz), 2.81 (2H, t, J 7.5 Hz), 5.31 (1H, dd, J 6.5, 6.5 Hz), 6.56 (1H, d, J 8.5 Hz), 6.79 (1H, dd, J 8.5, 2.0 Hz), 7.00 (1H, d, J 2.0 Hz), 7.34 (1H, d, J 7.5 Hz), 7.62 (1H, d, J 7.5 Hz), 7.72 (1H, t, J 7.5 Hz), 7.75 (2H, d, J 8.5 Hz), 8.16 (2H, d, J 8.5 Hz).

EXAMPLE 125

3-{3,5-Bis(methyloxy)-4-[((1R)-1-{6-[4-(trifluoromethyl)phenyl]-2-pyridinyl}pentyl)oxy]phenyl}propanoic acid

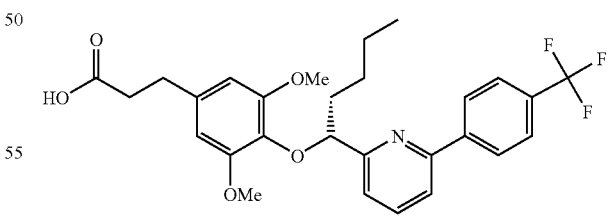

LC/MS: m/z 518.2 [M+H]⁺, $R_t$ 3.99 min.

¹H NMR (400 MHz; CDCl₃) δ: 0.89 (3H, t, J 7.5 Hz), 1.30-1.41 (2H, m), 1.41-1.52 (2H, m), 1.97-2.09 (1H, m), 2.09-2.22 (1H, m), 2.63 (2H, m), 2.85 (2H, m), 3.71 (6H, s), 5.28 (1H, dd, J 6.5, 6.5 Hz), 6.35 (2H, s), 7.60 (1H, dd, J 7.5, 1.5 Hz), 7.68 (2H, d, J 8.5 Hz), 7.71 (1H, dd, J 7.5, 1.5 Hz), 7.76 (1H, t, J 7.5 Hz), 8.06 (2H, d, J 8.5 Hz).

EXAMPLE 126

3-{2-(Methyloxy)-4-[((1R)-1-{6-[4-(trifluoromethyl)phenyl]-2-pyridinyl}pentyl)oxy]phenyl}propanoic acid

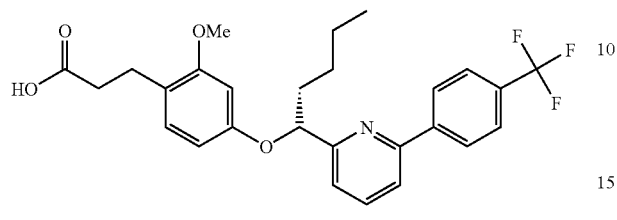

LC/MS: m/z 488.2 [M+H]+, R$_t$ 4.15 min.
$^1$H NMR (400 MHz; CDCl$_3$) δ: 0.92 (3H, t, J 7.5 Hz), 1.34-1.46 (2H, m), 1.46-1.53 (1H, m), 1.53-1.65 (1H, m), 1.98-2.08 (2H, m), 2.56 (2H, m), 2.80 (2H, m), 3.72 (3H, s), 5.30 (1H, dd, J 6.5, 6.5 Hz), 6.32 (1H, dd, J 8.5, 2.5 Hz), 6.52 (1H, d, J 2.5 Hz), 6.90 (1H, d, J 8.5, Hz), 7.38 (1H, d, J 7.5 Hz), 7.62 (1H, d, J 7.5 Hz), 7.70-7.76 (3H, m), 8.15 (2H, d, J 8.5 Hz).

General Procedure for Examples 127-130

The following compounds were prepared in a similar way to that described for Examples 123-126 except starting from alcohol (1R)-1-{6-[4-(trifluoromethyl)phenyl]-2-pyridinyl}-1-pentanol.

EXAMPLE 127

3-{3-Fluoro-4-[((1S)-1-{6-[4-(trifluoromethyl)phenyl]-2-pyridinyl}pentyl)oxy]phenyl}propanoic acid

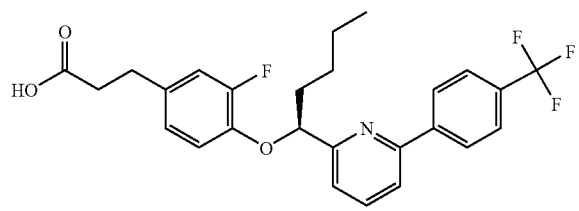

LC/MS and $^1$H NMR as described for Example 123.

EXAMPLE 128

3-{3-Methyl-4-[((1S)-1-{6-[4-(trifluoromethyl)phenyl]-2-pyridinyl}pentyl)oxy]phenyl}propanoic acid

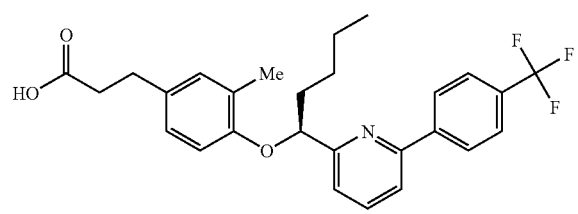

LC/MS and $^1$H NMR as described for Example 124.

EXAMPLE 129

3-{3,5-Bis(methyloxy)-4-[((1S)-1-{6-[4-(trifluoromethyl)phenyl]-2-pyridinyl}pentyl)oxy]phenyl}propanoic acid

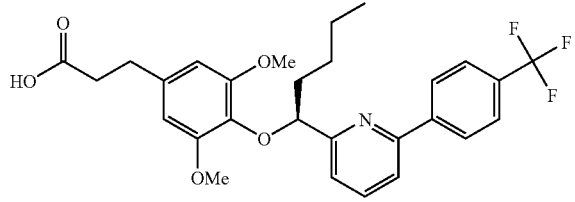

LC/MS and $^1$H NMR as described for Example 125.

EXAMPLE 130

3-{2-(Methyloxy)-4-[((1S)-1-{6-[4-(trifluoromethyl)phenyl]-2-pyridinyl}pentyl)oxy]phenyl}propanoic acid

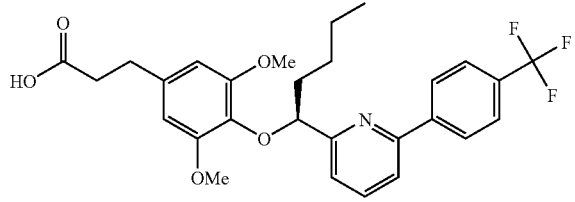

LC/MS and $^1$H NMR as described for Example 126.

EXAMPLE 131

3-{3-Chloro-5-(methyloxy)-4-[((1S)-1-{6-[4-(trifluoromethyl)phenyl]-2-pyridinyl}pentyl)oxy]phenyl}propanoic acid

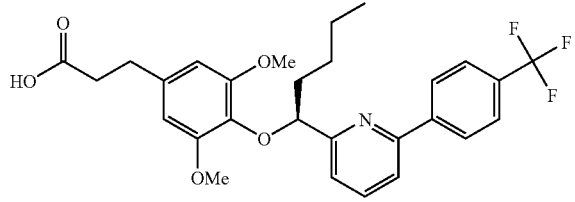

To a stirring solution of ethyl 3-{3-chloro-5-(methyloxy)-4-[((1S)-1-{6-[4-(trifluoromethyl)phenyl]-2-pyridinyl}pentyl)oxy]phenyl}propanoate (118 mg, 0.20 mmol) in THF (3 mL) and MeOH (3 mL) at ambient temperature was added NaOH (2N, 3 mL) and the mixture stirred for 2 h and then left to stand overnight. HCl (2N, 3 mL) was then added and the mixture reduced under vacuum.

The residue was then purified by SPE (silica, 5 g cartridge) with a pad of celite on the top, eluting with cyclohexane:EtOAc (gradient 20:1 to 0:1) to give the title compound (94 mg).

LC/MS: m/z 522.1 [M+H]+, $R_t$ 4.20 min.

1H NMR (400 MHz; CDCl3) δ: 0.88 (3H, t, J 7.0 Hz), 1.29-1.47 (4H, m), 2.02-2.14 (1H, m), 2.16-2.29 (1H, m), 2.63 (2H, m), 2.84 (2H, m), 3.69 (3H, s), 5.42 (1H, dd, J 6.5, 6.5 Hz), 6.59 (1H, d, J 2.0 Hz), 6.77 (1H, d, J 2.0 Hz), 7.64 (1H, d, J 7.5 Hz), 7.65 (1H, d, J 7.5 Hz), 7.69 (2H, d, J 8.0 Hz), 7.78 (1H, t, J 7.5 Hz), 8.07 (2H, d, J 8.0 Hz).

EXAMPLE 132

3-{3-Chloro-4-[((1R)-1-{6-[4-(trifluoromethyl)phenyl]-2-pyridinyl}pentyl)oxy]phenyl}propanoic acid

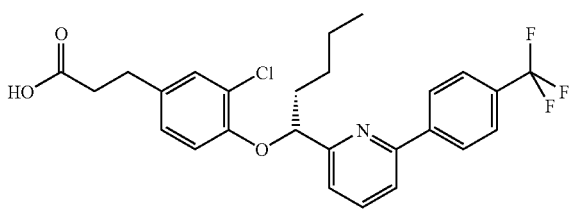

To a stirring solution of ethyl (2E)-3-{3-chloro-4-[((1R)-1-{6-[4-(trifluoromethyl)phenyl]-2-pyridinyl}pentyl)oxy]phenyl}-2-propenoate (54 mg, 0.10 mmol) in EtOAc (4 mL) under nitrogen at ambient temperature was added PtO2 (20 wt %, 11 mg) and the mixture stirred under an atmosphere of hydrogen for 5 h. The resulting mixture was then purified by SPE (silica, 5 g cartridge) with a pad of celite on the top, eluting with EtOAc. The filtrate was then reduced and purified further by SPE (silica, 5 g cartridge) eluting with cyclohexane:EtOAc (gradient 50:1 to 20:1) to give an inseparable mixture containing the desired material and some de-chlorinated compound (51 mg). This material was then dissolved in THF (2 mL) and MeOH (2 mL) at ambient temperature and treated with NaOH (2N, 2 mL). The resulting mixture was then stirred for 2 h and then left to stand overnight. HCl (2N, 2 mL) was then added and the mixture reduced under vacuum. The residue was then purified by SPE (silica, 5 g cartridge) with a pad of celite on the top, eluting with cyclohexane:EtOAc (gradient 20:1 to 0:1) to give a residue which was purified further by mass directed autoprep HPLC to give the title compound (30 mg).

LC/MS: m/z 492.2 [M+H]+, $R_t$ 4.28 min.

1H NMR (400 MHz; CDCl3) δ: 0.91 (3H, t, J 7.5 Hz), 1.33-1.45 (2H, m), 1.46-1.65 (2H, m), 2.03-2.15 (2H, m), 2.58 (2H, t, J 7.5 Hz), 2.80 (2H, t, J 7.5 Hz), 5.38 (1H, dd, J 7.5, 5.0 Hz), 6.71 (1H, d, J 8.5 Hz), 6.86 (1H, dd, J 8.5, 2.0 Hz), 7.21 (1H, d, J 2.0 Hz), 7.45 (1H, d, J 7.5 Hz), 7.64 (1H, d, J 7.5 Hz), 7.74 (2H, d, J 8.0 Hz), 7.78 (1H, t, J 7.5 Hz), 8.12 (2H, d, J 8.0 Hz).

EXAMPLE 133

3-{2-Chloro-4-[((1R)-1-{6-[4-(trifluoromethyl)phenyl]-2-pyridinyl}pentyl)oxy]phenyl}propanoic acid

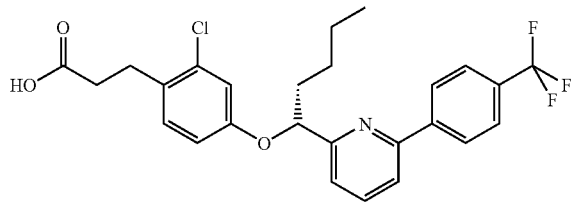

Prepared according to the procedure used to prepare Example 132 starting from ethyl (2E)-3-{2-chloro-4-[((1R)-{6-[4-(trifluoromethyl)phenyl]-2-pyridinyl}pentyl)oxy]phenyl}-2-propenoate (53 mg, 0.10 mmol) to afford the title compound (29 mg).

LC/MS: m/z 492.1 [M+H]+, $R_t$ 4.35 min.

1H NMR (400 MHz; CDCl3) δ: 0.91 (3H, t, J 7.5 Hz), 1.33-1.43 (2H, m), 1.43-1.62 (2H, m), 1.96-2.06 (2H, m), 2.61 (2H, m), 2.93 (2H, m), 5.26 (1H, dd, J 6.5, 6.5 Hz), 6.71 (1H, dd, J 8.5, 2.5 Hz), 6.97 (1H, d, J 2.5 Hz), 7.05 (1H, d, J 8.5 Hz), 7.35 (1H, d, J 8.0 Hz), 7.64 (1H, d, J 8.0 Hz), 7.74 (1H, t, J 8.0 Hz), 7.75 (2H, d, J 8.0 Hz), 8.14 (2H, d, J 8.0 Hz).

EXAMPLE 134

3-{3-Chloro-4-[((1S)-1-{6-[4-(trifluoromethyl)phenyl]-2-pyridinyl}pentyl)oxy]phenyl}propanoic acid

Prepared according to the procedure used to prepare Example 132 starting from ethyl (2E)-3-{3-chloro-4-[((1S)-1-{6-[4-(trifluoromethyl)phenyl]-2-pyridinyl}pentyl)oxy]phenyl}-2-propenoate (41 mg, 0.08 mmol) to afford the title compound (12 mg).

LC/MS and 1H NMR as described for Example 132.

EXAMPLE 135

3-{2-Chloro-4-[((1S)-1-{6-[4-(trifluoromethyl)phenyl]-2-pyridinyl}pentyl)oxy]phenyl}propanoic acid

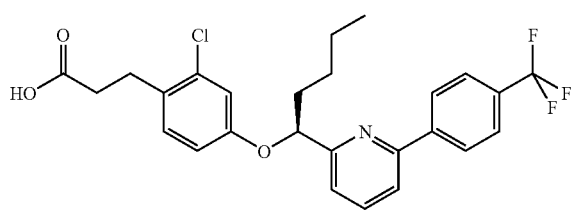

Prepared according to the procedure used to prepare Example 132 starting from ethyl (2E)-3-{2-chloro-4-[((1S)-1-{6-[4-(trifluoromethyl)phenyl]-2-pyridinyl}pentyl)oxy]phenyl}-2-propenoate (111 mg, 0.21 mmol) to afford the title compound (42 mg).

LC/MS and $^1$H NMR as described for Example 133.

General Procedure for Examples 136-141

To a solution of ethyl [(4-{[1-(3-bromo-2-methylphenyl)pentyl]oxy}-2-methylphenyl)oxy]acetate (75 mg, 0.17 mmol) in DME (4 mL) under nitrogen at room temperature was added the appropriate boronic acid (0.20 mmol), water (2 mL) and sodium carbonate (46 mg, 0.43 mmol). The reaction vessel was flushed with nitrogen, Pd(PPh$_3$)$_4$ (4 mg, 0.003 mmol) added and the resulting mixture heated to 80° C. and stirred for 18 h. The reaction mixture was allowed to cool and the solvents removed under vacuum. (Genevac) and the residue purified by SPE (10 g, C$_{18}$ cartridge), eluting with MeCN:H$_2$O gradient (1:19 to 9:1). The fractions containing UV active material collected and concentrated by Genevac. Further purification by SPE (10 g, aminopropyl cartridge), eluting with DCM, CHCl$_3$, Et$_2$O, EtOAc, MeOH and then NH$_3$:MeOH (1:9). The NH$_3$/MeOH fraction was shaken with 2M HCl (4.5 mL) and DCM (10 mL) at room temperature for 2 h, passed through a hydrophobic frit, combined with the MeOH fraction and concentrated under vacuum to afford the title compounds, with further purification by mass directed autoprep HPLC where appropriate.

EXAMPLE 136

{[2-Methyl-4-({1-[2-methyl-4'-(trifluoromethyl)-3-biphenylyl]pentyl}oxy)phenyl]oxy}acetic acid

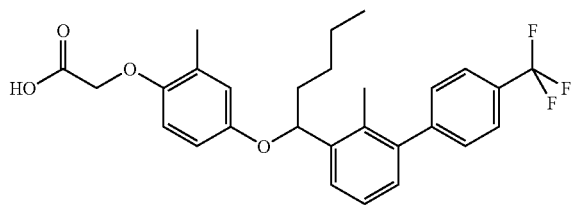

LC/MS: m/z 504.2 [M+NH$_4$]$^+$, R$_t$ 4.32 min.

$^1$H NMR (400 MHz; MeOD-d$^4$) δ: 0.93 (3H, t, J 7.5 Hz), 1.32-1.54 (3H, m), 1.54-1.66 (1H, m), 1.73-1.83 (1H, m), 1.83-1.96 (1H, m), 2.17 (3H, s), 2.23 (3H, s), 4.37 (2H, s), 5.30 (1H, dd, 8.5, 4.0 Hz), 6.47 (1H, dd, J 9.0, 3.0 Hz), 6.59 (1H, d, J 9.0 Hz), 6.65 (1H, d, J 3.0 Hz), 7.06 (1H, d, J 7.5 Hz), 7.19 (1H, t, J 7.5 Hz), 7.42 (1H, d, J 7.5 Hz), 7.46 (2H, d, J 8.0 Hz), 7.71 (2H, d, J 8.0 Hz).

EXAMPLE 137

[(4-{[1-(4'-Chloro-2-methyl-3-biphenylyl)pentyl]oxy}-2-methylphenyl)oxy]acetic acid

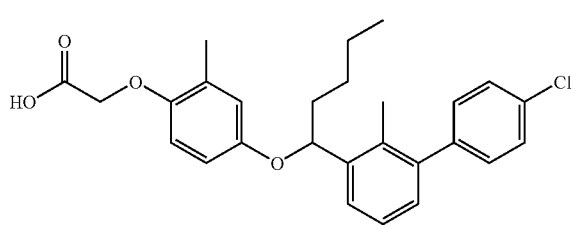

LC/MS: m/z 470.3 [M+NH$_4$]$^+$, R$_t$ 4.41 min.

$^1$H NMR (400 MHz; MeOD-d$^4$) δ: 0.92 (3H, t, J 7.5 Hz), 1.32-1.53 (3H, m), 1.53-1.66 (1H, m), 1.72-1.83 (1H, m), 1.83-1.96 (1H, m), 2.16 (3H, s), 2.23 (3H, s), 4.51 (2H, s), 5.29 (1H, dd, 8.5, 4.0 Hz), 6.47 (1H, dd, J 9.0, 3.0 Hz), 6.60 (1H, d, J 9.0 Hz), 6.66 (1H, d, J 3.0 Hz), 7.04 (1H, d, J 7.5 Hz), 7.16 (1H, t, J 7.5 Hz), 7.24 (2H, d, J 8.5 Hz), 7.39 (3H, m).

EXAMPLE 138

[(4-{[1-(2,4'-Dimethyl-3-biphenylyl)pentyl]oxy}-2-methylphenyl)oxy]acetic acid

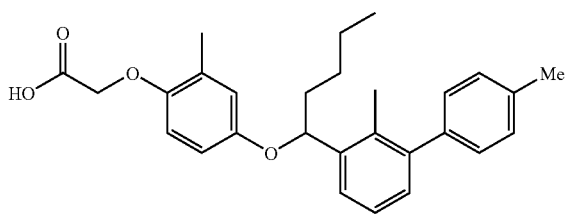

LC/MS: m/z 450.3 [M+NH$_4$]$^+$, R$_t$ 4.34 min.

$^1$H NMR (400 MHz; MeOD-d$^4$) δ: 0.92 (3H, t, J 7.5 Hz), 1.30-1.52 (3H, m), 1.52-1.65 (1H, m), 1.70-1.81 (1H, m), 1.81-1.93 (1H, m), 2.16 (3H, s), 2.22 (3H, s), 2.37 (3H, s), 4.39 (2H, s), 5.27 (1H, dd, J 8.5, 4.0), 6.46 (1H, dd J 9.0, 3.0 Hz), 6.59 (1H, d, J 9.0 Hz), 6.64 (1H, d, J 3.0 Hz), 7.01 (1H, d, J 7.5, 1.0 Hz), 7.12 (1H, t, J 7.5 Hz), 7.12 (2H, d, J 8.0 Hz), 7.20 (2H, d, J 8.0 Hz), 7.33 (1H, dd, J 7.5, 1.0 Hz).

EXAMPLE 139

[(4-{[1-(4'-Cyano-2-methyl-3-biphenylyl)pentyl]oxy}-2-methylphenyl)oxy]acetic acid

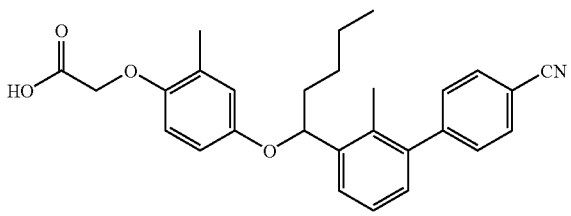

LC/MS: m/z 461.3 [M+NH$_4$]$^+$, R$_t$ 4.07 min.

$^1$H NMR (400 MHz; MeOD-d$^4$) δ: 0.93 (3H, t, J 7.5 Hz), 1.34-1.53 (3H, m), 1.53-1.66 (1H, m), 1.74-1.84 (1H, m), 1.84-1.96 (1H, m), 2.16 (3H, s), 2.23 (3H, s), 4.53 (2H, s), 5.31 (1H, dd, J 8.5, 4.0 Hz), 6.48 (1H, dd, J 9.0 Hz, 3.0 Hz), 6.61 (1H, d, J 9.0 Hz), 6.67 (1H, d, J 3.0 Hz), 7.06 (1H, d, J 7.5 Hz), 7.21 (1H, t, J 7.5 Hz), 7.43 (1H, d, J 7.5 Hz), 7.47 (2H, d, J 8.5 Hz), 7.78 (2H, d, J8.5 Hz).

EXAMPLE 140

{[2-Methyl-4-({1-[2-methyl-4'-(methyloxy)-3-biphenylyl]pentyl}oxy)phenyl]oxy}acetic acid

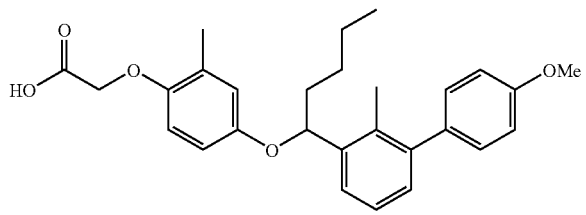

LC/MS: m/z 466.3 [M+NH$_4$]$^+$, R$_t$ 4.18 min.

$^1$H NMR (400 MHz; MeOD-d$^4$) δ: 0.92 (3H, t, J 7.5 Hz), 1.30-1.52 (3H, m), 1.52-1.65 (1H, m), 1.71-1.81 (1H, m), 1.81-1.93 (1H, m), 2.17 (3H, s), 2.22 (3H, s), 3.81 (3H, s), 4.34 (2H, s), 5.27 (1H, dd, J 8.5, 4.0 Hz), 6.45 (1H, dd, J 9.0, 3.0 Hz), 6.59 (1H, d, J 9.0 Hz), 6.64 (1H, d, J 3.0 Hz), 6.95 (2H, d, J 9.0 Hz), 7.02 (1H, dd, J 7.5, 1.0 Hz), 7.11 (1H, t, J 7.5 Hz), 7.16 (2H, d, J 9.0 Hz), 7.33 (1H, dd, J 7.5, 1.0 Hz).

EXAMPLE 141

[(4-{[1-(4'-Fluoro-2-methyl-3-biphenylyl)pentyl]oxy}-2-methylphenyl)oxy]acetic acid

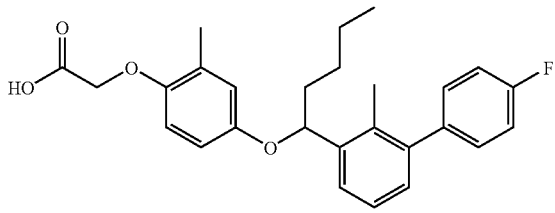

LC/MS: m/z 454.3 [M+NH$_4$]$^+$, R$_t$ 4.22 min.

$^1$H NMR (400 MHz; MeOD-d$^4$) δ: 0.92 (3H, t, J 7.5 Hz), 1.30-1.52 (3H, m), 1.52-1.65 (1H, m), 1.70-1.82 (1H, m), 1.82-1.95 (1H, m), 2.16 (3H, s), 2.22 (3H, s), 4.39 (2H, s), 5.28 (1H, dd, J 8.5, 4.0 Hz), 6.46 (1H, dd, J 9.0, 3.0 Hz), 6.59 (1H, d, J 9.0 Hz), 6.64 (1H, d, J 3.0 Hz), 7.03 (1H, dd, J 7.5, 1.0 Hz), 7.09-7.17 (3H, m), 7.22-7.29 (2H, m), 7.37 (1H, d, J 7.5, 1.0 Hz).

EXAMPLE 142

({2-Methyl-4-[(2-(propyloxy)-1-{6-[4-(trifluoromethyl)phenyl]-2-pyridinyl}ethyl)oxy]phenyl}oxy)acetic acid

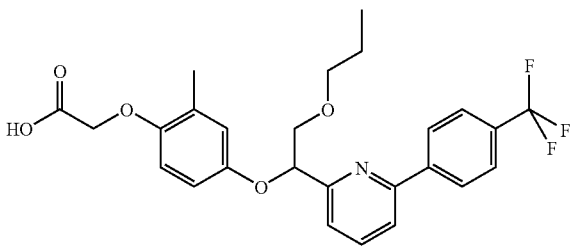

NaH (60% dispersion in mineral oil, 9.6 mg, 0.241 mmol) was washed with cyclohexane (3×1 mL) under nitrogen and the resulting powdery residue treated with THF (1 mL) and the resulting mixture cooled to 0° C. Ethyl ({4-[(2-hydroxy-1-{6-[4-(trifluoromethyl)phenyl]-2-pyridinyl}ethyl)oxy]-2-methylphenyl}oxy)acetate (88 mg, 0.185 mmol) in THF (1.85 mL) was then added drop-wise over 2 min. 1-Iodopropane (0.024 mL, 0.241 mmol) was then added and the resulting mixture allowed to warm to ambient temperature over 18 h. The reaction had caused hydrolysis of the ester and not alkylation so the mixture was reduced and purified by SPE (silica, 5 g cartridge) eluting with cyclohexane:EtOAc (+1% HCOOH) (gradient 10:1 to 1:10) then EtOAc:MeOH (1:1) to give the acid (66 mg, 0.148 mmol). This material was re-subjecting to the conditions described above using NaH (60% dispersion in mineral oil, 15.4 mg, 0.384 mmol) and 1-iodopropane (0.037 mL, 0.384 mmol) and the resulting solution reduced under vacuum. The residue was then partitioned between EtOAc (30 mL) and saturated aqueous NH$_4$OH (50 mL) and the layers separated. The aqueous was re-extracted with EtOAc (30 mL) and the combined organic layer washed with brine (30 mL) and reduced to give an oil. Purification by SPE (silica, 5 g cartridge) eluting with cyclohexane:EtOAc (+1% HCOOH) (gradient 10:1 to 1:10) then EtOAc:MeOH (1:1) afforded an oil which was further purified by mass directed autoprep HPLC to afford the title compound (5 mg).

LC/MS: m/z 490.1 [M+H]$^+$, R$_t$ 4.25 min.

$^1$H NMR (400 MHz; CDCl$_3$) δ: 0.86 (3H, t, J 7.5 Hz), 1.58 (2H, m), 2.19 (3H, s), 3.51 (2H, m), 3.91 (1H, dd, J 11.0, 7.0 Hz), 3.98 (1H, dd, J 11.0, 3.0 Hz), 4.52 (2H, s), 5.44 (1H, d, J 7.0, 3.0 Hz), 6.56 (1H, d, J 9.0 Hz), 6.64 (1H, dd, J 9.0, 3.0 Hz), 6.83 (1H, d, J 3.0 Hz), 7.42 (1H, d, J 7.5 Hz), 7.65 (1H, d, J 7.5 Hz), 7.73 (1H, t, J 7.5 Hz), 7.73 (2H, d, J 8.0 Hz), 8.14 (2H, d, J 8.0 Hz).

EXAMPLE 143

({4-[(2-(Ethyloxy)-1-{6-[4-(trifluoromethyl)phenyl]-2-pyridinyl}ethyl)thio]-2-methylphenyl}oxy)acetic acid (Enantiomer 1)

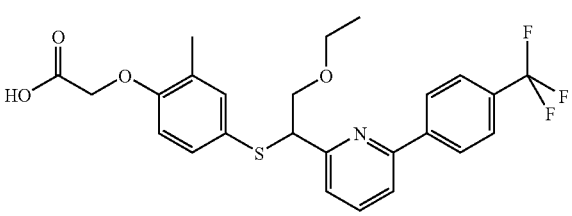

A solution of the ethyl ({4-[(2-(ethyloxy)-1-{6-[4-(trifluoromethyl)phenyl]-2-pyridinyl}ethyl)thio]-2-methylphenyl}oxy)acetate (Enantiomer 1) (12 mg, 0.023 mmol) in THF (1 mL) and MeOH (1 mL) was treated with aqueous NaOH (2N, 1 mL) and the resulting mixture agitated at ambient temperature for 15 h. Aqueous HCl (2N, 1 mL) was then added and the organic solvents removed under vacuum using a Genevac. The residue was the then made up to 2 mL by the addition of water and then extracted using DCM (3×3 mL) in an hydrophobic frit. The residue was reduced and then purified further by mass directed autoprep HPLC to afford the title compound as an oil (7 mg).

LC/MS: m/z 492.2 [M+H]$^+$, R$_t$ 4.09 min.

$^1$H NMR (400 MHz; CDCl$_3$) δ: 1.12 (3H, t, J 7.0 Hz), 2.17 (3H, s), 3.50 (2H, m), 3.93 (1H, dd, J 10.0, 6.0 Hz), 4.11 (1H, dd, J 10.0, 8.0 Hz), 4.44 (1H, dd, J 8.0, 6.0 Hz), 4.60 (2H, s), 6.56 (1H, d, J 8.5 Hz), 7.15 (1H, dd, J 8.5, 2.0 Hz), 7.18

(1H, d, J 2.0 Hz), 7.27 (1H, d, J 7.5 Hz), 7.61 (1H, d, J 7.5 Hz), 7.67-7.73 (3H, m), 8.04 (2H, d, J 8.0 Hz).

EXAMPLE 144

({4-[(2-(Ethyloxy)-1-{6-[4-(trifluoromethyl)phenyl]-2-pyridinyl}ethyl)thio]-2-methylphenyl}oxy)acetic acid (Enantiomer 2)

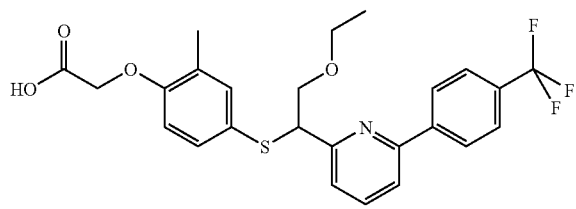

Prepared according to the procedure used to prepare Example 143 (Enantiomer 1) starting from ethyl ({4-[(2-(ethyloxy)-1-{6-[4-(trifluoromethyl)phenyl]-2-pyridinyl}ethyl)thio]-2-methylphenyl}oxy)acetate (Enantiomer 2) (13.7 mg, 0.026 mmol) to give, after further purification by mass directed autoprep HPLC, the title compound (9.1 mg).

LC/MS and $^1$H NMR as described for Example 143

The following intermediates and ligands were prepared for the binding and transfection assays described below:

(i) ({2-Methyl-4-[({4-methyl-2-[4-(trifluoromethyl)phenyl]-1,3-thiazol-5-yl}methyl)thio]phenyl}oxy)acetic acid.

This compound was used as a PPAR delta reference in the transfection assays described below and was prepared according to the method reported in WO200100603-A1

(ii) 2-Methyl-2-[(4-{[({4-methyl-2-[4-(trifluoromethyl)phenyl]-1,3-thiazol-5-yl}carbonyl)amino]methyl}phenyl)oxy]propanoic acid.

This compound was used as a PPAR alpha reference in the transfection assay described below and was prepared according to method reported in WO200140207-A1

(iii) 5-{[4-{(2-[Methyl(2-pyridinyl)amino]ethyl}oxy)phenyl]methyl}-1,3-thiazolidine-2,4-dione This compound was used as a PPAR gamma reference in the transfection assay described below and was prepared according to method reported in J. Med. Chem. 1994, 37(23), 3977

Binding Assay:

Compounds were tested for their ability to bind to hPPAR gamma, hPPAR alpha or hPPAR delta using a Scintillation Proximity Assay (SPA). The PPAR ligand binding domain (LBD) was expressed in E. coli as polyHis tagged fusion proteins and purified. The LBD was then labelled with biotin and immobilised on streptavidin-modified scintillation proximity beads. The beads were then incubated with a constant amount of the appropriate radioligand (3H-BRL 49653 for PPAR gamma, and labelled GW 2433 (see Brown, P. J et al. Chem. Biol., 4, 909-918 (1997) for the structure and synthesis of this ligand) for PPAR alpha and PPAR delta and variable concentrations of test compound, and after equilibration the radioactivity bound to the beads was measured by a scintillation counter. For each compound tested, plots of ligand concentration vs. CPM of radioligand bound were constructed and apparent Ki values were estimated from nonlinear least squares fit of the data assuming simple competitive binding. The details of this assay have been reported elsewhere (see, Blanchard, S. G. et. al. Development of a Scintillation Proximity Assay for Peroxisome Proliferator-Activated Receptor gamma Ligand Binding Domain. Anal. Biochem., 257, 112-119 (1998)).

Transfection Assay:

Compounds were screened for functional potency in transient transfection assays in CV-1 cells for their ability to activate the PPAR subtypes (transactivation assay). A previously established chimeric receptor system was utilized to allow comparison of the relative transcriptional activity of the receptor subtypes on the same target gene and to prevent endogenous receptor activation from complicating the interpretation of results. See, for example, Lehmann, J. M.; Moore, L. B.; Smith-Oliver, T. A.; Wilkison, W. O.; Willson, T. M.; Kliewer, S. A., An antidiabetic thiazolidinedione is a high affinity ligand for peroxisome proliferator-activated receptor gamma (PPARgamma), J. Biol. Chem., 270, 12953-6 (1995). The ligand binding domains for murine and human PPAR alpha, PPAR gamma, and PPAR delta were each fused to the yeast transcription factor GAL4 DNA binding domain. CV-1 cells were transiently transfected with expression vectors for the respective PPAR chimera along with a reporter construct containing five copies of the GAL4 DNA binding site driving expression of secreted placental alkaline phosphatase (SPAP) and beta-galactosidase. After 16 h, the medium was exchanged to DME medium supplemented with 10% delipidated fetal calf serum and the test compound at the appropriate concentration. After an additional 24 h, cell extracts were prepared and assayed for alkaline phosphatase and beta-galactosidase activity. Alkaline phosphatase activity was corrected for transfection efficiency using the beta-galactosidase activity as an internal standard (see, for example, Kliewer, S. A., et. al. Cell 83, 813-819 (1995)). Rosiglitazone (BRL 49653) was used as a positive control in the hPPAR gamma assay. The positive control in the hPPAR alpha assays was 2-methyl-2-[(4-{[({4-methyl-2-[4-(trifluoromethyl)phenyl]-1,3-thiazol-5-yl}carbonyl)amino]methyl}phenyl)oxy]propanoic acid. The positive control for PPAR delta assays was ({2-methyl-4-[({4-methyl-2-[4-(trifluoromethyl)phenyl]-1,3-thiazol-5-yl}methyl)thio]phenyl}oxy)acetic acid.

All of the above acid Examples showed at least 50% activation of PPARδ relative to the positive control at concentrations of $10^{-7}$ M or less.

We claim:

1. A compound of formula (I) or a pharmaceutically acceptable salt, or hydrolysable ester thereof,

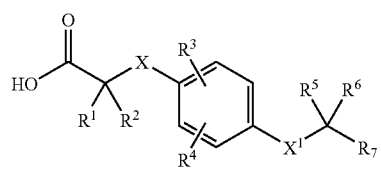

(1)

wherein:
$R^1$ and $R^2$ are independently H or $C_{1-3}$ alkyl;
X represents a O or $(CH_2)_n$ where n is 0, 1 or 2;
$R^3$ and $R^4$ independently represent H, $C_{1-3}$ alkyl, —OCH$_3$, —CF$_3$, allyl, or halogen;
$X^1$ represents O, S, SO$_2$, SO, or CH$_2$;
$R^5$ and $R^6$ independently represent hydrogen, $C_{1-6}$ alkyl (including branched alkyl and optionally substituted by one or more halogens or $C_{1-6}$alkoxy), or together with the carbon atom to which they are bonded form a 3-6 membered cycloalkyl ring; and
R⁷ is

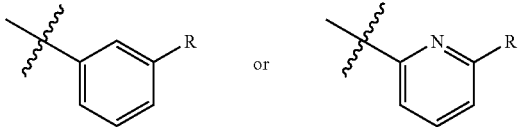

wherein R is para —C₆H₄CF₃, para —C₆H₄Me, para —C₆H₄CN or para —C₆H₄Cl.

2. A compound according to claim 1 wherein R¹ and R² are both H or both methyl.

3. A compound according to claim 2 wherein R¹ and R² are both H.

4. A compound according to claim 1 wherein X is O.

5. A compound according to claim 1 wherein R³ and R⁴ are independently H or C₁₋₃ alkyl.

6. A compound according to claim 5 wherein one of R³ and R⁴ is H and the other is not.

7. A compound according to claim 6 wherein the substituent group which is not H is positioned ortho to the X moiety.

8. A compound according to claim 6 wherein one of R³ and R⁴ is methyl.

9. A compound according to claims 1 wherein X¹ is O or S.

10. A compound according to claim 1 wherein R⁵ and R⁶ are independently H or C₁₋₆ alkyl (optionally substituted by C₁₋₆ alkoxy).

11. A compound according to claim 10 wherein one of R⁵ and R⁶ is H and the other is not.

12. A compound according to claim 11 wherein one of R⁵ and R⁶ is H and the other is butyl or ethyloxymethyl.

13. A compound selected from the group consisting of:
{[2-Methyl-4-({[4'-(trifluoromethyl)-3-biphenylyl]methyl}thio)phenyl]oxy}acetic acid;
{[2-Methyl-4-({[4-methyl-4'-(trifluoromethyl)-3-biphenylyl]methyl}thio)phenyl]oxy}acetic acid;
3-[2-Methyl-4-({[4'-(trifluoromethyl)-3-biphenylyl]methyl}oxy)phenyl]propanoic acid;
[(2-Methyl-4-{2-[4'-(trifluoromethyl)-3-biphenylyl]ethyl}phenyl)oxy]acetic acid;
({2-Methyl-4-[({6-[4-(trifluoromethyl)phenyl]-2-pyridinyl}methyl)thio]phenyl}oxy)acetic acid;
{[2-Methyl-4-({1-[4'-(trifluoromethyl)-3-biphenylyl]ethyl}thio)phenyl]oxy}acetic acid;
{[2-Methyl-4-({1-[4'-(trifluoromethyl)-4-biphenylyl]ethyl}thio)phenyl]oxy}acetic acid;
2-Methyl-2-({2-methyl-4-[(1-{6-[4-(trifluoromethyl)phenyl]-2-pyridinyl}pentyl)oxy]phenyl}oxy)propanoic acid;
{[2-Methyl-4-({1-[4'-(trifluoromethyl)-3-biphenylyl]pentyl}oxy)phenyl]oxy}acetic acid;
[(4-{[1-(4'-Chloro-3-biphenylyl)pentyl]oxy}-2-methylphenyl)oxy]acetic acid;
{[2-Methyl-4-({1-[4'-(trifluoromethyl)-4-biphenylyl]pentyl}oxy)phenyl]oxy}acetic acid;
[(4-{[1-(4'-Chloro-4-biphenylyl)pentyl]oxy}-2-methylphenyl)oxy]acetic acid;
{[2-Methyl-4-({(1R)-1-[4'-(trifluoromethyl)-4-biphenylyl]pentyl}thio)phenyl]oxy}acetic acid;
{[2-Methyl-4-({(1S)-1-[4'-(trifluoromethyl)-4-biphenylyl]pentyl}thio)phenyl]oxy}acetic acid;
({2-Methyl-4-[((1S)-1-{6-[4-(trifluoromethyl)phenyl]-2-pyridinyl}pentyl)oxy]phenyl}oxy)acetic acid;
({2-Methyl-4-[((1R)-1-{6-[4-(trifluoromethyl)phenyl]-2-pyridinyl}pentyl)oxy]phenyl}oxy)acetic acid;
({2-Methyl-4-[((1S)-1-{6-[4-(trifluoromethyl)phenyl]-2-pyridinyl}pentyl)thio]phenyl}oxy)acetic acid;
({2-Methyl-4-[((1R)-1-{6-[4-(trifluoromethyl)phenyl]-2-pyridinyl}pentyl)thio]phenyl}oxy)acetic acid;
({2-Methyl-4-[(1-{6-[4-(trifluoromethyl)phenyl]-2-pyridinyl}pentyl)sulfinyl]phenyl}oxy)acetic acid;
({2-Methyl-4-[(1-{6-[4-(trifluoromethyl)phenyl]-2-pyridinyl}pentyl)sulfonyl]phenyl}oxy)acetic acid;
{4-[(1-{6-[4-(Trifluoromethyl)phenyl]-2-pyridinyl}pentyl)oxy]phenyl}acetic acid;
({2-Methyl-4-[(1-{6-[4-(trifluoromethyl)phenyl]-2-pyridinyl}butyl)oxy]phenyl}oxy)acetic acid;
({4-[(1-{6-[4-(Trifluoromethyl)phenyl]-2-pyridinyl}pentyl)oxy]phenyl}oxy)acetic acid;
3-{4-[(1-{6-[4-(Trifluoromethyl)phenyl]-2-pyridinyl}pentyl)oxy]phenyl}propanoic acid;
{[4-({1-[6-(4-Chlorophenyl)-2-pyridinyl]pentyl}oxy)-2-methylphenyl]oxy}acetic acid;
({2-Methyl-4-[(1-{6-[4-(methyloxy)phenyl]-2-pyridinyl}pentyl)oxy]phenyl}oxy)acetic acid;
({4-[(1-{6-[4-(Ethyloxy)phenyl]-2-pyridinyl}pentyl)oxy]-2-methylphenyl}oxy)acetic acid;
{[2-Methyl-4-({1-[6-(4-methylphenyl)-2-pyridinyl]pentyl}oxy)phenyl]oxy}acetic acid;
{[4-({1-[6-(3,4-Dichlorophenyl)-2-pyridinyl]pentyl}oxy)-2-methylphenyl]oxy}acetic acid;
({2-Methyl-4-[(1-{6-[3-(trifluoromethyl)phenyl]-2-pyridinyl}pentyl)oxy]phenyl}oxy)acetic acid;
[(2-Methyl-4-{[1-(6-phenyl-2-pyridinyl)pentyl]oxy}phenyl)oxy]acetic acid;
{[4-({1-[6-(4-Acetylphenyl)-2-pyridinyl]pentyl}oxy)-2-methylphenyl]oxy}acetic acid;
{[4-({1-[6-(4-Fluorophenyl)-2-pyridinyl]pentyl}oxy)-2-methylphenyl]oxy}acetic acid;
{[4-({1-[6-(4-Cyanophenyl)-2-pyridinyl]pentyl}oxy)-2-methylphenyl]oxy}acetic acid;
({2-Methyl-4-[(1-{6-[4-(trifluoromethyl)phenyl]-2-pyridinyl}hexyl)oxy]phenyl}oxy)acetic acid;
({2-Methyl-4-[(4-methyl-1-{6-[4-(trifluoromethyl)phenyl]-2-pyridinyl}pentyl)oxy]phenyl}oxy)acetic acid;
({2-Methyl-4-[(3-methyl-1-{6-[4-(trifluoromethyl)phenyl]-2-pyridinyl}butyl)oxy]phenyl}oxy)acetic acid;
[(4-{[1-(3-Biphenylyl)pentyl]oxy}-2-methylphenyl)oxy]acetic acid;
{[4-({1-[4'-(Ethyloxy)-3-biphenylyl]pentyl}oxy)-2-methylphenyl]oxy}acetic acid;
[(4-{[1-(4'-Cyano-3-biphenylyl)pentyl]oxy}-2-methylphenyl)oxy]acetic acid;
[(2-Ethyl-4-{[1-(6-phenyl-2-pyridinyl)pentyl]oxy}phenyl)oxy]acetic acid;
{[4-({1-[6-(4-Chlorophenyl)-2-pyridinyl]pentyl}oxy)-2-ethylphenyl]oxy}acetic acid;
({2-Ethyl-4-[(1-{6-[4-(ethyloxy)phenyl]-2-pyridinyl}pentyl)oxy]phenyl}oxy)acetic acid;
{[4-({1-[6-(4-Cyanophenyl)-2-pyridinyl]pentyl}oxy)-2-ethylphenyl]oxy}acetic acid;
({2-Ethyl-4-[(1-{6-[4-(trifluoromethyl)phenyl]-2-pyridinyl}pentyl)oxy]phenyl}oxy)acetic acid;
4-{4-[(1-{6-[4-(Trifluoromethyl)phenyl]-2-pyridinyl}pentyl)oxy]phenyl}butanoic acid;
{[4-({(1R)-1-[6-(4-Chlorophenyl)-2-pyridinyl]pentyl}oxy)-2-methylphenyl]oxy}acetic acid;

{[4-({(1R)-1-[6-(4-Cyanophenyl)-2-pyridinyl]
pentyl}oxy)-2-methylphenyl]oxy}acetic acid;
({2-methyl-4-[((1R)-1-{6-[4-(methyloxy)phenyl]-2-
pyridinyl}pentyl)oxy]phenyl}oxy)acetic acid;
{[4-({(1R)-1-[6-(4-Acetylphenyl)-2-pyridinyl]
pentyl}oxy)-2-methylphenyl]oxy}acetic acid;
({4-[((1R)-1-{6-[4-Acetyl-3-(methyloxy)phenyl]-2-
pyridinyl}pentyl)oxy]-2-methylphenyl}oxy)acetic
acid;
{[4-({(1S)-1-[6-(4-Chlorophenyl)-2-pyridinyl]
pentyl}oxy)-2-methylphenyl]oxy}acetic acid;
{[4-({(1S)-1-[6-(4-Cyanophenyl)-2-pyridinyl]
pentyl}oxy)-2-methylphenyl]oxy}acetic acid;
({2-Methyl-4-[((1S)-1-{6-[4-(methyloxy)phenyl]-2-
pyridinyl}pentyl)oxy]phenyl}oxy)acetic acid;
{[4-({(1S)-1-[6-(4-Acetylphenyl)-2-pyridinyl]
pentyl}oxy)-2-methylphenyl]oxy}acetic acid;
({4-[((1S)-1-{6-[4-Acetyl-3-(methyloxy)phenyl]-2-
pyridinyl}pentyl)oxy]-2-methylphenyl}oxy)acetic
acid;
({2-Methyl-4-[((1R)-3-(methyloxy)-1-{6-[4-(trifluorom-
ethyl)phenyl]-2-pyridinyl}propyl)oxy]phenyl}oxy)
acetic acid;
[(4-{[(1R)-1-[6-(4-Chlorophenyl)-2-pyridinyl]-3-(methy-
loxy)propyl]oxy}-2-methylphenyl)oxy]acetic acid;
({2-Methyl-4-[((1S)-3-(methyloxy)-1-{6-[4-(trifluorom-
ethyl)phenyl]-2-pyridinyl}propyl)oxy]phenyl}oxy)
acetic acid;
[(4-{[(1S)-1-[6-(4-Chlorophenyl)-2-pyridinyl]-3-(methy-
loxy)propyl]oxy}-2-methylphenyl)oxy]acetic acid;
({4-[((1R)-2-(Ethyloxy)-1-{6-[4-(trifluoromethyl)phe-
nyl]-2-pyridinyl}ethyl)oxy]-2-methylphenyl}oxy)ace-
tic acid;
({4-[((1R)-2-(Ethyloxy)-1-{6-[4-(methyloxy)phenyl]-2-
pyridinyl}ethyl)oxy]-2-methylphenyl}oxy)acetic acid;
[(4-{[(1R)-1-[6-(4-Acetylphenyl)-2-pyridinyl]-2-(ethy-
loxy)ethyl]oxy}-2-methylphenyl)oxy]acetic acid;
[(4-{[(1R)-1-[6-(4-Cyanophenyl)-2-pyridinyl]-2-(ethy-
loxy)ethyl]oxy}-2-methylphenyl)oxy]acetic acid;
[(4-{[(1R)-1-[6-(4-Chlorophenyl-2-pyridinyl]-2-(ethy-
loxy)ethyl]oxy}-2-methylphenyl)oxy]acetic acid;
({4-[((1S)-2-(Ethyloxy)-1-{6-[4-(trifluoromethyl)phe-
nyl]-2-pyridinyl}ethyl)oxy]-2-methylphenyl}oxy)ace-
tic acid;
({4-[((1S)-2-(Ethyloxy)-1-{6-[4-(methyloxy)phenyl]-2-
pyridinyl}ethyl)oxy]-2-methylphenyl}oxy)acetic acid;
[(4-{[(1S)-1-[6-(4-Acetylphenyl)-2-pyridinyl]-2-(ethy-
loxy)ethyl]oxy}-2-methylphenyl)oxy]acetic acid;
[(4-{[(1S)-1-[6-(4-Cyanophenyl)-2-pyridinyl]-2-(ethy-
loxy)ethyl]oxy}-2-methylphenyl)oxy]acetic acid;
[(4-{[(1S)-1-[6-(4-Chlorophenyl)-2-pyridinyl]-2-(ethy-
loxy)ethyl]oxy}-2-methylphenyl)oxy]acetic acid;
{[4-({(1R)-2-(Ethyloxy)-1-[6-(3-fluoro-4-methylphe-
nyl)-2-pyridinyl]ethyl}oxy)-2-methylphenyl]
oxy}acetic acid;
{[4-({(1R)-2-(Ethyloxy)-1-[6-(4-methylphenyl)-2-py-
ridinyl]ethyl}oxy)-2-methylphenyl]oxy}acetic acid;
({4-[((1R)-2-(Ethyloxy)-1-{6-[4-(1-methylethyl)phenyl]-
2-pyridinyl}ethyl)oxy]-2-methylphenyl}oxy)acetic
acid;
[(4-{[(1R)-1-[6-(4-Cyano-3-fluorophenyl)-2-pyridinyl]-
2-(ethyloxy)ethyl]oxy}-2-methylphenyl)oxy]acetic
acid;
({4-[((1R)-2-(Ethyloxy)-1-{6-[4-(ethyloxy)phenyl]-2-
pyridinyl}ethyl)oxy]-2-methylphenyl}oxy)acetic acid;
{[4-({(1R)-2-(Ethyloxy)-1-[6-(2-fluoro-4-methylphe-
nyl)-2-pyridinyl]ethyl}oxy)-2-methylphenyl]
oxy}acetic acid;
{[4-({(1R)-2-(Ethyloxy)-1-[6-(4-fluorophenyl)-2-pyridi-
nyl]ethyl}oxy)-2-methylphenyl]oxy}acetic acid;
[(4-{[(1R)-2-(Ethyloxy)-1-(6-{4-[(1-methylethyl)oxy]
phenyl}-2-pyridinyl)ethyl]oxy}-2-methylphenyl)oxy]
acetic acid;
[(4-{[(1R)-1-[6-(4-Chloro-3-methylphenyl)-2-pyridinyl]-
2-(ethyloxy)ethyl]oxy}-2-methylphenyl)oxy]acetic
acid;
[(4-{[(1R)-1-[6-(3-Chloro-4-cyanophenyl)-2-pyridinyl]-
2-(ethyloxy)ethyl]oxy}-2-methylphenyl)oxy]acetic
acid;
[(4-{[(1R)-1-[6-(4-Cyano-3-methylphenyl)-2-pyridinyl]-
2-(ethyloxy)ethyl]oxy}-2-methylphenyl)oxy]acetic
acid;
({4-[((1R)-2-(Ethyloxy)-1-{6-[3-fluoro-4-(methyloxy)
phenyl]-2-pyridinyl}ethyl)oxy]-2-methylphenyl}oxy)
acetic acid;
[(4-{[(1R)-1-[6-(4-Cyano-2-fluorophenyl)-2-pyridinyl]-
2-(ethyloxy)ethyl]oxy}-2-methylphenyl)oxy]acetic
acid;
[(4-{[(1R)-1-[6-(4-Cyano-2-methylphenyl)-2-pyridinyl]-
2-(ethyloxy)ethyl]oxy}-2-methylphenyl)oxy]acetic
acid;
{[4-({(1S)-2-(Ethyloxy)-1-[6-(3-fluoro-4-methylphenyl)-
2-pyridinyl]ethyl}oxy)-2-methylphenyl]oxy}acetic
acid;
{[4-({(1S)-2-(Ethyloxy)-1-[6-(4-methylphenyl)-2-pyridi-
nyl]ethyl}oxy)-2-methylphenyl]oxy}acetic acid;
({4-[((1S)-2-(Ethyloxy)-1-{6-[4-(1-methylethyl)phenyl]-
2-pyridinyl}ethyl)oxy]-2-methylphenyl}oxy)acetic
acid;
[(4-{[(1S)-1-[6-(4-Cyano-3-fluorophenyl)-2-pyridinyl]-
2-(ethyloxy)ethyl]oxy}-2-methylphenyl)oxy]acetic
acid;
({4-[((1S)-2-(Ethyloxy)-1-{6-[4-(ethyloxy)phenyl]-2-
pyridinyl}ethyl)oxy]-2-methylphenyl}oxy)acetic acid;
{[4-({(1S)-2-(Ethyloxy)-1-[6-(2-fluoro-4-methylphenyl)-
2-pyridinyl]ethyl}oxy)-2-methylphenyl]oxy}acetic
acid;
{[4-({(1S)-2-(Ethyloxy)-1-[6-(4-fluorophenyl)-2-pyridi-
nyl]ethyl}oxy)-2-methylphenyl]oxy}acetic acid;
[(4-{[(1S)-2-(Ethyloxy)-1-(6-{4-[(1-methylethyl)oxy]
phenyl}-2-pyridinyl)ethyl]oxy}-2-methylphenyl)oxy]
acetic acid;
[(4-{[(1S)-1-[6-(4-Chloro-3-methylphenyl)-2-pyridinyl]-
2-(ethyloxy)ethyl]oxy}-2-methylphenyl)oxy]acetic
acid;
[(4-{[(1S)-1-[6-(3-Chloro-4-cyanophenyl)-2-pyridinyl]-
2-(ethyloxy)ethyl]oxy}-2-methylphenyl)oxy]acetic
acid;
[(4-{[(1S)-1-[6-(4-Cyano-3-methylphenyl)-2-pyridinyl]-
2-(ethyloxy)ethyl]oxy}-2-methylphenyl)oxy]acetic
acid;
({4-[((1S)-2-(Ethyloxy)-1-{6-[3-fluoro-4-(methyloxy)
phenyl]-2-pyridinyl}ethyl)oxy]-2-methylphenyl}oxy)
acetic acid;
[(4-{[(1S)-1-[6-(4-Cyano-2-fluorophenyl)-2-pyridinyl]-
2-(ethyloxy)ethyl]oxy}-2-methylphenyl)oxy]acetic
acid;
[(4-{[(1S)-1-{6-[4-Cyano-3-(methyloxy)phenyl]-2-py-
ridinyl}-2-(ethyloxy)ethyl]oxy}-2-methylphenyl)oxy]
acetic acid;
3-{2-Methyl-4-[((1S)-1-{6-[4-(trifluoromethyl)phenyl]-
2-pyridinyl}pentyl)oxy]phenyl}propanoic acid;

3-{2-Methyl-4-[((1S)-1-{6-[4-(methyloxy)phenyl]-2-pyridinyl}pentyl)oxy]phenyl}propanoic acid;
3-[4-({(1S)-1-[6-(4-Acetylphenyl)-2-pyridinyl]pentyl}oxy)-2-methylphenyl]propanoic acid;
3-[4-({(1S)-1-[6-(4-Cyanophenyl)-2-pyridinyl]pentyl}oxy)-2-methylphenyl]propanoic acid;
3-[4-({(1S)-1-[6-(4-Chlorophenyl)-2-pyridinyl]pentyl}oxy)-2-methylphenyl]propanoic acid;
3-{2-Methyl-4-[((1R)-1-{6-[4-(trifluoromethyl)phenyl]-2-pyridinyl}pentyl)oxy]phenyl}propanoic acid;
3-{2-Methyl-4-[((1R)-1-{6-[4-(methyloxy)phenyl]-2-pyridinyl}pentyl)oxy]phenyl}propanoic acid;
3-[4-({(1R)-1-[6-(4-Acetylphenyl)-2-pyridinyl]pentyl}oxy)-2-methylphenyl]propanoic acid;
3-[4-({(1R)-1-[6-(4-Cyanophenyl)-2-pyridinyl]pentyl}oxy)-2-methylphenyl]propanoic acid;
3-[4-({(1R)-1-[6-(4-Chlorophenyl-2-pyridinyl]pentyl}oxy)-2-methylphenyl]propanoic acid;
3-{3,5-Dimethyl-4-[(1-{6-[4-(trifluoromethyl)phenyl]-2-pyridinyl}pentyl)oxy]phenyl}propanoic acid;
3-{3-(Methyloxy)-5-propyl-4-[(1-{6-[4-(trifluoromethyl)phenyl]-2-pyridinyl}pentyl)oxy]phenyl}propanoic acid;
3-{3-Propyl-4-[(1-{6-[4-(trifluoromethyl)phenyl]-2-pyridinyl}pentyl)oxy]phenyl}propanoic acid;
3-{3-(Ethyloxy)-4-[(1-{6-[4-(trifluoromethyl)phenyl]-2-pyridinyl}pentyl)oxy]phenyl}propanoic acid;
3-{4-[((1R)-1-{6-[4-(Trifluoromethyl)phenyl]-2-pyridinyl}pentyl)oxy]phenyl}propanoic acid;
3-{3-(Methyloxy)-4-[((1R)-1-{6-[4-(trifluoromethyl)phenyl]-2-pyridinyl}pentyl)oxy]phenyl}propanoic acid;
{4-[((1R)-1-{6-[4-(Trifluoromethyl)phenyl]-2-pyridinyl}pentyl)oxy]phenyl}acetic acid;
{3-Chloro-4-[((1R)-1-{6-[4-(trifluoromethyl)phenyl]-2-pyridinyl}pentyl)oxy]phenyl}acetic acid;
{3-(Methyloxy)-4-[((1R)-1-{6-[4-(trifluoromethyl)phenyl]-2-pyridinyl}pentyl)oxy]phenyl}acetic acid;
3-{4-[((1S)-1-{6-[4-(Trifluoromethyl)phenyl]-2-pyridinyl}pentyl)oxy]phenyl}propanoic acid;
3-{3-(Methyloxy)-4-[((1S)-1-{6-[4-(trifluoromethyl)phenyl]-2-pyridinyl}pentyl)oxy]phenyl}propanoic acid;
{4-[((1S)-1-{6-[4-(Trifluoromethyl)phenyl]-2-pyridinyl}pentyl)oxy]phenyl}acetic acid;
{3-Chloro-4-[((1S)-1-{6-[4-(trifluoromethyl)phenyl]-2-pyridinyl}pentyl)oxy]phenyl}acetic acid;
{3-(Methyloxy)-4-[((1S)-1-{6-[4-(trifluoromethyl)phenyl]-2-pyridinyl}pentyl)oxy]phenyl}acetic acid;
3-{3-Fluoro-4-[((1R)-1-{6-[4-(trifluoromethyl)phenyl]-2-pyridinyl}pentyl)oxy]phenyl}propanoic acid;
3-{3-Methyl-4-[((1R)-1-{6-[4-(trifluoromethyl)phenyl]-2-pyridinyl}pentyl)oxy]phenyl}propanoic acid;
3-{3,5-Bis(methyloxy)-4-[((1R)-1-{6-[4-(trifluoromethyl)phenyl]-2-pyridinyl}pentyl)oxy]phenyl}propanoic acid;
3-{2-(Methyloxy)-4-[((1R)-1-{6-[4-(trifluoromethyl)phenyl]-2-pyridinyl}pentyl)oxy]phenyl}propanoic acid;
3-{3-Fluoro-4-[((1S)-1-{6-[4-(trifluoromethyl)phenyl]-2-pyridinyl}pentyl)oxy]phenyl}propanoic acid;
3-{3-Methyl-4-[((1S)-1-{6-[4-(trifluoromethyl)phenyl]-2-pyridinyl}pentyl)oxy]phenyl}propanoic acid;
3-{3,5-Bis(methyloxy)-4-[((1S)-1-{6-[4-(trifluoromethyl)phenyl]-2-pyridinyl}pentyl)oxy]phenyl}propanoic acid;
3-{2-(Methyloxy)-4-[((1S)-1-{6-[4-(trifluoromethyl)phenyl]-2-pyridinyl}pentyl)oxy]phenyl}propanoic acid;
3-{3-Chloro-5-(methyloxy)-4-[((1S)-1-{6-[4-(trifluoromethyl)phenyl]-2-pyridinyl}pentyl)oxy]phenyl}propanoic acid;
3-{3-Chloro-4-[((1R)-1-{6-[4-(trifluoromethyl)phenyl]-2-pyridinyl}pentyl)oxy]phenyl}propanoic acid;
3-{2-Chloro-4-[((1R)-1-{6-[4-(trifluoromethyl)phenyl]-2-pyridinyl}pentyl)oxy]phenyl}propanoic acid;
3-{3-Chloro-4-[((1S)-1-{6-[4-(trifluoromethyl)phenyl]-2-pyridinyl}pentyl)oxy]phenyl}propanoic acid;
3-{2-Chloro-4-[((1S)-1-{6-[4-(trifluoromethyl)phenyl]-2-pyridinyl}pentyl)oxy]phenyl}propanoic acid;
{[2-Methyl-4-({1-[2-methyl-4'-(trifluoromethyl)-3-biphenylyl]pentyl}oxy)phenyl]oxy}acetic acid;
[(4-{[1-(4'-Chloro-2-methyl-3-biphenylyl)pentyl]oxy}-2-methylphenyl)oxy]acetic acid;
[(4-{[1-(2,4'-dimethyl-3-biphenylyl)pentyl]oxy}-2-methylphenyl)oxy]acetic acid;
[(4-{[1-(4'-Cyano-2-methyl-3-biphenylyl)pentyl]oxy}-2-methylphenyl)oxy]acetic acid;
{[2-Methyl-4-({1-[2-methyl-4'-(methyloxy)-3-biphenylyl]pentyl}oxy)phenyl]oxy}acetic acid;
[(4-{[1-(4'-Fluoro-2-methyl-3-biphenylyl)pentyl]oxy}-2-methylphenyl)oxy]acetic acid;
({2-Methyl-4-[(2-(propyloxy)-1-{6-[4-(trifluoromethyl)phenyl]-2-pyridinyl}ethyl)oxy]phenyl}oxy)acetic acid; and
({4-[(2-(Ethyloxy)-1-{6-[4-(trifluoromethyl)phenyl]-2-pyridinyl}ethyl)thio]-2-methylphenyl}oxy)acetic acid.

14. A pharmaceutical composition comprising a compound according to claim 1 and a pharmaceutically acceptable diluent or carrier.

* * * * *

UNITED STATES PATENT AND TRADEMARK OFFICE
CERTIFICATE OF CORRECTION

PATENT NO. : 7,338,960 B2
APPLICATION NO. : 10/518679
DATED : March 4, 2008
INVENTOR(S) : Bell et al.

Page 1 of 2

It is certified that error appears in the above-identified patent and that said Letters Patent is hereby corrected as shown below:

On the Title page:

An inventor's residence in Item (75) should read as follows:

Item (75)   Inventors

-- Romain Luc Marie Gosmini, Les Ulis (FR); --

On the Title page Item (56) should include additional cited references as follows:

Item (56)   References Cited

-- FOREIGN PATENT DOCUMENTS

| | | |
|---|---|---|
| EP | 1 067 109 | 1/2001 |
| EP | 1 132 376 | 9/2001 |
| EP | 1 283 039 | 2/2003 |
| WO | 97/31907 | 9/1997 |
| WO | 99/11255 | 3/1999 |
| WO | 00/64876 | 11/2000 |
| WO | 01/36351 | 5/2001 -- |

On The Title Page, Item (56) should read as follows:

OTHER PUBLICATIONS

-- Gentles, R.G., et al., "Standardization Protocols and Optimized Precursor Sets for the Efficient Application of Automated Parallel Synthesis to Lead Optimization: A Mitsunobu Example," Journal of Combinatorial Chemistry (2002), Vol. 4(5), pgs. 442-456.

Kuchar, M., et al., "Benzyloxyarylalipatic Acids: Synthesis and Quantitative Relations between Structure and Antiinflammatory Activity," Collection of Czechoslovak Chemical Communications, Academic Press, London, GB, 1982, Vol. 47; pgs. 2514-2524.

Kuchar, M., et al., "The Effects of Lipophilicity on the Inhibition of Denaturation of Serum Albumin and on the Activation of Fibrinolysis Observed with a Series of Benzyloxyarylalipatic Acids," Collection of Czechoslovak Chemical Communications, Academic Press, London, GB, 1983, Vol. 48, pgs. 1077-1088. --

UNITED STATES PATENT AND TRADEMARK OFFICE
CERTIFICATE OF CORRECTION

PATENT NO. : 7,338,960 B2
APPLICATION NO. : 10/518679
DATED : March 4, 2008
INVENTOR(S) : Bell et al.

It is certified that error appears in the above-identified patent and that said Letters Patent is hereby corrected as shown below:

Claim 9 (Column 143, Lines 28-29) should read as follows:

-- 9. A compound according to claim 1 wherein $X^1$ is O or S. --

Signed and Sealed this

Twenty-first Day of October, 2008

JON W. DUDAS
*Director of the United States Patent and Trademark Office*